(12) United States Patent
Leblond et al.

(10) Patent No.: US 9,200,016 B2
(45) Date of Patent: Dec. 1, 2015

(54) SUBSTITUTED 6, 7-DIALKOXY-3-ISOQUINOLINE DERIVATIVES AS INHIBITORS OF PHOSPHODIESTERASE 10 (PDE 10A)

(71) Applicant: Allergan, Inc., Irvine, CA (US)

(72) Inventors: Bertrand Leblond, Paris (FR); Thierry Taverne, St. Martin les Boulogne sur Mer (FR); Cedric Chauvignac, Nogent sur Marne (FR); Eric Beausoleil, Paris (FR); Anne-Sophie Casagrande, Draveli (FR); Laurent Desire, Paris (FR); Matthew P. Pando, Paris (FR); John E. Donello, Dana Point, CA (US); Rong Yang, Mission Viejo, CA (US)

(73) Assignees: Allergan, Inc., Irvine, CA (US); Exonhit Therapeutics, SA, Paris (FR)

( * ) Notice: Subject to any disclaimer, the term of this patent is extended or adjusted under 35 U.S.C. 154(b) by 0 days.

(21) Appl. No.: 14/097,808

(22) Filed: Dec. 5, 2013

(65) Prior Publication Data
US 2015/0158895 A1    Jun. 11, 2015

(51) Int. Cl.
| | | |
|---|---|---|
| A01N 43/42 | (2006.01) |
| A61K 31/41 | (2006.01) |
| C07D 491/00 | (2006.01) |
| C07D 498/00 | (2006.01) |
| C07D 515/00 | (2006.01) |
| C07F 9/62 | (2006.01) |
| C07D 217/02 | (2006.01) |
| C07D 401/06 | (2006.01) |
| C07D 401/14 | (2006.01) |
| C07D 405/06 | (2006.01) |
| C07D 409/06 | (2006.01) |
| C07D 413/06 | (2006.01) |
| C07D 471/04 | (2006.01) |
| C07D 491/056 | (2006.01) |
| C07F 9/6558 | (2006.01) |

(52) U.S. Cl.
CPC ............... *C07F 9/62* (2013.01); *C07D 217/02* (2013.01); *C07D 401/06* (2013.01); *C07D 401/14* (2013.01); *C07D 405/06* (2013.01); *C07D 409/06* (2013.01); *C07D 413/06* (2013.01); *C07D 471/04* (2013.01); *C07D 491/056* (2013.01); *C07F 9/65583* (2013.01)

(58) Field of Classification Search
None
See application file for complete search history.

(56) References Cited

U.S. PATENT DOCUMENTS

| | | | |
|---|---|---|---|
| 6,919,337 B2 * | 7/2005 | Bhalay et al. ............... 514/234.2 |
| 2003/0032579 A1 | 2/2003 | Lebel |
| 2008/0300240 A1 | 12/2008 | Bergmann |
| 2010/0016303 A1 | 1/2010 | Ritzen |

FOREIGN PATENT DOCUMENTS

| | | |
|---|---|---|
| JP | 2011-201873 | 10/2011 |
| WO | 01-41807 | 6/2001 |
| WO | 2003-000693 | 1/2003 |
| WO | 03-14116 | 2/2003 |
| WO | 2004-002484 | 1/2004 |
| WO | 2004-005290 | 1/2004 |
| WO | 2004-005291 | 1/2004 |
| WO | 2005-002579 | 1/2005 |
| WO | 2005-003129 | 1/2005 |
| WO | 2005-012485 | 2/2005 |
| WO | 2005-082883 | 9/2005 |
| WO | 2005-120514 | 12/2005 |
| WO | 2006-011040 | 2/2006 |
| WO | 2006-028957 | 3/2006 |
| WO | 2006-034491 | 3/2006 |
| WO | 2006-034512 | 3/2006 |
| WO | 2006-070284 | 7/2006 |
| WO | 2006-071988 | 7/2006 |
| WO | 2006-072828 | 7/2006 |
| WO | 2006-075012 | 7/2006 |
| WO | 2006-089815 | 8/2006 |
| WO | 2007-022280 | 2/2007 |
| WO | 2007-085954 | 8/2007 |
| WO | 2007-096743 | 8/2007 |
| WO | 2007-098169 | 8/2007 |

(Continued)

OTHER PUBLICATIONS

Dyke et al., 27(2) Tetrahedron 281-9 (1971) (CAS Abstract).*

(Continued)

*Primary Examiner* — Timothy R Rozof
(74) *Attorney, Agent, or Firm* — Jonathan Bass

(57) ABSTRACT

The invention relates to compounds of the formula

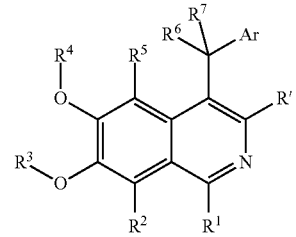

or a pharmaceutically acceptable salt thereof, wherein R', $R^1$ through $R^7$ and Ar are as defined herein. These compounds are useful as inhibitors of phosphodiesterase 10 (PDE10A) which are useful in treating central nervous system diseases such as psychosis and also in treating, for example, obesity, type II diabetes, metabolic syndrome, glucose intolerance, pain and ophthalmic diseases.

13 Claims, 1 Drawing Sheet

(56) References Cited

FOREIGN PATENT DOCUMENTS

| | | |
|---|---|---|
| WO | 2007-098214 | 8/2007 |
| WO | 2007-100880 | 9/2007 |
| WO | 2007-103260 | 9/2007 |
| WO | 2007-103370 | 9/2007 |
| WO | 2007-103554 | 9/2007 |
| WO | 2007-137819 | 12/2007 |
| WO | 2007-137820 | 12/2007 |
| WO | 2008-004117 | 1/2008 |
| WO | 2008-006372 | 1/2008 |
| WO | 2008-020302 | 2/2008 |
| WO | 2008-032171 | 3/2008 |
| WO | 2008-046342 | 4/2008 |
| WO | 2009-025823 | 2/2009 |
| WO | 2009-025839 | 2/2009 |
| WO | 2009-029214 | 3/2009 |
| WO | 2009-036766 | 3/2009 |
| WO | 2009-068320 | 6/2009 |
| WO | 2009-070583 | 6/2009 |
| WO | 2009-070584 | 6/2009 |
| WO | 2009-143178 | 11/2009 |
| WO | 2009-152825 | 12/2009 |
| WO | 2009-158393 | 12/2009 |
| WO | 2009-158467 | 12/2009 |
| WO | 2009-158473 | 12/2009 |
| WO | 2010-006130 | 1/2010 |
| WO | 2010-017236 | 2/2010 |
| WO | 2010-027097 | 3/2010 |
| WO | 2010-054253 | 5/2010 |
| WO | 2010-054260 | 5/2010 |
| WO | 2010-057126 | 5/2010 |
| WO | 2010-062559 | 6/2010 |
| WO | 2010-063610 | 6/2010 |
| WO | 2010-077992 | 7/2010 |
| WO | 2010-090737 | 8/2010 |
| WO | 2010-094762 | 8/2010 |
| WO | 2010-097367 | 9/2010 |
| WO | 2010-117926 | 10/2010 |
| WO | 2010-128995 | 11/2010 |
| WO | 2010-138430 | 12/2010 |
| WO | 2010-138577 | 12/2010 |
| WO | 2010-138585 | 12/2010 |
| WO | 2010-138833 | 12/2010 |
| WO | 2010-145668 | 12/2010 |
| WO | 2011-022213 | 2/2011 |
| WO | 2011-036127 | 3/2011 |
| WO | 2011-051324 | 5/2011 |
| WO | 2011-051342 | 5/2011 |
| WO | 2011-053559 | 5/2011 |
| WO | 2011-072694 | 6/2011 |
| WO | 2011-072695 | 6/2011 |
| WO | 2011-072696 | 6/2011 |
| WO | 2011-072697 | 6/2011 |
| WO | 2011-089132 | 7/2011 |
| WO | 2011-105628 | 9/2011 |
| WO | 2011-110545 | 9/2011 |
| WO | 2011-112828 | 9/2011 |
| WO | 2011-117264 | 9/2011 |
| WO | 2011-132048 | 10/2011 |
| WO | 2011-132051 | 10/2011 |
| WO | 2011-138657 | 11/2011 |
| WO | 2011-143365 | 11/2011 |
| WO | 2011-143366 | 11/2011 |
| WO | 2011-143495 | 11/2011 |
| WO | 2011-150156 | 12/2011 |
| WO | 2011-154327 | 12/2011 |
| WO | 2011-163355 | 12/2011 |
| WO | 2012-000519 | 1/2012 |
| WO | 2012-007006 | 1/2012 |
| WO | 2012-112946 | 8/2012 |

OTHER PUBLICATIONS

Berge, Stephen M., Pharmaceutical Salts, Journal of Pharmaceutical Sciences, Jan. 1977, 1-19, 66 (1), US.

Cantin, Louis-David et al, PDE-10A Inhibitors as Insulin Secretagogues, Bioorganic & Medicinal Chemistry Letters, 2007, 2869-2873, 17.

Fujishige, Kotomi et al, Cloning and Characterization of a Novel Human Phosphodiesterase That Hydrolyzes Both cAMP and cGMP (PDE10A), Journal of Biological Chemistry, Jun. 25, 1999, 18438-18445, 274 (26).

Fujishige, Kotomi et al, Striatum- and Testis-Specific Phosphodiesterase PDE10A, Eur. J. Biochem., 1999, 1118-1127, 266.

Hamblin, Nicole et al, Pyrazolopyridines as a Novel Structural Class of Potent and Selective PDE4 Inhibitors, Bioorganic & Medicinal Chemistry Letters, 2008, 4237-4241, 18.

Ji, Yining et al, Innate C—H Trifluoromethylation of Heterocycles, PNAS, Aug. 2011, 14411-14415, 108(35).

Kalluraya, Balakrishna et al, One Pot Reaction: Synthesis, Characterization and Biological Activity of 3-Alkyl/Aryl-9-Substituted 1,2,4-triazolo[3,4-b][1,3,4]quinolino Thiadiazepines, Indian Journal of Chemistry, Jan. 2003, 211-214, 42B.

Kehler, Jan et al, The Potential Therapeutic Use of Phosphodiesterase 10 Inhibitors, Expert Opin. Ther. Patents, 2007, 147-158, 17 (2).

Kehler, Jan, Phosphodiesterase 10A Inhibitors: a 2009-2012 Patent Update, Expert Opin. Ther. Patents, 2013, 31-45, 23(1).

Kotera, Jun et al, Characterization and Phosphorylation of PDE10A2, a Novel Alternative Splice Variant of Human Phosphodiesterase That Hydrolyzes cAMP and cGMP, Biochemical and Biophysical Research Communications, 1999, 551-557, 261.

Langlois, Bernard et al, Trifluoromethylation of Aromatic Compounds with Sodium Trifluoromethanesulfinate Under Oxidative Conditions, Tetrahedron Letters, 1991, 7525-7528, 32(51).

Loughney, K. et al, Isolation and Characterization of PDE10A, a Novel Human 3', 5'-Cyclic Nucleotide Phosphodiesterase, Gene, 1999, 109-117, 234.

Menniti, Frank et al, Immunohistochemical Localization of PDE10A in the Rat Brain, Brain Research, 2003, 113-126, 985.

Nagib, David et al, Trifluoromethylation of Arenes and Heteroarenes by Means of Photoredox Catalysis, Nature, Dec. 2011, 224-228, 480.

Seeger, T.F., PDE10A mRNA in situ Hybridization Mapping in the Rodent Brian: Apparent Co-Localization With Dopaminoceptive Neurons, Neuroscience, 2000, 345.10, 26.

Singh, Mrityunjay et al, Synthesis of Diastereomeric 2,4-disubstituted pyrano[2,3-b]quinolines from 3-formyl-2quinolones Through O—C Bond Formation Via Intramolecular Electrophilic Cyclization, Tetrahedron Letters, 2007, 5987-5990, 48.

Soderling, Scott et al, Isolation and Characterization of a Dual-Substrate Phosphodiesterase Gene Family: PDE10A, Proc. Natl. Acad. Sci., Jun. 1999, 7071-7076, 96.

Wolloscheck, Tanja et al, Phosphodiesterase10A: Abundance and Circadian Regulation in the Retina and Photoreceptor of the Rat, Brian Research, 2011, 42-50, 1376.

\* cited by examiner

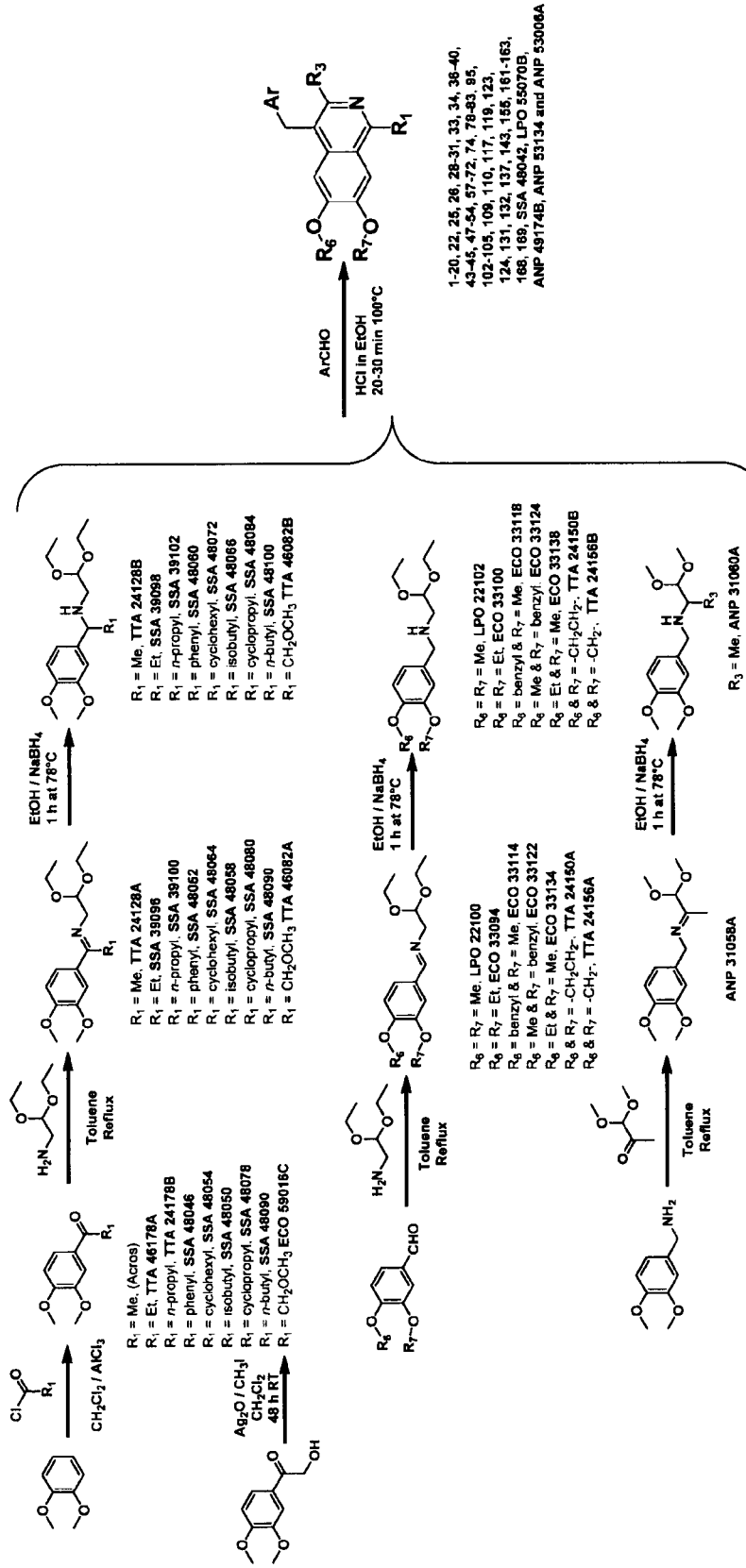

SUBSTITUTED 6, 7-DIALKOXY-3-ISOQUINOLINE DERIVATIVES AS INHIBITORS OF PHOSPHODIESTERASE 10 (PDE 10A)

BACKGROUND OF THE INVENTION

Phosphodiesterases (PDEs) are a class of intracellular enzymes involved in the hydrolysis of the nucleotides cyclic adenosine monophosphate (cAMP) and cyclic guanosine monophosphates (cGMP) into their respective nucleotide monophosphates. The cyclic nucleotides cAMP and cGMP are synthesized by adenylyl and guanylyl cyclases, respectively.

The cAMP and cGMP function as intracellular second messengers regulating a vast array of intracellular processes particularly in neurons of the central nervous system. In neurons, this includes the activation of cAMP and cGMP-dependent kinases and subsequent phosphorylation of proteins involved in acute regulation of synaptic transmission as well as in neuronal differentiation and survival. The complexity of cyclic nucleotide signaling is indicated by the molecular diversity of the enzymes involved in the synthesis and degradation of cAMP and cGMP.

There are at least ten families of adenylyl cyclases, two of guanylyl cyclases, and eleven of phosphodiesterases. Furthermore, different types of neurons are known to express multiple isozymes of each of these classes, and there is good evidence for compartmentalization and specificity of function for different isozymes within a given neuron.

A principal mechanism for regulating cyclic nucleotide signaling is by phosphodiesterase-catalyzed cyclic nucleotide catabolism. There are 11 known families of PDEs encoded by 21 different genes. Each gene typically yields multiple splice variants that further contribute to the isozyme diversity. The PDE families are distinguished functionally based on cyclic nucleotide substrate specificity, mechanism(s) of regulation, and sensitivity to inhibitors. Furthermore, PDEs are differentially expressed throughout the organism, including in the central nervous system. As a result of these distinct enzymatic activities and localization, different PDEs' isozymes can serve distinct physiological functions. Furthermore, compounds that can selectively inhibit distinct PDE families or isozymes may offer particular therapeutic effects, fewer side effects, or both.

PDE10 is identified as a unique family based on primary amino acid sequence and distinct enzymatic activity. Homology screening of EST databases revealed human PDE10A as the first member of the PDE10 family of PDEs (Fujishige et al., *J. Biol. Chem.*, 274, 18438-18445, 1999; Loughney, K. et al., *Gene*, 234, 109-117, 1999). The murine homologue has also been cloned (Soderling, S. et al., *Proc. Natl. Acad. Sci. USA*, 96, 7071-7076, 1999) and N-terminal splice variants of both the rat and human genes have been identified (Kotera, J. et al., *Biochem. Biophys. Res. Comm.*, 261, 551-557, 1999; Fujishige, K. et al., *Eur. J. Biochem.*, 266, 1118-1127, 1999). There is a high degree of homology across species. The mouse PDE10A1 is a 779 amino acid protein that hydrolyzes both cAMP and cGMP to AMP and GMP, respectively. The affinity of PDE10 for cAMP (Km=0.05 µM) is higher than for cGMP (Km=3 µM). However, the approximately 5-fold greater Vmax for cGMP over cAMP has lead to the suggestion that PDE10 is a unique cAMP-inhibited cGMPase (Fujishige et al., *J. Biol. Chem.*, 274, 18438-18445, 1999).

PDE10A also is uniquely localized in mammals relative to other PDE families. mRNA for PDE10 is highly expressed only in testis and brain (Fujishige, K. et al., *Eur J Biochem.*, 266, 1118-1127, 1999; Soderling, S. et al., *Proc. Natl. Acad. Sci.*, 96, 7071-7076, 1999; Loughney, K. et al., *Gene*, 234, 109-117, 1999).

These initial studies indicated that within the brain PDE10A expression is highest in the striatum (caudate and putamen), n. accumbens, and olfactory tubercle. More recently, a detailed analysis has been made of the expression pattern in rodent brain of PDE10 mRNA (Seeger, T. F. et al., *Abst. Soc. Neurosci.*, 26, 345.10, 2000) and PDE10 protein (Menniti, F. S., Stick, CA₁ Seeger, T. F., and Ryan, A. M., Immunohistochemical localization of PDE10 in the rat brain, William Harvey Research Conference 'Phosphodiesterase in Health and Disease', Porto, Portugal, Dec. 5-7, 2001).

PDE10A was shown to be highly expressed in retinal neurons including photoreceptors. The levels of PDE10A transcript and protein display daily rhythms which could be seen in preparations of the whole retina (Wolloscheck T. et al, *Brain Res.*, 2011, 1376, 42-50. Epub 2010 Dec. 29). These findings place PDE10A in the context of the visual system and suggest an important role of PDE10A in the adaptation of cyclic nucleotide signaling to daily changes in light intensity in retinal neurons including photoreceptors.

The tissue distribution of PDE10A indicates that PDE10A inhibitors can be used to raise levels of cAMP and/or cGMP within cells that express the PDE10 enzyme, especially neurons that comprise the basal ganglia, and the PDE10A inhibitors of the present invention would therefore be useful in treating a variety of associated neuropsychiatric conditions involving the basal ganglia such as neurological and psychiatric disorders, schizophrenia, bipolar disorder, obsessive compulsive disorder, and the like, and may have the benefit of not possessing unwanted side effects, which are associated with the current therapies on the market.

US 2003/0032579 discloses a method for treating certain neurologic and psychiatric disorders with the PDE10A inhibitor papaverine. In particular, the method relates to psychotic disorders such as schizophrenia, delusional disorders and drug-induced psychosis; to anxiety disorders such as panic and obsessive-compulsive disorder; and to movement disorders including Parkinson's disease and Huntington's disease. Other indications which may be treated using a PDE10A inhibitor are described in WO 20055120514.

A variety of therapeutic uses for PDE inhibitors has been reported including obtrusive lung disease, allergies, hypertension, angina, congestive heart failure, depression and erectile dysfunction (WO 2001041807, incorporated herein by reference). Furthermore, publications (WO 2005120514, WO 2005012485, Cantin et al., *Bioorg. & Med. Chem. Lett.*, 17, 2869-2873, 2007) suggest that PDE10A inhibitors may be useful for treatment of obesity and non-insulin dependent diabetes.

WO2012/112946 discloses substituted 6,7-dialkoxy-3-isoquinolinol derivatives as inhibitors of phosphodiesterase 10 (PDE10A).

WO 2011110545, WO 2011051342 (Janssen Pharmaceutica NV) disclose respectively imidazo[1,2-a]pyrazine derivatives, imidazo[1,2-b]pyridazine derivatives PDE10A inhibitors useful for the treatment or prevention of neurological, psychiatric and metabolic disorders in which the PDE10 enzyme is involved.

WO 2012007006, WO 2012000519, WO 2011072695, WO 2011072697, WO 2011072694, WO 2011072696, WO 2010145668 (H. Lundbeck A/S) disclose respectively triazolo- and pyrazoloquinazoline derivatives, aryl- and heteroarylamide derivatives, phenylimidazole derivatives comprising an ethynylene linker, heteroaromatic aryl triazole derivatives, heteroaromatic phenylimidazole derivatives, 2-arylimidazole derivatives, novel phenylimidazole derivatives as PDE10A inhibitors reported to be useful for the treatment of psychiatric and neurodegenerative disorders including schizophrenia as well as bipolar disorders, anxiety, stress disorders and Alzheimer's, Parkinson's and Huntington's disease, dementia and attention deficit/hyperactivity disorder.

WO 2011150156 (Sunovion Pharmaceuticals Inc.) discloses heteroaryl compounds as PDE10A inhibitors useful for the treatment, prevention, and/or management of various disorders, such as CNS disorders and metabolic disorders, including, but not limited to, e.g., neurological disorders, psychosis, schizophrenia, obesity, and diabetes.

WO 2010138833 (Biotie Therapies GmbH—Wyeth) discloses substituted imidazo[1,5-a]quinoxalines as PDE10A inhibitors useful in treating central nervous system diseases such as psychosis and also in treating, for example, obesity, type 2 diabetes, metabolic syndrome, glucose intolerance, and pain.

WO 2011053559 or WO 2011022213 or WO 2010138430 and WO 2010138585 or WO 2010138430 (Merck & Co., Inc.) disclose respectively aryl or amino or alkoxy tetrahydropyridopyrimidine derivatives or pyrimidinones as PDE10A inhibitors useful for the treatment of neurological and psychiatric disorders including schizophrenia, delusional disorders, drug induced psychosis, anxiety, movement, mood and neurodegenerative disorders.

WO 2010138577 (Merck & Co., Inc.) discloses radiolabeled pyrimidinone compounds which are useful as radiotracers for quantitative imaging of PDE10A in mammals.

WO 2011138657, WO 2011132051, and WO 2011132048 (Glenmark Pharmaceuticals SA) disclose respectively aryl substituted olefinic compounds, tricyclic compounds, and heteroaryl compounds as PDE10A inhibitors reported to be useful for the treatment of schizophrenia.

WO 2011163355 & WO 2010090737 (Takeda Pharmaceutical Co., Ltd.) disclose respectively fused heterocyclic compounds and pyridazinone compounds as PDE10A inhibitors useful for the treatment of schizophrenia.

WO 2010128995 (EnVivo Pharmaceuticals, Inc.) discloses phenoxymethyl heterocyclic compounds as PDE10A inhibitors useful for the treatment of schizophrenia, bipolar disorder, Huntington's disease, obesity and metabolic syndrome, among other disorders.

WO 2010117926 (Schering Corp.) discloses substituted triazolopyridines and analogs thereof as PDE10A inhibitors reported to be useful for the treatment of schizophrenia, psychosis, Alzheimer's disease, bipolar disorder, depression, obesity, diabetes and metabolic syndrome.

WO 2011051324 and WO 2010097367 (Janssen Pharmaceutica NV) disclose radiolabeled fluorinated azole PDE10A ligands reported to be useful in positron emission tomography imaging and quantification of PDE10A enzymes.

WO 2011117264, WO 2011089132 & WO 2011154327, WO 2011036127, and WO 2010094762 & WO 2010063610 (F. Hoffmann-La Roche AG) disclose respectively N-(imidazopyrimidin-7-yl)-heteroarylamide derivatives, nitrogen-containing heteroaryl derivatives, novel imidazopyridines, and heteroaryl substituted pyridazinone derivatives as PDE10A inhibitors reported to be useful for the treatment of schizophrenia, cognitive disorders, anxiety, substance abuse and dependence, Parkinson's disease, mood disorders, neurodegenerative disorders, stroke, diabetes and cancer, among other disorders.

WO 2011143366, WO 2011143365, WO 2011143495, WO 2010077992, and WO 2010057126 (Amgen Inc.) disclose respectively heteroaryloxycarbocyclyl compounds, nitrogen heterocyclic compounds, heteroaryloxyheterocyclyl compounds, aminopyridine and carboxypyridine compounds, and pyridine and pyrimidine derivatives as PDE10A inhibitors that are considered to have potential in the treatment of psychiatric disorders such as schizophrenia, bipolar disorder, obsessive-compulsive disorder, obesity, non-insulin dependent diabetes.

WO 2010062559 (Schering Corp.) discloses substituted pyrazoloquinolines and derivatives thereof as PDE10A inhibitors for the treatment of PDE10-modulated disorders.

WO 2010138833, WO 2010054253 & WO 2010054260 (Biotie Therapies GmbH—Wyeth) disclose respectively substituted imidazo[1,5-a]quinoxalines and triazine derivatives as inhibitors of phosphodiesterases, particularly PDE10A and PDE2A, described as useful for the treatment of pain, cognitive disorders, diabetes, obesity, extrapyramidal disorders, epilepsy and psychiatric disorders such as depression, anxiety, schizophrenia and attention deficit/hyperactivity disorders.

JP 2011201873, WO 2011105628, and WO 2010027097 (Mitsubishi Tanabe Pharma Corp.) disclose respectively trisubstituted pyrimidine compounds, pyrazolopyrimidine compounds, and tri-substituted pyrimidine compounds and their use as PDE10A inhibitors reported to be useful for the treatment of schizophrenia, anxiety, drug addiction, cognitive and mood disorders.

WO 2011112828 and WO 2010017236 (Omeros Corp.) disclose PDE10A inhibitors described as useful for the treatment of neurological and psychiatric disorders such as schizophrenia and post-traumatic stress disorder as well as Parkinson's disease, Huntington's disease, Alzheimer's disease, encephalitis, phobias, epilepsy, pain, sleep disorders, bipolar disorder and multiple sclerosis.

US 2010016303 & WO 2009152825 (H. Lundbeck A/S) disclose novel phenylimidazole derivatives as PDE10A enzyme inhibitors to be useful in the treatment of psychiatric and neurological disorders such as schizophrenia, cognition deficits, Parkinson's disease, Alzheimer's disease, Huntington's disease and substance abuse, among others.

WO 2010006130 (EnVivo Pharmaceuticals, Inc.) discloses vicinal substituted cyclopropyl compounds as PDE10A inhibitors.

WO 2009158473, WO 2009158467 & WO 2009158393 (EnVivo Pharmaceuticals, Inc.) disclose respectively 5- and 6 membered heterocyclic compounds, disubstituted phenyls compounds and 1,2-disubstituted heterocyclic compounds as PDE10A inhibitors described as useful for the treatment of schizophrenia, Huntington's disease, obesity and metabolic syndrome.

WO 2009070583 (Wyeth) discloses pyrido(3,2-e)pyrazines as inhibitors of PDE10A that are considered to have potential in the treatment of psychosis, mood diseases, anxiety, neurodegenerative disorders, obesity, diabetes, metabolic diseases, pain.

WO 2009068320 & WO 2009070584 (Biotie Therapies GmbH) disclose aryl and heteroaryl fused imidazo[1,5-a]pyrazines as inhibitors of PDE10A that are active compounds for treating central nervous system diseases of mammals, including humans.

WO 2009152825 & WO 2009036766 (H. Lundbeck A/S) disclose respectively novel phenylimidazole derivatives and cyanoisoquinoline derivatives as PDE10A inhibitors.

WO 2009143178, WO 2008064342 & US 2008300240 (Omeros Corp.) disclose quinoline derivatives as PDE10A inhibitors active in psychotic, anxiety, movement disorders and/or neurological disorders such as Parkinson's disease, Huntington's disease, Alzheimer's disease, encephalitis, phobias, epilepsy, aphasia, Bell's palsy, cerebral palsy, sleep disorders, pain, Tourette syndrome, schizophrenia, delusional disorders, drug-induced psychosis and panic and obsessive-compulsive disorders.

WO 2009025839 & WO 2009025823 (Amgen Inc.) disclose cinnoline derivatives as PDE10A inhibitors that are considered to have potential in the treatment of psychiatric disorders such as schizophrenia, bipolar disorder and obsessive-compulsive disorder.

WO 2009029214 (Amgen Inc.—Memory Pharmaceuticals Corp.) discloses isoquinolone derivatives as PDE10A inhibitors that are considered to have potential in the treatment of schizophrenia, bipolar disorder, obsessive-compulsive disorder, obesity and diabetes.

WO 2008032171 (Matrix Laboratories Ltd.) discloses dibenzofuran as inhibitors of PDE4 and PDE10A with potential utility in the treatment of asthma, chronic obstructive pulmonary disease, allergic rhinitis, atopic dermatitis, multiple sclerosis, Huntington disease, Alzheimer's disease, Parkinson's disease, schizophrenia and depression, among other disorders.

WO 2008020302 (Pfizer Products Inc.) discloses heteroaromatic quinoline-based compounds as selective PDE10A inhibitors.

WO 2008006372 (H. Lundbeck A/S) discloses 6,7-dialkoxyquinazoline and 6,7-dialkoxyisoquinoline derivatives as PDE10A inhibitors that are considered to have potential in the treatment of psychiatric and neurological disorders such as schizophrenia, cognition deficits, Parkinson's disease, Alzheimer's disease, dementia, epilepsy, multiple sclerosis and Huntington's diseases.

WO 2008004117 & WO 2006072828 (Pfizer Products Inc.) disclose respectively selective azole compounds and heteroaromatic quinoline compounds as PDE10A inhibitors that are considered to have potential in the treatment of psychotic, anxiety, movement, mood and neurodegenerative disorders and obesity.

WO 2007137819 & WO 2007137820 (Biotie Therapies GmbH) disclose respectively 4-amino-pyrido(3,2-e)pyrazines and pyrido(3,2-e)pyrazines as PDE10A inhibitors. More particularly, the inventions relate to the treatment of neurologic and psychiatric disorders, for example psychosis and disorders comprising cognitive deficits as symptoms.

WO 2007103370, WO 2007103260, WO 2007100880 & WO 2007022280 (Amgen Inc.—Memory Pharmaceuticals Corp.) disclose quinazoline derivatives as PDE10A inhibitors that are considered to have potential in the treatment of schizophrenia, bipolar disorder and obsessive-compulsive disorder. Further applications include obesity and non-insulin diabetes.

WO 2007103554, WO 2007098214 & WO 2007098169 (Amgen Inc.—Memory Pharmaceuticals Corp.) disclose cinnoline derivatives as PDE10A inhibitors that are considered to have potential in the treatment psychiatric disorders such as schizophrenia, bipolar disorders and obsessive-compulsive disorder.

WO 2007096743 & WO 2007085954 (Pfizer Products Inc.) disclose respectively substituted quinazolines and aminophthalazine compounds as PDE10A inhibitors that are considered to have potential in the treatment of psychotic disorders, anxiety disorders, movement disorders such as Parkinson and Huntington diseases, mood disorders, obesity and drug addiction.

WO 2006089815 & WO 2006075012 (Nycomed GmbH) disclose novel pyrrolodihydroisoquinolines as PDE10A inhibitors with potential utility in the treatment of neurological and psychiatric disorders, in diabetes therapy and in the regulation of fertility.

WO 2006071988 & WO 2006028957 (Memory Pharmaceuticals Corp.) disclose respectively thienopyrimidine derivatives and 4-substituted-4,6-dialkoxy-cinnoline derivatives as PDE10A inhibitors that are considered to have potential in the treatment of psychosis, including schizophrenia, bipolar disorder and obsessive-compulsive disorder, Alzheimer's disease and movement disorders such as Parkinson's disease. Other conditions include epilepsy, multiple sclerosis, Huntington's disease, disorders relating to the basal ganglia, diabetes and obesity.

WO 2006070284 & WO 2006011040 (Pfizer Products Inc.) disclose respectively pyrrolidyl derivatives of heteroaromatic compounds, and quinazolin-4-yl-piperidine and cinnolin-4-yl derivatives as PDE10A inhibitors that are considered to have potential in the treatment of CNS disorders, including schizophrenia, delusional disorders, drug-induced psychosis, anxiety, mood and movement disorders, neurodegenerative disorders and drug addiction.

WO 2005082883 (Pfizer Products Inc.) discloses tetrahydroisoquinolinyl derivatives of quinazoline and isoquinoline as PDE10A inhibitors that are claimed for use in the treatment of psychotic disorders, anxiety and movement disorders including Parkinson's disease and Huntington's disease, among other conditions.

WO 2006034512 & WO 2006034491 (Bayer Pharmaceuticals Corp.) disclose PDE10A inhibitors described as useful for the treatment of diabetes and related disorders. Pyrrolodihydroisoquinolines and variants thereof are disclosed as inhibitors of PDE10A in WO 2005003129 and WO 2005002579 (Nycomed GmbH).

WO 2004005291 & WO 2004005290 (Bayer Healthcare AG) disclose hetero-cyclically substituted imidazotriazines as PDE10A inhibitors described as useful for the treatment of neurodegenerative conditions, particularly Parkinson's disease and schizophrenia, and cancer.

WO 2004002484 (Kyowa Hakko Kirin Co., Ltd.) discloses quinoline derivatives as PDE10A inhibitors with potential in the treatment of Parkinson's disease, dyskinesia, anxiety, stress, mood and cognitive disorders, drug abuse, schizophrenia, cerebrovascular disorders, erectile dysfunction, diabetes, ischemic cardiopathies, renal disorders, peripheral vascular disease, hypertension, urinary incontinence, autoimmune diseases, respiratory disorders, allergies, pain, osteoporosis, cancer.

WO 2003014116 (Bayer Healthcare AG) discloses pyrrolo[2.1-a]isoquinoline derivatives as PDE10A inhibitors with potential in the treatment of cancer. WO 2003000693 (Bayer Healthcare AG) discloses imidazotriazines for use as PDE10A inhibitors considered to have potential in the treatment of Parkinson's disease.

All the above-mentioned publications are incorporated herein by reference.

However, these disclosures do not pertain to the compounds of the invention, which are structurally unrelated to any of the known PDE10A inhibitors (Kehler, J. et al., *Expert Opin. Ther. Patents*, 17, 147-158, 2007, Kehler, J., *Expert Opin. Ther. Patents*, 23, 31-45, 2013 and above cited patent literature), and which have now been found by the inventors to be highly active and selective PDE10A enzyme inhibitors.

The compounds of the invention offer alternatives to current marketed treatments for neurodegenerative and/or psychiatric disorders, which are not efficacious in all patients.

SUMMARY OF THE INVENTION

The present invention provides compounds that are PDE10A enzyme inhibitors, in particular selective PDE10A enzyme inhibitors. The present invention further provides compounds which have such activity. The invention also provides an effective treatment, in particular long-term treatment, of a human patient, without causing the side effects typically associated with current therapies for neurological and psychiatric disorders. Further aspects of the invention will become apparent upon reading the present specification.

In one aspect, the present invention relates to compounds of Formula (I):

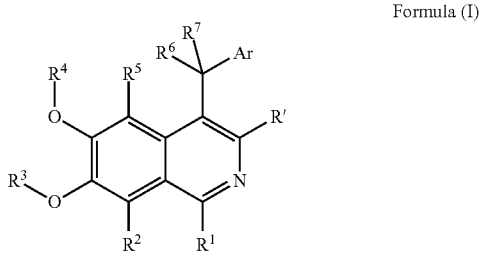

Formula (I)

or a pharmaceutically acceptable salt, thereof, wherein:

$R^1$ is selected from the group of H, optionally substituted ($C_1$-$C_6$)alkyl, optionally substituted ($C_3$-$C_6$)cycloalkyl and optionally substituted aryl;

$R_2$ is H;

$R_3$ and $R_4$ independently represent a ($C_1$-$C_3$)alkyl group;

$R_5$ is H;

$R_6$ and $R_7$ are independently H;

R' is H or ($C_1$-$C_6$)alkyl;

Ar is selected from the group consisting of: an optionally substituted fused nine- to ten-membered heteroaryl, optionally substituted benzo-fused aryl, optionally substituted benzo-fused heteroaryl, optionally substituted benzo-fused hetorocyclyl, and optionally substituted benzo-fused cycloalkyl, wherein two optional substituents at adjacent positions of each of said optionally substituted fused nine- to ten-membered heteroaryl, optionally substituted benzo-fused aryl, optionally substituted benzo-fused heteroaryl, optionally substituted benzo-fused hetorocyclyl, and optionally substituted benzo-fused cycloalkyl can be taken together with the atoms to which they are attached to form an aryl.

In another aspect, the present invention relates to compounds of Formula (IA):

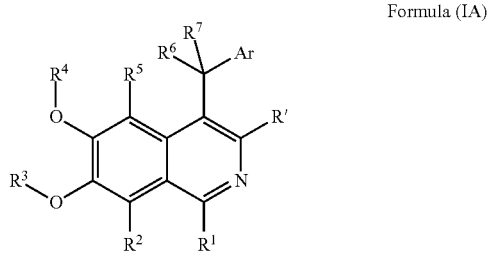

Formula (IA)

or a pharmaceutically acceptable salt thereof, wherein:

$R^1$ is selected from the group of H, ($C_1$-$C_6$)alkyl, ($C_3$-$C_6$) cycloalkyl and aryl;

$R_2$ is H;

$R_3$ and $R_4$ independently represent a ($C_1$-$C_3$)alkyl group;

$R_5$ is H;

$R_6$ and $R_7$ are independently H;

R' is H or ($C_1$-$C_6$)alkyl; and

Ar is selected from the group consisting of: an optionally substituted fused nine- to ten-membered heteroaryl, optionally substituted benzo-fused aryl, optionally substituted benzo-fused heteroaryl, optionally substituted benzo-fused hetorocyclyl, and optionally substituted benzo-fused cycloalkyl, wherein two optional substituents at adjacent positions of each of said optionally substituted fused nine- to ten-membered heteroaryl, optionally substituted benzo-fused aryl, optionally substituted benzo-fused heteroaryl, optionally substituted benzo-fused hetorocyclyl, and optionally substituted benzo-fused cycloalkyl can be taken together with the atoms to which they are attached to form an aryl; and pharmaceutically acceptable salts, tautomer forms, solvates and esters thereof.

In another aspect, the present invention provides a pharmaceutical composition comprising at least one compound of Formula (I) or Formula (IA) as set forth above, or a pharmaceutically acceptable salt thereof, and at least one pharmaceutically acceptable carrier.

In another aspect, the present invention provides a method for inhibiting PDE10A in a mammal, comprising administering to said mammal in need thereof, a therapeutically effective amount of at least one compound of Formula (I) or (IA) as set forth above or a pharmaceutically acceptable salt thereof.

In another aspect, the present invention provides a method for treating a disease in a mammal modulated by PDE10A, comprising administering to said mammal in need thereof, a therapeutically effective amount of at least one compound of Formula (I) or (IA) as set forth above or a pharmaceutically acceptable salt thereof.

BRIEF DESCRIPTION OF THE DRAWING

FIG. 1 shows synthetic routes used for the preparation of intermediary compounds TTA 24126B. SSA 39008, SSA 39102, SSA 48060, SSA 48072, SSA 48066, SSA 40084, SSA 48100, TTA 46082B, LPO 22102, ECO 33100, ECO 33118, ECO 33124, ECO 33138, TTA 24150B, TTA 24156B and ANP 31060A

DETAILED DESCRIPTION OF THE INVENTION

Within the context of the present application, the term "alkyl", alone or in combination with other groups, denotes linear or branched saturated hydrocarbon radical containing preferably from 1 to 10 carbon atoms, in particular from 1 to 6 carbon atoms, more particularly from 1 to 4 carbon atoms, unless otherwise indicated. Examples of alkyl groups having from 1 to 6 carbon atoms inclusive are methyl, ethyl, propyl (e.g., n-propyl, iso-propyl), butyl (e.g., tert-butyl, sec-butyl, n-butyl), pentyl (e.g., neo-pentyl), hexyl (e.g., n-hexyl), 2-methylbutyl, 2-methylpentyl and the other isomeric forms thereof. "Alkyl" may be unsubstituted or optionally substituted by one or more "ring system substituents" as defined herein below.

The term "halogen" denotes a chlorine, bromine, iodine or fluorine atom.

The term "acetylaminoalkyl" denotes a $CH_3CONH$-alkyl group.

The term "alkoxy" denotes an alkyl-O— group, with alkyl as defined above. Examples of alkoxy groups are methoxy, ethoxy, n-propyloxy, isopropyloxy and sec-butyloxy.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" also includes heterocyclyl rings as described above wherein =O replaces two available hydrogens on the same ring carbon atom. Example of such moiety is pyrrolidone, having the structure:

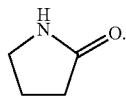

The term "aryl" refers to monocyclic or polycyclic (e.g. having 2, 3 or 4 fused rings) aromatic hydrocarbons such as, for example, phenyl, naphthyl, antracenyl, phenanthrenyl and the like. In some embodiments, an aryl group has from 5 to 20 carbons, in particular from 6 to 14 carbon atoms. Most preferred aryl groups are mono- or bi-cyclic and comprises from 6 to 14 carbon atoms, such as phenyl, a-naphthyl, β-naphthyl, antracenyl. The aryl group can be optionally substituted with one or more "ring system substituents" which may be the same or different, and are as defined herein.

The term "aryloxy" denotes an aryl-O— group, with aryl as defined above.

The term "heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen, phosphorus or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —SF$_5$, —OSF$_5$ (for aryl), —O—C(O)-alkyl, —O—C(O)-aryl, —O—C(O)-cycloalkyl, —NY$_1$—S(=O)$_2$N(Y$_2$)$_2$, —C(=N—CN)—NH$_2$, —C(=NH)—NH$_2$, —C(=NH)—NH(alkyl), oxime (e.g., =N—OH), —NY$_1$Y$_2$, -alkyl-NY$_1$Y$_2$, —C(O)NY$_1$Y$_2$, —SO$_2$NY$_1$Y$_2$ and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

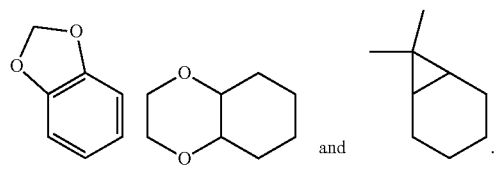

The term "optionally substituted" means optional substitution (i.e., unsubstituted or substituted) with the specified groups, radicals or moieties.

In one embodiment, in Formula (I) or (IA), R$^3$ and R$^4$ are both methyl. In another embodiment, in Formula (I) or (IA), the optionally substituted (C$_1$-C$_6$)alkyl of R$_1$ is selected from the group consisting of ethyl, n-propyl, n-butyl, and isobutyl; the optionally substituted aryl is optionally substituted phenyl; and the optionally substituted (C$_3$-C$_6$)cycloalkyl is selected from the group consisting of cyclopropyl and cyclohexyl.

In another embodiment, in Formula (I) or (IA), R$_1$ is selected from the group consisting of ethyl, n-propyl, n-butyl, isobutyl, phenyl, cyclopropyl, and cyclohexyl.

In another embodiment, in Formula (I) or (IA), R' is selected from the group consisting of H and methyl.

In another embodiment, in Formula (I) or (IA), Ar is a fused nine to ten-membered heteroaryl and is an optionally substituted pyrazolo-pyridyl (e.g.,

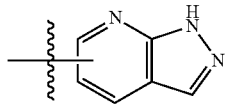

that is attached to the carbon bearing the $R^6$ and $R^7$ groups through a carbon atom of the pyridyl ring.

In another embodiment, in Formula (I) or (IA), Ar is an optionally substituted benzo-fused aryl and is napthyl, wherein said naphthyl is unsubstituted or substituted with a $(C_1-C_6)$alkoxy.

In another embodiment, in Formula (I) or (IA), Ar is an optionally substituted benzo-fused heteroaryl, which is attached to the carbon bearing the $R^6$ and $R^7$ groups either through a carbon atom of the benzene ring or through a carbon atom of the heteroaryl ring, and wherein two optional substituents at adjacent positions of said benzofused heteroaryl can be taken together with the atoms to which they are attached to form an aryl.

In another embodiment, in Formula (I) or (IA), Ar is an optionally substituted said benzo-fused heteroaryl is selected from the group consisting of quinolinyl, benzofuranyl, benzopyrrolyl, benzothiophenyl, benzimidazolyl, dibenzofuranyl, carbazolyl, 4H-chromen-4-only (e.g.,

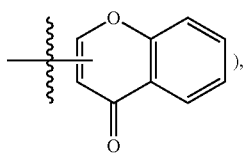

benzo[d]oxazolyl (e.g.,

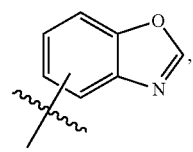

and benzo[d]oxazol-2(3H)-only (e.g.,

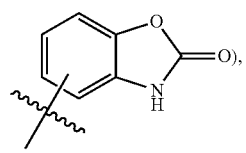

each of which is unsubstituted or substituted with at least one substituent selected from the group consisting of halogen, haloalkyl, cyano, optionally substituted aryl, -aryl-$(C_1-C_6)$alkyl-OH, -aryl-C(=O)—OH, -aryl-CN, -aryl-OH, —NH$_2$, —NH$(C_1-C_6)$alkyl, N$((C_1-C_6)$alkyl$))_2$, hydroxy, hydroxy-$(C_1-C_6)$alkyl, —O—$(C_1-C_6)$alkyl-tetrazolyl (e.g., —O—$(C_1-C_6)$alkyl-(1H-tetrazol-5-yl), —O—$(C_1-C_6)$alkyl-NH—C(=O)—$(C_1-C_6)$alkyl, —O—$(C_1-C_6)$alkyl-N$((C_1-C_6)$alkyl)-C(=O)—$(C_1-C_6)$alkyl, —C(=O)—$(C_1-C_6)$alkyl $(C_1-C_6)$alkoxy, $(C_1-C_6)$alkyl, —O—$(C_1-C_6)$alkyl-pyridyl, —O—$(C_1-C_6)$alkyl-C(=O)—O—$(C_1-C_6)$alkyl, —O—$(C_1-C_6)$alkyl-OH, —O—$(C_1-C_6)$alkyl-C(=O)—NH$_2$, —O—$(C_1-C_6)$alkyl-C(=O)—OH, —O—$(C_1-C_6)$alkyl-C(=O)—NH—$(C_1-C_6)$alkyl), —O—$(C_1-C_6)$alkyl-C(=O)—NH—$((C_1-C_6)$cycloalkyl), —NH—$(C_1-C_6)$alkyl, —NHS(=O)$_2$NH$_2$, —NHS(=O)$_2$NH—$(C_1-C_6)$alkyl, —NHS(=O)$_2$—$(C_1-C_6)$alkyl, —N$((C_1-C_6)$alkyl)-S(=O)$_2$—$(C_1-C_6)$alkyl, —NH—C(=O)—$(C_1-C_6)$alkyl-OH, —NH—C(=O)—C(=O)—O—$(C_1-C_6)$alkyl, —NH—C(=O)—C(=O)—NH$_2$, —NH—C(=O)—NH$_2$, —NH—C(=O)—$(C_1-C_6)$alkyl-O—C(=O)—$(C_1-C_6)$alkyl, —NH—C(=O)—$(C_1-C_6)$alkyl, —P(=O)(OH)$_2$, —N-pyrrolidin-2-one, and —NH—$(C_1-C_6)$alkyl-NH—C(=O)—$(C_1-C_6)$alkyl.

In another embodiment, in Formula (I) or (IA), Ar is an optionally substituted said benzo-fused heteroaryl is selected from the group consisting of quinolinyl, benzofuranyl, benzopyrrolyl, benzothiophenyl, benzimidazolyl, dibenzofuranyl, carbazolyl, 4H-chromen-4-onyl (e.g.,

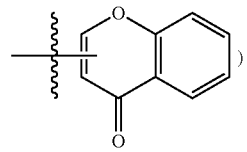

and benzo[d]oxazol-2(3H)-onyl (e.g.,

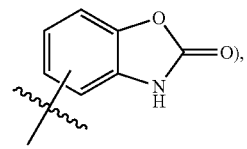

each of which is unsubstituted or substituted with at least one substituent selected from the group consisting of halogen, hydroxy, $(C_1-C_6)$alkoxy, $(C_1-C_6)$alkyl, —O—$(C_1-C_6)$alkyl-pyridyl, —O—$(C_1-C_6)$alkyl-C(=O)—O—$(C_1-C_6)$alkyl, —O—$(C_1-C_6)$alkyl-OH, —O—$(C_1-C_6)$alkyl-C(=O)—O—NH$_2$, —NH—$(C_1-C_6)$alkyl, —NHSO$_2$NH$_2$, and —NH—$(C_1-C_6)$alkyl-NH—C(=O)—$(C_1-C_6)$alkyl.

In another embodiment, in Formula (I) or (IA), Ar is a benzo-fused hetorocyclyl, which is attached to the carbon bearing the $R^6$ and $R^7$ groups through a carbon atom of the benzene ring of said benzo-fused heterocyclyl.

In another embodiment, in Formula (I) or (IA), Ar is a benzo-fused hetorocyclyl, which is attached to the carbon bearing the $R^6$ and $R^7$ groups through a carbon atom of the benzene ring of said benzo-fused heterocyclyl, wherein said benzo-fused heterocyclyl is selected from the group consisting of indolinyl, chromanyl (e.g.,

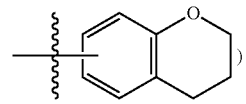

including alkylchromanyl and dialkyl chromanyl (e.g.,

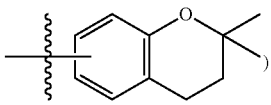

)

and optionally substituted dihydro-2H-benzo[b][1,4]oxazinyl (e.g.,

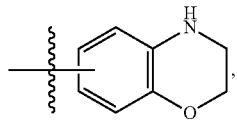

, each of which is unsubstituted or substituted at a nitrogen or carbon atom with at least one —($C_1$-$C_6$)alkyl.

In another embodiment, in Formula (I) or (IA), Ar is a benzo-fused cycloalkyl, which is attached to the carbon bearing the $R^6$ and $R^7$ groups through a carbon atom of the benzene ring of said benzo-fused cycloalkyl.

In another embodiment, in Formula (I) or (IA), Ar is a benzo-fused cycloalkyl, which is attached to the carbon bearing the $R^6$ and $R^7$ groups through a carbon atom of the benzene ring of said benzo-fused cycloalkyl, wherein said benzo-fused cycloalkyl is fluorenyl.

Specific compounds of formula (I) or (IA) which fall within the scope of the present invention include each of compounds 1 to 171 presented in the following "Examples" part. The invention thus relates to a compound of formula (I), selected in the group consisting of compounds 1 to 171 or a pharmaceutically acceptable salt thereof:

6,7-dimethoxy-4-(naphthalen-2-ylmethyl)isoquinoline hydrochloride 1,
3-((6,7-dimethoxyisoquinolin-4-yl)methyl)quinoline dihydrochloride 2,
4-(benzo[b]thiophen-5-ylmethyl)-6,7-dimethoxyisoquinoline hydrochloride 3,
4-((9H-fluoren-2-yl)methyl)-6,7-dimethoxyisoquinoline hydrochloride 4,
2-((6,7-dimethoxyisoquinolin-4-yl)methyl)quinoline dihydrochloride 5,
6-((6,7-dimethoxyisoquinolin-4-yl)methyl)quinoline dihydrochloride 6,
2-((6,7-dimethoxyisoquinolin-4-yl)methyl)quinolin-8-ol dihydrochloride 7,
3-((6,7-dimethoxyisoquinolin-4-yl)methyl)-7-methoxyquinoline dihydrochloride 8,
6,7-dimethoxy-4-((6-methoxynaphthalen-2-yl)methyl)isoquinoline hydrochloride 9,
4-(dibenzo[b,d]furan-2-ylmethyl)-6,7-dimethoxyisoquinoline hydrochloride 10,
6,7-dimethoxy-4-((1-methylindolin-5-yl)methyl)isoquinoline hydrochloride 11,
7-((6,7-dimethoxyisoquinolin-4-yl)methyl)-4-methyl-3,4-dihydro-2H-benzo[b][1,4]oxazine hydrochloride 12,
3-((6,7-dimethoxyisoquinolin-4-yl)methyl)-N,N-dimethylquinolin-2-amine dihydrochloride 13,
3-((6,7-dimethoxyisoquinolin-4-yl)methyl)-9-ethyl-9H-carbazole hydrochloride 14,
4-((1H-benzo[d]imidazol-5-yl)methyl)-6,7-dimethoxyisoquinoline dihydrochloride 15,
4-((4-chloro-1-ethyl-1H-pyrazolo[3,4-b]pyridin-5-yl)methyl)-6,7-dimethoxyisoquinoline dihydrochloride 16,
4-((4-ethoxy-1-ethyl-1H-pyrazolo[3,4-b]pyridin-5-yl)methyl)-6,7-dimethoxyisoquinoline dihydrochloride 17,
5-((6,7-dimethoxyisoquinolin-4-yl)methyl)-1-ethyl-1H-pyrazolo[3,4-b]pyridin-4-ol dihydrochloride 18,
2-chloro-3-((6,7-dimethoxyisoquinolin-4-yl)methyl)quinoline dihydrochloride 19,
3-((6,7-dimethoxyisoquinolin-4-yl)methyl)quinolin-2-ol hydrochloride 20,
2-((6,7-dimethoxyisoquinolin-4-yl)methyl)-8-methoxyquinoline dihydrochloride 21,
6,7-dimethoxy-3-methyl-4-(naphthalen-2-ylmethyl)isoquinoline hydrochloride 22,
2-((6,7-dimethoxyisoquinolin-4-yl)methyl)-8-(pyridin-4-ylmethoxy)quinoline trihydrochloride 23,
2-((6,7-dimethoxyisoquinolin-4-yl)methyl)-8-(pyridin-3-ylmethoxy)quinoline trihydrochloride 24,
6,7-dimethoxy-1-methyl-4-(naphthalen-2-ylmethyl)isoquinoline hydrochloride 25,
3-((6,7-dimethoxy-1-methylisoquinolin-4-yl)methyl)quinoline dihydrochloride 26,
2-((6,7-dimethoxyisoquinolin-4-yl)methyl)-8-ethoxyquinoline dihydrochloride 27,
3-((6,7-diethoxyisoquinolin-4-yl)methyl)quinoline dihydrochloride 28,
3-((6-ethoxy-7-methoxyisoquinolin-4-yl)methyl)quinoline dihydrochloride 31,
2-((6,7-dimethoxyisoquinolin-4-yl)methyl)-8-propoxyquinoline dihydrochloride 32,
4-(dibenzo[b,d]furan-2-ylmethyl)-6,7-dimethoxy-1-methylisoquinoline hydrochloride 33,
4-((2,2-dimethylchroman-6-yl)methyl)-6,7-dimethoxyisoquinoline hydrochloride 34,
4-(dibenzo[b,d]furan-2-ylmethyl)-6,7-dimethoxyisoquinoline 2-oxide 35,
4-(dibenzo[b,d]furan-2-ylmethyl)-6-ethoxy-7-methoxyisoquinoline hydrochloride 37,
4-(dibenzo[b,d]furan-2-ylmethyl)-1-ethyl-6,7-dimethoxyisoquinoline hydrochloride 39,
4-(dibenzo[b,d]furan-2-ylmethyl)-6,7-dimethoxy-1-propylisoquinoline hydrochloride 40,
ethyl 2-((2-((6,7-dimethoxyisoquinolin-4-yl)methyl)quinolin-8-yl)oxy)acetate dihydrochloride 41,
2-((2-((6,7-dimethoxyisoquinolin-4-yl)methyl)quinolin-8-yl)oxy)ethanol dihydrochloride 42,
3-((6,7-dimethoxy-3-methylisoquinolin-4-yl)methyl)quinoline dihydrocloride 43,
3-((6,7-dimethoxy-1-propylisoquinolin-4-yl)methyl)quinoline dihydrochloride 44,
2-((6,7-dimethoxy-1-propylisoquinolin-4-yl)methyl)quinolin-8-ol dihydrochloride 45,
2-((2-((6,7-dimethoxyisoquinolin-4-yl)methyl)quinolin-8-yl)oxy)acetamide 46,
3-((6,7-dimethoxy-1-propylisoquinolin-4-yl)methyl)quinolin-2-ol dihydrochloride 47,
6-((6,7-dimethoxyisoquinolin-4-yl)methyl)-2-methylquinoline dihydrochloride 48,
3-((6,7-dimethoxy-1-propylisoquinolin-4-yl)methyl)-6-methoxyquinolin-2-ol dihydrochloride 49,
3-((1-ethyl-6,7-dimethoxyisoquinolin-4-yl)methyl)quinoline dihydrochloride 50,
3-((1-ethyl-6,7-dimethoxyisoquinolin-4-yl)methyl)-6-methoxyquinolin-2-ol dihydrochloride 51,
3-((6,7-dimethoxy-1-propylisoquinolin-4-yl)methyl)-6-ethoxyquinolin-2-ol dihydrochloride 52, 3-((6,7-dimethoxyisoquinolin-4-yl)methyl)-6-methoxyquinolin-2-ol dihydrochloride 53,
3-((6,7-dimethoxy-1-propylisoquinolin-4-yl)methyl)-6-methylquinolin-2-ol dihydrochloride 54,
2-((3-((6,7-dimethoxy-1-propylisoquinolin-4-yl)methyl)-6-methoxyquinolin-2-yl)oxy)acetonitrile 55,
N-(2-((3-((6,7-dimethoxy-1-propylisoquinolin-4-yl)methyl)-6-methoxyquinolin-2-yl)oxy)ethyl)acetamide dihydrochloride 56,
6-((6,7-dimethoxy-1-propylisoquinolin-4-yl)methyl)-2-methylquinoline dihydrochloride 57,
6-((1-ethyl-6,7-dimethoxyisoquinolin-4-yl)methyl)-2-methylquinoline dihydrochloride 58,
6-((6,7-dimethoxy-1-phenylisoquinolin-4-yl)methyl)-2-methylquinoline dihydrochloride 59,
6-((1-cyclohexyl-6,7-dimethoxyisoquinolin-4-yl)methyl)-2-methylquinoline dihydrochloride 60,
3-((1-isobutyl-6,7-dimethoxyisoquinolin-4-yl)methyl)quinoline dihydrochloride 61,
3-((1-cyclopropyl-6,7-dimethoxyisoquinolin-4-yl)methyl)quinoline dihydrochloride 62,
3-((6,7-dimethoxy-1-phenylisoquinolin-4-yl)methyl)quinoline dihydrochloride 63,
3-((1-butyl-6,7-dimethoxyisoquinolin-4-yl)methyl)quinoline dihydrochloride 64,
4-(isoquinolin-3-ylmethyl)-6,7-dimethoxy-1-propylisoquinoline dihydrochloride 65,
4-(isoquinolin-3-ylmethyl)-6,7-dimethoxyisoquinoline dihydrochloride 66,
6-((1-butyl-6,7-dimethoxyisoquinolin-4-yl)methyl)-2-methylquinoline dihydrochloride 67,
6-((1-isobutyl-6,7-dimethoxyisoquinolin-4-yl)methyl)-2-methylquinoline dihydrochloride 68,
3-((6,7-dimethoxy-1-propylisoquinolin-4-yl)methyl)-7-methylquinoline dihydrochloride 69,
3-((1-butyl-6,7-dimethoxyisoquinolin-4-yl)methyl)-7-methylquinoline 70,
1-ethyl-4-(isoquinolin-3-ylmethyl)-6,7-dimethoxyisoquinoline dihydrochloride 72,
2-((2-((6,7-dimethoxy-1-propylisoquinolin-4-yl)methyl)quinolin-8-yl)oxy)acetamide dihydrochloride 73,
3-((6,7-dimethoxyisoquinolin-4-yl)methyl)-7-methylquinoline 74,
2-((2-((6,7-dimethoxy-1-propylisoquinolin-4-yl)methyl)quinolin-8-yl)oxy)ethanol 75,
N-(2-((3-((6,7-dimethoxy-1-propylisoquinolin-4-yl)methyl)-6-methoxyquinolin-2-yl)amino)ethyl)acetamide dihydrochloride 76,
3-((6,7-dimethoxy-1-propylisoquinolin-4-yl)methyl)-N-ethyl-6-methoxyquinolin-2-amine dihydrochloride 77,
6-((1-cyclopropyl-6,7-dimethoxyisoquinolin-4-yl)methyl)-2-methylquinoline dihydrochloride 78,
3-((6,7-dimethoxyisoquinolin-4-yl)methyl)-6-methyl-4H-chromen-4-one hydrochloride 79,
3-((6,7-dimethoxyisoquinolin-4-yl)methyl)-4H-chromen-4-one hydrochloride 80,
6-((6,7-dimethoxyisoquinolin-4-yl)methyl)-3-methylbenzo[d]oxazol-2(3H)-one hydrochloride 81,
2-((1-ethyl-6,7-dimethoxyisoquinolin-4-yl)methyl)quinolin-8-ol 82,
6-((6,7-dimethoxy-1-propylisoquinolin-4-yl)methyl)-3-methylbenzo[d]oxazol-2(3H)-one dihydrochloride 82,
2-((1-ethyl-6,7-dimethoxyisoquinolin-4-yl)methyl)quinolin-8-ol 83,
N-(2-((1-ethyl-6,7-dimethoxyisoquinolin-4-yl)methyl)quinolin-8-yl)sulfamide 84,
N-(2-((1-propyl-6,7-dimethoxyisoquinolin-4-yl)methyl)quinolin-8-yl)sulfamide 85,
N-(2-((1-ethyl-6,7-dimethoxyisoquinolin-4-yl)methyl)quinolin-8-yl)methanesulfonamide 86,
1-(2-((1-ethyl-6,7-dimethoxyisoquinolin-4-yl)methyl)quinolin-8-yl)urea 87,
N-(2-((1-ethyl-6,7-dimethoxyisoquinolin-4-yl)methyl)quinolin-8-yl)acetamide 88,
N-(2-((1-ethyl-6,7-dimethoxyisoquinolin-4-yl)methyl)quinolin-8-yl)ethanesulfonamide 89,
2-((1-ethyl-6,7-dimethoxyisoquinolin-4-yl)methyl)quinoline-8-carbonitrile 90,
2-((1-ethyl-6,7-dimethoxyisoquinolin-4-yl)methyl)quinoline-8-carboxamide 91,
ethyl 2-((2-((1-ethyl-6,7-dimethoxyisoquinolin-4-yl)methyl)quinolin-8-yl)amino)-2-oxoacetate 92,
$N^1$-(2-((1-ethyl-6,7-dimethoxyisoquinolin-4-yl)methyl)quinolin-8-yl)oxalamide 93,
N-((2-((1-ethyl-6,7-dimethoxyisoquinolin-4-yl)methyl)quinolin-8-yl)methyl)sulfamide 94,
3-((1-ethyl-6,7-dimethoxyisoquinolin-4-yl)methyl)quinolin-6-ol 95,
3-((1-ethyl-6,7-dimethoxyisoquinolin-4-yl)methyl)quinolin-6-amine 96,
1-(3-((1-ethyl-6,7-dimethoxyisoquinolin-4-yl)methyl)quinolin-6-yl)pyrrolidin-2-one 97,
$N^1$-(3-((1-ethyl-6,7-dimethoxyisoquinolin-4-yl)methyl)quinolin-6-yl)oxalamide 98,
N-(3-((1-ethyl-6,7-dimethoxyisoquinolin-4-yl)methyl)quinolin-6-yl)methanesulfonamide 99,
N-(3-((1-ethyl-6,7-dimethoxyisoquinolin-4-yl)methyl)quinolin-6-yl)sulfamide 100,
N-(3-((1-ethyl-6,7-dimethoxyisoquinolin-4-yl)methyl)quinolin-6-yl)-N-ethylmethanesulfonamide 101,
3-((6,7-dimethoxyisoquinolin-4-yl)methyl)-6-fluoro-4H-chromen-4-one hydrochloride 102,
6-chloro-3-((6,7-dimethoxyisoquinolin-4-yl)methyl)-4H-chromen-4-one hydrochloride 103,
6,8-dichloro-3-((6,7-dimethoxyisoquinolin-4-yl)methyl)-4H-chromen-4-one hydrochloride 104,
6-((6,7-dimethoxy-1-methylisoquinolin-4-yl)methyl)-2-methylquinoline dihydrochloride 105,
5-((6,7-dimethoxyisoquinolin-4-yl)methyl)benzo[d]oxazol-2(3H)-one hydrochloride 106,
5-((6,7-dimethoxyisoquinolin-4-yl)methyl)-3-ethylbenzo[d]oxazol-2(3H)-one hydrochloride 107,
2-((2-((6,7-dimethoxy-1-propylisoquinolin-4-yl)methyl)quinolin-8-yl)oxy)acetic acid dihydrochloride 108,
3-((6,7-dimethoxy-1-propylisoquinolin-4-yl)methyl)-6-fluoro-4H-chromen-4-one hydrochloride 109,
3-((6,7-dimethoxy-1-propylisoquinolin-4-yl)methyl)-6-methyl-4H-chromen-4-one hydrochloride 110,
6-((6,7-dimethoxyisoquinolin-4-yl)methyl)benzo[d]oxazol-2(3H)-one hydrochloride 111,
6-((6,7-dimethoxyisoquinolin-4-yl)methyl)-3-ethylbenzo[d]oxazol-2(3H)-one hydrochloride 112,
3-((6,7-dimethoxyisoquinolin-4-yl)methyl)-N-ethyl-6-methoxyquinolin-2-amine dihydrochloride 113,
5-((6,7-dimethoxyisoquinolin-4-yl)methyl)-2-phenylbenzo[d]oxazole 114,
methyl 4-(5-((6,7-dimethoxyisoquinolin-4-yl)methyl)benzo[d]oxazol-2-yl)benzoate 115,
2-((2-((1-ethyl-6,7-dimethoxyisoquinolin-4-yl)methyl)quinolin-8-yl)oxy)acetamide 116,
3-((6,7-dimethoxy-1-methylisoquinolin-4-yl)methyl)-7-methylquinoline 117, sodium 3-((2-((6,7-dimethoxy-1-propylisoquinolin-4-yl) methyl)quinolin-8-yl)oxy)propanoate 118,
N-(2-((1-(methoxymethyl)-6,7-dimethoxyisoquinolin-4-yl) methyl)quinolin-8-yl)sulfamide 119,
2-((2-((6,7-dimethoxy-1-methylisoquinolin-4-yl)methyl) quinolin-8-yl)oxy)acetamide 120,
8-((1H-tetrazol-5-yl)methoxy)-2-((6,7-dimethoxy-1-propyl-isoquinolin-4-yl)methyl)quinoline 121,
sodium 3-((2-((1-ethyl-6,7-dimethoxyisoquinolin-4-yl)me-thyl)quinolin-8-yl)oxy)propanoate 122,
2-((1-cyclopropyl-6,7-dimethoxyisoquinolin-4-yl)methyl) quinolin-8-ol 123,
2-((6,7-dimethoxy-3-methylisoquinolin-4-yl)methyl)quino-lin-8-ol 124,
2-((2-((6,7-dimethoxy-1-propylisoquinolin-4-yl)methyl) quinolin-8-yl)oxy)-N-methylacetamide 125,
N-cyclopropyl-2-((2-((6,7-dimethoxy-1-propylisoquinolin-4-yl)methyl)quinolin-8-yl)oxy)acetamide 126,
8-((1H-tetrazol-5-yl)methoxy)-2-((1-ethyl-6,7-dimethoxy-isoquinolin-4-yl)methyl)quinoline 127,
ethyl 2((2-((1-ethyl-6,7-dimethoxyisoquinolin-4-yl)methyl) quinolin-8-yl)oxy)acetate 128,
3-((6,7-dimethoxy-1-propylisoquinolin-4-yl)methyl)-6-methoxy-N-methylquinolin-2-amine 129,
2-((2-((1-cyclopropyl-6,7-dimethoxyisoquinolin-4-yl)me-thyl)quinolin-8-yl)oxy)acetamide 130,
2-((6,7-dimethoxy-1-methylisoquinolin-4-yl)methyl)quino-lin-8-ol 131,
2-((6,7-dimethoxy-1-propylisoquinolin-4-yl)methyl)-5-(tri-fluoromethyl)quinolin-8-ol 132,
2-((2-((6,7-dimethoxy-1-propylisoquinolin-4-yl)methyl)-5-(trifluoromethyl)quinolin-8-yl)oxy)acetamide 133,
2-((2-((6,7-dimethoxy-1-propylisoquinolin-4-yl)methyl) quinolin-8-yl)oxy)-2-methylpropanamide 134,
2-((2-((1-ethyl-6,7-dimethoxyisoquinolin-4-yl)methyl) quinolin-8-yl)oxy)ethanol 135,
N-(2-((2-(((6,7-dimethoxy-1-propylisoquinolin-4-yl)methyl) quinolin-8-yl)oxy)ethyl)acetamide 136,
3-((6,7-dimethoxyisoquinolin-4-yl)methyl)quinolin-6-ol 137,
2-((3-((6,7-dimethoxyisoquinolin-4-yl)methyl)quinolin-6-yl)oxy)acetamide 138,
2-((2-((6,7-dimethoxy-1-propylisoquinolin-4-yl)methyl) quinolin-8-yl)oxy)acetamide 139,
2-((6,7-dimethoxy-1-propylisoquinolin-4-yl)methyl)quino-lin-8-yl acetate 140,
(4-(5-((6,7-dimethoxyisoquinolin-4-yl)methyl)benzo[d]ox-azol-2-yl)phenyl)methanol 141,
(4-(5-((6,7-dimethoxyisoquinolin-4-yl)methyl)benzo[d]ox-azol-2-yl)phenyl)methanol 142,
3-((6,7-dimethoxy-1-propylisoquinolin-4-yl)methyl)quino-lin-6-ol 143,
2-((3-((6,7-dimethoxy-1-propylisoquinolin-4-yl)methyl) quinolin-6-yl)oxy)acetamide 144,
potassium 4-(5-((6,7-dimethoxyisoquinolin-4-yl)methyl) benzo[d]oxazol-2-yl)benzoate 145,
4-(5-((6,7-dimethoxyisoquinolin-4-yl)methyl)benzo[d]ox-azol-2-yl)benzoic acid 146,
5-((6,7-dimethoxy-1-propylisoquinolin-4-yl)methyl)benzo [d]oxazol-2(3H)-one 147,
2-(5-((6,7-dimethoxy-1-propylisoquinolin-4-yl)methyl)-2-oxobenzo[d]oxazol-3(2H)-yl)acetamide 148,
4-(5-((6,7-dimethoxy-1-propylisoquinolin-4-yl)methyl)benzo[d]ox-azol-2-yl)aniline 149,
2-((3-((6,7-dimethoxyisoquinolin-4-yl)methyl)quinolin-6-yl)oxy)acetic acid 150,
(3-(5-((6,7-dimethoxyisoquinolin-4-yl)methyl)benzo[d]ox-azol-2-yl)phenyl)methanol 151,
2-((6,7-dimethoxy-1-methylisoquinolin-4-yl)methyl)quino-lin-8-amine 152,
4-(5-((6,7-dimethoxyisoquinolin-4-yl)methyl)benzo[d]ox-azol-2-yl)benzonitrile 153,
(2-(5-((6,7-dimethoxyisoquinolin-4-yl)methyl)benzo[d]ox-azol-2-yl)phenyl)methanol 154,
3-((6,7-dimethoxy-1-methylisoquinolin-4-yl)methyl)quino-lin-6-ol 155,
(2-(6,7-dimethoxy-1-methyl-isoquinolin-4-ylmethyl)-quinolin-8-yl)-sulfamide 156,
2-((6,7-dimethoxyisoquinolin-4-yl)methyl)quinolin-8-amine 157,
2-((2-((6,7-dimethoxy-1-propylisoquinolin-4-yl)methyl) quinolin-8-yl)amino)-2-oxoethyl acetate 158,
(2-(6,7-dimethoxy-1-methyl-isoquinolin-4-ylmethyl)-quinolin-8-yl)-sulfamide 159,
N-(2-((6,7-dimethoxy-1-propylisoquinolin-4-yl)methyl) quinolin-8-yl)-2-hydroxyacetamide 160,
3-((6,7-dimethoxyisoquinolin-4-yl)methyl)-5-(trifluorom-ethyl)quinolin-6-ol 161,
3-((6,7-dimethoxy-1-propylisoquinolin-4-yl)methyl)-5-(tri-fluoromethyl)quinolin-6-ol 162,
2-((6,7-dimethoxy-1-(methoxymethyl)isoquinolin-4-yl)me-thyl)quinolin-8-ol 163,
2-((2-((6,7-dimethoxy-1-(methoxymethyl)isoquinolin-4-yl) methyl)quinolin-8-yl)oxy)acetamide 164,
Ethyl 2-((2-((6,7-dimethoxy-1-(methoxymethyl)isoquino-lin-4-yl)methyl)quinolin-8-yl)oxy)acetate 165,
2-((2-((6,7-dimethoxy-1-(methoxymethyl)isoquinolin-4-yl) methyl)quinolin-8-yl)oxy)ethanol 166,
2-((6,7-dimethoxy-1-(methoxymethyl)isoquinolin-4-yl)me-thyl)quinolin-8-amine 167,
3-((6,7-dimethoxy-1-(methoxymethyl)isoquinolin-4-yl)me-thyl)quinolin-6-ol 168,
3-((6,7-dimethoxy-1-(methoxymethyl)isoquinolin-4-yl)me-thyl)-5-(trifluoromethyl)quinolin-6-ol 169,
(4-(6-((6,7-dimethoxyisoquinolin-4-yl)methyl)benzo[d]ox-azol-2-yl)phenyl)methanol 170,
and sodium 3-((6,7-dimethoxy-1-propylisoquinolin-4-yl) methyl)quinolin-6-yl phosphate 171; or a pharmaceuti-cally acceptable salt thereof.

The compounds according to the present invention may be prepared by various methods known to those skilled in the art. General and specific methods for the preparation of compounds of formula (I) and (IA) are described herein below.

The intermediary compounds TTA 24128B, SSA 39098, SSA 39102, SSA 48060, SSA 48072, SSA 48066, SSA 40084, and SSA 48100 were prepared in three synthetic steps from veratrole: a Friedel and Crafts acylation of veratrole in anhydrous dichloromethane with the desired commercially available acid chloride in presence of aluminium trichloride followed by an amination of the obtained ketone with aminoacetaldehyde diethyl acetal, preferentially under reflux in toluene (110° C. for 4 h), using a Dean Stark apparatus and finally the reduction of the obtained iminoacetal using sodium borohydride in refluxing ethanol (78° C.) (Reaction scheme 1).

TTA 46082B was prepared in three synthetic steps from 1-(3,4-dimethoxyphenyl)-2-hydroxyethanone (CAS#37803-48-8): a methylation of 1-(3,4-dimethoxyphenyl)-2-hydroxy-ethanone in anhydrous dichloromethane in presence of silver (I) oxide and iodomethane at RT for 48 h gave 2-methoxy-1-(3,4-dimethoxyphenyl)ethanone ECO 59016. ECO 59016 was then treated with aminoacetaldehyde diethyl acetal, preferentially under reflux in toluene (110° C. for 4 h), using a Dean Stark apparatus followed by a subsequent reduction of the obtained iminoacetal TTA 46082A using sodium borohydride in refluxing at reflux (78° C.) to give TTA 46082B (Reaction scheme 1).

The intermediates LPO 22102, ECO 33100, ECO 33118, ECO 33124, ECO 33138, TTA 24150B and TTA 24156B were prepared in two synthetic steps by amination of the corresponding commercially available aldehydes with aminoacetaldehyde diethyl acetal, preferentially under reflux in toluene at 110° C. for 4 hours using a Dean Stark apparatus, followed by a subsequent reduction of the obtained iminoacetals using sodium borohydride in refluxing ethanol (78° C.) (reaction scheme 1). The intermediary compound ANP 31060A was prepared in two steps by amination of (3,4-dimethoxyphenyl)methanamine with 1,1-dimethoxypropan-2-one, preferentially in refluxing toluene (110° C. for 4 h) and using a Dean Stark apparatus, followed by a subsequent reduction of the obtained (E)-1-(3,4-dimethoxyphenyl)-N-(1,1-dimethoxypropan-2-ylidene)methanamine using sodium borohydride in refluxing ethanol (78° C.) (reaction scheme 1).

The compounds 1-20, 22, 25, 26, 28-31, 33, 34, 36-40, 43-45, 47-54, 57-72, 74, 78-83, 95, 102-105, 109, 110, 117, 119, 123, 124, 131, 132, 137, 143, 155, 161-163, 168, 169 and intermediates SSA 48042, LPO 55070B, ANP 49174B, ANP 53134 and ANP 53006A were prepared from the corresponding aromatic aldehydes (1 equivalent) and the corresponding aminoacetaldehyde diethyl or dimethyl acetals (1 equivalent) in a one to one mixture of absolute EtOH and a 37% HCl solution, preferentially at 90-110° C. for 15-30 min and in an ace pressure tube (Aldrich). After neutralization and purification of the obtained free base by column chromatography (SiO$_2$), when needed, the free base (1 equivalent) was dissolved in MeOH and a 1.75 N HCl solution in MeOH (2.1 eq×number of basic nitrogen) was added and all the volatiles were evaporated to give the desired isoquinolines as hydrochloride salts (reaction scheme 1).

The aromatic aldehydes used to obtain the compounds of the invention were commercially available or can be prepared following the synthetic routes described in reaction scheme 2.

The aldehydes LPO 43162A and ANP 49046 were prepared following the procedure described by Sing, Mrityunjay et al., *Tetrahedron letters*, 48(34), 5987-90, 2007 and the aldehyde LPO 43136A from the procedure described by Kalluraya, Balakhrishna et al., *Indian Journal of Chemistry*, 42B (1), 211-214, 2003.

The 7-methoxy- and 7-methyl-quinoline-3-carbaldehydes were prepared following the procedure described by Tom, Norma J. et al., *Synthesis*, (9), 1351-1355, 2001.

The masked aldehyde 3-(1,3-dioxolan-2-yl)-7-methylquinoline SSA 48104 was prepared in two steps from 2-chloro-7-methylquinoline-3-carbaldehyde by treatment with ethane-1,2-diol in presence of p-toluenesulfonic acid (PTSA) in toluene followed by a reduction of the chlorine atom of the obtained 2-chloro-3-(1,3-dioxolan-2-yl)-7-methylquinoline SSA 48098 by hydrogenation catalyzed by Pd/C 10% in presence of K$_2$CO$_3$ as base and MeOH as solvent.

The masked aldehyde 3-(1,3-dioxolan-2-yl)-quinolin-6-ol LPO 55016 was obtained via a similar method as for SSA 48104 from 2-chloro-6-hydroxyquinoline-3-carbaldehyde LPO 50188A. LPO 50188A itself was prepared by treatment of 2-chloro-6-methoxyquinoline-3-carbaldehyde by boron tribromide (BBr$_3$) in dichloromethane. Finally quinolin-6-ol LPO 55016 was O-alkylated by treatment with ethyl 2-bromoacetate and cesium carbonate as a base in acetone for 2 hours at 85° C. to yield ethyl 2-((3-(1,3-dioxolan-2-yl)quinolin-6-yl)oxy)acetate LPO 55070A (reaction scheme 2). The masked aldehyde 3-(1,3-dioxolan-2-yl)-8-(trifluoromethyl) quinolin-5-ol LPO 50180C was prepared by radical trifluoromethylation of dioxolane TTA 46034 using a methodology developed by Langlois B. et al., *Tetrahedron Lett.*, (32), 51, 7525-7528, 1991 and modified by Baran P. et al., *PNAS*, 108, 35, 14411-14415, 2011 (reaction scheme 2).

The masked aldehyde 3-(dimethoxymethyl)-5-(trifluoromethyl)quinolin-6-ol ECO 55152 was prepared by radical trifluoromethylation via photoredox catalysis of dimethylacetal ECO 55108C using a methodology developed by MacMillan D. et al., *Nature*, 480, 224-228, 2011 (reaction scheme 2).

The 4-chloro-1-ethyl-1H-pyrazolo[3,4-b]pyridine-5-carbaldehyde SAO 33058 was obtained in two steps from ethyl 4-chloro-1-ethyl-1H-pyrazolo[3,4-b]pyridine-5-carboxylate (described by Hamblin, J. Nicole et al., *Bioorg. Med. Chem. Lett.*, 18(14), 4237-41, 2008).

Reduction of 4-chloro-1-ethyl-1H-pyrazolo[3,4-b]pyridine-5-carboxylate by LiBH$_4$ in THF provided the alcohol SAO 33034 that was oxidized in aldehyde SAO 33058 using Dess-Martin periodinane reagent in dichloromethane for 1 hour at 4° C. then overnight at RT (reaction scheme 2).

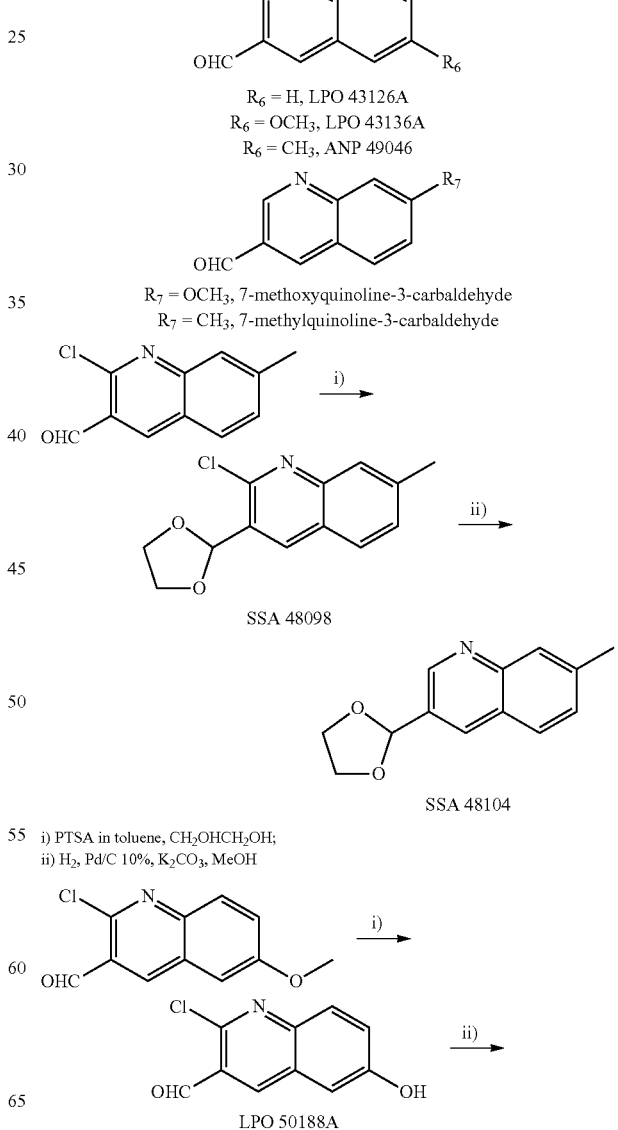

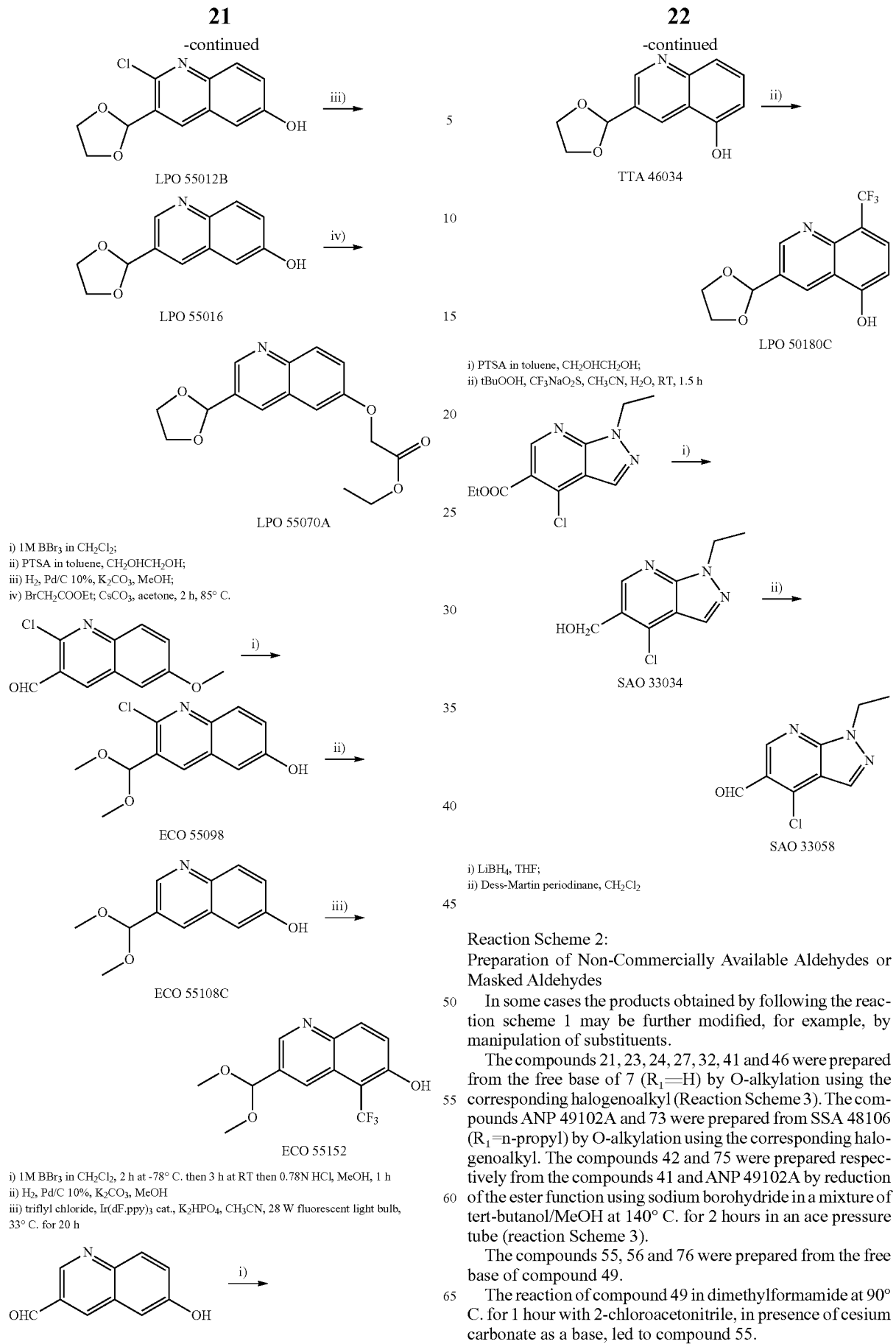

Reaction Scheme 2:
Preparation of Non-Commercially Available Aldehydes or Masked Aldehydes In some cases the products obtained by following the reaction scheme 1 may be further modified, for example, by manipulation of substituents.

The compounds 21, 23, 24, 27, 32, 41 and 46 were prepared from the free base of 7 ($R_1$=H) by O-alkylation using the corresponding halogenoalkyl (Reaction Scheme 3). The compounds ANP 49102A and 73 were prepared from SSA 48106 ($R_1$=n-propyl) by O-alkylation using the corresponding halogenoalkyl. The compounds 42 and 75 were prepared respectively from the compounds 41 and ANP 49102A by reduction of the ester function using sodium borohydride in a mixture of tert-butanol/MeOH at 140° C. for 2 hours in an ace pressure tube (reaction Scheme 3).

The compounds 55, 56 and 76 were prepared from the free base of compound 49.

The reaction of compound 49 in dimethylformamide at 90° C. for 1 hour with 2-chloroacetonitrile, in presence of cesium carbonate as a base, led to compound 55.

Reaction Scheme 3: Preparation of compounds 21, 23, 24, 27, 32, 41, 42, 46, 73 and 75

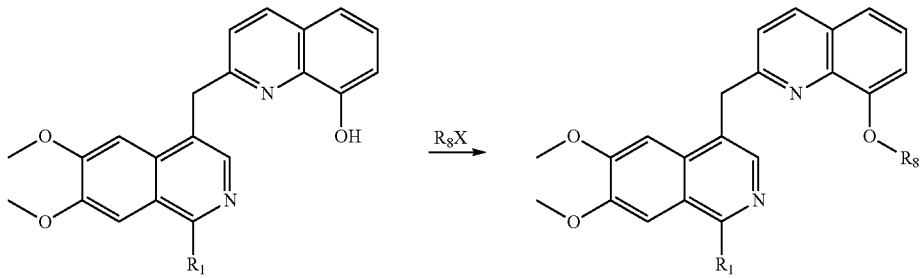

R$_1$ = H, free base of 7
R$_1$ = n-propyl, SSA 48106

| R$_8$X | R$_1$ = H | | R$_1$ = n-propyl |
|---|---|---|---|
| CH$_3$I | R$_8$ = CH$_3$, 21 | R$_8$ = —CH$_2$COOEt, ANP 49102A | tBUOH, MeOH, NaBH$_4$ 2 h, 140° C. |
| 4-picolyl chloride hydrochloride | R$_8$ = 4-picolyl, 23 | | |
| 3-picolyl chloride hydrochloride | R$_8$ = 3-picolyl, 24 | | |
| EtBr | R$_8$ = ethyl, 27 | R$_8$ = —CH$_2$CONH$_2$, 73 | |
| 1-bromopropane | R$_8$ = n-propyl, 32 | | |
| BrCH$_2$COOEt | R$_8$ = —CH$_2$COOEt, 41 | | |
| BrCH$_2$CONH$_2$ | R$_8$ = —CH$_2$CONH$_2$, 46 | | |

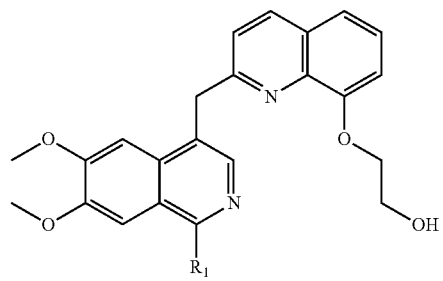

R$_1$ = H, 42
R$_1$ = n-propyl, 75

The compound 55 can be hydrogenated in presence of hydrogen and 10% Pd/C as catalyst in methanol at room temperature to yield compound LPO 43180. The compound LPO 43180 was acetylated for 2 hours at 4° C. in tetrahydrofuran with acetic anhydride, in presence of triethylamine as base, to give the free base of compound 56 that was subsequently transformed in its dihydrochloride salt by treatment with a 1.75 N HCl solution in methanol at room temperature (reaction scheme 4).

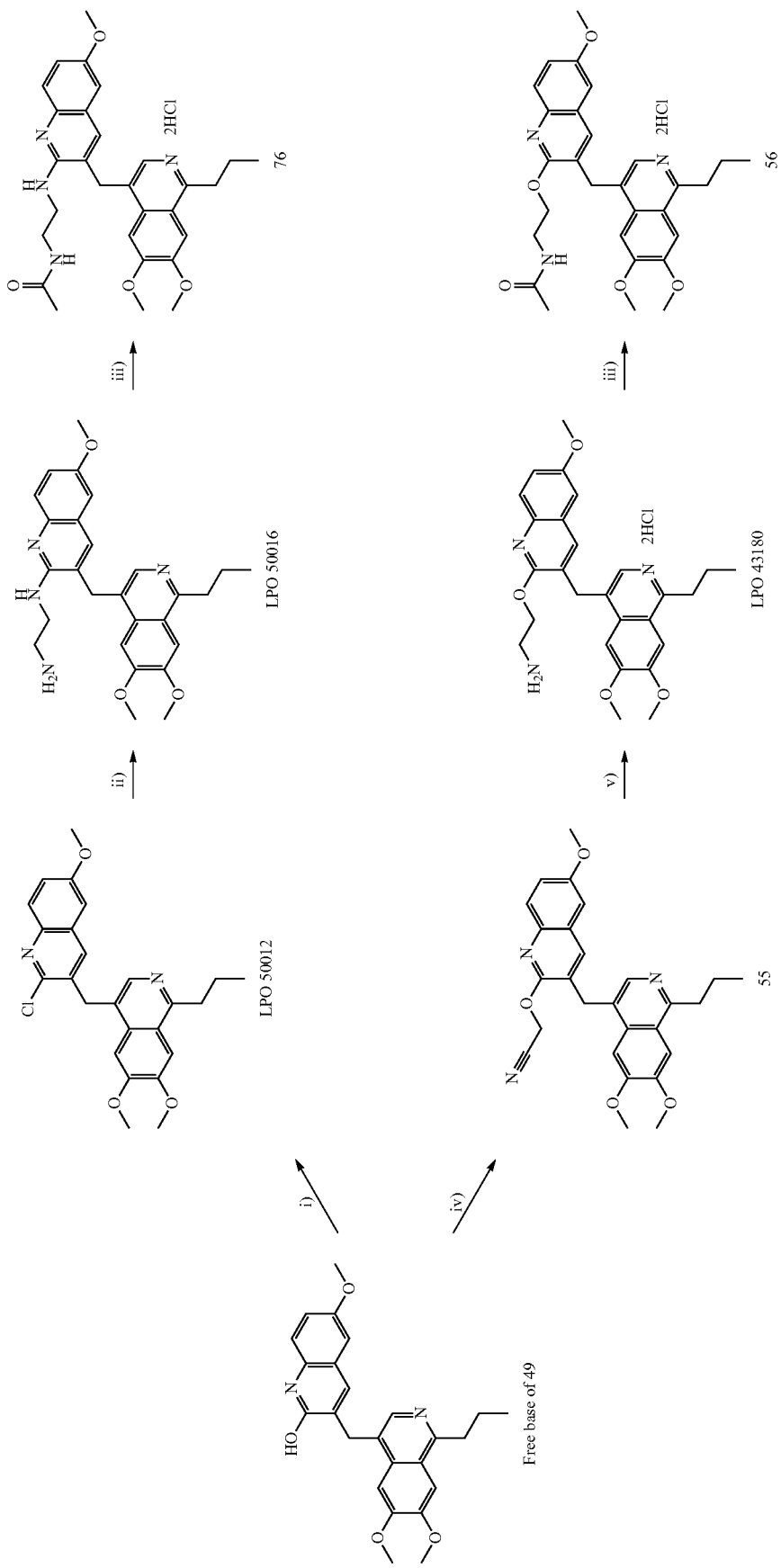
i) POCl₃, 2 h at 100° C.;
ii) Pd(OAc)₂, tBuXPhos, NH₂CH₂CH₂NH₂, tBuOK, toluene, 8 h at 100° C.;
iii) Ac₂O, Et₃N, THF, 4° C. for 2 h then 1.75N HCl solution in MeOH, MeOH, RT;
iv) 2-chloroacetonitrile, Cs₂CO₃, DMF, 90° C. for 1 h;
v) H₂/Pd/C, MeOH, HCl.

Reaction Scheme 4:
Preparation of Compounds 55, 56 and 76

The treatment of compound 49 with phosphorus oxychloride for 2 hours at 100° C. gave the aryl chloro derivative LPO 50012. The compound LPO 50016 was prepared by a Buchwald-Hartwig reaction of the compound LPO 50012 preferentially at 100° C. for 8 hours in toluene with ethylenediamine, in presence of palladium(II) acetate as catalyst, 2-(di-tert-butylphosphino)biphenyl (JohnPhos) as ligand, and potassium tert-butoxide as base. The acetylation of compound LPO 50016 for 2 hours at 4° C. in tetrahydrofuran with acetic anhydride, in presence of triethylamine as base, gave the free base of compound 76 that was subsequently transformed in its dihydrochloride salt by treatment with a 1.75 N hydrochloride solution in methanol at room temperature (reaction scheme 4).

and LPO50042C by a Buchwald-Hartwig reaction, at 170° C. for 5 hours (77) or 100° C. for 6 hours (113) in toluene with a 2 N solution of diethylamine in tetrahydrofuran, in presence of palladium(II) acetate as catalyst, JohnPhos as ligand, and potassium tert-butoxide as base. The obtained free bases were transformed into their corresponding dihydrochloride salt 77 and 113 by treatment with a 1.76 N hydrochloride solution in methanol for 15 minutes at 4° C. (reaction scheme 5). The compound 129 was preferentially obtained from LPO 50012 by a Buchwald-Hartwig reaction at 145° C. for 25 min in toluene with a 2 N solution of diethylamine in tetrahydrofuran, in presence of palladium(II) acetate as catalyst, 2-(di-tert-butylphosphinobiphenyl) as ligand, and potassium tert-butoxide as base (reaction scheme 5).

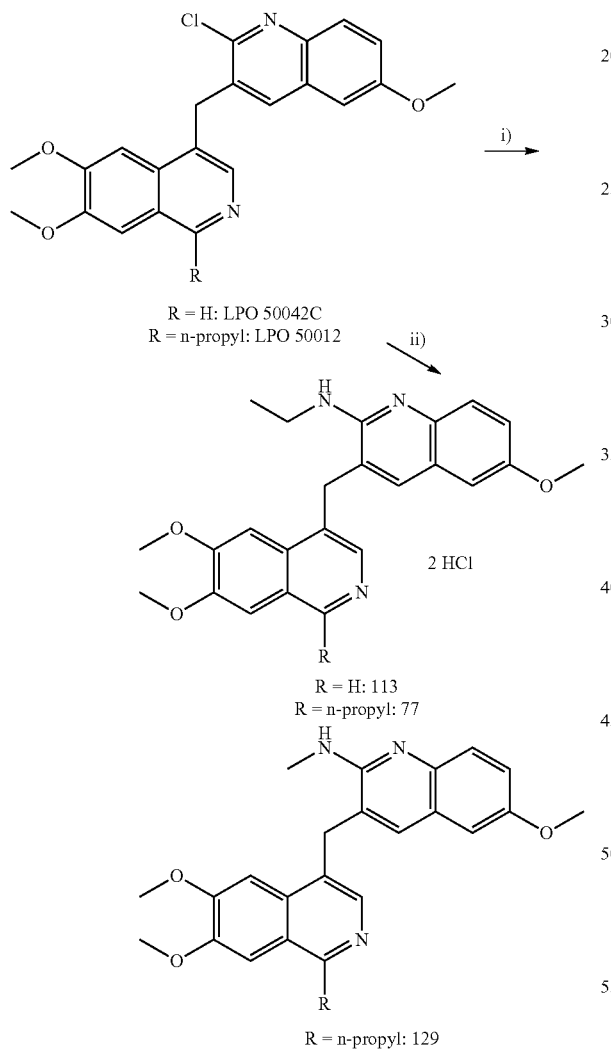

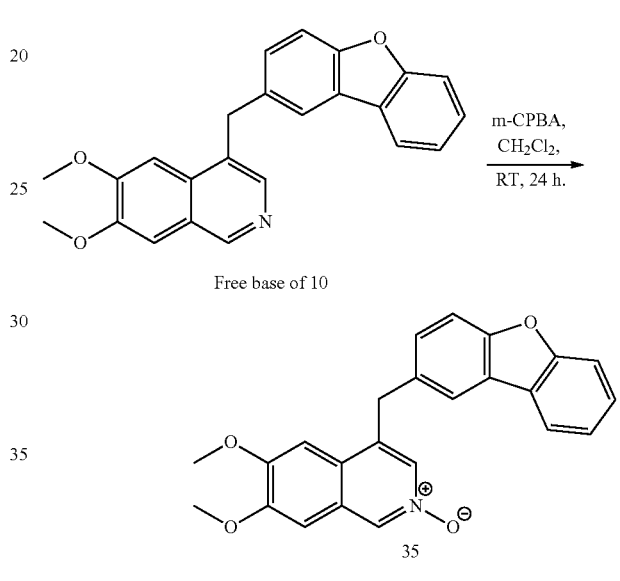

Reaction Scheme 6:
Preparation of Compound 35

The N-oxide derivative 35 was prepared from the free base of compound 10 by oxidation using preferentially meta-chloroperbenzoic acid in dichloromethane for 24 hours (reaction scheme 6).

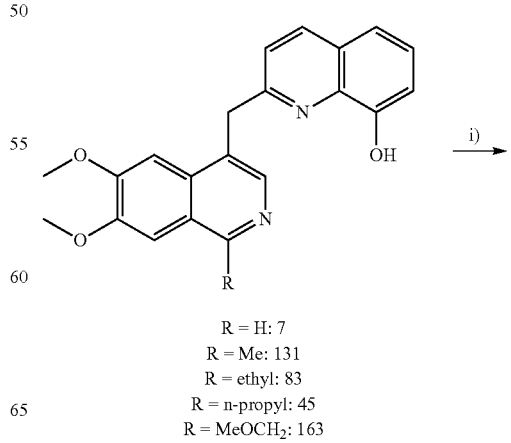

Reaction Scheme 5:
Preparation of Compounds 77, 113 and 129.

The compounds 77 and 113 were preferentially respectively prepared from the aryl chloro derivative LPO 50012

-continued

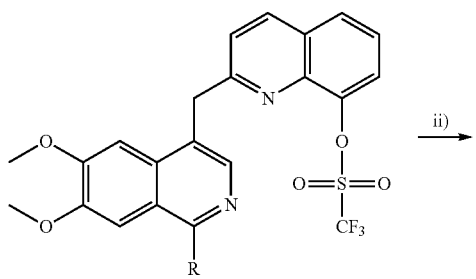

R = H: ANP 57032A 53%
R = Me: ANP 53184A 52%
R = ethyl: RBO 51116 80%
R = n-propyl: LPO 55036C 72%
R = MeOCH$_2$: ECO 59060 47%

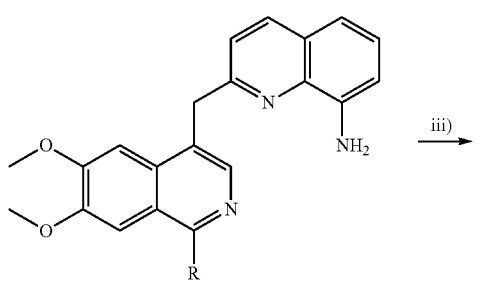

R = H: 157 60&
R = Me: 152 16%
R = ethyl: RBO 51118B 80%
R = n-propyl: LPO 55056D 65%
R = MeOCH$_2$: 167 20%

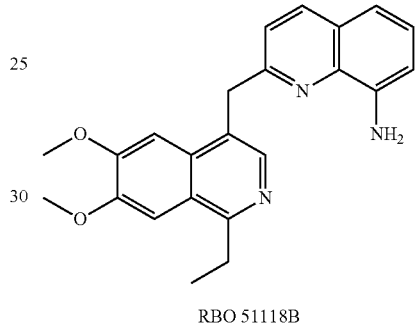

R = H: 159 2%
R = Me: 156 22%
R = ethyl: 84 47% (recryst. in CH$_3$CN: 27%)
R = n-propyl: 85 53%
R = MeOCH$_2$: 119 10% i) N-phenyl-bis(trifluoromethanesulfonimide), Et$_3$N, DMF, RT or 40° C., 16 h.
ii) i. Benzophenone imine, Cs$_2$CO$_3$, BINAP, Pd$_2$(dba)$_3$, anh. toluene, reflux, overnight. ii. THF, 5N or 3N HCl, RT, 1-4 h. iii. NaHCO$_3$ to reach pH = 7.
iii) Sulfamide, 1,4-dioxane, reflux, 15-16 h.

Reaction Scheme 7:
Preparation of Compounds 84, 85, 119, 152, 156, 157, 159 and 167.

The sulfamide derivatives 159, 156, 84, 85 and 119 were prepared respectively from phenols 7, 131, 83, 45 and 163 in three steps (reaction scheme 7). The phenols 7, 131, 83, 45 and 163 were treated in DMF with N-phenyl-bis(trifluoromethanesulfonimide) in presence of triethylamine at RT or 40° C. to give, respectively, the triflates ANP 57032A, ANP 53184A, RBO 51116, LPO 55036C and ECO 59060. Palladium-catalyzed amination (Buchwald-Hartwig reaction) overnight between the triflates ANP 57032A, ANP 53184A, RBO 51116, LPO 55036C and ECO 59060 and benzophenone imine, using a catalyst consisting of a combination of tris(dibenzylideneacetone)dipalladium(0) and BINAP in presence of cesium carbonate in refluxing dry toluene, afforded respectively, after HCl hydrolysis in tetrahydrofuran at RT for 1 to 4 hours, anilines 157, 152, RBO 51118B, LPO 55056D and 167. A final treatment of anilines 157, 152, RBO 51118B, LPO 55056D and 167 with sulfamide for 15-16 hours in refluxing 1,4-dioxane gave respectively, after purification, sulfamides 159, 156, 84, 85 and 119 (reaction scheme 7).

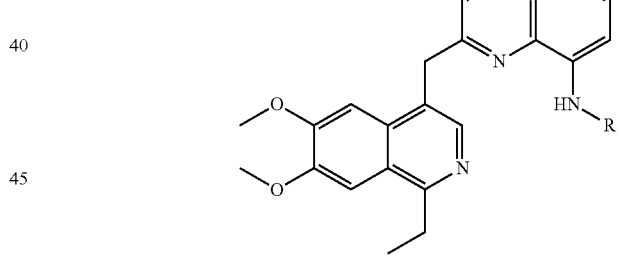

RBO 51118B i) R = SO$_2$CH$_3$, 86 (83%)
ii) R = SO$_2$C$_2$H$_5$, 89 (40%)
iii) R = COCH$_3$, 88 (60%)
iv) R = CONH$_2$, 87 (43%)
v) R = COCONH$_2$, 93 (61%)

i) Methane sulfonyl chloride, pyridine, CH$_2$Cl$_2$, MW at 70° C., 30 min, 83%.
ii) Ethane sulfonyl chloride, pyridine, CH$_2$Cl$_2$, MW at 70° C., 3 h, 40%.
iii) Ac$_2$O, pyridine, NMP, THF, RT, 15 h, 60%.
iv) KOCN, AcOH, Water, 40° C., 3 h, 43%.
v) 2-amino-2-oxoacetyl chloride, Et$_3$N, THF, RT, 15 h, 30%.

Reaction Scheme 8:
Preparation of Compounds 86-89 and 93.

The compounds 86-89 and 93 were prepared from aniline RBO 51118B as described in reaction scheme 8.

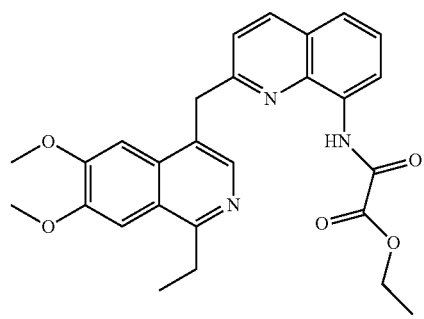

92 iv) ↑

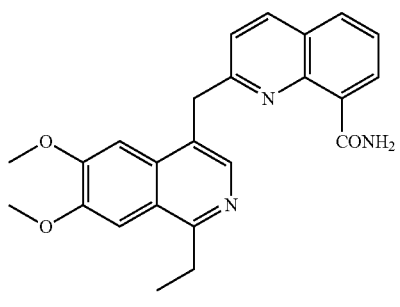

91 v) ↑

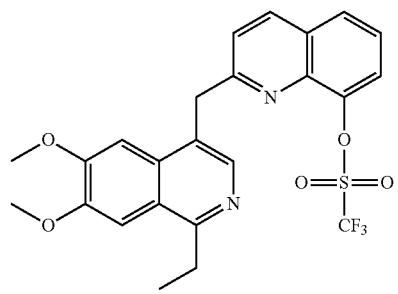

RBO 51116 i) →

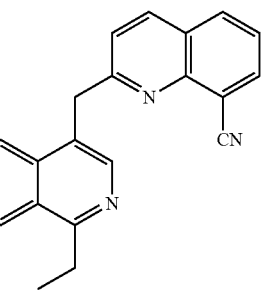

90 ii) →

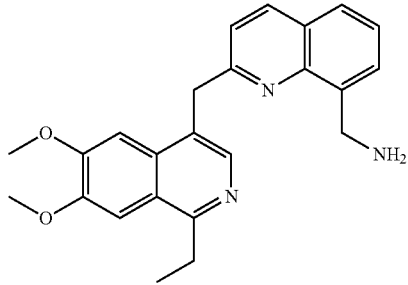 [SMILES: CCc1ncc(Cc2ccc3cccc(CN)c3n2)c2cc(OC)c(OC)cc12]

RBO 51194 iii) →

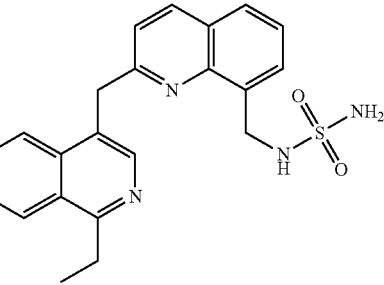

94 i) Zn(CN)$_2$, Pd(PPh$_3$)$_4$, DMF, MW, 180° C., 10 min, 44%.
ii) DIBAL-H, THF, -78° C. to RT, 5 h then NH$_4$Cl, 53%.
iii) Sulfamide, 1,4-dioxane, reflux, 2 h, 7%.
iv) Pd$_2$(dba)$_3$, Xantphos, ethyl oxamate, Cs$_2$CO$_3$, 1,4-dioxane, reflux, 4 h, 61%.
v) H$_2$O$_2$ 35%, EtOH, 0.5 N NaOH, reflux, 72 h, 47%.

Reaction Scheme 9:
Preparation of Compounds 90-92 and 94.

The amide 91 was prepared by basic hydrolysis of the nitrile 90 that was prepared from triflate RBO 51116 as described in reaction scheme 9. The compounds 92 and 94 were also prepared from triflate RBO 51116 as described in reaction scheme 9.

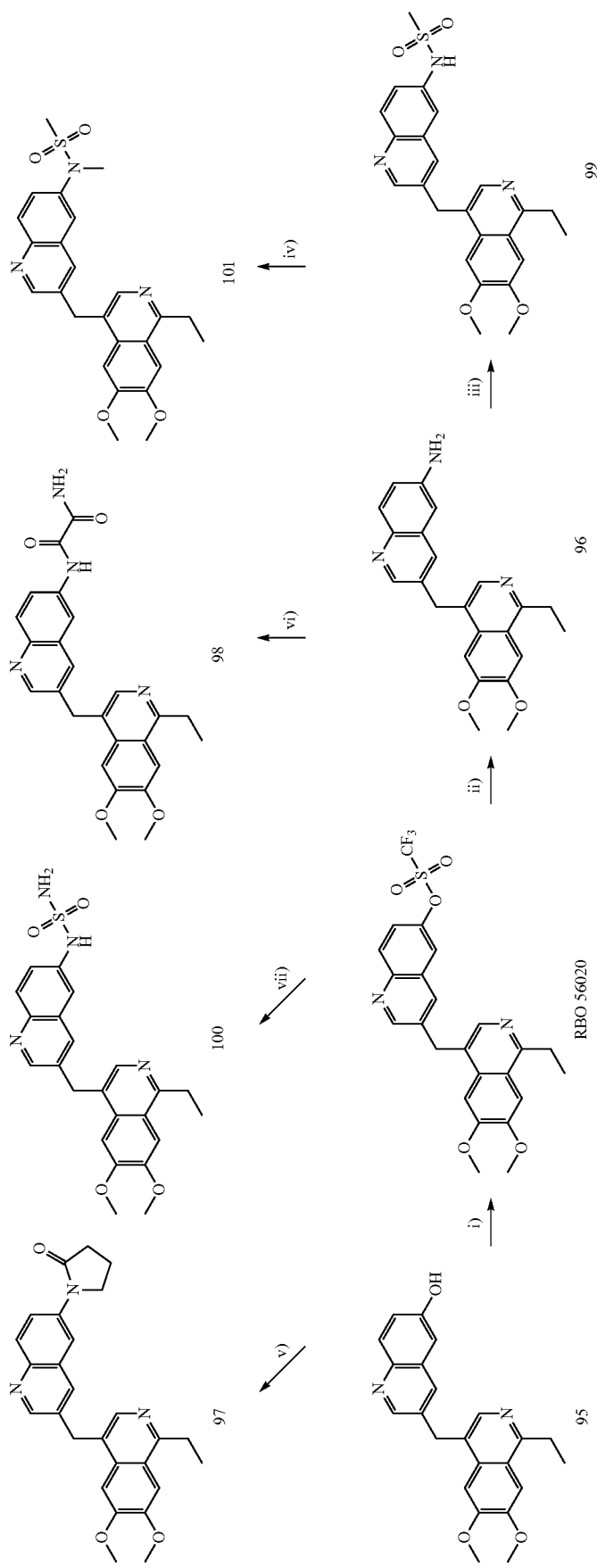

i) N-phenyl bis-trifluoromethane sulfonimide, Et₃N, DMF, 25° C., 15 h, 80%.
ii) i. Pd₂(dba)₃, Xantphos, tert-butyl carbamate, Cs₂CO₃, THF, MW, 140° C., 25 min. ii. TFA, CH₂Cl₂, 25° C., 15 h NaHCO₃, 63%.
iii) Methane sulfonyl chloride, pyridine, CH₂Cl₂, MW at 70° C., 70 min, 47%.
iv) CH₃I, Cs₂CO₃, CH₃CN, MW, 80° C., 11 min, 35%.
v) Pd₂(dba)₃, Xantphos, pyrrolidinone, Cs₂CO₃, 1,4-dioxane, MW, 160° C., 5 min, 71%.
vi) 2-Amino-2-oxoacetyl chloride RBO 56082, Et₃N, THF, RT overnight, 45%.
vii) Sulfamide, 1,4-dioxane, reflux, 15 h, 2.5%.

Reaction Scheme 10:
Preparation of Compounds 96 to 101.
The compounds 96 to 101 were prepared as described in reaction scheme 10.
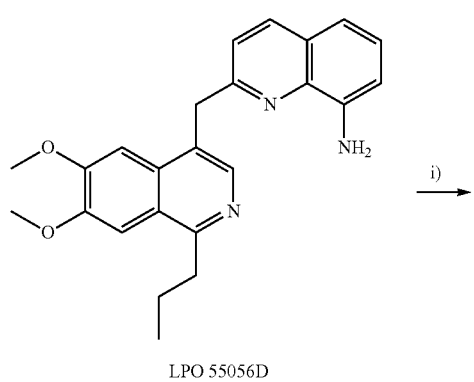
LPO 55056D
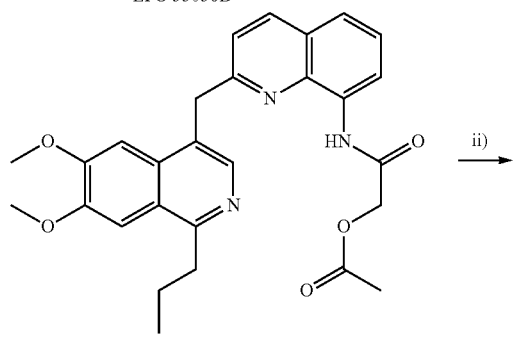
158
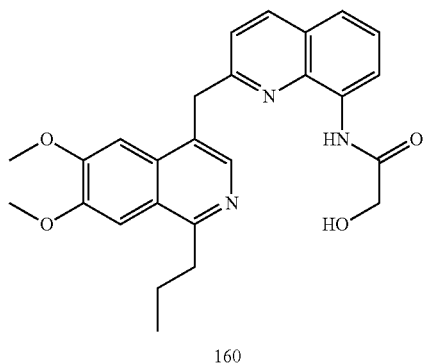
160
i) Acetoxyacetylchloride, pyridine, dry THF, 0° C. to RT, 1 h, 95%.
ii) 2 M LiOH in THF, 70° C., THF, 2 h, 73%.
Reaction Scheme 11:
Preparation of Compounds 158 and 160.
The compounds 158 and 160 were prepared as described in reaction scheme 11.

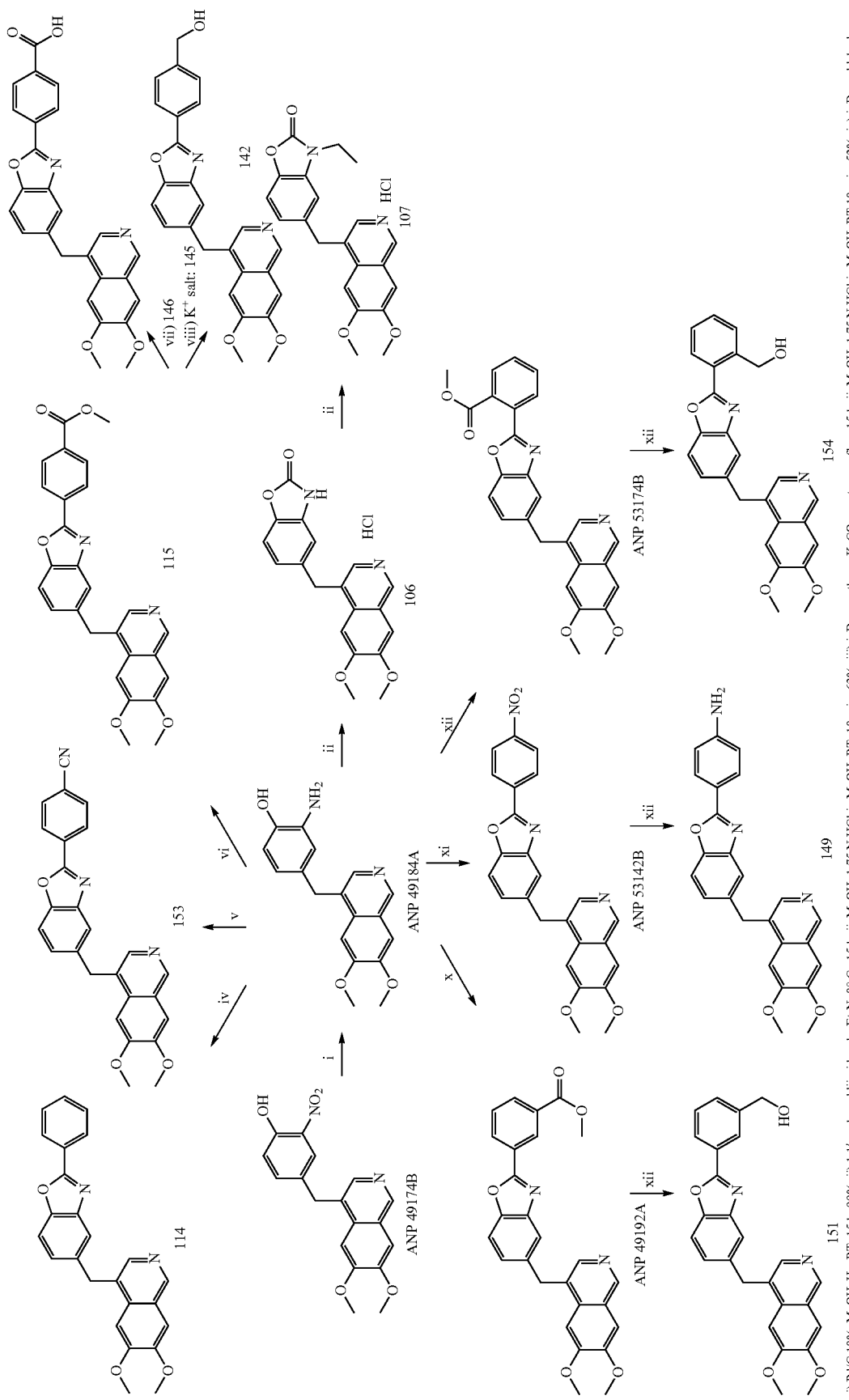

Reaction Scheme 12:
Preparation of Compounds 106, 107, 114, 115, 142, 145, 146, 149, 151, 153 and 154.

The compounds 106, 107, 114, 115, 142, 145, 146, 149, 151, 153 and 154 were prepared as described in Reaction Scheme 12.

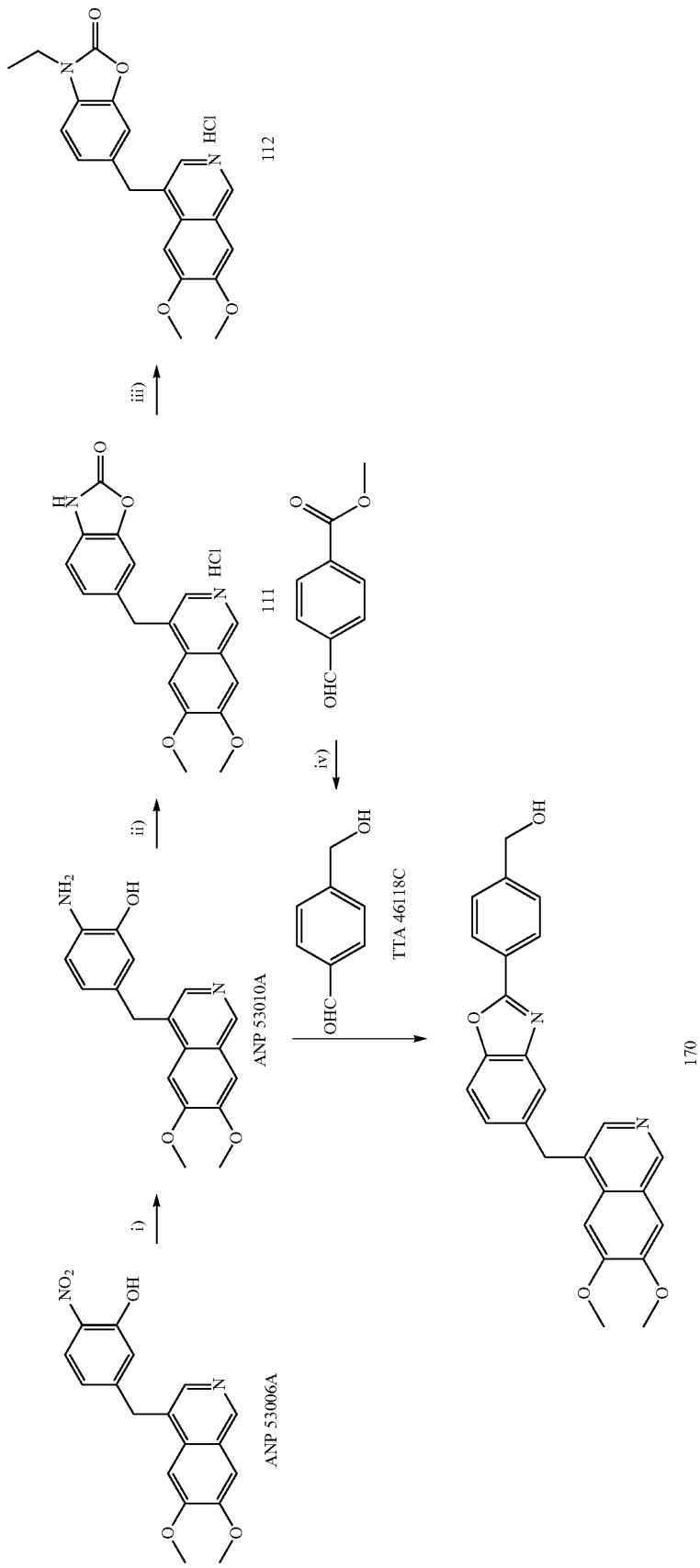
i) Pd/C 10%, MeOH, H₂, RT, 15 h, 94%.
ii) i. 1,1'-Carbonyldiimidazole, Et₃N, 0° C. to RT, 15 h. ii. MeOH, 1.75 N HCl in MeOH, RT, 10 min, 34%.
iii) i. Bromoethane, K₂CO₃, acetone, reflux, 15 h. ii. MeOH, 1.75 N HCl in MeOH, RT, 10 min, 52%.
iv) i. PTSA, ethane-1,2-diol, toluene, reflux, 4 h. ii. LiAlH₄, THF, 0° C. to RT, 4 h, 82%. iii. 1.5 N HCl, MeOH, 30° C., 1 h, 79%.
v) i. TTA 46118C, MeOH, RT, 15 h. ii. DDQ, CH₂Cl₂, RT, 2 h, 4%.

Reaction Scheme 13:
Preparation of Compounds 106, 111 and 112.
The compounds 111, 112 and 170 were prepared as described in reaction Scheme 13.
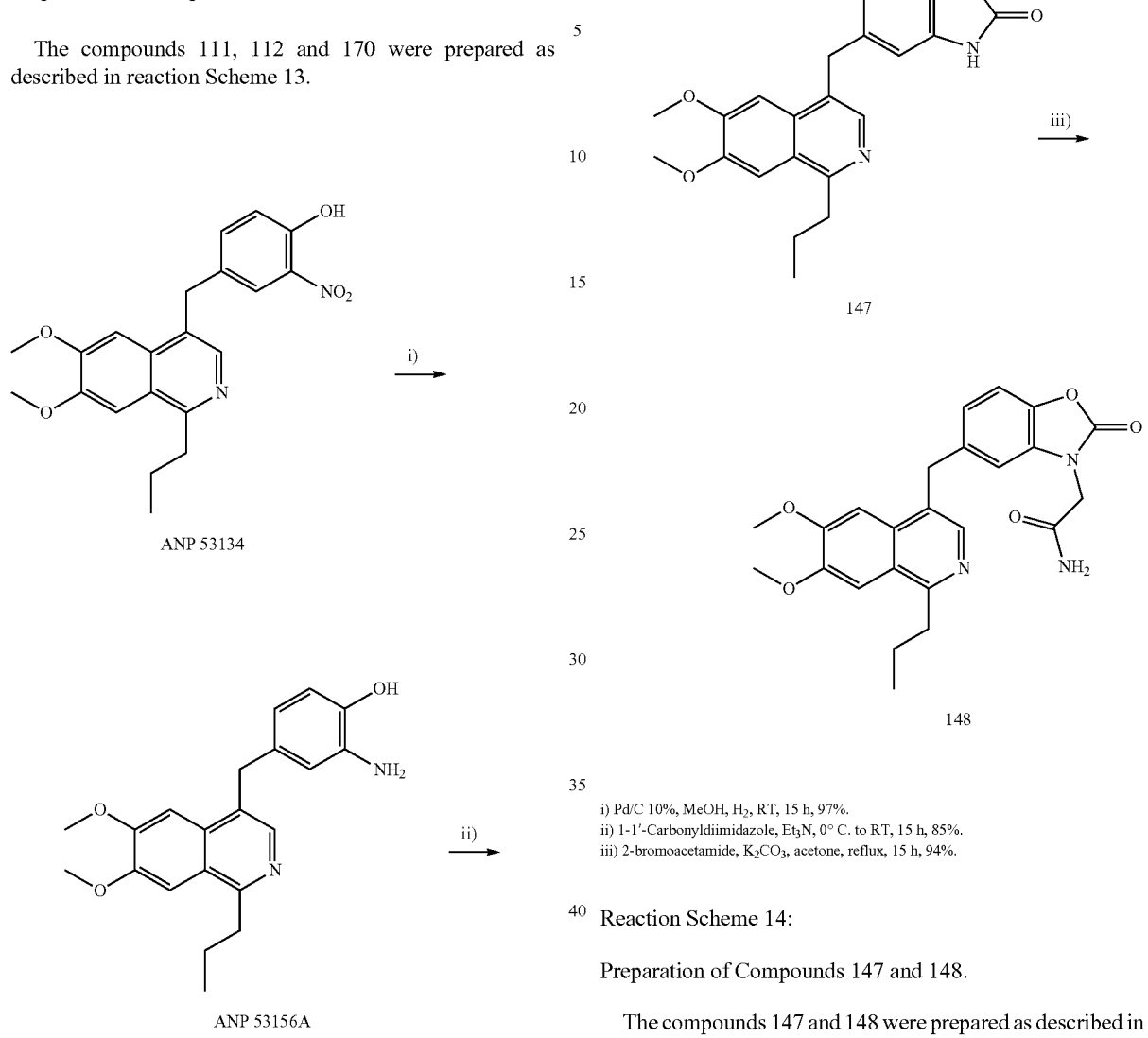
i) Pd/C 10%, MeOH, H₂, RT, 15 h, 97%.
ii) 1-1'-Carbonyldiimidazole, Et₃N, 0° C. to RT, 15 h, 85%.
iii) 2-bromoacetamide, K₂CO₃, acetone, reflux, 15 h, 94%.
Reaction Scheme 14:
Preparation of Compounds 147 and 148.
The compounds 147 and 148 were prepared as described in reaction scheme 14.
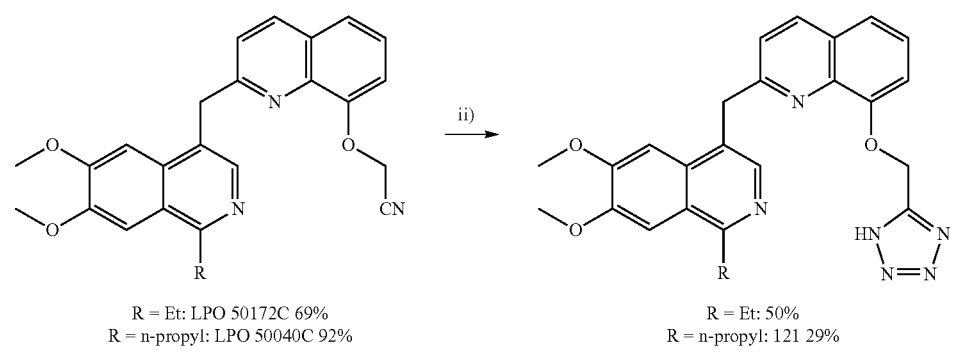

-continued

R = H: 7
R = Me: 131
R = Et: 83
R = n-propyl: 45
R = MeOCH₂: 163
R = cyclopropyl: 123 iv) i, iii: n =1, R = H: 41 (2HCl) 20%
iv) i: n = 1, R = Et: 128 81%
iv) i: n = 1, R = n-propyl: ANP 49102A 51%
iv) i: n = 1, R = MeOCH₂: 165 80%
iv) ii: n = 2, R = Et: LPO 50164C 78%
iv) ii: n = 2, R = n-propyl: LPO 50156C 46% v) i: n =1, R = H: 150 13%
v) ii. iii: n = 1, R = n-propyl: 108 (2 HCl) 78%
v) ii: n = 2, R = Et: 122 (Na⁺ salt) 36%
v) ii: n = 2, R = n-propyl: 118 (Na⁺ salt) 31%

R = H: 46 (2HCl) 13%
R = Me: 120 17%
R = Et: 116 47%
R = n-propyl: 139 25%
R = MeOCH₂: 164 72%
R = cyclopropyl: 130 71%

R = H: 42 61%
R = Et: 135 10%
R = n-propyl: 75 24%
R = MeOCH₂: 166 55% i) Chloroacetonitrile, Cs₂CO₃, acetone, reflux, 15 h, 69-92%.
ii) Sodium azide, NH₄Cl, DMF, 100° C., 2.5 h, 29-50%.
iii) 2-Bromoacetamide, Cs₂CO₃, DMF, 80° C., 7-15 h, 13-72%.
iv) i. Ethyl 2-bromoacetate, Cs₂CO₃, DMF, 65° C., 15 h, 20-81%. ii. Ethyl 3-bromopropionate, Et₃N, Cs₂CO₃, DMF, MW at 150° C., 35-45 min, 46-78%. iii. MeOH, 1.75 N HCl in MeOH, RT, 10 min.
v) i. 37%, HCl, AcOH, 110° C., 2 h, then NaHCO₃, 13%. ii. NaOH, H₂O, MeOH, 30-40° C., 1 h, 31-78%. iii) MeOH, 1.75 N HCl in MeOH, RT, 10 min.
vi) Bromoethanol, KI, Cs₂CO₃, DMF, 90° C., 15 h, 10%.
vii) NaBH₄, tBuOH, MeOH, 100-140° C., 2 h, 24-61%.

Reaction Scheme 15:
Preparation of Compounds 41, 42, 46, 108, 116, 118, 120, 122, 128, 130, 135, 139, 148, 164, 165 and 166.

The compounds 41, 42, 46, 108, 116, 118, 120, 122, 128, 130, 135, 139, 148, 164, 165 and 166 were prepared as described in reaction scheme 15.

47
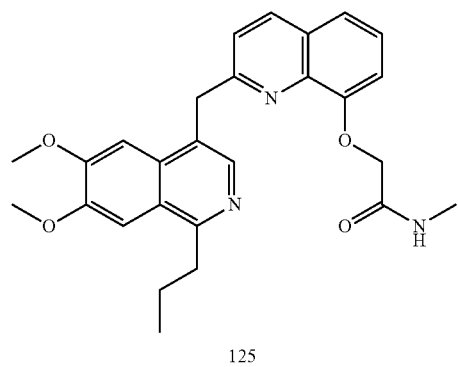
125
48
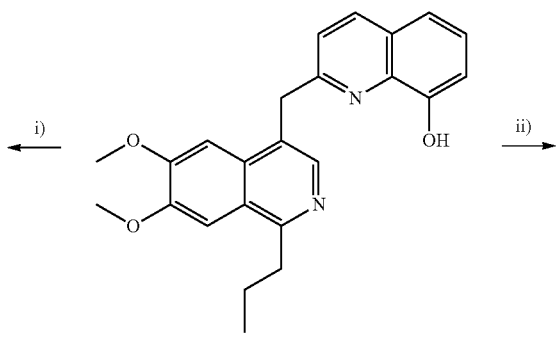
45 (free base)
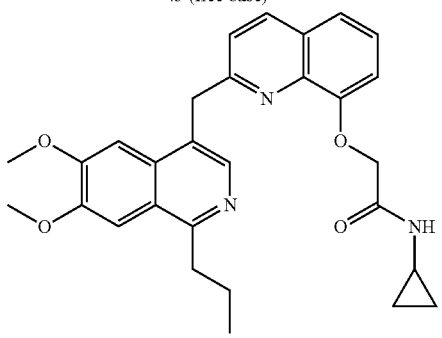
126
i) 2-Chloro-N-methylacetamide, Cs$_2$CO$_3$, acetone, reflux, 15 h, 51%.
ii) 2-Chloro-N-cyclopropylacetamide, Cs$_2$CO$_3$, acetone, reflux, 15 h, 37%.
Reaction Scheme 16:
Preparation of Compounds 125 and 126.
The compounds 165 and 166 were prepared as described in reaction scheme 16.

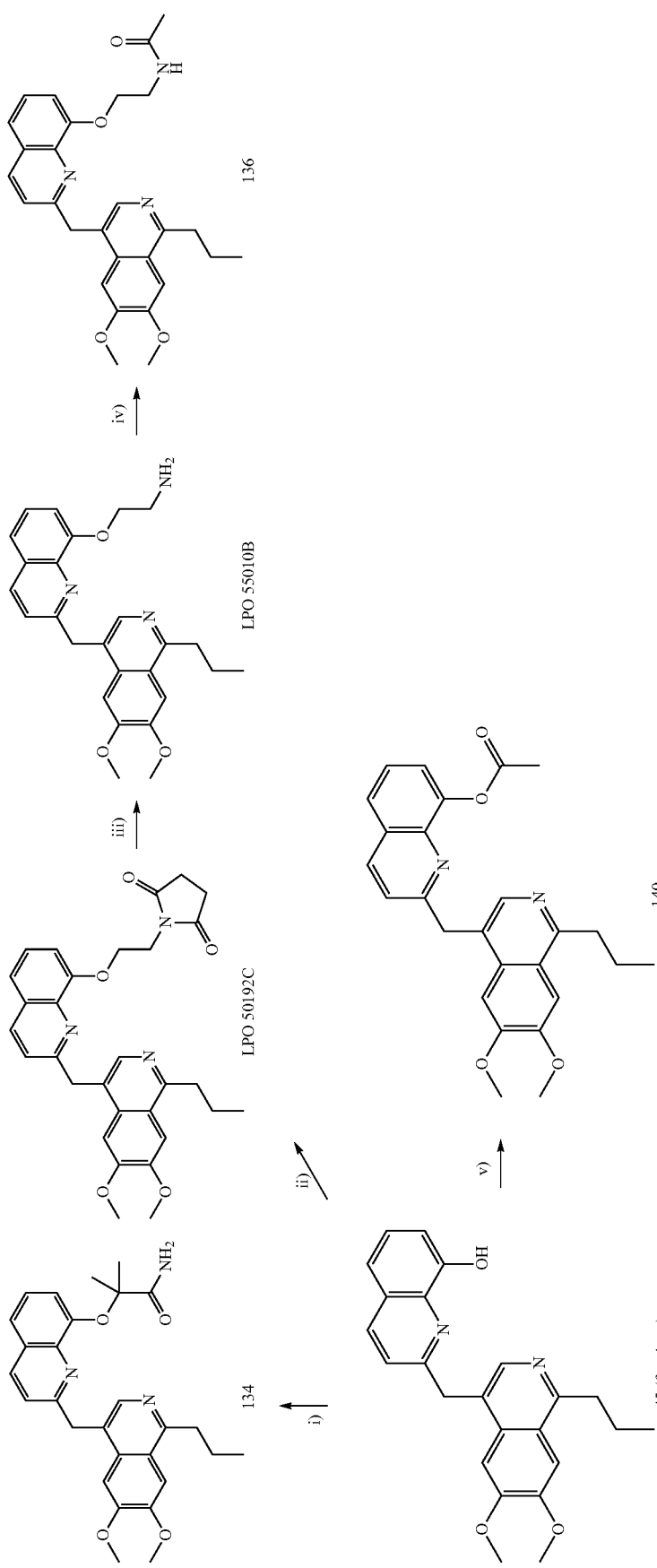
i) 2-Bromo-2-methylpropionamide, Cs₂CO₃, acetone, reflux, 4 h, 60%.
ii) N-(2-bromoethyl)phthalimide, Cs₂CO₃, DMF, MW at 150° C., 10 min, 13%.
iii) Hydrazine monohydrate, EtOH, 80° C., 2 h, 90%.
iv) Ac₂O, pyridine, CH₂Cl₂, RT, 2 h, 34%.
v) Ac₂O, DMAP, CH₂Cl₂, RT, 15 h, 59%.

Reaction Scheme 17:
Preparation of Compounds 45, 134, 136 and 140.
The compounds 45, 134, 136 and 140 were prepared as described in reaction scheme 17.
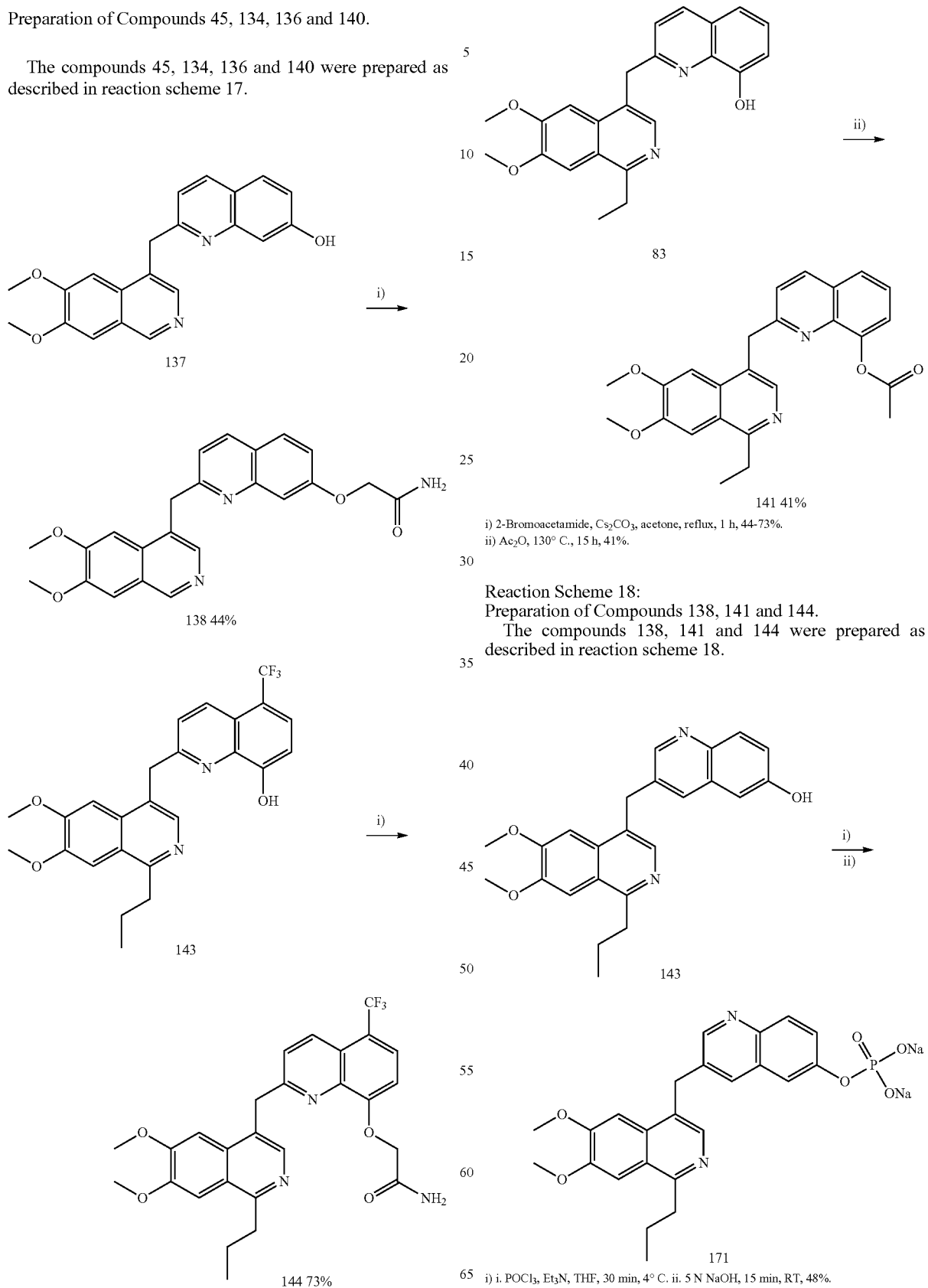
i) 2-Bromoacetamide, Cs$_2$CO$_3$, acetone, reflux, 1 h, 44-73%.
ii) Ac$_2$O, 130° C., 15 h, 41%.
Reaction Scheme 18:
Preparation of Compounds 138, 141 and 144.
The compounds 138, 141 and 144 were prepared as described in reaction scheme 18.
i) i. POCl$_3$, Et$_3$N, THF, 30 min, 4° C. ii. 5 N NaOH, 15 min, RT, 48%.

Reaction Scheme 19:
Preparation of Compound 171.

The compound 171 was prepared as described in reaction scheme 19.

It should be understood that other ways of producing these compounds may be designed by the skilled person, based on common general knowledge and following guidance contained in this application.

Another object of the present invention is the intermediate compounds used for the preparation of compounds of formula (I) or (IA). In particular, the present invention relates to the intermediate compounds herein below mentioned in the examples.

Included within the scope of the invention are all stereoisomers, tautomeric forms, salts and solvates of the compound of formula (I) or (IA).

The compounds according to the invention can be in the form of salts, particularly acid or base salts, preferably compatible with pharmaceutical use (i.e. pharmaceutically acceptable salts of the compounds of the invention). It will be appreciated by those skilled in the art that non-pharmaceutically acceptable salts of compounds of formula (I) or (IA) are also part of the present invention, since such non-pharmaceutically acceptable salts can be useful as intermediates in the preparation of pharmaceutically acceptable salts.

Salts of compounds of the invention include pharmaceutically acceptable acid addition salts, pharmaceutically acceptable base addition salts, pharmaceutically acceptable metal salts, ammonium, and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, ketoglutarates and the like. Further examples of pharmaceutically acceptable inorganic or organic acid addition salts include the pharmaceutically acceptable salts listed in *J. Pharm. Sci.*, 66, 2, 1977 which is incorporated herein by reference. Examples of metal salts include lithium, sodium, potassium, magnesium salts and the like. Base salts include, but are not limited to, those formed with pharmaceutically acceptable cations, such as sodium, potassium, lithium, calcium, magnesium, ammonium and alkylammonium. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like. Other examples of organic bases include lysine, arginine, guanidine, diethanolamine, choline and the like.

The pharmaceutically acceptable salts can in particular be prepared by reacting the compound of formula (I) or (IA) with acids such as hydrochloric acid, hydrobromic acid, nitric acid, sulfuric acid, phosphoric acid, p-toluenesulphonic acid, methanesulfonic acid, fonic acid, acetic acid, citric acid, maleic acid, salicylic acid, hydroxynaphthoic acid, ascorbic acid, palmitic acid, succinic acid, benzoic acid, benzenesulfonic acid, tartaric acid and the like in solvents like ethyl acetate, ether, alcohols, acetone, THF, dioxane, etc. Mixture of solvents may also be used.

Compounds of Formula (I) or (IA) may have optical centers and therefore may occur in different enantiomeric and diastereomeric configurations. The present invention includes all enantiomers, diastereomers, and other stereoisomers of such compounds of Formula (I) or (IA), as well as racemic compounds and racemic mixtures and other mixtures of stereoisomers thereof.

The compounds according to the present invention may be prepared by various methods known to those skilled in the art. General and specific methods for the preparation of compounds of formula (I) or (IA) are described herein below.

The compounds of the invention can be administered alone, but are generally administered with a pharmaceutical carrier, with respect to standard pharmaceutical practice (such as described in Remington's Pharmaceutical Sciences, Mack Publishing), in either single or multiple doses. The invention thus also includes a pharmaceutical composition comprising, in a pharmaceutically acceptable carrier, a compound of formula (I) or (IA).

Suitable pharmaceutical carriers include inert solid diluents or fillers, sterile aqueous solutions and various organic solvents. The pharmaceutical compositions formed thereby can then be readily administered in a variety of dosage forms such as tablets, powders, lozenges, liquid preparations, syrups, injectable solutions and the like. These pharmaceutical compositions can optionally contain additional ingredients such as flavorings, binders, excipients and the like. Thus, the compound of the invention may be formulated for oral, ocular, buccal, intranasal, parenteral (e.g. intravenous, intramuscular or subcutaneous), transdermal (e.g. patch) or rectal administration, or in a form suitable for administration by inhalation or insufflation. The pharmaceutical compositions of the invention can be formulated either as solid or liquid compositions.

For oral administration, the pharmaceutical compositions may take the form of, for example, tablets or capsules prepared by conventional means with pharmaceutically acceptable excipients such as binding agents (e.g. pregelatinized maize starch, polyvinylpyrrolidone or hydroxypropyl methylcellulose); fillers (e.g. lactose, microcrystalline cellulose or calcium phosphate); lubricants (e.g. magnesium stearate, talc or silica); disintegrants (e.g. potato starch or sodium starch glycolate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl p-hydroxybenzoates or sorbic acid).

For buccal administration, the composition may take the form of tablets or lozenges formulated in conventional manner.

The compounds of the invention may be formulated for parenteral administration by injection, including using conventional catheterization techniques or infusion. Formulations for injection may be presented in unit dosage form, e.g. in ampoules or in multi-dose containers, with an added preservative. They may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g. sterile pyrogen-free water, before use. When a product solution is required, it can be made by dissolving the isolated inclusion complex in water (or other aqueous medium) in an amount sufficient to generate a solution of the required strength for oral or parenteral administration to patients. The compounds may be formulated for fast dispersing dosage forms, which are designed to release the active ingredient in the oral cavity. These have often been formulated using rapidly soluble gelatin-based matrices. These dosage forms are well known and can be used to deliver a wide range of drugs. Most fast dispersing dosage forms utilize gelatin as a carrier or structure-forming agent. Typically, gelatin is used to give sufficient strength to the dosage form to prevent breakage during removal from packaging, but once placed in the mouth, the gelatin allows immediate dissolution of the dosage form. Alternatively, various starches are used to the same effect. The compounds of the invention may also be formulated in rectal compositions such as suppositories or retention enemas, e.g. containing conventional suppository bases such as cocoa butter or other glycerides.

The dosages and dosage regimen in which the compounds of formula (I) are administered will vary according to the pharmacodynamic characteristics of the particular agent and its mode and route of administration; the age, health and weight of the recipient; the nature and extent of the symptoms; the kind of concurrent treatment; the frequency of treatment; and the effect desired. Accordingly, optimal therapeutic concentrations will be best determined at the time and place through routine experimentation.

The compounds according to the invention can be used enterally or parenterally. Orally, the compounds according to the invention are suitably administered in the amount from about 0.1 mg per day to 1,000 mg per day. For parenteral, sublingual, intranasal, or intrathecal administration, the compounds according to the invention are suitably used in the amount from about 0.5 to about 100 mg/day; for depo administration and implants from about 0.5 mg/day to about 50 mg/day; for topical administration from about 0.5 mg/day to about 200 mg/day; for rectal administration from about 0.5 mg to about 500 mg. In a preferred aspect, the therapeutically effective amounts for oral administration is from about 1 mg/day to about 100 mg/day; and for parenteral administration from about 5 to about 50 mg daily. In a more preferred aspect, the therapeutically effective amounts for oral administration are from about 5 mg/day to about 50 mg/day.

The compounds of the present invention can also be administered intraocularly (e.g., intravitreally (e.g., through injection) subconjunctivally, or injection into subtenon space).

For intravitreal administration, the weight of the device (i.e., drug plus carrier/vehicle/excipient) is typically 1 mg (which for example may be administered with a 22 G needle) and the drug load is normally 10-50%. The drug dose range for intravitreal administration is normally about 100-500 µg. However, the drug load can be stretched to 2-65%, i.e., a drug dose range of 20-650 µg can be used. However, the device weight may be 1.5 mg, and for this a drug dose range of 20-975 µg can be used.

Another way of intravitreal delivery is by injecting drug suspension formulation. For this, the dose range is 10-600 ug.

An intraocular implant comprising a therapeutically effective amount of a compound of Formula (I) or (IA) (the therapeutic component; the active pharmaceutical ingredient (API)), and a drug release sustaining polymer component associated with the therapeutic compound can also be administered by intraocular means. As used herein, an "intraocular implant" refers to a device or element that is structured, sized, or otherwise configured to be place in an eye. Intraocular implants are generally biocompatible with physiological conditions of an eye and do not cause adverse side effects. Intraocular implants may be place in an eye without disrupting vision of the eye.

The implant may be solid, semisolid, or viscoelastic. The drug release sustaining component is associated with the therapeutic component to sustain release of an amount of the therapeutic component into an eye in which the implant is placed.

The therapeutic component may be released from the implant by diffusion, erosion, dissolution or osmosis. The drug release sustaining component may comprise one or more biodegradable polymers or one or more non-biodegradable polymers. Examples of biodegradable polymers of the present implants may include poly-lactide-co-glycolide (PLGA and PLA), polyesters, poly (ortho ester), poly(phosphazine), poly(phosphate ester), polycaprolactone, natural polymers such as gelatin or collagen, or polymeric blends. The amount of the therapeutic component is released into the eye for a period of time greater than about one week after the implant is placed in the eye and is effective in reducing or treating an ocular condition.

In one embodiment, the intraocular implant comprises a therapeutic component and a biodegradable polymer matrix. The therapeutic component is associated with a biodegradable polymer matrix that degrades at a rate effective to sustain release of an amount of the therapeutic component from the implant effective to treat an ocular condition. The intraocular implant is biodegradable or bioerodible and provides a sustained release of the therapeutic component in an eye for extended periods of time, such as for more than one week, for example for about one month or more and up to 5 about six months or more. The implant may be configured to provide release of the therapeutic component in substantially one direction, or the implant may provide release of the therapeutic component from all surfaces of the implant.

The biodegradable polymer matrix of the foregoing implant may be a mixture of biodegradable polymers or the matrix may comprise a single type of biodegradable polymer. For example, the matrix may comprise a polymer selected from the group consisting of polylactides, poly(lactide-co-glycolides), polycaprolactones, and combinations thereof.

In another embodiment, the intraocular implant comprises the therapeutic component and a polymeric outer layer covering the therapeutic component. The polymeric outer layer includes one or more orifices or openings or holes that are effective to allow a liquid to pass into the implant, and to allow the therapeutic component to pass out of the implant.

The therapeutic component is provided in a core or interior portion of the implant, and the polymeric outer layer covers or coats the core. The polymeric outer layer may include one or more non-biodegradable portions. The implant can provide an extended release of the therapeutic component for more than about two months, and for more than about one year, and even for more than about five or about ten years. One example of such a polymeric outer layer covering is disclosed in U.S. Pat. No. 6,331,313.

In one embodiment, the present implant provides a sustained or controlled delivery of the therapeutic component at a maintained level despite the rapid elimination of the therapeutic component from the eye. For example, the present implant is capable of delivering therapeutically effective amounts of the therapeutic component for a period of at least about 30 days to about a year despite the short intraocular half-lives that may be associated with the therapeutic component. Plasma levels of the therapeutic component obtained after implantation may be extremely low, thereby reducing issues or risks of systemic toxicity. The controlled delivery of the therapeutic component from the present implants would permit the therapeutic component to be administered into an eye with reduced toxicity or deterioration of the blood-aqueous and blood-retinal barriers, which may be associated with intraocular injection of liquid formulations containing the therapeutic component.

A method of making the present implant involves combining or mixing the therapeutic component with a biodegradable polymer or polymers. The mixture may then be extruded or compressed to form a single composition. The single composition may then be processed to form individual implants suitable for placement in an eye of a patient.

Another method of making the present implant involves providing a polymeric coating around a core portion containing the therapeutic component, wherein the polymeric coating has one or more holes. The implant may be placed in an ocular region to treat a variety of ocular conditions, such as treating, preventing, or reducing at least one symptom associated with nonexudative age related macular degeneration (ARMD), exudative age related macular degeneration, choroidal neovascularization, acute macular neuroretinopathy, cystoid macular edema, diabetic macular edema, Behcet's disease, diabetic retinopathy, retinal arterial occlusive The daily dose may be administered as single dose or in divided doses and, in addition, the upper limit can also be exceeded when this is found to be indicated.

The present invention also relates to a compound of formula (I) or (IA), or a composition comprising a compound of formula (I) or (IA), for use as a medicament. Indeed, the compounds according to the invention have been found to have pharmacologically important properties which can be used therapeutically. The compounds of the invention can be used alone, in combination with each other or in combination with other active compounds.

The compounds of the invention are inhibitors selective for PDE10A. The invention thus also relates to a compound of formula (I) or (IA) or a pharmaceutical composition comprising the same, for use in a method for the treatment of a disease selected in the group consisting of the diseases or groups of diseases described below, where inhibition of PDE10 would be efficient in the treatment of said diseases.

The present invention also pertains to a pharmaceutical composition for use in the potential treatment of certain psychotic disorders and conditions such as schizophrenia, delusional disorders and drug induced psychosis; to anxiety disorders such as panic and obsessive-compulsive disorder; and to movement disorders including Parkinson's disease and Huntington's disease, comprising an amount of a compound of formula (I) or (IA) effective in inhibiting PDE10A.

In another embodiment, the invention relates to a pharmaceutical composition for potentially treating psychotic disorders and condition such as schizophrenia, delusional disorders and drug induced psychosis; anxiety disorders such as panic and obsessive-compulsive disorder; and movement disorders including Parkinson's disease and Huntington's disease, comprising an amount of a compound of formula (I) effective in treating said disorder or condition.

The invention also relates to a compound of formula (I) or (IA), for use in the potential treatment of certain psychotic disorders and conditions such as schizophrenia, delusional disorders and drug induced psychosis; to anxiety disorders such as panic and obsessive-compulsive disorder; and to movement disorders including Parkinson's disease and Huntington's disease.

Examples of psychotic disorders that can potentially be treated according to the present invention include, but are not limited to, schizophrenia, for example of the paranoid, disorganized, catatonic, undifferentiated, or residual type; schizophreniform disorder; schizoaffective disorder, for example of the delusional type or the depressive type; delusional disorder; substance-induced psychotic disorder, for example psychosis induced by alcohol, amphetamine, cannabis, cocaine, hallucinogens, inhalants, opioids, or phencyclidine; personality disorder of the paranoid type; and personality disorder of the schizoid type. Examples of movement disorders that can potentially be treated according to the present invention include but are not limited to Huntington's disease and dyskinesia associated with dopamine agonist therapy, Parkinson's disease, restless leg syndrome, and essential tremor.

Other disorders that can potentially be treated according to the present invention are obsessive/compulsive disorders, Tourette's syndrome and other tic disorders.

In another embodiment, the invention relates to a method for potentially treating an anxiety disorder or condition in a mammal which method comprises administering to said mammal an amount of a compound of formula (I) or (IA) effective in inhibiting PDE10A.

The invention also provides a method for potentially treating an anxiety disorder or condition in a mammal which method comprises administering to said mammal an amount of a compound of formula (I) or (IA) effective in treating said disorder or condition.

The invention also relates to a compound of formula (I) or (IA), for use in the potential treatment of an anxiety disorder or condition in a mammal.

Examples of anxiety disorders that can potentially be treated according to the present invention include, but are not limited to, panic disorder; agoraphobia; a specific phobia; social phobia; obsessive-compulsive disorder; post-traumatic stress disorder; acute stress disorder; and generalized anxiety disorder.

The invention further provides a method of potentially treating a drug addiction, for example an alcohol, amphetamine, cocaine, or opiate addiction, in a mammal, including a human, which method comprises administering to said mammal an amount of a compound of formula (I) or (IA) effective in treating drug addiction. The invention also provides a method of treating a drug addiction, for example an alcohol, amphetamine, cocaine, or opiate addiction, in a mammal, including a human, which method comprises administering to said mammal an amount of a compound of formula (I) or (IA) effective in inhibiting PDE10A.

The invention also relates to a compound of formula (I) or (IA), for use in the treatment of a drug addiction, for example an alcohol, amphetamine, cocaine, or opiate addiction, in a mammal, including a human.

A "drug addiction", as used herein, means an abnormal desire for a drug and is generally characterized by motivational disturbances such a compulsion to take the desired drug and episodes of intense drug craving.

The invention further provides a method of potentially treating a disorder comprising as a symptom a deficiency in attention and/or cognition in a mammal, including a human, which method comprises administering to said mammal an amount of a compound of formula (I) or (IA) effective in treating said disorder. The invention also provides a method of potentially treating a disorder or condition comprising as a symptom a deficiency in attention and/or cognition in a mammal, including a human, which method comprises administering to said mammal an amount of a compound of formula (I) or (IA) effective in inhibiting PDE10A.

The invention also provides a method of potentially treating a disorder or condition comprising as a symptom a deficiency in attention and/or cognition in a mammal, including a human, which method comprises administering to said mammal an amount of a compound of formula (I) or (IA) effective in treating said disorder or condition.

The invention also relates to a compound of formula (I) or (IA), for use in the potential treatment of a disorder or condition comprising as a symptom a deficiency in attention and/or cognition in a mammal, including a human.

The phrase "deficiency in attention and/or cognition" as used herein in "disorder comprising as a symptom a deficiency in attention and/or cognition" refers to a subnormal functioning in one or more cognitive aspects such as memory, intellect, or learning and logic ability, in a particular individual relative to other individuals within the same general age population. "Deficiency in attention and/or cognition" also refers to a reduction in any particular individual's functioning in one or more cognitive aspects, for example as it occurs in age-related cognitive decline. Examples of disorders that comprise as a symptom a deficiency in attention and/or cognition that can be treated according to the present invention are dementia, for example Alzheimer's disease, multi-infarct dementia, alcoholic dementia or other drug-related dementia, dementia associated with intracranial tumors or cerebral trauma, dementia associated with Huntington's disease or Parkinson's disease, or AIDS-related dementia; delirium; amnestic disorder; post-traumatic stress disorder; mental retardation; a learning disorder, for example reading disorder, mathematics disorder, or a disorder of written expression; attention-deficit/hyperactivity disorder; and age-related cognitive decline.

The invention also provides a method of potentially treating a mood disorder or mood episode in a mammal, including a human, comprising administering to said mammal an amount of a compound of formula (I) or (IA) effective in treating said disorder or episode.

The invention also provides a method of potentially treating a mood disorder or mood episode in a mammal, including a human, comprising administering to said mammal an amount of a compound of formula (I) or (IA) effective in inhibiting PDE10A.

The invention also relates to a compound of formula (I) or (IA), for use in the treatment of a mood disorder or mood episode in a mammal, including a human Examples of mood disorders and mood episodes that can be treated according to the present invention include, but are not limited to, major depressive episode of the mild, moderate or severe type, a manic or mixed mood episode, a hypomanic mood episode; a depressive episode with atypical features; a depressive episode with melancholic features; a depressive episode with catatonic features; a mood episode with post-partum onset; post-stroke depression; major depressive disorder; dysthymic disorder; minor depressive disorder; pre-menstrual dysphoric disorder; post-psychotic depressive disorder of schizophrenia; a major depressive disorder superimposed on a psychotic disorder such as delusional disorder or schizophrenia; a bipolar disorder, for example bipolar I disorder, bipolar II disorder, and cyclothymic disorder.

The invention further provides a method of potentially treating a neurodegenerative disorder or condition in a mammal, including a human, which method comprises administering to said mammal an amount of a compound of formula (I) or (IA) effective in treating said disorder or condition. The invention further provides a method of potentially treating a neurodegenerative disorder or condition in a mammal, including a human, which method comprises administering to said mammal an amount of a compound of formula (I) or (IA) effective in inhibiting PDE10A. The invention also provides to a compound of formula (I) or (IA), for use in the treatment of a neurodegenerative disorder or condition in a mammal, including a human.

As used herein, and unless otherwise indicated, a "neurodegenerative disorder or condition" refers to a disorder or condition that is caused by the dysfunction and/or death of neurons in the central nervous system. The treatment of these disorders and conditions can be facilitated by administration of an agent which prevents the dysfunction or death of neurons at risk in these disorders or conditions and/or enhances the function of damaged or healthy neurons in such a way as to compensate for the loss of function caused by the dysfunction or death of at-risk neurons. The term "neurotrophic agent" as used herein refers to a substance or agent that has some or all of these properties.

Examples of neurodegenerative disorders and conditions that can potentially be treated according to the present invention include, but are not limited to, Parkinson's disease; Huntington's disease; dementia, for example Alzheimer's disease, multi-infarct dementia, AIDS-related dementia, and Fronto temperal Dementia; neurodegeneration associated with cerebral trauma; neurodegeneration associated with stroke, neurodegeneration associated with cerebral infarct; hypoglycemia-induced neurodegeneration; neurodegeneration associated with epileptic seizure; neurodegeneration associated with neurotoxin poisoning; and multi-system atrophy.

In one embodiment of the invention, the neurodegenerative disorder is Parkinson's disease or Alzheimer's disease.

In one embodiment of the present invention, the neurodegenerative disorder or condition comprises neurodegeneration of striatal medium spiny neurons in a mammal, including a human.

In a further embodiment of the present invention, the neurodegenerative disorder or condition is Huntington's disease.

The invention also provides a pharmaceutical composition for potentially treating psychotic disorders, delusional disorders and drug induced psychosis; anxiety disorders, movement disorders, mood disorders, neurodegenerative disorders, obesity, and drug addiction, comprising an amount of a compound of formula (I) or (IA) effective in treating said disorder or condition.

The invention also provides a method of potentially treating a disorder selected from psychotic disorders, delusional disorders and drug induced psychosis; anxiety disorders, movement disorders, obesity, mood disorders, and neurodegenerative disorders, which method comprises administering an amount of a compound of formula (I) or (IA) effective in treating said disorder.

The invention also provides to a compound of formula (I) or (IA), for use in the potential treatment of a disorder selected from psychotic disorders, delusional disorders and drug induced psychosis; anxiety disorders, movement disorders, obesity, mood disorders, and neurodegenerative disorders.

The invention also provides a method of potentially treating disorders selected from the group consisting of: dementia, Alzheimer's disease, multi-infarct dementia, alcoholic dementia or other drug-related dementia, dementia associated with intracranial tumors or cerebral trauma, dementia associated with Huntington's disease or Parkinson's disease, or AIDS-related dementia; delirium; amnestic disorder; post-traumatic stress disorder; mental retardation; a learning disorder, for example reading disorder, mathematics disorder, or a disorder of written expression; attention-deficit/hyperactivity disorder; age-related cognitive decline, major depressive episode of the mild, moderate or severe type; a manic or mixed mood episode; a hypomanic mood episode; a depressive episode with atypical features; a depressive episode with melancholic features; a depressive episode with catatonic features; a mood episode with postpartum onset; post-stroke depression; major depressive disorder; dysthymic disorder; minor depressive disorder; premenstrual dysphoric disorder; post-psychotic depressive disorder of schizophrenia; a major depressive disorder superimposed on a psychotic disorder comprising a delusional disorder or schizophrenia; a bipolar disorder comprising bipolar I disorder, bipolar II disorder, cyclothymic disorder, Parkinson's disease; Huntington's disease; Fronto temperal Dementia; neurodegeneration associated with cerebral trauma; neurodegeneration associated with stroke; neurodegeneration associated with cerebral infarct; hypoglycemia-induced neurodegeneration; neurodegeneration associated with epileptic seizure; neurodegeneration associated with neurotoxin poisoning; multi-system atrophy, paranoid, disorganized, catatonic, undifferentiated or residual type; schizophreniform disorder; schizoaffective disorder of the delusional type or the depressive type; delusional disorder; substance-induced psychotic disorder, psychosis induced by alcohol, amphetamine, cannabis, cocaine, hallucinogens, obesity, inhalants, opioids, or phencyclidine; personality disorder of the paranoid type; and personality disorder of the schizoid type, which method comprises administering an amount of a compound of Formula (I) or (IA) effective in treating said disorders. The invention thus also provides a compound of formula (I) or (IA), for use in the treatment of the diseases mentioned in the previous sentence.

The invention also provides a method for the potential treatment of psychotic disorders, delusional disorders and drug induced psychosis; anxiety disorders, movement disorders, mood disorders, neurodegenerative disorders, obesity, and drug addiction which method comprises administering an amount of a compound of formula (I) or (IA) effective in inhibiting PDE10A.

The invention also provides a method for the potential treatment of diseases of the retina, which method comprises administering an amount of a compound of formula (I) or (IA) effective in inhibiting PDE10A. By "diseases of the retina," the applicants mean any condition of the retina which impairs the normal functioning of the retina, its surrounding tissues, or the eye. These include macular degeneration, myopic retinal degeneration, diabetic retinopathy, choroidal neovascularization, macular edema (also referred to as cystoid macular edema and macular swelling), epiretinal membrane (macular pucker), macular hole, retinitis (such as retinitis pigmentosa), macular dystrophies (such as Stargardt's juvenile macular degeneration, Best's vitelliform dystrophy, cone dystrophies, and pattern dystrophy of the retinal pigmented epithelium), retinal detachment, retinal trauma, retinal tumors and retinal diseases associated with them, congenital hypertrophy of the retinal pigmented epithelium, acute posterior multifocal placoid pigment epitheliopathy, acute retinal pigment epithelitis, and uveitis (including iritis, pars planitis, choroiditis, retinitis, and chorioretinitis).

According to a particular aspect, the invention relates to a compound of formula (I) or a composition comprising a compound of formula (I) or (IA), for use in a method for the potential treatment of type I or type II diabetes, impaired glucose tolerance, impaired fasting glucose, metabolic syndrome, metabolism related disorders including excess of body weight or excess of body fat in obese patients, psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attention disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma and breast cancer, pain, ophthalmic diseases such as macular degeneration/retinal degeneration, including wet Age Related Macular Degeneration (ARMD), dry ARMD, retinitis pigmentosa, choroidal neovascularization, vascular diseases/exudative diseases, retinopathy, including diabetic retinopathy, uveitis/retinitis/choroiditis, Stargard's disease, macular edema, retinal detachment, trauma, systemic disorders with associated retinal dystrophies, cone dystrophies, dystrophy of the retinal pigmented epithelium, myopic retinal degeneration, acute retinal pigment epithelitis, retinal tumors, retinal disease associated with tumors.

The invention further relates to a method for the potential treatment of type I or type II diabetes, impaired glucose tolerance, impaired fasting glucose, metabolic syndrome, metabolism related disorders including excess of body weight or excess of body fat in obese patients, psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attention disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma and breast cancer, pain, ophthalmic diseases such as macular degeneration/retinal degeneration, including wet Age Related Macular Degeneration (ARMD), dry ARMD, geographic atrophy, retinitis pigmentosa, choroidal neovascularization, vascular diseases/exudative diseases, retinopathy, including diabetic retinopathy, uveitis/retinitis/choroiditis, Stargard's disease, macular edema, retinal detachment, trauma, systemic disorders with associated retinal dystrophies, cone dystrophies, dystrophy of the retinal pigmented epithelium, myopic retinal degeneration, acute retinal pigment epithelitis, retinal tumors, retinal disease associated with tumors, which method comprises administering an amount of a compound of formula (I) or (IA) effective in inhibiting PDE10A.

The invention further relates to a method for the potential treatment of type I or type II diabetes, impaired glucose tolerance, impaired fasting glucose, metabolic syndrome, metabolism related disorders including excess of body weight or excess of body fat in obese patients, psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attention disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma and breast cancer, pain, ophthalmic diseases such as macular degeneration/retinal degeneration, including wet Age Related Macular Degeneration, dry ARMD, geographic atrophy, retinitis pigmentosa, choroidal neovascularization, vascular diseases/exudative diseases, retinopathy, including diabetic retinopathy, uveitis/retinitis/choroiditis, Stargard's disease, macular edema, retinal detachment, trauma, systemic disorders with associated retinal dystrophies, cone dystrophies, dystrophy of the retinal pigmented epithelium, myopic retinal degeneration, acute retinal pigment epithelitis, retinal tumors, retinal disease associated with tumors, which method comprises administering an amount of a compound of Formula (I) or (IA) effective in treating said disorders.

The term "treating", as in "a method of treating a disorder", refers to reversing, alleviating, or inhibiting the progress of the disorder to which such term applies, or one or more symptoms of the disorder. As used herein, the term also encompasses, depending on the condition of the patient, preventing the disorder, including preventing onset of the disorder or of any symptoms associated therewith, as well as reducing the severity of the disorder or any of its symptoms prior to onset. "Treating" as used herein refers also to preventing a recurrence of a disorder.

The following examples illustrate the invention. However, it is to be understood that the invention is not limited to the details provided in these examples.

EXAMPLES

Example 1

Preparation of Compounds According to the Invention

General $^1$H-NMR and $^{13}$C-NMR spectra were recorded at ambient temperature with an Advance 300 (Bruker) spectrometer.

The compounds were analyzed by reverse phase high performance liquid chromatography (HPLC) using a Waters Autopurification System equipped with a Waters 2525 Pump, a Waters 2696 photodiode array detector. The Method A (10 min) was performed with an XTerra™ column (5 µm, C18, 4.5×50 mm, Model #186000482) or an XBridge™ column (5 µm, C18, 4.5×50 mm, Model #186003113). Solvent A was $H_2O$ with 0.05% TFA and solvent B was $CH_3CN$ with 0.05% TFA. The 10 min gradient run was realized using 1.0 mL min$^{-1}$ with 5% B in A (0.0-1.0 min), 5% to 100% B in A (1.0-7.0 min), 100% to 5% B in A (7.0-7.5 min), 5 B in A (7.5-10.0 min). The 5 min gradient run was realized using 1.0 mL min$^{-1}$ with 5% B in A (0.0-0.25 min), 5% to 100% B in A (0.25-3.0 min), 100% to 5% B in A (3.0-4.0 min), 5% B in A (4.0-5.0 min).

Melting points were measured with a Büchi B-545 melting point apparatus and were uncorrected. Microwave reactions were performed in a Biotage Initiator 60 EXP microwave reactor.

To isolate reaction products the solvent were removed by evaporation using a vacuum rotatory evaporator, unless otherwise indicated, the water bath temperature did not exceed 40° C.

General Procedure for Friedel-Crafts Acylation of 1,2-Dimethoxybenzene (Veratrole): Preparation of Compounds TTA 24178a, TTA 24178B, SSA 48078, SSA 48050, SSA 48090, SSA 48054, and SSA 48046

In a 100 mL round bottom flask at −4° C., $AlCl_3$ was dissolved in anhydrous $CH_2Cl_2$ and the desired acyl chloride was added portionwise (see conditions in table 1). After complete addition, the mixture was stirred at −4° C. for 5 min under a nitrogen atmosphere and a solution of veratrole in anhydrous $CH_2Cl_2$ was slowly added drop wise over 15 min (see conditions in table 1). The reaction mixture was stirred at 0° C. for 1 h (see conditions in table 1) and was poured into a 3 N HCl solution (typically 15 mL) and $CH_2Cl_2$ (typically 180 mL) was added. After extraction, the combined separated organic layers were washed with brine (typically 50 mL), dried over $MgSO_4$, filtered and evaporated to give after further drying the desired acylated compound. When necessary, the acylated compound was purified by column chromatography ($SiO_2$, see conditions in table 1).

General Procedure for Preparation of Iminoacetals: Preparation of Compounds LPO 22100, ANP 31058A, TTA 24128A, SSA 39096, SSA 39100, SSA 48080, SSA 48058, SSA 48092, SSA 48064, SSA 48052, ECO 33094, ECO 33114, ECO 33122, ECO 33134, TTA 24150A, TTA 24156A and TTA 46082A The aromatic aldehyde or ketone and aminoacetaldehyde diethyl acetal were placed in a 500 mL round-bottom flask and toluene was added (see conditions in table 1). The mixture was heated under reflux in a Dean-Stark apparatus (around 4 h, see conditions in table 1) until complete separation of water was achieved. Toluene was then evaporated to give after drying the desired iminoacetal in almost quantitative yield. The iminoacetal ANP 31058A was prepared from 3,4-dimethoxybenzylamine (23.2 mmol) and pyruvic aldehyde dimethyl acetal (35.5 mmol) using the same general procedure (see conditions in table 1).

General Procedure for Reduction of Iminoacetals to Aminoacetals: Preparation of Compounds LPO 22102, ANP 31060A, TTA 24128B, SSA 39098, SSA 39102, SSA 48084, SSA 48066, SSA 48100, SSA 48072, SSA 48060, ECO 33100, ECO 33118, ECO 33124, ECO 33138, TTA 241508, TTA 241568 and TTA 46082B The desired iminoacetal was dissolved in EtOH and $NaBH_4$ was added portion wise over a 0.5 h period and the reaction mixture was refluxed for 1 h (see conditions in table 2). The reaction mixture was concentrated under reduced pressure and the obtained residue was poured into water (typically 250 mL). This mixture was extracted using $CH_2Cl_2$ (typically 3×100 mL) and the combined organic layers were washed with $H_2O$ (typically 2×150 mL), brine (typically 50 mL), dried over $Mg_2SO_4$ and evaporated to give after further drying under vacuum the desired aminoacetal.

TABLE 1

| Compound | FORMULA | Conditions for Friedel-Crafts Acylation | Work-Up & Purification | Analysis |
|---|---|---|---|---|
| TTA 24178A | (structure: 1-(3,4-dimethoxyphenyl)propan-1-one) | AlCl₃ (17.4 g, 130 mmol); CH₂Cl₂ (50 mL); propionyl chloride (6.5 mL, 75.0 mmol); veratrole (8.5 g, 62 mmol) in CH₂Cl₂ (20 mL); 40 min at −5° C. then 20 min at 0° C. | Reaction was quenched at −10° C. with a slow addition of 3N HCl (60 mL). | 1-(3,4-dimethoxyphenyl)propan-1-one (11.8 g); MW: 194.23; Yield: 98%; White Solid, Mp (° C.): 58.8; $^1$H-NMR (CDCl$_3$, δ): 1.22 (t, 3H, J = 7.3 Hz, CH$_3$), 2.97 (q, 2H, J = 7.3 Hz, CH$_2$), 3.94 (s, 3H, OMe), 3.95 (s, 3H, OMe), 6.89 (d, 1H, J = 8.4 Hz, ArH), 7.54 (d, 1H, J = 1.9 Hz, ArH), 7.60 (dd, 1H, J = 8.3 Hz, J = 1.9 Hz, ArH); $^{13}$C-NMR (CDCl$_3$, δ): 8.4, 31.1, 55.8, 55.9, 109.9, 110.0, 122.4, 130.0, 148.9, 153.0, 199.3; MS-ESI m/z (% rel. Int.): 195.1 ([MH]$^+$ 100); HPLC: Method A, detection UV 254 nm, RT = 4.64 min, peak area 98%. |
| TTA 24178B | (structure: 1-(3,4-dimethoxyphenyl)butan-1-one) | AlCl₃ (17.4 g, 130 mmol); CH₂Cl₂ (50 mL); butyryl chloride (7.8 mL, 75 mmol); veratrole (8.5 g, 62 mmol) in CH₂Cl₂ (20 mL); 40 min at −5° C. then 20 min at 0° C. | Reaction was quenched at −10° C. with a slow addition of 3N HCl (60 mL). | 1-(3,4-dimethoxyphenyl)butan-1-one (12.6 g); MW: 208.25; Yield: 93%; White Solid, Mp (° C.): 67.7; $^1$H-NMR (CDCl$_3$, δ): 1.11 (t, 3H, J = 7.4 Hz, CH$_3$), 1.76 (sext., 2H, J = 7.4 Hz, CH$_2$), 2.91 (t, 2H, J = 7.4 Hz, COCH$_2$), 3.94 (s, 3H, OMe), 3.95 (s, 3H, OMe), 6.88 (d, 1H, J = 8.3 Hz, ArH), 7.54 (d, 1H, J = 1.7 Hz, ArH), 7.59 (dd, 1H, J = 8.3 Hz, J = 1.5 Hz, ArH); $^{13}$C-NMR (CDCl$_3$, δ): 13.9, 18.1, 40.0, 55.9, 56.0, 109.9, 110.0, 122.6, 130.3, 148.9, 153.0, 199.0; MS-ESI m/z (% rel. Int.): 209.1 (100); HPLC: Method A, detection UV 254 nm, RT = 5.10 min, peak area 98%. |
| SSA 48078 | (structure: cyclopropyl(3,4-dimethoxyphenyl)methanone) | AlCl₃ (4 g, 30 mmol); CH₂Cl₂ (18 mL); cyclopropane carbonyl chloride (1.40 mL, 15.4 mmol); veratrole (1.85 mL, 15.4 mmol) in CH₂Cl₂ (4 mL); 15 min at −4° C. then 0° C. for 1 h. | Reaction was quenched at −10° C. with a slow addition of 3N HCl (15 mL). | cyclopropyl(3,4-dimethoxyphenyl)methanone (3.15 g); MW: 106.24; Yield: Quantitative; Pale Yellow Oil; $^1$H-NMR (CDCl$_3$, δ): 1.01-1.04 (m, 2H, CH$_2$), 1.19-1.24 (m, 2H, CH$_2$), 2.62-2.67 (m, 1H, CH), 3.95 (d, 6H, J = 7.0 Hz, 2xOMe), 6.91 (d, 1H, J = 8.0 Hz, ArH), 7.54 (d, 1H, J = 2.0 Hz, ArH), 7.69 (dd, 1H, J = 8.0 Hz, J = 2.0 Hz, ArH); $^{13}$C-NMR (CDCl$_3$, δ): 11.3, 16.6, 56.0, 76.6, 110.3, 120.8, 122.6, 131.2, 149.0, 153.1, 199.0; MS-ESI m/z (% rel. Int.): 207.1 ([MH]$^+$, 100); HPLC: Method A, detection UV 254 nm, RT = 4.63 min, peak area 97%. |
| SSA 48050 | (structure: 1-(3,4-dimethoxyphenyl)-3-methylbutan-1-one) | AlCl₃ (4 g, 30 mmol); CH₂Cl₂ (18 mL); isovaleryl chloride (1.88 mL, 15.4 mmol); veratrole (1.85 mL, 15.4 mmol, 1 eq) in CH₂Cl₂ (4 mL); 15 min at 4° C. then 0° C. for 1 h. | Reaction was quenched at −10° C. with a slow addition of 3N HCl (15 mL). | 1-(3,4-dimethoxyphenyl)-3-methylbutan-1-one (3.37 g); MW: 222.29; Yield: Quantitative; Pale Yellow Oil; $^1$H-NMR (CDCl$_3$, δ): 0.99 (dd, 6H, J = 7.0 Hz & J = 2.0 Hz, 2xCH$_3$), 2.21-2.33 (m, 1H, CH), 2.78 (d, 2H, J = 7.0 Hz, CH$_2$), 3.94 (s, 6H, 2xOMe), 6.86-6.92 (m, 1H, ArH), 7.53-7.59 (m, 2H, 2xArH); $^{13}$C-NMR (CDCl$_3$, δ): 22.8, 25.5, 56.0, 109.9, 110.3, 122.8, 130.7, 149.0, 153.1, 198.9; MS-ESI m/z (% rel. Int.): 223.2 ([MH]$^+$, 100); HPLC: Method A, detection UV 254 nm, RT = 5.39 min, peak area 95%. |
| SSA 48090 | (structure: 1-(3,4-dimethoxyphenyl)pentan-1-one) | AlCl₃ (4 g, 30 mmol); CH₂Cl₂ (18 mL); valeryl chloride (1.84 mL, 15.4 mmol); veratrole (1.85 mL, 15.4 mmol) in CH₂Cl₂ (4 mL); 15 min at −4° C. then 0° C. for 1 h. | Reaction was quenched at −10° C. with a slow addition of 3N HCl (15 mL). | 1-(3,4-dimethoxyphenyl)pentan-1-one (3.45 g); MW: 222.29; Yield: Quantitative; Pale Yellow Oil; $^1$H-NMR (CDCl$_3$, δ): 0.94 (t, 3H, J = 7.0 Hz, CH$_3$), 1.38-1.47 (sextuplet, 2H, J = 7.0 Hz, CH$_2$), 1.58-1.77 (quintuplet, 2H, J = 7.0 Hz, CH$_2$), 2.93 (t, 2H, J = 7.0 Hz, CH$_2$), 3.94 (s, 3H, OMe), 3.95 (s, 3H, OMe), 6.90 (s, 1H, ArH), 7.54 (d, 1H, J = 2.0 Hz, ArH), 7.60 (dd, 1H, J = 8.0 Hz, J = 2.0 Hz, ArH); $^{13}$C-NMR (CDCl$_3$, δ): 13.6, 22.2, 26.8, 37.9, 56.0, 110.3, 120.8, 122.7, 130.4, 149.1, 153.1, 199.3; MS-ESI m/z (% rel. Int.): 207.1 ([MH]$^+$, 100); HPLC: Method A, detection UV 254 nm, RT = 4.63 min, peak area 97%. |

TABLE 1-continued

| Compound | FORMULA | Conditions for Friedel-Crafts Acylation | Work-Up & Purification | Analysis |
|---|---|---|---|---|
| SSA 48054 | cyclohexyl(3,4-dimethoxyphenyl)methanone structure | AlCl₃ (4 g, 30 mmol); CH₂Cl₂ (18 mL); cyclohexane carbonyl chloride (2.07 mL, 15.4 mmol); veratrole (1.85 mL, 15.4 mmol) in CH₂Cl₂ (4 mL); 15 min at −4° C. then 0° C. for 1 h. | Reaction was quenched at −10° C. with a slow addition of 3N HCl (15 mL). | cyclohexyl(3,4-dimethoxyphenyl)methanone (3.95 g); MW: 248.32; Yield: Quantitative; Pale Yellow Oil; ¹H-NMR (CDCl₃, δ): 1.38-1.54 (m, 6H, 3xCH₂), 1.73-1.96 (m, 4H, 2xCH₂), 3.19-3.28 (m, 1H, CH), 3.94 (s, 6H, 2xOMe), 6.88-6.93 (m, 1H, ArH), 7.43 (d, 1H, J = 2.0 Hz, ArH), 7.57 (dd, 1H, J = 8.0 Hz, J = 2.0 Hz, ArH); ¹³C-NMR (CDCl₃, δ): 25.3, 25.9, 28.8, 29.7, 45.2, 56.0, 110.0, 110.7, 122.6, 129.5, 149.1, 153.1, 180.7, 202.5; MS-ESI m/z = 249.2 ([MH]⁺, 100); HPLC: Method A, detection UV 254 nm, RT = 5.88 min, peak area 92%. |
| SSA 48046 | (3,4-dimethoxyphenyl)(phenyl)methanone structure | AlCl₃ (4 g, 30 mmol); CH₂Cl₂ (18 mL); benzoyl chloride (1.78 mL, 15.4 mmol); veratrole (1.85 mL, 15.4 mmol) in CH₂Cl₂ (4 mL); 15 min at −4° C. then 0° C. for 1 h 15. | Reaction was quenched at −10° C. with a slow addition of 3N HCl (15 mL). Chromatography: (SiO₂, cyclohexane:EtOAc = 10:0 to 8:2). | (3,4-dimethoxyphenyl)(phenyl)methanone (932 mg); MW: 242.28; Yield: 27% (EtOAc:cyclohexane = 85:15); 1H-NMR (CDCl₃, δ): 3.95 (s, 3H, OMe), 3.97 (s, 3H, OMe), 6.88 (d, 1H, J = 8.0 Hz, ArH), 7.38 (dd, 1H, J = 8.0, J = 2.0 Hz, ArH), 7.48-7.55 (m, 3H, 3xArH), 7.57-7.59 (m, 1H, ArH), 7.75-7.81 (m, 1H, ArH); ¹³C-NMR (CDCl₃, δ): 56.0, 56.1, 109.8, 112.2, 125.5, 128.2, 128.5, 129.7, 130.2, 130.3, 131.9, 138.3, 149.1, 153.1, 195.6; MS-ESI m/z (% rel. Int.): 243.2 ([MH]⁺, 100); HPLC: Method A, detection UV 254 nm, RT = 5.24 min, peak area 98%. |

| Compound | FORMULA | Conditions for Amination | | Analysis |
|---|---|---|---|---|
| LPO 22100 | (E)-N-(3,4-dimethoxybenzylidene)-2,2-diethoxyethanamine structure | 3,4-dimethoxy-benzaldehyde (10 g, 59.58 mmol); toluene (120 mL); aminoacetaldehyde diethyl acetal (13.5 mL, 90.99 mmol); 150° C. for 4 h. | | (E)-N-(3,4-dimethoxybenzylidene)-2,2-diethoxyethanamine (16.02 g); MW: 281.35; Yield: 100%; Beige Solid; MS-ESI m/z (% rel. Int.): 282.2 ([MH]⁺, 23), 236.2 (100). ¹H-NMR (CDCl₃, δ): 1.21 (t, 3H, J = 7.1 Hz, CH₃), 3.53-3.64 (m, 2H, OCH₂), 3.69-3.92 (m, 2H, OCH₂ & CH₂), 3.80 (s, 3H, OCH₃), 3.92 (s, 3H, OCH₃), 4.79 (t, 1H, J = 5.4 Hz, CH), 6.88 (d, 1H, J = 8.2 Hz, ArH), 7.17 (dd, 1H, J = 8.2 Hz & 1.9 Hz, ArH), 7.42 (d, 1H, J = 1.9 Hz, ArH), 8.20 (s, 1H, CH=N), ¹³C-NMR (CDCl₃, δ): 15.34 (2xC), 55.92 (2xC), 62.36, 62.58, 64.42, 102.25, 108.92, 110.46, 123.12, 129.57, 149.33, 151.42, 162.86. |
| ANP 31058A | (E)-1-(3,4-dimethoxyphenyl)-N-(1,1-dimethoxypropan-2-ylidene)methanamine structure | 3,4-dimethoxy-benzylamine (4 g, 23.20 mmol); toluene (50 mL); pyruvic aldehyde dimethylacetal (4.20 mL, 35.52 mmol); 150° C. for 4 h. | | (E)-1-(3,4-dimethoxyphenyl)-N-(1,1-dimethoxypropan-2-ylidene)methanamine (5.74 g); MW: 267.32; Yield: 92%; Yellow Oil; ¹H-NMR (CDCl₃, δ): 1.93 (s, 3H, CH₃), 4.43 (s, 6H, 2xCH₃), 3.88 (s, 6H, 2xOCH₃), 4.48 (s, 2H, CH₂), 4.54 (s, 1H, CH), 6.84-6.88 (m, 3H, 3xArH). |
| TTA 24128A | (E)-N-(1-(3,4-dimethoxyphenyl)ethylidene)-2,2-diethoxyethanamine structure | 1-(3,4-dimethoxyphenyl)-ethanone (2.0 g, 11.0 mmol); toluene (g, 33.0 mmol); aminoacetaldehyde diethyl acetal (4.4 g, 33.0 mmol); 170° C. for 6 h. | | (E)-N-(1-(3,4-dimethoxyphenyl)ethylidene)-2,2-diethoxyethanamine (3.2 g); MW: 295.37; Yield: quantitative; Brown Oil; ¹H-NMR (CDCl₃, δ): 1.25 (t, 6H, J = 7.1 Hz, 2xCH₃), 2.22 (s, 3H, CH₃), 3.62-3.83 (m, 6H, 2xOCH₂ & NCH₂), 3.91 (s, 3H, OMe), 3.92 (s, 3H, OMe), 4.91 (t, 1H, J = 5.5 Hz, CH), 6.84 (d, 1H, J = 8.4 Hz, ArH), 7.29 (dd, 1H, J = 8.4 Hz, J = 2.0 Hz, ArH), 7.53 (d, 1H, J = 2.00 Hz, ArH). |

TABLE 1-continued

| Compound | FORMULA | Conditions for Friedel-Crafts Acylation | Work-Up & Purification | Analysis |
|---|---|---|---|---|
| SSA 39096 | | TTA 24178A (2.0 g, 10 mmol); toluene (30 mL); aminoacetaldehyde diethyl acetal (4.1 g, 30 mmol); 170° C. for 2 h. | | (E)-N-(1-(3,4-dimethoxyphenyl)propylidene)-2,2-diethoxyethanamine (4.06 g); MW: 309.41; Yield: quantitative; Pale Yellow Oil; $^1$H-NMR (CDCl$_3$, δ): 1.13 (t, 3H, J = 7.0 Hz, CH$_3$), 1.21 (t, 6H, J = 7.4 Hz, 2xCH$_3$), 3.51 (q, 2H, J = 7.2 Hz, CH$_2$), 3.60 (m, 2H, CH$_2$), 3.69 (q, 4H, J = 7.1 Hz, 2xCH$_2$), 3.91 (s, 6H, 2xCH$_3$), 4.92 (t, 1H, J = 5.5 Hz, CH), 6.84 (m, 1H, ArH), 7.28 (m, 1H, ArH), 7.51 (m, 1H, ArH). |
| SSA 39100 | | TTA 24178B (2.1 g, 10 mmol); toluene (30 mL); aminoacetaldehyde diethyl acetal (4.1 g, 30 mmol); 180° C. for 2 h. | | (E)-N-(1-(3,4-dimethoxyphenyl)butylidene)-2,2-diethoxyethanamine (3.63 g); MW: 323.44; Yield: quantitative; Yellow Oil; $^1$H-NMR (CDCl$_3$, δ): 1.00 (t, 3H, J = 7.0 Hz, CH$_3$), 1.21 (m, 6H, 2xCH$_3$), 1.55 (sextuplet, 2H, J = 8.0 Hz, CH$_2$), 3.55 (m, 2H, CH$_2$), 3.68 (m, 4H, 2xCH$_2$), 3.83 (m, 2H, CH$_2$), 3.93 (m, 6H, 2xCH$_3$), 4.90 (t, 1H, J = 6.0 Hz, CH), 6.89 (m, 1H, ArH), 7.28 (m, 1H, ArH), 7.59 (m, 1H, ArH); $^{13}$C-NMR (CDCl$_3$, δ): 13.6, 15.3 (2xC), 15.4, 20.5, 55.6, 55.8 (2xC), 62.3, 62.9, 102.9, 109.7, 110.0, 119.7, 132.9, 148.9, 150.3, 169.1. |
| SSA 48080 | | SSA 48078 (3.12 g, 15.1 mmol); toluene (40 mL); aminoacetaldehyde diethyl acetal (6.60 mL, 45.4 mmol); 170° C. for 4 h. | | (E)-N-(cyclopropyl(3,4-dimethoxyphenyl)methylene)-2,2-diethoxyethanamine (4.52 g); MW: 321.42; Yield: 94%; Brown Oil; $^1$H-NMR (CDCl$_3$, δ): 0.78-0.81 (m, 2H, CH$_2$), 1.00-1.03 (m, 2H, CH$_2$), 1.20 (m, 6H, 2xCH$_3$), 2.61-2.68 (m, 1H, CH), 2.80 (d, 2H, J = 5.1 Hz, CH$_2$), 3.49-3.60 (m, 2H, OCH$_2$), 3.62-3.76 (m, 2H, OCH$_2$), 3.86 (d, 6H, J = 8 Hz, 2xOCH$_3$), 4.75 (t, 1H, J = 5.1 Hz, CH), 6.69 (d, 1H, J = 8.3 Hz, ArH), 6.84-6.93 (m, 2H, 2xArH). |
| SSA 48058 | | SSA 48050 (3.37 g, 15.1 mmol); toluene (45 mL); aminoacetaldehyde diethyl acetal (6.61 mL, 45.4 mmol); 170° C. for 4 h. | | (E)-N-(1-(3,4-dimethoxyphenyl)-3-methylbutylidene)-2,2-diethoxyethanamine (6.59 g); MW: 337.46; Yield: quantitative; Yellow Oil; $^1$H-NMR (CDCl$_3$, δ): 0.90 (d, 6H, J = 6.6 Hz, 2xCH$_3$), 1.17-1.27 (m, 6H, 2xCH$_3$), 1.91-2.05 (m, 1H, CH), 2.61 (d, 2H, J = 7.4 Hz, CH$_2$), 3.49-3.60 (m, 2H, OCH$_2$), 3.63-3.74 (m, 2H, OCH$_2$), 3.76-3.84 (m, 2H, CH$_2$), 3.88 (q, 6H, J = 7.1 Hz, 2xOCH$_3$), 4.90 (t, 1H, J = 5.5 Hz, CH), 6.84-6.91 (m, 2H, 2xArH), 7.49 (d, 1H, J = 2 Hz, ArH). |
| SSA 48092 | | SSA 48090 (3.42 g, 15.4 mmol); toluene (45 mL); aminoacetaldehyde diethyl acetal (6.71 mL, 46.2 mmol); 170° C. for 4 h. | | E)-N-(1-(3,4-dimethoxyphenyl)pentylidene)-2,2-diethoxyethanamine (7.65 g); MW: 337.46; Yield: quantitative; Yellow Oil; $^1$H-NMR (CDCl$_3$, δ): 0.90 (m, 2H, CH$_3$), 1.16-1.27 (m, 9H, 3xCH$_3$), 1.31-1.76 (m, 4H, 2xCH$_2$), 2.79 (d, 2H, J = 5.5 Hz, CH$_2$), 3.41-3.59 (m, 2H, OCH$_2$), 3.60-3.75 (m, 2H, OCH$_2$), 3.68-3.95 (m, 6H, 2xOCH$_3$), 4.93 (t, 1H, J = 5.4 Hz, CH), 6.69-6.90 (m, 3H, 3xArH). |
| SSA 48064 | | SSA 48054 (3.95 g, 15.9 mmol); toluene (50 mL; aminoacetaldehyde diethyl acetal (6.94 mL, 47.7 mmol); 170° C. for 4 h. | | (E)-N-(cyclohexyl(3,4-dimethoxyphenyl)methylene)-2,2-diethoxyethanamine (7.08 g); MW: 363.50; Yield: quantitative; $^1$H-NMR (CDCl$_3$, δ): 1.21 (m, 6H, 2xCH$_3$), 1.28-1.84 (m, 10H, 5xCH$_2$), 2.40-2.51 (m, 1H, CH), 3.36 (d, 2H, J = 5.5 Hz, CH$_2$), 3.49-3.60 (m, 2H, OCH$_2$), 3.62-3.76 (m, 2H, OCH$_2$), 3.86 (s, 6H, OCH$_3$), 3.88 (s, 6H, OCH$_3$), 4.80 (t, 1H, J = 5.6 Hz, CH), 6.62-6.91 (m, 3H, 3xArH). |

TABLE 1-continued

| Compound | FORMULA | Conditions for Friedel-Crafts Acylation | Work-Up & Purification | Analysis |
|---|---|---|---|---|
| SSA 48052 | (structure) | SSA 48046 (932 mg, 3.85 mmol); toluene (12 mL); aminoacetaldehyde diethyl acetal (1.68 mL, 11.55 mmol); 170° C. for 4 h. | | (E)-N-((3,4-dimethoxyphenyl)(phenyl)methylene)-2,2-diethoxyethanamine (1.56 g); MW: 357.45; Yield: quantitative; Yellow Oil; $^1$H-NMR (CDCl$_3$, δ): 1.21 (m, 6H, 2xCH$_3$), 3.52-3.74 (m, 6H, CH$_2$ & 2xOCH$_2$), 3.88 (q, 6H, J = 7.1 Hz, OCH$_3$), 4.91 (t, J = 5.0 Hz, 1H, CH), 6.68-6.74 (m, 2H, ArH), 7.16 (dd, 1H, J = 7.8 & J = 2.2 Hz, ArH), 7.34-7.44 (m, 3H, 3xArH), 7.56 (d, 1H, J = 2.0 Hz, ArH), 7.62 (dd, 1H, J = 7.0 & J = 2.0 Hz, ArH). |
| ECO 33094 | (structure) | 3,4-diethoxybenzaehyde (4.11 g, 30.9 mmol); toluene (45 mL); aminoacetaldehyde diethylacetal (4.37 mL, 20.6 mmol); 150° C. for 4 h. | | (E)-N-(3,4-diethoxybenzylidene)-2,2-diethoxyethanamine (6.31 g); MW: 311.42; Yield: 98%; Brown Oil; $^1$H-NMR (CDCl$_3$, δ) : 1.22 (t, 6H, J = 7.0 Hz, 2xCH$_3$), 1.49 (t, 6H, J = 19.0 Hz, 2xCH$_3$), 2.75 (d, 2H J = 5.6 Hz, CH$_2$CH), 3.48-3.78 (m, 4H, 2xCH$_2$O), 3.75 (s, 2H, CH$_2$N), 4.13 (q, 4H, J = 14 Hz & J = 7.0 Hz, 2xCH$_2$O), 4.65 (t, 1H, J = 5.4 Hz, CH(OEt)$_2$), 6.76-6.95 (m, 3H, 3xArH), 8.2 (s, 1H, CH=N); MS-ESI m/z (% rel. Int.): 312.4 ([MH]$^{+1}$, 15), 220.3 (55), 179.2 (100); HPLC: Method A, detection UV 254 nm, RT = 4.29 min, peak area 98%. |
| ECO 33114 | (structure) | 4-(benzyloxy)-3-methoxybenzaldehyde (5.00 g, 20.6 mmol); toluene (100 mL); aminoacetaldehyde diethylacetal (4.50 mL, 31.0 mmol); 150° C. for 4 h. | | (E)-N-(4-(benzyloxy)-3-methoxybenzylidene)-2,2-diethoxyethanamine (7.94 g); MW: 357.45; Yield: quantitative; Brown Oil; $^1$H-NMR (CDCl$_3$, δ): 1.22 (t, 6H, J = 7.0 Hz, 2xCH$_3$), 3.52-3.63 (m, 2H, CH$_2$N), 3.67-3.78 (m, 4H, 2xCH$_2$O), 3.94 (d, 3H J = 2.3 Hz, CH$_3$O), 4.76-4.80 (m, 1H, CH(OEt)$_2$), 5.20 (s, 2H, ArCH$_2$O), 6.86-6.90 (m, 1H, ArH), 7.07-7.11 (m, 1H, ArH), 7.25-7.44 (m, 6H, 6xArH), 8.17 (s, 1H, CH=N). |
| ECO 33122 | (structure) | 4-ethoxy-3-methoxybenzaldehyde (5.00 g, 27.7 mmol); toluene (100 mL); aminoacetaldehyde diethylacetal (6.00 mL, 41.6 mmol); 150° C. for 4 h. | | (E)-N-(3-(benzyloxy)-4-methoxybenzylidene)-2,2-diethoxyethanamine (8.19 g); MW: 357.45; Yield: quantitative; Brown Oil; MS-ESI m/z (% rel. Int.): 358.3 ([MH]$^{+1}$, 52), 312.2 (100). HPLC: Method A, detection UV 254 nm, RT = 5.30 min. |
| ECO 33134 | (structure) | 4-ethoxy-3-methoxybenzaldehyde (5.00 g, 27.7 mmol); toluene (100 mL); aminoacetaldehyde diethylacetal (6.00 mL, 41.6 mmol); 150° C. for 4 h. | | (E)-2,2-diethoxy-N-(4-ethoxy-3-methoxybenzylidene)ethanamine (10.23 g); MW: 295.38; Yield: quantitative; Pale Yellow Oil; $^1$H-NMR (CDCl$_3$, δ): 1.18-1.25 (m, 6H, 2xCH$_3$), 1.47-1.51 (m, 3H, CH$_3$), 3.52-3.77 (m, 6H, 3xCH$_2$O), 3.93 (s, 3H, CH$_3$O), 4.14 (q, 2H, J = 7.0 Hz, CH$_2$N), 4.80 (t, 1H, J = 5.6 Hz, CHO), 6.86-6.89 (m, 1H, ArH), 7.13-7.16 (m, 1H, ArH), 7.42 (m, 1H, ArH), 8.19 (s, 1H, CH=N). |
| TTA 24150A | (structure) | 2,3-dihydrobenzo[b][1,4]dioxine-6-carbaldehyde (3.00 g, 18.3 mmol); toluene (80 mL); aminoacetaldehyde diethyl acetal (3.65 g, 27.4 mmol); 170° C. for 4 h | | (E)-N-((2,3-dihydrobenzo[b][1,4]dioxin-6-yl)methylene)-2,2-diethoxyethanamine (5.10 g); MW: 279.33; Yield: quantitative; Pale Yellow Oil; $^1$H-NMR (CDCl$_3$, δ): 1.20 (t, 6H, J = 7.0 Hz, 2xCH$_3$), 3.55-3.63 (m, 2H, CH$_2$N), 3.68-3.74 (m, 4H, 2xCH$_2$O), 4.25-4.30 (m, 4H, 2xCH$_2$O), 4.77 (t, 1H, J = 5.4 Hz, CH(OEt)$_2$), 6.88, (d, 1H, J = 8.3 Hz, ArH), 7.22 (dd, 1H, J = 8.3 Hz, J = 2.0 Hz, ArH), 7.28 (d, 1H, J = 2.0 Hz, ArH), 8.15 (s, 1H, CH=N); $^{13}$C-NMR (CDCl$_3$, δ): 15.4, (2xC), 62.7 (2xC), 64.2, 64.5 (2xC), 102.3, 116.8, 117.3, 121.9, 130.2, 143.7, 145.9, 162.5. |

TABLE 1-continued

| Compound | FORMULA | Conditions for Friedel-Crafts Acylation | Work-Up & Purification | Analysis |
|---|---|---|---|---|
| TTA 24156A |  | TTA 24152B (885 mg, 5.9 mmol); toluene (35 mL); aminoacetaldehyde diethyl acetal (1.18 g, 8.8 mmol); 170° C. for 4 h. | | (E)-N-(Benzo[d][1,3]dioxol-5-ylmethylene)-2,2-diethoxyethanamine (1.55 g); MW: 265.30; Yield: 99%; Pale Yellow Oil; $^1$H-NMR (CDCl$_3$, δ): 1.18-1.25 (m, 6H, 2xCH$_2$CH$_3$), 3.53-3.63 (m, 2H, CH$_2$N), 3.68-3.78 (m, 4H, 2xCH$_2$O), 4.77 (t, 1H, J = 5.4 Hz, CH(OEt)$_2$), 6.00 (s, 2H, OCH$_2$O), 6.81-6.86 (m, 1H, ArH), 7.10-7.15 (m, 1H, ArH), 7.35-7.37 (m, 1H, ArH), 8.17 (s, 1H, CH=N); $^{13}$C-NMR (CDCl$_3$, δ): 15.3 (2xC), 62.7 (2xC), 64.3, 101.4, 102.2, 106.6, 108.0, 124.4, 131.1, 148.2, 149.9, 162.4. |
| TTA 46082A | 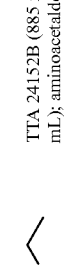 | In Dean-Stark apparatus: 1-(3,4-dimethoxyphenyl)-2-methoxyethanone (1.92 g, 9.13 mmol); toluene (50 mL); aminoacetaldehyde diethyl acetal (3.70 g, 24.70 mmol); 150° C. for 6 h. | | E)-N-(1-(3,4-dimethoxyphenyl)-2-methoxyethylidene)-2,2-diethoxyethanamine (3.00 g); MW: 325.40; Yield: 98%; Brown Oil ; $^1$H-NMR (CDCl$_3$, δ): 1.17-1.26 (m, 6H, CH$_3$); 2.90-2.92 (m, 4H, 2xCH$_2$); 3.36-4.91 (m, 14H, NCH$_2$, CH(OEt$_2$), OCH$_2$, 3xOCH$_3$); 6.93-6.95 (m, 1H, ArH), 7.35 (dd, 1H, J = 8.4 Hz & 2.0 Hz, ArH), 7.48 (d, 1H, J = 1.9 Hz, ArH) |

TABLE 2

| COM-POUND | FORMULA | Conditions for Reduction | Analysis |
|---|---|---|---|
| LPO 22102 | (structure) | LPO 22100 (16.02 g, 56.93 mmol); EtOH (100 mL); NaBH4 (4.30 g, 113.88 mmol); RT for 0.5 h then 100° C. for 1 h. | N-(3,4-dimethoxybenzyl)-2,2-diethoxyethanamine (14.0 g); MW: 283.37; Yield: 87%; Yellow Oil; $^1$H-NMR (CDCl$_3$, δ): 1.17-1.25 (t, 6H, 2xCH$_3$), 1.57 (s, 1H, NH), 2.75 (d, 2H, J = 5.6 Hz, ArCH$_2$N), 3.48-3.58 (m, 2H, CH$_2$), 3.64-3.74 (m; 2H, CH$_2$), 3.75 (s, 2H, CH$_2$), 3.86 (s, 3H, OCH$_3$), 3.88 (s, 3H, OCH$_3$), 4.61-4.64 (m, 1H, CH); 6.80-6.89 (m, 3H, 3xArH); MS-ESI m/z (% rel. Int.): 284.3 ([MH]$^+$, 23), 151.1 (100); HPLC: Method A, detection UV 254 nm, RT = 3.9 min, peak area 99.9%. |
| ANP 31060A | (structure) | ANP 31058A (5.74 g, 21.47 mmol); EtOH (35 mL); NaBH4 (1.62 g, 42.94 mmol) RT for 0.5 h then 100° C. for 1 h. | N-(3,4-dimethoxybenzyl)-1,1-dimethoxypropan-2-amine; MW: 269.34; Yield: 84%; Yellow Oil; $^1$H-NMR (CDCl$_3$, δ): 1.10 (d, 3H, J = 6.4 Hz, CH$_3$), 2.81-2.86 (m, 1H, NCH), 3.36 (s, 3H, CH$_3$), 3.39 (s, 3H, CH$_3$), 3.64 (d, 1H, J = 12.9 Hz, NCH$_2$); 3.86 (d, 1H, J = 16.8 Hz, NCH$_2$); 3.87 (s, 3H, CH$_3$); 3.89 (s, 3H, CH$_3$); 4.14 (d, 1H, J = 6.3 Hz, OCH), 6.83-6.88 (m, 3H, 3xArH). |
| TTA 24128B | (structure) | TTA 24128A (3.2 g, 11.0 mmol); EtOH (35 mL); NaBH$_4$ (0.79 g, 20.9 mmol); RT for 0.5 h then 100° C. for 1 h. | N-(1-(3,4-dimethoxyphenyl)ethyl)-2,2-diethoxyethanamine (2.9 g); MW: 297.39; Yield: 90%; Brown Oil; $^1$H-NMR (CDCl$_3$, δ): 1.16-1.24 (m, 6H, 2xCH$_3$), 1.35 (d, 3H, J = 6.5 Hz, CH$_3$), 2.52-2.67 (m, 2H, NCH$_2$), 3.46-3.75 (m, 5H, 2xOCH2 & NCH), 3.89 (s, 3H, OMe), 3.92 (s, 3H, OMe), 4.56 (t, 1H, J = 5.5 Hz, OCH), 6.83 (m, 2H, 2xArH), 6.89 (d, 1H, J = 1.0 Hz, ArH). MS-ESI m/z (% rel. Int.): 298.3 ([MH]$^+$, 20), 165.1 (100). |
| SSA 39098 | (structure) | SSA 39096 (4.06 g, 10 mmol); EtOH (35 mL); NaBH$_4$ (0.72 g, 19 mmol); RT for 0.5 h then 100° C. for 1 h. | N-(2,2-diethoxyethyl)-1-(3,4-dimethoxyphenyl)propan-1-amine (3.5 g); MW: 311.42; Yield: 87%; Pale Yellow Oil; $^1$H-NMR (CDCl$_3$, δ): 0.78 (t, 3H, J = 7.5 Hz CH$_3$), 1.11-1.22 (m, 6H, 2xCH$_3$), 1.52-1.76 (m, 2H, CH$_2$), 2.53 (t, 1H, J = 6.0 Hz, CH), 3.35-3.70 (m, 4H, 2xCH$_2$), 3.83 (s, 3H, OCH$_3$), 3.85 (s, 3H, OCH$_3$), 4.52 (t, 1H, J = 5.4 Hz, CH), 6.77 (s, 2H, 2xArH), 6.83 (s, 1H, ArH); $^{13}$C-NMR (CDCl$_3$, δ): 10.7, 15.3, 31.0, 44.6, 49.8, 55.7, 61.7, 62.2, 64.7, 102.0, 103.9, 109.8, 110.7, 119.7, 136.5, 147.8, 149.0; MS-ESI m/z (% rel. Int.): 312 ([MH]$^+$, 10), 220 (10), 179.1 (100); HPLC: Method A, detection UV 254 nm, RT = 3.82 min, peak area 99.9%. |

TABLE 2-continued

| COMPOUND | FORMULA | Conditions for Reduction | Analysis |
|---|---|---|---|
| SSA 39102 | (structure) | SSA 39100 (3.63 g, 10 mmol); EtOH (35 mL); NaBH$_4$ (0.72 g, 19 mmol); RT for 0.5 h then 100° C. for 1 h. | N-(2,2-diethoxyethyl)-1-(3,4-dimethoxyphenyl)butan-1-amine (3.62 g); MW: 325.45; Yield: Quantitative; Yellow Oil; $^1$H-NMR (CDCl$_3$, δ): 0.86 (m, 3H, CH$_3$), 1.21 (m, 6H, 2xCH$_3$), 1.67-1.56 (m, 2H, CH$_2$), 2.52 (t, 1H, J = 5.0 Hz, CH), 3.51-3.43 (m, 4H, 2xCH$_2$), 3.69-3.56 (m, 2H, CH$_2$), 3.89 (m, 6H, 2xCH$_3$), 4.54 (t, 1H, J = 5.0 Hz, CH), 6.78 (d, 2H, 2xArH), 6.85 (s, 1H, ArH); $^{13}$C-NMR (CDCl$_3$, δ): 13.9, 15.2 (2xC), 19.4, 40.5, 49.7, 55.7 (2xC), 61.7, 62.2, 62.8, 102.0, 109.7, 110.7, 119.6, 136.8, 147.8, 149.0; MS-ESI m/z (% rel. Int.): 326.2 ([MH]$^+$, 8), 194.1 (20), 193.1 (100); HPLC: Method A, detection UV 254 nm, RT = 4.02 min, peak area 99.9%. |
| SSA 48084 | (structure) | SSA 48080 (4.51 g, 14 mmol); EtOH (25 mL); NaBH$_4$ (0.80 g, 21.1 mmol); RT for 0.5 h then 100° C. for 1 h. | N-(cyclopropyl(3,4-dimethoxyphenyl)methyl)-2,2-diethoxyethanamine (4.13 g); MW: 323.44; Yield: 91%; Yellow Oil; $^1$H-NMR (CDCl$_3$, δ): 0.34-0.63 (m, 4H, 2xCH$_2$), 1.15-1.24 (m, 6H, 2xCH$_3$), 2.51-2.68 (m, 1H, CH), 2.77 (d, 2H, J = 5.0 Hz, CH$_2$), 3.43-3.54 (m, 2H, CH$_2$), 3.56-3.69 (m, 2H, CH$_2$), 3.87 (m, 6H, 2xOMe), 3.95 (d, 1H, J = 8.0 Hz, CH), 4.41 (t, 1H, J = 6.0 Hz, CH), 6.82-7.00 (m, 3H, 3xArH); $^{13}$C-NMR (CDCl$_3$, δ): 2.8, 4.9, 15.4, 19.1, 49.9, 55.8, 62.2, 62.9, 68.3, 102.1, 110.1, 110.9, 120.5, 136.6, 149.0; MS-ESI m/z (% rel. Int.): 324.4 ([MH]$^+$, 8), 191.2 (100). |
| SSA 48066 | (structure) | SSA 48058 (6.58 g, 19.5 mmol); EtOH (40 mL); NaBH$_4$ (1.40 g, 37.0 mmol); RT for 0.5 h then 100° C. for 1 h. | N-(2,2-diethoxyethyl)-1-(3,4-dimethoxyphenyl)-3-methylbutan-1-amine (4.24 g); MW: 339.48; Yield: Quantitative; Yellow Oil; $^1$H-NMR (CDCl$_3$, δ): 0.85 (d, 3H, J = 6.0 Hz, CH$_3$), 0.91 (d, 3H, J = 6.0 Hz, CH$_3$), 1.14-1.23 (m, 6H, 2xCH$_3$), 1.46-1.50 (m, 1H, CH), 1.52-1.57 (m, 2H, CH$_2$), 2.74 (t, 2H, J = 4.0 Hz, CH$_2$), 3.43-3.48 (m, 2H, CH$_2$), 3.50-3.54 (m, 1H, CH), 3.62-3.69 (m, 2H, CH$_2$), 3.84 (s, 3H, OMe), 3.86 (s, 3H, OMe), 4.53 (t, 1H, J = 6.0 Hz, CH), 6.80-6.89 (m, 3H, 3xArH); $^{13}$C-NMR (CDCl$_3$, δ): 15.3, 22.3, 22.5, 24.8, 47.6, 49.7, 55.7, 60.9, 61.6, 62.2, 102.0, 109.1, 110.9, 119.6, 137.0, 149.1; MS-ESI m/z (% rel. Int.): 340.3 ([M + H]$^+$, 14), 207.2 (100). |
| SSA 48100 | (structure) | SSA 48092 (7.65 g, 22.7 mmol); EtOH (40 mL); NaBH$_4$ (1.29 g, 34 mmol); RT for 0.5 h then 100° C. for 1 h. | N-(2,2-diethoxyethyl)-1-(3,4-dimethoxyphenyl)pentan-1-amine (5.33 g); MW: 339.48; Yield: 69%; Yellow Oil; $^1$H-NMR (CDCl$_3$, δ): 0.84 (t, 2H, J = 7.0 Hz, CH$_3$), 1.15-1.27 (m, 9H, 3xCH$_2$), 1.51-1.74 (m, 4H, 2xCH$_2$), 2.55 (t, 2H, J = 5.4 Hz, CH$_2$), 3.41-3.59 (m, 3H, CH & OCH$_2$), 3.60-3.75 (m, 2H, OCH$_2$), 3.86 (s, 3H, OMe), 3.88 (s, 3H, OMe), 4.55 (t, 1H, J = 5.4 Hz, CH), 6.79-6.92 (m, 3H, 3xArH); $^{13}$C-NMR (CDCl$_3$, δ): 14.0, 15.4, 22.7, 28.6, 38.1, 44.7, 49.9, 55.9, 61.8, 62.3, 63.2, 102.2, 109.9, 110.9, 119.7, 147.9; MS-ESI m/z (% rel. Int.): 340.4 ([MH]$^+$, 10), 207.2 (100). |

TABLE 2-continued

| COMPOUND | FORMULA | Conditions for Reduction | Analysis |
|---|---|---|---|
| SSA 48072 | (structure) | SSA 48064 (7.08 g, 19.5 mmol); EtOH (40 mL); NaBH$_4$ (1.40 g, 37 mmol); RT for 0.5 h then 100° C. for 1 h. | N-(cyclohexyl(3,4-dimethoxyphenyl)methyl)-2,2-diethoxyethanamine (4.76 g); MW: 365.52; Yield: 68%; Yellow oil; $^1$H-NMR (CDCl$_3$, δ): 0.72-1.03 (m, 2H, CH$_2$), 1.07-1.24 (m, 8H, 2xCH$_3$ & CH$_2$), 1.31-1.40 (m, 2H, CH$_2$), 1.42-1.56 (m, 1H, CH), 1.60-1.93 (m, 4H, 2xCH$_2$), 2.48 (d, 2H, J = 5.0 Hz, CH$_2$), 3.23 (d, 1H, J = 8.0 Hz, CH), 3.43-3.54 (m, 2H, CH$_2$), 3.56-3.69 (m, 2H, CH$_2$), 3.86 (s, 3H, OCH$_3$), 3.88 (s, 3H, OCH$_3$), 4.53 (t, 1H, J = 6.0 Hz, CH), 6.74-6.90 (m, 3H, 3xArH); $^{13}$C-NMR (CDCl$_3$, δ): 15.4, 26.3, 26.5, 29.9, 30.3, 44.3, 50.0, 55.8, 62.2, 62.9, 63.6, 102.1, 110.6, 110.7, 120.5, 135.6, 148.9; MS-ESI m/z (% rel. Int.): 366.3 ([MH]$^+$, 20), 233.2 (100). |
| SSA 48060 | (structure) | SSA 48052 (1.56 g, 4.36 mmol); EtOH (9 mL); NaBH$_4$ (414 mg, 10.93 mmol); RT for 0.5 h then 100° C. for 1 h. | N-((3,4-dimethoxyphenyl)(phenyl)methyl)-2,2-diethoxyethanamine (1.20 g); MW: 359.47; Yield: 76%; Green Oil; $^1$H-NMR (CDCl$_3$, δ): 1.21 (t, 6H, J = 7.0 Hz, 2xCH$_2$CH$_3$), 2.74 (d, 2H, J = 6.0 Hz, CH$_2$), 3.47-3.57 (m, 2H, CH$_2$), 3.62-3.72 (m, 2H, CH$_2$), 3.84 (d, 6H, J = 2.0 Hz, 2xOMe), 4.65 (t, 1H, J = 6.0 Hz, CH), 4.78 (s, 1H, CH), 6.78 (d, 1H, J = 8.0 Hz, ArH), 6.90-6.95 (m, 2H, 2xArH), 7.18-7.23 (m, 1H, ArH), 7.27-7.33 (m, 2H, 2xArH), 7.40 (d, 2H, J = 7.0 Hz, 2xArH); $^{13}$C-NMR (CDCl$_3$, δ): 15.4, 50.4, 55.9, 62.2, 66.9, 90.1, 102.1, 110.5, 111.1, 119.5, 127.0, 127.2, 128.4, 140.2, 149.1; MS-ESI m/z (% rel. Int.): 360.3 ([MH]$^+$, 4), 227.2 (100); HPLC: Method A, detection UV 254 nm, RT = 4.13 min, peak area 92%. |
| ECO 33100 | (structure) | ECO 33094 (6.74 g, 20.6 mmol); EtOH (50 mL); NaBH$_4$ (1.47 g, 39.1 mmol); RT for 0.5 h then 100° C. for 1 h. | N-(3,4-diethoxybenzyl)-2,2-diethoxyethanamine (6.31 g); MW: 311.42; Yield: 98% ; Brown Oil; $^1$H-NMR (CDCl$_3$, δ): 1.22 (t, 6H, J = 7.0 Hz, 2xCH$_2$CH$_3$), 1.49 (t, 6H, J = 19 Hz, CH$_3$CH$_2$O), 2.75 (d, 2H J = 5.6 Hz, CH$_3$CH), 3.48-3.78 (m, 4H, 2xCH$_3$CH$_2$O), 3.75 (s, 2H, CH$_2$N), 4.13 (q, 4H, J = 14 Hz, J = 7.0 Hz, CH$_3$CH$_2$O), 4.65 (t, 1H, J = 5.4 Hz, CH(OEt)$_2$), 6.76-6.95 (m, 3H, 3xArH); MS-ESI m/z (% rel. Int.): 312.4 ([MH]$^+$, 15), 220.3 (55), 179.2 (100); HPLC: Method A, detection UV 254 nm, RT = 4.29 min, peak area 98%. |
| ECO 33118 | (structure) | ECO 33114 (9.60 g, 20.6 mmol); EtOH (60 mL); NaBH$_4$ (1.48 g, 31.9 mmol); RT for 0.5 h then 100° C. for 1 h. | N-(4-(benzyloxy)-3-methoxybenzyl)-2,2-diethoxyethanamine (6.75 g); MW: 359.47; Yield: 91%, Yellow Oil; $^1$H-NMR (CDCl$_3$, δ): 1.20 (m, 6H, 2xCH$_2$CH$_3$), 2.74 (d, 2H J = 5.5 Hz, NCH$_2$), 3.52-3.60 (m, 4H, 2xCH$_2$O), 3.74 (s, 2H, PhCH$_2$O), 3.89 (s, 3H, OMe), 4.00 (s, 2H, CH$_2$N), 4.08 (m, 2H, CH$_2$N), 4.61 (t, 1H, J = 5.6 Hz, CHO), 5.14 (s, 2H, CH$_2$O), 6.75-6.91 (m, 3H, 3xArH) 7.25-7.36 (m, 5H, 5xArH); MS-ESI m/z (% rel. Int.): 360.3 ([MH]$^+$, 30%; 268.2 (100%); HPLC: Method A, detection UV 254 nm, RT = 5.04 min, peak area 99.9%. |

TABLE 2-continued

| COMPOUND | FORMULA | Conditions for Reduction | Analysis |
|---|---|---|---|
| ECO 33124 | (structure) | ECO 33122 (8.19 g, 22.9 mmol); EtOH (60 mL); NaBH₄ (1.65 g, 43.5 mmol); RT for 1 h then 100° C. for 1 h. | N-(3-(benzyloxy)-4-methoxybenzyl)-2,2-diethoxyethanamine (6.78 g); MW: 359.47; Yield: 82%; Yellow Oil; ¹H-NMR (CDCl₃, δ): 1.20 (t, 6H J = 7.0 Hz, 2xCH₂CH₃), 2.71 (d, 2H J = 5.5 Hz, NCH₂), 3.49-3.70 (m, 6H, 2xCH₂O & CH₂N), 3.88 (s, 3H, OMe), 4.61 (t, 1H, J = 5.6 Hz CHO), 5.15 (s, 2H, PhCH₂O), 6.85-6.92 (m, 3H, 3xArH), 7.29-7.46 (m, 5H, 5xArH); MS-ESI m/z (% rel. Int.): 360.3 ([MH]⁺, 46), 227.2 (100); HPLC: Method A, detection UV 254 nm, RT = 5.17 min, peak area 99.9%. |
| ECO 33138 | (structure) | ECO 33134 (8.50 g, 28.7 mmol); EtOH (60 mL); NaBH₄ (2.07 g, 54.61 mmol) RT for 0.5 h then 100° C. for 1 h. | 2,2-diethoxy-N-(4-ethoxy-3-methoxybenzyl)ethanamine (7.08 g); MW: 297.40; Yield: 82%; Yellow Oil; ¹H-NMR (CDCl₃, δ): 1.18 (m, 6H, 2xCH₂CH₃), 1.45 (m, 3H, CH₃CH₂O), 2.75 (d, 2H J = 5.5 Hz, NCH₂), 3.48-3.71 (m, 4H, 2xCH₂O), 3.75 (s, 2H, CH₂N), 3.90 (s, 3H, OMe), 4.09 (q, 2H, J = 7 Hz, CH₂O), 4.61 (t, 1H, J = 5.6 Hz, CHO), 6.81 (s, 1H, ArH), 6.89 (s, 1H, ArH); MS-ESI m/z (% rel. Int.): 298.3 ([MH]⁺, 60%), 165.2 (100%); HPLC: Method A, detection UV 254 nm, RT = 4.47 min, peak area 99.9%. |
| TTA 24150B | (structure) | TTA 24150A (5.1 g, 18.3 mmol); EtOH (60 mL); NaBH₄ (1.31 g, 34.8 mmol) RT for 0.5 h then 100° C. for 1 h. | N-((2,3-dihydrobenzo[b][1,4]dioxin-6-yl)methyl)-2,2-diethoxyethanamine (4.9 g); MW: 281.35; Yield: 95%; Yellow Oil; ¹H-NMR (CDCl₃, δ): 1.20 (t, 6H, J = 7.1 Hz, 2xCH₂CH₃), 1.53 (s, 1H, NH), 2.73 (d, 2H, J = 5.6 Hz, NCH₂), 3.48-3.58 (m, 2H, CH₂O), 3.63-3.73 (m, 4H, CH₂O & CH₂N), 4.24 (s, 4H, OCH₂), 4.61 (t, 1H, J = 5.6 Hz, CH(OEt)₂), 6.76-6.83 (m, 3H, 3xArH); ¹³C-NMR (CDCl₃, δ): 15.4 (2xC), 51.5, 53.3, 62.3 (2xC), 64.3 (2xC) 102.2, 116.9, 117.0, 121.1, 133.6, 142.5, 143.4; MS-ESI m/z (% rel. Int.): 282.2 ([MH]⁺, 20), 190.1 (100); HPLC: Method A, detection UV 254 nm, RT = 3.64 min, peak area 96%. |
| TTA 24156B | (structure) | TTA 24156A (1.55 g, 5.8 mmol); EtOH (30 mL); NaBH₄ (440 mg, 11.7 mmol); RT for 0.5 h then 100° C. for 1 h | N-(benzo[d][1,3]dioxol-5-ylmethyl)-2,2-diethoxyethanamine (1.33 g); MW: 267.32; Yield: 86%; Pale Yellow Oil; ¹H-NMR (CDCl₃, δ): 1.21 (t, 6H, J = 7.1 Hz, 2xCH₂CH₃), 1.56 (s, 1H, NH), 2.72 (d, 2H, J = 5.6 Hz, NCH₂), 3.48-3.58 (m, 2H, CH₂O), 3.64-3.74 (m, 4H, CH₂O & CH₂N), 4.60 (t, 1H, J = 5.6 Hz, CH(OEt)₂), 5.93 (s, 2H, OCH₂O), 6.75-6.83 (m, 3H, 3xArH); ¹³C-NMR (CDCl₃, δ): 15.4 (2xC), 51.4, 53.6, 62.3 (2xC), 100.8, 102.2, 108.6, 121.2, 134.3, 146.5, 147.7; MS-ESI m/z (% rel. Int.): 268.2 ([MH]⁺, 10), 176.1 (100); HPLC: Method A, detection UV 254 nm, RT = 3.65 min, peak area 96%. |
| TTA 46082B | (structure) | TTA 46082A (3.00 g, 9.13 mmol); EtOH (70 mL); NaBH₄ (691 mg, 18.20 mmol); 100° C. for 1 h. | N-(2,2-diethoxyethyl)-1-(3,4-dimethoxyphenyl)-2-methoxyethanamine (2.90 g); MW: 327.42; Yield: 97%; Brown Oil; ¹H-NMR CDCl₃, δ): 1.17-1.26 (m, 6H, (2xCH₃), 2.90-2.92 (m, 4H, 2xCH₂), 3.36-4.91 (m, 14H, NCH₂, CH(OEt₂), OCH₃, 3xOCH₃); 6.93-6.95 (m, 1H, ArH), 7.35 (dd, 1H, J = 8.4 Hz & 2.0 Hz, ArH), 7.48 (d, 1H, J = 1.9 Hz, ArH). MS-ESI m/z (% rel. Int.): 328.2 ([MH]⁺¹, 100); HPLC: Method A, detection UV 254 nm, RT = 3.81 min, peak area 88.2%. |

Preparation of Compounds 1-169

General Procedure A for Preparation of Compounds 1-20, 22, 25, 26, 28-31, 33, 34, 36-40, 43-45, 47-54, 57-72, 74, 78-83, 95, 102-105, 109, 110, 117, 119, 123, 124, 131, 132, 137, 143, 155, 161-163, 168, 169 and Compounds SSA 48042, LPO 55070B, ANP 491748, ANP 53134 and ANP 53006A A solution of 37% aqueous HCl was added to a mixture of the corresponding aromatic aldehyde (or masked aldehyde) and aminoacetaldehyde diethyl acetal (in absolute EtOH (see conditions in tables 3 and 7). The reaction mixture was stirred in an ace pressure tube (Aldrich) according to the conditions described in tables 3 and 7. The reaction mixture was immediately cooled at 4° C. and concentrated to dryness under reduced pressure. EtOAc (typically 200 mL) was added to the residue and this mixture was poured into a 1 M aqueous $K_2CO_3$ solution (typically 50 mL). The separated organic layer was washed with brine (typically 20 mL), dried over $MgSO_4$, filtered and evaporated to give a residue. This residue was purified by column chromatography ($SiO_2$, see exact conditions in tables 3 and 7). After evaporation, if the hydrochloride salt was needed, the obtained free base (1 eq.) was dissolved in MeOH (2 mL) and a 1.75 N HCl solution in MeOH (2.1 eq.×number of basic nitrogen) was added (see conditions in tables 3 and 7). The desired isoquinoline, either as a free base or a hydrochloride salt, was obtained after further drying under vacuum.

TABLE 3

| Compound | FORMULA | General Procedure and Conditions | Work-Up & Purification | Analysis |
|---|---|---|---|---|
| SSA 48042 | (structure: 6-methoxy-2-hydroxyquinoline linked via CH₂ to 6,7-dimethoxyisoquinoline) | A LPO 22102 (1.26 g, 4.44 mmol); SSA 48036 (1.06 g, 4.44 mmol); 37% aqueous HCl (3.6 mL); EtOH (3.6 mL); 95° C. for 25 min. | Chromatography SiO₂, CH₂Cl₂:MeOH = 100:0 to 96:4 | 3-((6,7-dimethoxyisoquinolin-4-yl)methyl)-6-methoxyquinolin-2-ol (566 mg); MW: 376.42; Yield: 34%; Pale Yellow Solid; Mp (° C.): 243.7; R$_f$: 0.20 (CH₂Cl₂:MeOH = 96:4); ¹H-NMR (DMSO-d₆): 3.71 (s, 3H, OCH₃), 3.97 (s, 3H, OCH₃), 4.04 (s, 3H, OCH₃), 5.39 (s, 3H, OCH₃), 4.40 (s, 2H, CH₂), 7.06-7.12 (m, 2H, 2xArH), 7.26 (d, 1H, ArH, J = 8.8 Hz), 7.73 (d, 2H, 2xArH, J = 13.41 Hz), 7.92 (s, 1H, ArH), 8.47 (s, 1H, ArH), 9.44 (s, 1H, ArH), 11.93 (s, 1H, OH); MS-ESI m/z (% rel. Int.): 377.4 ([MH]⁺, 100); HPLC: Method A, detection UV 254 nm, RT = 3.70 min, peak area 98.7%. |
| LPO 55070B | (structure: quinoline with OCH₂COOEt linked via CH₂ to isoquinoline with two OMe) | A LPO 22102 (996 mg, 3.51 mmol); LPO 55070A (969 mg, 3.19 mmol); 37% aqueous HCl (6 mL); EtOH (6 mL); 90° C. for 30 min then evaporation; dry HCl (1.0 g, 27.4 mmol); EtOH (10 mL); 90° C. for 20 min. | Chromatography SiO₂, CH₂Cl₂:MeOH = 100:0 to 98:2 | ethyl 2-(3-((6,7-dimethoxyisoquinolin-4-yl)methyl)quinolin-6-yl)oxy)acetate (120 mg); MW: 432.47; Yield: 8%; Yellow Solid; ¹H-NMR (CDCl₃, δ): 1.27 (t, 3H, J = 7.1 Hz, CH₃), 3.83 (s, 3H, OCH₃), 4.02 (s, 3H, OCH₃), 4.26 (q, 2H, J = 7.1 Hz, OCH₂), 4.47 (s, 2H, CH₂), 4.67 (s, 2H, CH₂), 6.82 (d, 1H, J = 2.8 Hz, ArH), 7.02 (s, 1H, ArH), 7.24 (s, 1H, ArH), 7.39 (dd, 1H, J = 9.2 Hz, J = 2.8 Hz, ArH), 7.62 (d, 1H, J = 1.2 Hz, ArH), 7.99 (d, 1H, J = 9.2 Hz, ArH), 8.36 (s, 1H, ArH), 8.83 (d, 1H, J = 2.1 Hz, ArH), 9.03 (s, 1H, ArH); ¹³C-NMR (CDCl₃, δ): 14.11, 33.90, 55.97, 56.05, 61.51, 65.50, 101.61, 106.08, 106.21, 121.75, 124.91, 127.22, 128.82, 130.96, 131.16, 133.07, 133.57, 142.83, 143.53, 149.46, 149.82, 150.20, 153.15, 156.19, 168.44; MS-ESI m/z (% rel. Int.): 433.3 ([MH]⁺, 100); HPLC: Method A, detection UV 254 nm, RT = 4.10 min, peak area 95.2%. |
| ANP 49174B | (structure: 4-hydroxy-3-nitrophenyl linked via CH₂ to 6,7-dimethoxyisoquinoline) | A LPO 22102 (678 mg, 2.39 mmol); 4-hydroxy-3-nitrobenzaldehyde (400 mg, 2.39 mmol); 37% aqueous HCl (6 mL); EtOH (6 mL); 90° C. for 25 min. | Chromatography SiO₂, CH₂Cl₂:MeOH = 100:0 to 98:2 | 4-((6,7-dimethoxyisoquinolin-4-yl)methyl)-2-nitrophenol (214.5 mg); MW: 340.33; Yield: 26%; Yellow Solid; ¹H-NMR (CD₃OD, δ): 3.89 (s, 3H, OCH₃), 4.00 (s, 3H, OCH₃), 4.28 (s, 2H, CH₂), 6.98 (s, 1H, ArH), 7.05 (d, 1H, ArH, J = 8.6 Hz), 7.21 (s, 1H, ArH), 7.40 (dd, 1H, ArH, J = 2.2 Hz, J = 8.6 Hz), 7.96 (d, 1H, ArH, J = 2.2 Hz), 8.26 (s, 1H, ArH), 8.98 (s, 1H, ArH); MS-ESI m/z (% rel. Int.): 341.2 ([MH]⁺¹, 100); HPLC: Method A, detection UV 254 nm, RT = 3.98 min, peak area 97.2%. |

TABLE 3-continued

| Compound | FORMULA | General Procedure and Conditions | Work-Up & Purification | Analysis |
|---|---|---|---|---|
| ANP 53134 | 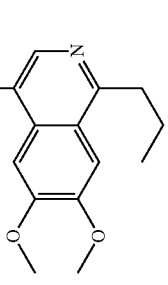 | A LPO 22102 (2.0 g, 6.14 mmol); 4-hydroxy-3-nitrobenzaldehyde (1.03 g, 6.14 mmol); 37% aqueous HCl (15 mL); EtOH (15 mL); 90° C. for 25 min. | Precipitation in MeOH; Chromatography SiO$_2$, CH$_2$Cl$_2$:MeOH = 100:0 to 99: | 4-((6,7-dimethoxy-1-propylisoquinolin-4-yl)methyl)-2-nitrophenol (1.00 g) MW: 382.41; Yield: 43%; Yellow Solid; R$_f$: 0.25 (CH$_2$Cl$_2$: MeOH = 99:1); MS-ESI m/z (% rel. Int.): 383.3 ([MH]$^{+1}$, 100), 384.3 (22), 385.4 (4); HPLC: Method A, detection UV 254 nm, RT = 4.64 min, peak area 95.5%. |
| ANP 53006A | 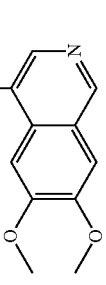 | A LPO 22102 (2.0 g, 6.14 mmol); 3-hydroxy-4-nitrobenzaldehyde (500 mg, 5.9 mmol); 37% aqueous HCl (14 mL); EtOH (14 mL); 90° C. for 25 min. | Chromatography SiO$_2$, CH$_2$Cl$_2$:MeOH = 100:0 to 98:2 | 5-((6,7-dimethoxyisoquinolin-4-yl)methyl)-2-nitrophenol (293 mg); MW: 340.33; Yield: 14%; Yellow Solid; R$_f$: 0.30 (CH$_2$Cl$_2$:MeOH = 98:2); $^1$H-NMR (CDCl$_3$, δ): 3.90 (s, 3H, OCH$_3$), 4.03 (s, 3H, OCH$_3$), 4.36 (s, 2H, CH$_2$), 6.86 (d, 1H, ArH, J = 8.7 Hz), 6.96 (m, 2H, 2xArH), 7.27 (s, 1H, ArH), 8.03 (d, 1H, ArH, J = 8.7 Hz), 8.23 (s, 1H, ArH), 8.96 (s, 1H, ArH); MS-ESI m/z (% rel. Int.): 341.2 ([MH]$^{+1}$, 100); HPLC: Method A, detection UV 254 nm, RT = 4.03 min, peak area 99.5%. |

General Procedures B for Preparation of Compounds 21, 23, 24, 27, 32, 41, 46, 55, 73, 107, 112, 116, 120, 125, 126, 128, 130, 133, 134, 135, 138, 139, 143, 148, 164 & 165 and Compounds LPO 55070A, LPO 50156C, LPO 50172C, LPO 50040C, LPO 50164C, ANP 49102A & LPO 50192C.

a) O-Alkylation Using 107, 112, 116, 120, 125, 126, 128, 130, 133, 134, 135, 138, 139, 143, 148, 164 & 165) and Compounds LPO 55070A, LPO 50156C, LPO 50172C, LPO 50040C, LPO 50164C, ANP 49102A & LPO 50192C.

To a stirred mixture of the hydroxyquinoline derivative, $Cs_2CO_3$ or $K_2CO_3$ as base, and acetone, acetonitrile or DMF as solvent was added the desired halogeno-derivative (see tables 4 and 7 for conditions). The resulting mixture was stirred between 1 h to 40 h at RT to 90° C. or heated under microwave irradiation (see tables 4 and 7 for conditions). After cooling, the reaction mixture was partitioned between EtOAc (typically 200 mL) and a 1 M $K_2CO_3$ solution (typically 30 mL). The organic layer was separated, washed with $H_2O$ (typically 30 mL), brine (typically 30 mL), dried over $MgSO_4$, filtered and concentrated to dryness under reduced pressure. The residue was purified by column chromatography ($SiO_2$, see tables 4 and 7 for conditions). After evaporation of the solvents, if a hydrochloride salt was needed, the obtained free base (1 eq) was dissolved in MeOH (1 mL) and a 1.75 N HCl solution in MeOH (2.1 eq×number of basic nitrogen) was added. The desired O-alkylated isoquinoline derivative was obtained as a free base or hydrochloride salt after further drying under vacuum.

b) O-Alkylation Using KOH in $H_2O$/DME (Compounds 21 and 24)

To a stirred mixture of the hydroxyquinoline derivative and KOH in a mixture of $H_2O$ and DME was added the desired halogeno-derivative (see conditions in table 7). The resulting mixture was stirred between 24 h to 55 h at RT then partitioned between EtOAc (200 mL) and a 1 M $K_2CO_3$ solution (30 mL). The organic layer was separated, washed with $H_2O$ (30 mL), brine (30 mL), dried over $MgSO_4$, filtered and concentrated to dryness under reduced pressure. The residue was purified by column chromatography ($SiO_2$, see conditions in table 7). After evaporation of the solvents, the obtained free base (1 eq) was dissolved in MeOH (1 mL) and a 1.75 N HCl solution in MeOH (2.1 eq×number of basic nitrogen) was added. All the volatiles were evaporated to give the desired O-alkylated isoquinoline derivative 21 or 24 as a hydrochloride salt (see table 7) after further drying under vacuum.

TABLE 4

| Compound | FORMULA | General Procedure & Conditions for O-Alkylation | Work-Up & Purification | Analysis |
|---|---|---|---|---|
| LPO 55070A | (structure) | B (a) LPO 55016 (800 mg, 3.68 mmol); Cs₂CO₃ (1.32 g, 4.05 mmol); ethyl 2-bromoacetate (820 μL, 7.37 mmol); acetone (36 mL); 85° C. for 2 h. | Not purified | ethyl 2-((3-(1,3-dioxolan-2-yl)quinolin-6-yl)oxy)acetate (969 mg); MW: 303.31; Crude Yield: 6%; Brown Solid; MS-ESI m/z (% rel. Int.): 304.3 ([MH]$^{+1}$, 100); HPLC: Method A, detection UV 54 nm, RT = 3.76 min, peak area 85.7%. |
| LPO 50156C | (structure) | B (a) 45 (245 mg, 0.63 mmol); Cs₂CO₃ (308 mg, 0.95 mmol); Et₃N (185 μL, 1.33 mmol); ethyl 3-bromopropanoate (88.5 μL, 0.69 mmol); DMF (4 mL); 150° C. for 35 min (microwave). | Chromatography SiO₂, cyclohexane:EtOAc = 100:0 to 50:50 | ethyl 3-((2-((6,7-dimethoxy-1-propylisoquinolin-4-yl)methyl)quinolin-8-yl)oxy)propanoate (144 mg); MW: 488.57; Crude Yield: 46%; Yellow Solid; MS-ESI m/z (% rel. Int.): 489.3 ([MH]$^{+1}$, 100); HPLC: Method A, detection UV 254 nm, RT = 4.85 min, peak area 60.2%. |
| LPO 50172C | (structure) | B (a) 83 (200 mg, 0.53 mmol); Cs₂CO₃ (191.4 mg, 0.59 mmol); Et₃N (185 μL, 1.33 mmol); 2-chloroacetonitrile (67.8 μL, 1.07 mmol); Acetone (10 mL); 80° C. for 15 h. | Chromatography SiO₂, cyclohexane:EtOAc = 50:50 to 0:100 | 2-((2-((1-ethyl-6,7-dimethoxyisoquinolin-4-yl)methyl)quinolin-8-yl)oxy)acetonitrile (161 mg); MW: 413.47; Yield: 69%; Yellow Solid; $^{1}$H-NMR (CDCl₃, δ): 1.45 (t, 3H, J = 7.5 Hz, CH₃), 3.24 (q, 2H, J = 7.5 Hz, OCH₂), 3.91 (s, 3H, OCH₃), 3.98 (s, 3H, OCH₃), 4.68 (s, 2H, CH₂), 5.17 (s, 2H, OCH₂), 7.25-7.31 (m, 3H, 3xArH), 7.34-7.49 (m, 2H, 2xArH), 7.55 (s, 1H, ArH), 7.96 (d, 1H, J = 8.40 Hz, ArH), 8.42 (s, 1H, ArH); MS-ESI m/z (% rel. Int.): 414.2 ([MH]$^{+1}$, 100); HPLC: Method A, detection UV 254 nm, RT = 4.03 min, peak area 90.6%. |
| LPO 50040C | (structure) | B (a) 45 (300 mg, 0.77 mmol); Cs₂CO₃ (277 mg, 0.85 mmol); 2-chloroacetonitrile (98 μL, 1.54 mmole); Acetone (18 mL); 56° C. for 1 h. | Chromatography SiO₂, cyclohexane:EtOAc = 50:50 to 20:80 | 2-((2-((6,7-dimethoxy-1-propylisoquinolin-4-yl)methyl)quinolin-8-yl)oxy)acetonitrile (305 mg); MW: 427.50; Yield: 92%; Brown Solid; $^{1}$H-NMR (CDCl₃, δ): 1.07 (t, 3H, CH₃, J = 7.35 Hz), 1.9 (q, 2H, CH₂, J = 7.6 Hz), 3.18 (t, 2H, CH₂, J = 7.6 Hz), 3.90 (s, 3H, OCH₃), 3.98 (s, 3H, OCH₃), 4.68 (s, 2H, CH₂), 5.17 (s, 2H, CH₂), 7.26-7.31 (m, 3H, 3xArH), 7.42-7.53 (m, 3H, 3xArH), 7.99 (d, 1H, ArH, J = 8.55 Hz), 8.41 (s, 1H, ArH); $^{13}$C-NMR (CDCl₃, δ): 14.37, 22.58, 37.52, 41.32, 55.51, 55.88, 56.02, 103.53, 104.15, 113.83, 115.25, 122.06, 122.84, 123.12, 125.63, 125.90, 128.33, 132.19, 136.81, 139.67, 141.57, 149.51, 151.74, 152.32, 159.30, 160.52; MS-ESI m/z (% rel. Int.): 428.2 ([MH]$^{+1}$, 100); HPLC: Method A, detection UV 254 nm, RT = 4.22 min, peak area 99.5%. |

TABLE 4-continued

| Compound | FORMULA | General Procedure & Conditions for O-Alkylation | Work-Up & Purification | Analysis |
|---|---|---|---|---|
| LPO 50164C | 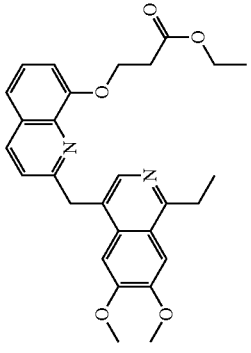 | B (a) 83 (200 mg, 0.53 mmol); Cs$_2$CO$_3$ (261 mg, 0.80 mmol), Et$_3$N (246.6 µL, 1.76 mmol); ethyl 3-bromopropanoate (75 µL, 0.59 mmol); DMF (4 mL); 150° C. for 45 min (microwave). | Chromatography SiO$_2$, cyclohexane:EtOAc = 50:50 to 30:70 | ethyl 3-((2-((1-ethyl-6,7-dimethoxyisoquinolin-4-yl)methyl)quinolin-8-yl)oxy)propanoate (199 mg); MW: 474.55; Crude Yield: 78%; Yellow Solid; MS-ESI m/z (% rel. Int.): 475.3 ([MH]$^{+1}$, 100); HPLC: Method A, detection UV 254 nm, RT = 4.74 min, peak area 50.2%. |
| ANP 49102A | 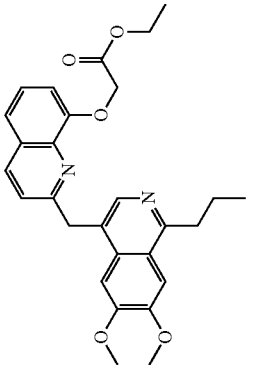 | B (a) 45 (322 mg, 0.83 mmol); Cs$_2$CO$_3$ (780 mg, 2.40 mmol); ethyl bromoacetate (129 µL, 1.16 mmol); DMF (5 mL); 40° C. for 7 h. | Chromatography SiO$_2$, cyclohexane:EtOAc = 90:10 to 0:100 | ethyl 2-((2-((6,7-dimethoxy-1-propylisoquinolin-4-yl)methyl)quinolin-8-yl)oxy)acetate (200 mg); MW: 474.55; Yield: 51%; Yellow Solid; R$_f$: 0.25 (EtOAc); $^1$H-NMR (CDCl$_3$, δ): 1.07 (t, 3H, CH$_3$, J = 7.4 Hz), 1.31 (t, 3H, CH$_3$, J = 7.1 Hz), 1.90 (sext, 2H, CH$_2$, J = 7.8 Hz), 3.17 (q, 2H, CH$_2$, J = 7.7 Hz), 3.91 (s, 3H, OCH$_3$), 3.98 (s, 3H, OCH$_3$), 4.30 (q, 2H, OCH$_2$, J = 7.1 Hz), 4.70 (s, 2H, CH$_2$), 4.97 (s, 2H, OCH$_2$), 6.96-6.99 (m, 1H, ArH), 7.24-7.30 (m, 2H, 2xArH), 7.36-7.38 (m, 2H, 2xArH), 7.66 (s, 1H, ArH), 7.93 (d, 1H, ArH, J = 7.50 Hz), 8.42 (s, 1H, ArH); MS-ESI m/z (% rel. Int.): 475.1 ([MH]$^{+1}$, 100); HPLC: Method A, detection UV 254 nm, RT = 4.37 min, peak area 99.0%. |
| LPO 50192C | 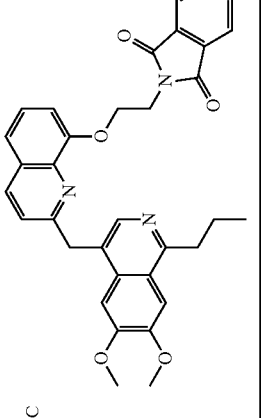 | B (a) 45 (300 mg, 0.77 mmol); Cs$_2$CO$_3$ (377.3 mg, 1.16 mmol); N-(2-bromoethyl)phthalimide (392.4 mg, 1.55 mmol); DMF (3 mL); 150° C. for 10 min (microwave). | Chromatography SiO$_2$, CH$_2$Cl$_2$:MeOH = 100:0 to 98:2 | 2-(2-((2-((6,7-dimethoxy-1-propylisoquinolin-4-yl)methyl)quinolin-8-yl)oxy)ethyl)isoindoline-1,3-dione (58.3 mg); MW: 561.63; Yield: 13%; White Solid; R$_f$ = 0.30 (CH$_2$Cl$_2$:MeOH = 98:2); $^1$H-NMR (CDCl$_3$, δ): 1.08 (t, 3H, CH$_3$, J = 7.4 Hz), 1.91 (sext, 2H, CH$_2$, J = 7.4 Hz), 3.18 (t, 2H, CH$_2$, J = 7.7 Hz), 3.86 (s, 3H, OCH$_3$), 3.98 (s, 3H, OCH$_3$), 4.29 (t, 2H, CH$_2$, J = 6.6 Hz), 4.55 (t, 2H, OCH$_2$, J = 6.6 Hz), 4.61 (s, 2H, OCH$_2$), 7.16-7.41 (m, 6H, 6xArH), 7.55 (s, 1H, ArH), 7.69-7.73 (m, 2H, 2xArH), 7.84-7.89 (m, 3H, 3xArH), 8.38 (s, 1H, ArH); MS-ESI m/z (% rel. Int.): 562.3 ([MH]$^{+1}$, 100); HPLC: Method A, detection UV 254 nm, RT = 5.01 min, peak area 95.2%. |

General Procedures C to Prepare Compounds 56, 76, 136, 140, 141, 158, 93, 106, 111, 147.

a) Preparation of 56, 76, 136, 140, 141, 158 (Acylation Using Acetic Anhydride or an Acyl Chloride)

The amino derivative LPO 43180, LPO 50016B, LPO 55010B, free base of 45, 83 or LPO 55056D and triethylamine, DMAP or pyridine were dissolved in anhydrous THF or in $CH_2Cl_2$ and acetic anhydride (or acetoxyacetyl chloride for 158) was slowly added (see conditions in table 7). After complete addition, the reaction mixture was stirred under a nitrogen atmosphere (see conditions in table 7). The reaction mixture was poured in 1 M aqueous $K_2CO_3$ (typically 10 mL) and dichloromethane (typically 100 mL) was added. The separated organic layer was washed with brine (typically 20 mL), dried over $MgSO_4$, filtered and evaporated to give a crude N-acetylated amine derivative. This crude compound was purified by column chromatography ($SiO_2$, see conditions in table 7) and solvents were evaporated. If a hydrochloride salt was needed, the obtained free base (1 eq) was dissolved in MeOH (1 mL) and a 1.75 N HCl solution in MeOH (2.1 eq×number of basic nitrogen) was added. The N-acetylated amine derivative 56, 76, 136, 140, 141 or 158 (see table 7) was obtained, as a free base or a dihydrochloride salt, after further drying under vacuum pump.

b) Preparation of Oxalamides 93 and 98
2-Amino-2-Oxoacetyl Chloride RBO 56082

To a solution of oxamic acid (500 mg, 5.61 mmol) in dry $CH_2Cl_2$ (20 mL) in a 50 mL round bottom flask equipped with a magnetic stirrer was added $SOCl_2$ (4.07 mL, 56.10 mmol) followed by 1 drop of DMF and the mixture was stirred under reflux for 3 h then cooled to 25° C. After concentration to dryness at 40° C. under vacuum, the residue was diluted with $CH_2Cl_2$ (20 mL) before concentration back to dryness (done twice), giving 633 mg of a pale yellow solid 2-amino-2-oxoacetyl chloride RBO 56082 that was used in the next step without further purification (quant. crude yield).

Oxalamides 93 and 98

To a solution of aminoquinoline RBO 51118B or 86 in THF in a 50 mL round bottom flask equipped with a magnetic stirrer was added $Et_3N$ followed by 2-amino-2-oxoacetyl chloride RBO 56082 (see conditions table 7). The mixture was stirred overnight at 25° C. All the volatiles were evaporated at 40° C. under vacuum and the residue was taken back in $CH_2Cl_2$ (30 mL) and the solution was washed with $H_2O$ (3×5 mL), brine (5 mL), dried over $Na_2SO_4$, filtered and concentrated at 40° C. under vacuum. Purification by column chromatography ($SiO_2$, see conditions in table 7) gave after evaporation and drying the oxalamide 93 or 98 (see table 7).

c) Preparation of Benzoxazolinones 106, 111 and 147 Using 1,1'-Carbonyl Diimidazole To a solution of 2-aminophenol derivative (ANP 49188A, ANP49184A or ANP 53156A) in anhydrous $CH_2Cl_2$ were added triethylamine and 1,1'-carbonyl diimidazole in anhydrous $CH_2Cl_2$ at 0-4° C. under nitrogen (see conditions table 7). The reaction mixture was stirred at 0-4° C. and then abandoned to RT 5 h or overnight (see conditions table 7). The precipitate that appeared was filtered and dried to give the desired benzoxazolinone 106. In case no precipitate was observed, the reaction mixture was evaporated and the residue was purified by column chromatography ($SiO_2$, see conditions table 7) to give the benzoxazolinone 111 or 147 (see table 7).

d) Preparation of Sulfonamides 86 and 99 Using Alkyl Sulfonyl Chloride

To a solution of RBO 51118B in $CH_2Cl_2$ in a 20 mL microwave vial equipped with a magnetic stirrer was added pyridine followed by methane- or ethane-sulfonyl chloride (see conditions table 7). The mixture was heated under microwave irradiation at 70° C. (see conditions table 7). After cooling to RT, the mixture was then washed with water (3×5 mL), brine (5 mL), dried over $Na_2SO_4$, filtered and concentrated at 40° C. under vacuum. Purification by column chromatography ($SiO_2$, see exact conditions table 7) gave after evaporation and drying the sulfonamide 86 or 99 (see table 7).

e) Preparation of Urea 87

To a solution of RBO 51118B (100 mg, 0.27 mmol) in AcOH (10 mL) in a 50 mL round bottom flask equipped with a magnetic stirrer was added a solution of potassium cyanate (21.9 mg, 0.27 mmol) in $H_2O$ (1 mL) and the mixture was stirred for 3 h at 40° C. AcOH was then removed at 40° C. under reduced pressure and the residue was taken up in $CH_2Cl_2$ (20 mL) before neutralisation with a saturated aqueous $NaHCO_3$ solution. The precipitate that formed was isolated by filtration and further washed with pentane (2×10 mL). After drying under vacuum, 48 mg of 1-(2-((1-ethyl-6,7-dimethoxyisoquinolin-4-yl)methyl)quinolin-8-yl)urea 87 (see table 7) were obtained as a white solid (43%).

General Procedures D to Prepare Compounds TTA 461188, 42, 75, 142, 149, 151, 154 and 166.

a) Preparation of Compounds TTA 46118B, 42, 75, 142, 151, 154, 166

The corresponding ester derivative TTA 46118A, 41 (free base), ANP 49102A, 115, ANP 53192A, ANP 531748 or 165 was dissolved in MeOH or tBuOH or THF and $NaBH_4$ or a solution of $LiAlH_4$ in THF was added at RT (see conditions in tables 5 and 7). The reaction mixture was stirred at 0° C. to RT or 140° C. (see conditions in tables 5 and 7). After cooling to RT, the reaction mixture was concentrated under reduced pressure and the residue was poured into water (typically 100 mL) and extracted with $CH_2Cl_2$ (typically 200 mL). The separated organic layer was washed with water (typically 2×30 mL), brine (typically 30 mL), dried over $Mg_2SO_4$, filtered and evaporated to give a crude compound. This crude compound was purified by column chromatography ($SiO_2$, see conditions tables 5 and 7). After evaporation of the solvents, if a hydrochloride salt was needed, the obtained free base (1 eq.) was dissolved in MeOH (1 mL) and a 1.75 N HCl solution in MeOH (2.1 eq×number of basic nitrogen) was added. The alcohol derivative TTA 46118B, 42, 75, 142, 151, 154 or 166 (see table 7) was obtained as a free base or a dihydrochloride salt after further drying under vacuum.

b) Preparation of Compound 149 and LPO 43180

To a solution of ANP 53142B or 55 in MeOH was added 10% Pd/C at RT under a hydrogen atmosphere (see conditions in table 7 and 5). The reaction mixture was stirred according to the conditions described in table 7 or 5. The mixture was filtered on celite and the filtrate was concentrated to dryness.

For reaction involving 55, crude LPO 43180 (see table 5) was obtained after further drying and was used without further purification in the next step.

For reaction involving ANP 53142B, the residue was purified by column chromatography ($SiO_2$, see conditions in table 7) to give, after evaporation and further drying, the aminophenyl derivative 149 (see table 7).

c) Preparation of Compounds SSA 48104, LPO 55016 and ECO 55108C

In a 100 mL round bottom flask, 2-chloro-3-[1,3]dioxolan-2-yl-7-methyl-quinoline, LPO 55012B or ECO 55098, 10% Pd/C and $K_2CO_3$ were dissolved in MeOH (see conditions in table 5). The reaction mixture was stirred under a hydrogen atmosphere according to the conditions described in table 5. The reaction mixture was filtered on celite and the celite cake was further washed with MeOH (5 mL). The obtained filtrate was evaporated to give a crude product. This crude product was purified by column chromatography (see conditions in table 5) to give, after evaporation and further drying, compounds SSA 48104, LPO 55016 or ECO 55108C (see table 5).

d) Preparation of Compound RBO 51194

To a solution of compound 90 (872 mg, 2.27 mmol) in THF (20 mL) in a 50 mL round bottom flask equipped with a magnetic stirrer at −78° C. was added dropwise DIBAL-H (1.0 M solution in THF, 9.00 mL, 9.00 mmol). After complete addition, the mixture was stirred for 20 min at −78° C., then for 30 min at −40° C. and then for 1 h at RT. Another portion of DIBAL-H (1.0 M solution in THF, 6.80 mL, 6.80 mmol) was then added at −78° C. and the mixture was further stirred for 3 h allowing the medium to slowly reach RT. After cooling to 0° C., the mixture was carefully hydrolysed with $H_2O$ (6 mL) and a saturated aqueous $NH_4Cl$ solution (10 mL) before stirring for 3 days at RT. The solid that had formed was filtered-off and the filtrate was concentrated to dryness at 40° C. under vacuum. The residue was taken up in $CH_2Cl_2$ (60 mL) and washed with $H_2O$ (3×15 mL), brine (15 mL), dried over $Na_2SO_4$, filtered and concentrated at 40° C. under vacuum. Purification by column chromatography ($SiO_2$ eluent $CH_2Cl_2$:MeOH=100:0 to 90:10) gave after evaporation and further drying RBO 51194 as a yellow solid (see table 5).

Procedures E to Prepare Compounds 35, 91 and SAO 33058 a) Preparation of Compound 35

To a solution of 4-(dibenzo[b,d]furan-2-ylmethyl)-6,7-dimethoxyisoquinoline 10 (600 mg, 1.62 mmol) in $CH_2Cl_2$ (40 mL) was added mCPBA (336 mg, 1.95 mmol) at RT under a nitrogen atmosphere. The reaction mixture was stirred at RT overnight and then this mixture was partitioned between $CH_2Cl_2$ (200 mL) and a 1 M $K_2CO_3$ aqueous solution (50 mL). The separated organic layer was washed with brine (50 mL), dried over $MgSO_4$, filtered and evaporated to give 4-dibenzofuran-2-ylmethyl-6,7-dimethoxy-isoquinoline 2-oxide 35 (see table 7) as yellow solid (645 mg, quant. yield).

b) Preparation of Compound 91

To a solution of quinolinecarbonitrile 90 (0.78 mmol) in EtOH (10 mL) in a 25 mL round bottom flask equipped with a magnetic stirrer was added 35% $H_2O_2$ (236 μL, 2.74 mmol) followed by a 0.5 M aqueous solution of NaOH (1.57 mL, 0.78 mmol). The mixture was heated at reflux for 3 days, then cooled to RT. After evaporation of the volatiles, the residue was taken back in $CH_2Cl_2$ (20 mL) and washed with water (3×5 mL), brine (5 mL), dried over $Na_2SO_4$, filtered and concentrated at 40° C. under vacuum. Purification by column chromatography ($SiO_2$, see exact conditions in table 7) gave after evaporation and further drying the desirated quinolinecarboxamide 91 (see table 7).

c) Preparation of Compound SAO 33058

(4-Chloro-1-ethyl-1H-pyrazolo[3,4-b]pyridin-5-yl)-methanol SAO 33034 (359 mg, 1.70 mmol) was dissolved in anhydrous $CH_2Cl_2$ (50 mL) at RT under nitrogen. Dess Martin Periodinane (755 mg, 1.78 mmol) was slowly added portionwise at 4° C. The reaction mixture was stirred for 1 h at 4° C. then overnight at RT. The solid was filtered off and $CH_2Cl_2$ (200 mL) was added to the mixture. After separation, the organic layer was washed with brine (20 mL), dried over $MgSO_4$, filtered and evaporated to give 4-chloro-1-ethyl-1H-pyrazolo[3,4-b]pyridine-5-carbaldehyde SAO 33058 (see table 5) as an off-white solid (711 mg, 100%).

Procedures F for Preparation of Compounds 108, 118, 122, 145, 146, 150 and 160)

a) Preparation of Compounds 108, 118, 122, 145, 146 and 160 (Saponification of Esters Using of KOH, NaOH or LiOH)

To a solution of KOH, NaOH or LiOH in MeOH:$H_2O$ or THF:$H_2O$ (1:1) was added a solution of the ester derivative in MeOH or THF at RT (see conditions in table 7). The reaction mixture was stirred according to the conditions described in table 7.

To obtain a sodium (118, 122) or a potassium (145) carboxylate: the solvent was evaporated and the residue was purified by column chromatography (RP 18; gradient $H_2O$:$CH_3CN$=10:0 to 7:3) to give after evaporation and further drying the desired salt 118, 122 or 145 (see table 7).

To obtain a carboxylic acid 108 or 146 or the 2-hydroxyacetamide 160: the solvent was evaporated and the residue was dissolved in $CH_2Cl_2$ (75 mL) and a 2 N HCl solution was added until pH=7-8. The organic layer was then washed with brine (20 mL), dried over $MgSO_4$, filtered and evaporated. The residue was purified by column chromatography ($SiO_2$, see conditions in table 7) to give after evaporation and further drying the desired compound (free base of 108, 146 or 160). To obtain the dihydrochloride salt 108, the free base of 108 (0.08 mmol) was dissolved in MeOH and a 1.76 N HCl methanolic solution (100 μL, 0.17 mmol) was added at 4° C. This solution was stirred at 4° C. for 10 min and then concentrated. The dihydrochloride salt 108 was obtained after further drying under vacuum (see table 7).

b) Preparation of Compound 150

The derivative LPO 55070A (120 mg, 0.28 mmol) was dissolved in a 37% aqueous HCl solution (1 mL) and AcOH (1 mL). The reaction mixture was stirred at 110° C. for 4 h. After cooling, the solvents were evaporated and the residue was poured in n-BuOH (60 mL) and a 1 M $K_2CO_3$ solution (30 mL) was added. The separated organic layer was washed with brine (20 mL), dried over $MgSO_4$, filtered and evaporated. The crude product was purified by column chromatography ($SiO_2$, see conditions in table 7) to give, after evaporation and further drying under vacuum, the acid 150 (see table 7).

Procedures G for Preparation of Compounds ANP 57032a, ANP 53184a, RBO 51116, LPO 55036C, ECO 59060, RBO 56020, LPO 50012 and LPO 50042C a) Preparation of Triflates ANP 57032a, ANP 53184a, RBO 51116, LPO 55036C, ECO 59060 and RBO 56020

To a solution of the corresponding hydroxyquinoline derivative 7 free base, 131, 83, 45, 163 or 95 in DMF (20 mL) were added N-phenyl bis-trifluoromethane sulfonimide and triethylamine (see conditions described in table 5). The reaction mixture was stirred according to the conditions described in table 5. DMF was removed under vacuum at 70° C. The residue was diluted in $CH_2Cl_2$ (typically 100 mL), washed with $H_2O$ (typically 3×30 mL), brine (typically 20 mL), dried over $Na_2SO_4$, filtered and concentrated at 40° C. under reduced pressure. The crude product was purified by column chromatography ($SiO_2$, see conditions in table 5) to give, after evaporation and further drying under vacuum, the triflates ANP 57032A, ANP 53184A, RBO 51116, LPO 55036C, ECO 59060 or RBO 56020 (see table 5).

b) Preparation of Compounds LPO 50012 and LPO 50042C

The 2-hydroxyquinoline derivative (free base of 49 or SSA 48042) was stirred in phosphoryl trichloride in an ace pressure tube (Aldrich) at 100-110° C. for 2 h (see conditions in table 5). After cooling, the mixture was poured in ice (10 g) and a 1 M aqueous $K_2CO_3$ solution (5 mL) and EtOAc (150 mL) were added. The separated organic layer was washed with brine (20 mL), dried over $MgSO_4$, filtered and evaporated. The crude product was purified by column chromatography ($SiO_2$, eluent cyclohexane:EtOAc=70:30 to 50:50) to give, after evaporation and further drying to the vacuum pump, the 2-chloroquinoline derivative LPO 50012 or LPO 50042C (see table 5).

TABLE 5

| Compound | FORMULA | General Procedure & Conditions | Work-Up & Purification | Analysis |
|---|---|---|---|---|
| TTA 46118B | 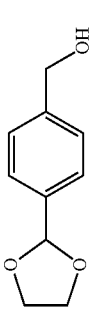 | D (a) TTA 46118A (4.8 g, 23.0 mmol); LiAlH₄ (3.5 g, 92.0 mmol); THF (130 mL); 0° C. to RT for 4 h. | Not purified | (4-(1,3-dioxolan-2-yl)phenyl)methanol (3.4 g); MW: 180.20; Yield: 82%; Colorless Oil; R$_f$: 0.15 (cyclohexane: EtOAc = 80:20); $^1$H-NMR (CDCl$_3$, δ): 2.22 (t, 1H, J = 5.85 Hz, OH), 3.98-4.13 (m, 4H, 2xCH2), 4.63 (d, 1H, J = 5.64 Hz, CH2), 5.79 (s, 1H, CH), 7.33 (d, 2H, J = 8.2 Hz, 2xArH), 7.44 (d, 2H, J = 8.1 Hz, 2xArH); $^{13}$C-NMR (CDCl$_3$, δ): 64.61, 65.26 (2xC), 103.58, 126.62 (2xC), 129.78 (2xC), 136.92, 142.20 ; MS-ESI m/z (% rel. Int.): 181.1 ([MH]$^{+1}$ 100), HPLC: Method A, detection UV 254 nm, RT = 3.19 min, peak area 90.0%. |
| LPO 43180 | 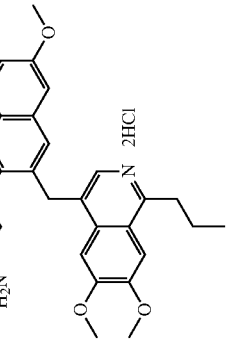 | D (b) LPO 55012B (50 mg, 0.109 mmol); MeOH (5 mL); 37% aqueous HCl (63 μL, 0.76 mmol); H₂ Pd/C 10% (12.8 mg, 0.12 mmol); RT for 3 h. | Filtration on celite | 2-(3-((6,7-dimethoxy-1-propylisoquinolin-4-yl)methyl)-6-methoxyquinolin-2-yl)oxy)ethanamine dihydrochloride (70.5 mg); MW: 534.47; Crude Yield: quantitative, Yellow Oil; MS-ESI m/z (% rel. Int.): 462.4 ([MH]$^{+1}$, 100); HPLC: Method A, detection UV 254 nm, RT = 3.78 min, peak area 80%. |
| SSA 48104 | 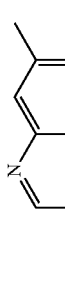 | D (c) 2-chloro-3-(1,3)dioxolan-2-yl-7-methyl-quinoline (1.33 g, 6.18 mmol); MeOH (15 mL); K₂CO₃ (1.2 g, 8.68 mmol); H₂; Pd/C 10% (225 mg, 0.20 mmol); 5 days at RT. | Filtration on celite then chromatography SiO$_2$ CH$_2$Cl$_2$:EtOAc = 100:0 to 90:10 | 3-(1,3-dioxolan-2-yl)-7-methylquinoline (595 mg); MW: 215.25; Yield: 45%; Off-white Solid; $^1$H-NMR (CDCl$_3$, δ): 2.57 (s, 3H, CH$_3$), 4.07-4.13 (m, 2H, CH$_2$), 4.15-4.21 (m, 2H, CH$_2$), 6.01 (s, 1H, CH), 7.39 (dd, 1H, J = 2.0 & 8.0 Hz, ArH), 7.72 (d, 1H, J = 8.0 Hz, ArH), 7.91 (s, 1H, ArH), 8.19 (d, 1H, J = 2.0 Hz, ArH), 9.96 (d, 1H, J = 3.0 Hz, ArH); $^{13}$C-NMR (CDCl$_3$, δ): 21.9, 65.4 (2xC), 102.4, 125.5, 127.7, 128.3, 129.2, 130.3, 133.8, 140.4, 148.7, 149.0; MS-ESI m/z (% rel. Int.): 216.2 ([MH]$^{+1}$, 100); HPLC: Method A, detection UV 254 nm, RT = 3.22 min, peak area 94%. |
| LPO 55016 | 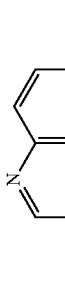 | D (c) LPO 55012B (435 mg, 1.73 mmol); MeOH (5 mL); K₂CO₃ (359 mg, 2.60 mmol); H₂; Pd/C 10% (184 mg, 0.17 mmol); RT for 3 h. | Filtration on celite | 3-(1,3-dioxolan-2-yl)quinolin-6-ol (248.9 mg); MW: 217.22; Yield: 66%; Pale Green Solid; MS-ESI m/z (% rel. Int.): 218.2 ([MH]$^{+1}$, 100); HPLC: Method A, detection UV 254 nm, RT = 2.88 min, peak area 90.8%. |
| ECO 55108C | 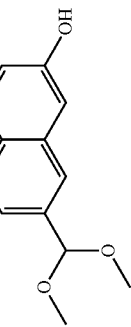 | D (c) ECO 55098 (1.0 g, 3.95 mmol); MeOH (20 mL); K₂CO₃ (819 mg, 5.93 mmol); H₂; Pd/C 10% (420 mg, 0.39 mmol); RT for 4.5 h. | Filtration on celite then chromatography SiO$_2$, CH$_2$Cl$_2$:EtOAc = 100:0 to 50:50 | 3-(dimethoxymethyl)quinolin-6-ol (609 mg); MW: 219.24; Yield: 69%, Pale Yellow Solid. $^1$H-NMR (CD$_3$OD, δ): 3.38 (s, 6H, 2xCH$_3$O), 5.89 (s, 1H, CHO), 7.21 (d, 1H, ArH), 7.39 (dd, 1H, ArH), 8.00 (d, 1H, ArH), 8.52 (s, 1H, ArH), 8.81 (s, 1H, ArH); MS-ESI m/z (% rel. Int.): 220.2 ([MH]$^{+1}$, 100); HPLC: Method A, detection UV 254 nm, RT = 3.32 min, peak area 95.8%. |

TABLE 5-continued

| Compound | FORMULA | General Procedure & Conditions | Work-Up & Purification | Analysis |
|---|---|---|---|---|
| RBO 51194 | (structure) | D (d) 90 (872 mg, 2.27 mmol); THF (20 mL); DIBAL-H (1.0 M in THF, 9.00 mL, 9.00 mmol); 20 min at −78° C. then 30 min at −40° C. and 1 h to RT; DIBAL-H (1.0 M in THF, 6.80 mL, 6.80 mmol) was then added at −78° C. and the mixture was abandoned for 3 h to slowly reach RT. | Chromatography SiO$_2$, eluent CH$_2$Cl$_2$:MeOH = 100:0 to 90:10 | 2-((1-ethyl-6,7-dimethoxyisoquinolin-4-yl)methyl)quinolin-8-yl)methanamine (467 mg); MW: 387.47; Yield: 53%; Yellow Solid; $^1$H NMR (CD$_3$OD δ): 1.41 (t, J = 6.0 Hz, 3H, CH$_3$), 3.26 (q, J = 6.0 Hz, 2H, CH$_2$), 3.78 (s, 3H, CH$_3$), 3.97 (s, 3H, CH$_3$), 4.37 (s, 2H, CH$_2$), 4.73 (s, 2H, CH$_2$), 7.33 (s, 1H, ArH), 7.46-7.52 (m, 3H, 3xArH), 7.66-7.69 (m, 1H, ArH), 7.84 (dd, 1H, J = 1.5 Hz & J = 9.0 Hz, ArH), 8.20-8.23 (m, 2H, 2xArH); MS-ESI m/z (% rel. int.): 388 ([MH]$^+$, 100); HPLC: Method A, detection UV 254 nm, RT = 4.12 min, peak area 95.0%. |
| SAO 33058 | (structure) | E (c) SAO 33034 (359 mg, 1.70 mmol); CH$_2$Cl$_2$ (50 mL); Dess Martin periodinane (755 mg, 1.78 mmol); 1 h at 4° C. then overnight at RT. | Filtration | 4-chloro-1-ethyl-1H-pyrazolo[3,4-b]pyridine-5-carbaldehyde (711 mg); MW: 209.64; Crude Yield: quantitative; Off-white Solid; $^1$H-NMR (CDCl$_3$, δ): 1.56 (t, 3H, J = 7.3 Hz, CH$_3$), 3.57-4.64 (q, 2H, J = 7.26 Hz, CH$_2$), 8.25 (s, 1H, ArH), 9.00 (s, 1H, ArH), 10.55 (s, 1H, HC═O); MS-ESI m/z (% rel. Int.): 210.2 ([MH]$^+$, 100); HPLC: Method A, detection UV 254 nm, RT = 5.44 min, peak area 97%. |
| ANP 57032A | (structure) | G (a) 7 (free base, 1.15 g, 3.33 mmol); N-phenyl bis-trifluoromethane sulfonimide (1.8 g, 5.04 mmol); Et$_3$N (931 μL, 6.66 mmol); DMF (5 mL); 40° C. for 15 h. | Chromatography SiO$_2$, CH$_2$Cl$_2$:MeOH = 100:0 to 98:2 | 2-((6,7-dimethoxyisoquinolin-4-yl)methyl)quinolin-8-yl trifluoromethanesulfonate (840 mg); MW: 478.44; Yield: 53%; Yellow Solid: R$_f$: 0.25 (CH$_2$Cl$_2$:MeOH = 98:2); $^1$H-NMR (CDCl$_3$, δ): 3.94 (s, 3H, OCH$_3$), 3.98 (s, 3H, OCH$_3$), 4.71 (s, 2H, CH$_2$), 7.17 (s, 1H, ArH), 7.39 (d, 1H, ArH, J = 8.6 Hz), 7.49-7.62 (m, 3H, 3xArH), 7.78 (d, 1H, ArH, J = 8.1 Hz), 8.04 (d, 1H, ArH, J = 8.6 Hz), 8.53 (s, 1H, ArH), 8.98 (s, 1H, ArH); $^{13}$C-NMR (CDCl$_3$, δ): 41.28, 55.97, 56.32, 102.65, 105.66, 116.86 (q, CF$_3$, J = 327.5 Hz), 121.06, 122.67, 124.87, 125.34, 125.58, 127.01, 127.93, 128.31, 131.83, 136.35, 140.12, 142.44, 145.79, 150.23, 153.24, 162.05. MS-ESI m/z (% rel. Int.): 479.2 ([MH]$^{+1}$, 100). HPLC: Method A, detection UV 254 nm, RT = 5.25 min, peak area 98.5%. |
| ANP 53184A | (structure) | G (a) 131 (1.00 g, 2.77 mmol); N-phenyl bis-trifluoromethane sulfonimide (1.50 g, 4.16 mmol); Et$_3$N (776 μL, 5.55 mmol); DMF (4 mL); 40° C. for 15 h. | Chromatography CH$_2$Cl$_2$:MeOH = 100:0 to 98:2 | 2-((6,7-dimethoxy-1-methylisoquinolin-4-yl)methyl)quinolin-8-yl trifluoromethanesulfonate (768 mg); MW: 492.47; Yield: 56%; White Solid; R$_f$: 0.25 (CH$_2$Cl$_2$:MeOH = 98:2); $^1$H-NMR (CDCl$_3$, δ): 2.89 (s, 3H, CH$_3$), 3.92 (s, 3H, OCH$_3$), 3.98 (s, 3H, OCH$_3$), 4.68 (s, 2H, CH$_2$), 7.24 (s, 1H, ArH), 7.37 (d, 1H, ArH, J = 8.6 Hz), 7.50 (t, 1H, ArH, J = 7.9 Hz), 7.56 (s, 1H, ArH), 7.59-7.61 (dd, 1H, ArH, J = 1.0 Hz, J = 7.7 Hz), 7.75-7.78 (dd, 1H, ArH, J = 1.2 Hz, J = 8.1 Hz), 8.01 (d, 1H, ArH, J = 8.6 Hz), 8.42 (s, 1H, ArH); $^{13}$C-NMR (CDCl$_3$, δ): 22.58, 41.32, 55.89, 56.23, 116.86, 121.02, 122.64, 123.32, 125.49, 125.59, 127.92, 128.31, 131.83, 136.25, 140.09, 141.52, 145.79, 149.61, 152.60, 155.80, 162.44; MS-ESI m/z (% rel. Int.): 493.2 ([MH]$^{+1}$, 100); HPLC: Method A, detection UV 254 nm, RT = 5.20 min, peak area 99.6%.? |

TABLE 5-continued

| Compound | FORMULA | General Procedure & Conditions | Work-Up & Purification | Analysis |
|---|---|---|---|---|
| RBO 51116 | (structure) | G (a) 83 (2.12 g, 5.61 mmol); N-phenylbis-trifluoromethane sulfonamide (3.03 g, 8.41 mmol); Et₃N (1.57 mL, 11.2 mmol); DMF (20 mL); 16 h at 25° C. | Chromatography SiO₂, CH₂Cl₂:EtOAc = 100:0 to 50:50 | 2-((1-ethyl-6,7-dimethoxyisoquinolin-4-yl)methyl)quinolin-8-yl trifluoromethanesulfonate (2.53 g); MW: 506.49; Yield: 80%; Pale Yellow Solid; Mp (° C.): 189.1-191.6; $^1$H NMR (CDCl₃, δ): 1.45 (t, J = 7.5 Hz, 3H, CH₃), 3.24 (q, J = 7.8 Hz, 2H, CH₂), 3.93 (s, 3H, CH₃), 3.98 (s, 3H, CH₃), 4.68 (s, 2H, CH₂), 7.31 (s, 1H, ArH), 7.38 (d, 1H, J = 8.7, ArH), 7.51 (d, 1H, J = 7.8, ArH), 7.60 (m, 2H, 2xArH), 7.77 (dd, 1H, J = 1.5 Hz, J = 8.1 Hz, ArH), 8.02 (d, 1H, J = 8.4 Hz, ArH), 8.46 (s, 1H, ArH); $^{13}$C-NMR (CDCl₃, δ): 13.19, 28.49, 41.30, 55.85, 56.18, 103.44, 103.97, 116.88, 120.99, 121.12, 122.52, 122.67, 125.40, 125.44, 127.88, 128.30, 132.17, 136.21, 140.08, 141.57, 145.77, 149.66, 152.56, 160.29, 162.41; MS-ESI m/z (% rel. int.): 507.2 ([MH]⁺, 100); HPLC: Method A, detection UV 254 nm, RT = 5.00 min, peak area 97.5% |
| LPO 55036C | (structure) | G (a) 5 (free base, 2.00 g, 5.14 mmol); N-phenyl bis-trifluoromethane sulfonimide (2.8 g 7.72 mmol); Et₃N (1.44 mL, 10.03 mmol); DMF (8 mL); overnight at 40° C. then N-phenyltrifluoromethanesulfonimide (700 mg, 1.93 mmol); Et₃N (600 μL, 4.30 mmol); 40° C. for another 5 h. | Chromatography SiO₂, CH₂Cl₂:EtOAc = 100:0 to 50:50 | 2-((6,7-dimethoxy-1-propylisoquinolin-4-yl)methyl)quinolin-8-yl trifluoromethanesulfonate (1.92 g); MW: 520.52; Yield: 85%; Pale Yellow Solid; Mp (° C.): 171.0; Rf: 0.30 (CH₂Cl₂:EtOAc = 5:5); $^1$H-NMR (CDCl₃, δ): 1.08 (t, 3H, J = 7.4 Hz, CH₃), 1.91 (sextuplet, 2H, J = 7.5 Hz CH₂), 3.18 (t, 2H, J = 7.8 Hz, CH₂), 3.92 (s, 3H, OMe), 3.98 (s, 3H, OMe), 4.67 (s, 2H, CH₂), 7.31 (s, 1H, ArH), 7.39 (d, 1H, J = 8.6 Hz, ArH), 7.52 (d, 1H, J = 1.3 Hz, ArH), 7.57-7.61 (m, 2H, 2xArH), 7.77 (dd, 1H, J = 8.1 Hz, J = 1.3 Hz, ArH), 8.02 (d, 1H, J = 8.6 Hz, ArH), 8.45 (s, 1H, ArH); $^{13}$C-NMR (CDCl₃, δ): 14.4, 22.6, 37.5, 41.4, 55.9, 56.2, 103.4, 104.1, 116.9, 121.0, 122.7, 122.8, 125.4, 125.5, 127.9, 128.3, 132.2, 136.3, 140.1, 141.6, 145.8, 149.6, 152.5, 159.4, 162.5; MS-ESI m/z (% rel. Int.): 521.3 ([MH]⁺¹, 100); HPLC: Method A, detection UV 254 nm, RT = 5.36 min, peak area 99%. |
| ECO 59060 | (structure) | G (a) 163 (840 mg, 2.15 mmol); N-phenyl bis-trifluoromethane sulfonimide (1.15 g, 3.23 mmol); Et₃N (601 μL, 4.30 mmol); DMF (6 mL); 37° C. for 15 h. | Chromatography SiO₂, CH₂Cl₂:MeOH = 100:0 to 98:2 | 2-((6,7-dimethoxy-1-(methoxymethyl)isoquinolin-4-yl)methyl)quinolin-8-yl trifluoromethanesulfonate (525 mg); MW: 522.49; Yield: 47%; Pale Yellow Solid; Mp (° C.): 171.9; $^1$H-NMR (CDCl₃, δ): 3.47 (s, 3H, CH₃O), 3.94 (s, 3H, CH₃O), 3.98 (s, 3H, CH₃O), 4.68 (s, 2H, CH₂), 5 00 (s, 2H, CH₂), 7 33 (d, 1H, J = 8.6 Hz, ArH), 7.49 (t, 1H, J = 8.0 Hz, ArH), 7.57 (m, 2H, 2xArH), 7.72 (d, 1H, J = 8.1 Hz, ArH), 7.96 (d, 1H, J = 8.6 Hz, ArH), 8.49 (s, 1H, ArH); $^{13}$C-NMR (CDCl₃, δ): 41.3, 55.8, 56.2, 58.3, 75.4, 102.5, 104.0, 116.8, 118.9 (J = 320.3 Hz, CF₃), 121.0, 122.6, 123.3, 125.5, 127.4, 127.9, 128.2, 132.5, 136.3, 140.0, 141.2, 145.7, 149.9, 152.8, 154.2, 162.0; MS-ESI m/z (% rel. Int.): 523.1 ([MH]⁺, 100); HPLC: Method A, detection UV 254 nm, RT = 4.90 min peak area 90.7 %. |
| RBO 56020 | (structure) | G (a) 95 (1.10 g, 2.94 mmol); DMF (15 mL); N-phenyl bis-trifluoromethane sulfonimide (1.57 g, 4.39 mmol); NEt₃ (0.79 mL, 5.68 mmol); overnight, RT | Chromatography SiO₂, CH₂Cl₂:EtOAc = 100:0 to 50:50 | 3-((1-ethyl-6,7-dimethoxyisoquinolin-4-yl)methyl)quinolin-6-yl trifluoromethanesulfonate (1.20 g); MW: 506.49; Yield: 80%; Off-White Solid; Rf: 0.2 (CH₂Cl₂:EtOAc = 50:50); $^1$H NMR (CD₃OD, δ): 1.43 (t, 3H, CH₃, J = 7.5 Hz), 3.22-3.29 (m, 2H, CH₂), 3.85 (s, 3H, OCH₃), 3.99 (s, 3H, OCH₃), 4.63 (s, 2H, CH₂), 7.25 (s, 1H, ArH), 7.51 (s, 1H, ArH), 7.69-7.72 (m, 1H, ArH), 7.94 (s, 1H, ArH), 8.14-8.23 (m, 3H, 3xArH), 8.98 (s, 1H, ArH); $^{13}$C NMR (CDCl₃, δ): 14.3, 29.1, 34.3, 56.4, 56.5, 103.7, 105.8, 120.0, 120.6 (q, J = 250.6 Hz), 123.9, 124.2, 127.9, 129.8, 132.2, 133.3, 136.7, 136.8, 141.5, 146.3, 148.9, 151.7, 154.2, 154.7, 161.9; MS-ESI m/z (% rel. int.): 507 ([MH]⁺, 100); HPLC: Method A, detection UV 254 nm, RT = 5.22 min, peak area 97.9%. |

TABLE 5-continued

| Compound | FORMULA | General Procedure & Conditions | Work-Up & Purification | Analysis |
|---|---|---|---|---|
| LPO 50012 | (structure) | G (b) 49 (free base, 316 mg, 0.76 mmol); POCl₃ (915 μL, 9.81 mmol); 100° C. for 2 h. | Chromatography SiO₂, cyclohexane:EtOAc = 70:30 to 50:50 | 2-chloro-3-((6,7-dimethoxy-1-propylisoquinolin-4-yl)methyl)-6-methoxyquinoline (241 mg); MW: 436.93; Yield: 73%; Pale Yellow Solid; Mp (° C.): 213.4; $R_f$: 0.15 (cyclohexane:EtOAc = 70:30); $^1$H-NMR (CDCl₃, δ): 1.12 (t, 3H, J = 7.4 Hz, CH₃), 1.93-2.01 (sextuplet, 2H, J = 7.7 Hz, CH₂), 3.24 (t, 2H, J = 7.7 Hz, CH₂), 3.80 (s, 3H, OCH₃), 3.85 (s, 3H, OCH₃), 4.03 (s, 3H, OCH₃), 4.50 (s, 2H, CH₂), 6.78 (d, 1H, J = 2.7 Hz, ArH), 6.98 (s, 1H, ArH), 7.29 (dd, 1H, J = 9.2 Hz, ArH), 7.40 (s, 1H, ArH), 7.47 (s, 1H, ArH), 7.88 (d, 2H, J = 9.2 Hz, ArH), 8.31 (s, 1H, 9.2 Hz, ArH); $^{13}$C-NMR (CDCl₃, δ): 14.4, 22.5, 33.4, 37.5, 55.5, 55.9, 56.0, 102.4, 104.5, 104.7, 122.8, 122.9, 125.0, 128.5, 129.5, 131.7, 132.1, 136.7, 142.2, 142.6, 148.1, 149.7, 152.7, 158.2, 159.5. MS-ESI m/z (% rel. Int.): 437.4/439.4 ([MH]$^{+1}$, 100/40); HPLC: Method A, detection UV 254 nm, RT = 4.69 min, peak area 99%. |
| LPO 50042C | (structure) | G (b) SSA 48042 (312 mg, 0.83 mmol); POCl₃ (1.0 mL, 10.77 mmol); 110° C. for 2 h. | Chromatography SiO₂, cyclohexane:EtOAc = 50:50 to 0:100 | 2-chloro-3-((6,7-dimethoxyisoquinolin-4-yl)methyl)-6-methoxyquinoline (191 mg); MW: 394.85; White Solid; Yield: 58%; $R_f$ = 0.30 (EtOAc); MS-ESI m/z (% rel. Int.): 395.3/397.3 ([MH]$^+$, 100/33); HPLC: Method A, detection UV 254 nm, RT = 4.33 min, peak area 99.5%. |

Procedures H for Preparation of Compounds 77, 113, 129, RBO 51118B, LPO 55056D, 152, 157, 167, 92, 96, 97 and 90 (Using Palladium)

a) Preparation of Compounds LPO 50016, 77, 113 and 129

A mixture of 2-chloroquinoline LPO 50012 or LPO 50042C, 2-(di-tert-butylphosphinobiphenyl), ethane-1,2-diamine or a 2 N EtNH$_2$ or MeNH$_2$ solution in THF, palladium (II) acetate, and tBuOK was dissolved in anhydrous toluene (see conditions in tables 6 and 7). The reaction mixture was stirred according the conditions described in tables 6 and 7. The solvent was evaporated and the residue was partitioned between CH$_2$Cl$_2$ (typically 175 mL) and a 1 M K$_2$CO$_3$ solution (typically 5 mL). The separated organic layer was washed with brine (20 mL), dried over MgSO$_4$, filtered and evaporated. The crude product was purified by column chromatography (SiO$_2$, see conditions in tables 6 and 7) to give, after evaporation and further drying under vacuum, the amino derivative LPO 50016, 77, 113 or 129.

b) Preparation of Compounds RBO 51118B, LPO 55056D, 152, 157 and 167

To a solution of the corresponding triflate RBO 51116, LPO 55036C, ANP 53184A, ANP 57032A or ECO 59060 in toluene were added Pd$_2$(dba)$_3$, (+/−)-2,2-bis(diphenylphosphino)-1,1-binaphthyl (BINAP), benzophenone imine and Cs$_2$CO$_3$ (see conditions in tables 6 and 7). The mixture was stirred according to the conditions described in tables 6 and 7. After cooling, the mixture was filtered through celite and the obtained cake was washed with EtOAc (typically 20 mL). After evaporation of all the volatiles, the residue was diluted with EtOAc (typically 30 mL), washed with brine (typically 3×10 mL), dried over Na$_2$SO$_4$, filtered and evaporated at 40° C. under vacuum. The obtained crude product was treated with a 5 N HCl solution (typically 2 mL) in THF (typically 20 mL) and stirred at RT for 4 h, then the reaction mixture was neutralized with a saturated aqueous NaHCO$_3$ solution to reach pH=7. The solvent were removed under reduced pressure and the resulting aqueous layer was extracted using CH$_2$Cl$_2$ (typically 3×75 mL). The organics layers were combined then washed with H$_2$O (typically 3×20 mL), brine (typically 3×20 mL), dried over Na$_2$SO$_4$, filtered and evaporated. The obtained residue was purified by flash chromatography (SiO$_2$, see conditions in tables 6 and 7) to give the aminoquinoline RBO 51118B, LPO 55056D, 152, 157 or 167 after further drying under vacuum pump.

c) Preparation of Compounds 92, 96, 97, and 152

To a solution of the corresponding triflate RBO 51116, RBO 56020 or ANP 53184A in 1,4-dioxane was added tert-butyl carbamate or pyrrolidinone, cesium carbonate, Xantphos and Pd$_2$dba$_3$ at RT under nitrogen flux (see conditions in table 7). The reaction mixture was stirred according to the conditions described in table 7. After cooling, the reaction mixture was filtrated on celite and the solvent was removed to give a residue. This residue was purified by column chromatography to give, after evaporation and drying, a tert-butyl carbamate intermediate (SiO$_2$, eluent: CH$_2$Cl$_2$:MeOH=100:0 to 98:2) or the pyrrolidinone 152 (SiO$_2$, eluent: CH$_2$Cl$_2$:EtOAc=100:0 to 0:100).

The obtained tert-butyl carbamate was then deprotected by stirring with a solution of TFA (1 mL) in CH$_2$Cl$_2$ (10 mL) for 1 h at RT. After concentration to dryness, the residue was taken back in EtOAc (150 mL) and a 1 M K$_2$CO$_3$ solution (50 mL) was added. The separated organic layer was washed with H$_2$O (3×20 mL), brine (3×20 mL), dried over Na$_2$SO$_4$, filtered and evaporated to provide a residue. This residue was purified by flash chromatography (SiO$_2$, see conditions in table 7) to give, after evaporation after further drying under vacuum, the aminoquinoline 92, 96 or 97 (see table 7).

d) Preparation of Nitrile 90

To a solution of the triflate RBO 51116 in DMF in a 20 mL microwave vial equipped with a magnetic stirrer was added Zn(CN)$_2$ followed by Pd(PPh$_3$)$_4$ (see exact conditions in table 7). The mixture was heated under microwave irradiation at 180° C. for 15 min then cooled to 25° C. The reaction mixture was then hydrolysed with a 2 M aq. H$_2$SO$_4$ solution (10 mL) at RT for 20 min. The mixture was filtered through celite and the cake was washed with CH$_2$Cl$_2$ (3×50 mL). After concentration to dryness, the residue was taken back in CH$_2$Cl$_2$ (50 mL) and neutralized with a saturated aqueous NaHCO$_3$ solution (until pH=9). The separated organic layer was washed with water (3×10 mL), brine (10 mL), dried over Na$_2$SO$_4$ filtered and concentrated. Purification by flash chromatography (SiO$_2$, see exact conditions in table 7) gave, after evaporation and further drying to the vacuum, the nitrile 90 (see table 7)

Procedure I for Preparation of Sulfamides 84, 85, 94, 100, 119, 156, 159

To a solution of the corresponding amino derivative RBO 51118B, LPO 55056D, RBO 51194, 96, 167, 152 or 157 in 1,4-dioxane (20 mL) was added sulfamide. The mixture was heated according to the conditions described in the table 7. After cooling to RT, the volatiles were removed at 50° C. under reduced pressure to provide a residue that was purified by flash chromatography (SiO$_2$, see exact conditions in table 7) to give, after evaporation and further drying under vacuum, the sulfamide 84, 85, 94, 100, 119, 156 or 159 (see table 7).

Procedure J for Preparation of Benzoxazoles LPO 55056D, ANP 53142B, ANP 53192A, 114, 115, 153 and 170

To a solution of ANP 49184A or ECO 59064 in MeOH was added the corresponding aldehyde at RT in an ace pressure tube (see aldehyde and conditions in tables 6 and 7). The reaction mixture was stirred according to the conditions described in tables 6 and 7. After cooling to RT, the solvent was evaporated and the residue was dissolved in CH$_2$Cl$_2$ and DDQ was added (see exact conditions in table 7). This reaction mixture was stirred at RT for 30 min and CH$_2$Cl$_2$ (100 mL) and a 1 M K$_2$CO$_3$ aqueous solution (20 mL) were added. The separated organic layer was washed with brine (50 mL), dried over MgSO$_4$, filtered and evaporated. The residue was purified by column chromatography (SiO$_2$, see exact conditions in tables 6 and 7) to give, after evaporation and further drying under vacuum, the benzoxazole LPO 55056D, ANP 53142B, ANP 53192A, 114, 115, 153 or 170 (see table 7).

Procedure K for Preparation of Tetrazoles 121 and 127

To a solution of the nitrile LPO 50040C or LPO 50172C in DMF were added ammonium chloride and sodium azide at RT in ace pressure tube (see conditions in table 7). The reaction mixture was stirred according to the conditions described in table 7. After cooling to RT, the solvent was evaporated and a 2 N HCl solution (2.5 mL) was added. This solution was stirred RT for 30 min, neutralized by a 1 M K$_2$CO$_3$ aqueous solution (35 mL) and extracted with n-butanol (70 mL). The separated organic layer was washed with brine (20 mL), dried over MgSO$_4$, filtered and evaporated. The residue was purified by column chromatography (SiO$_2$, see

TABLE 6

| Compound | FORMULA | General Procedure & Conditions | Work-Up & Purification | Analysis |
|---|---|---|---|---|
| LPO 50016 | (structure) | H (a) LPO 50012 (120 mg, 0.28 mmol); 2-(di-tert-butylphosphinobiphenyl) (0.8 mg, 2.75 μmol); ethane-1,2-diamine (27.6 μL, 0.41 mmol); Pd(OAc)$_2$ (0.6 mg, 2.75 μmol); tBuOK (43.2 mg, 0.38 mmol); toluene (1.5 mL); 100° C. for 8 h (microwave). | Not purified | N$^1$-(3-((6,7-dimethoxy-1-propylisoquinolin-4-yl)methyl)-6-methoxyquinolin-2-yl)ethane-1,2-diamine (); MW: 460.57; Yield: quantitative; Brown Solid; MS-ESI m/z ([MH]$^+$, 100); HPLC: Method A, detection UV 254 nm, RT = 3.36 mn, peak area 80%. |
| RBO 51118B | (structure) | H (b) RBO 51116 (500 mg, 0.99 mmol); THF (15 mL); Pd$_2$dba$_3$ (53 mg, 0.058 mmol); BINAP (123 mg, 0.20 mmol); benzophenone imine (364 μL, 2.17 mmol); Cs$_2$CO$_3$ (643 mg, 1.97 mmol); overnight under reflux (115° C.). | Chromatography SiO$_2$ EtOAc:CH$_2$Cl$_2$ = 100:0 to 50:50 | 2-((1-ethyl-6,7-dimethoxyisoquinolin-4-yl)methyl)quinolin-8-amine (300 mg); MW: 373.45; Yield: 80%; Pale Yellow Solid; Mp (° C.): 231.3-233.8; $^1$H NMR (CDCl$_3$, δ): 1.45 (t, J = 7.5 Hz, 3H, CH$_3$), 3.24 (q, J = 7.8 Hz, 2H, CH$_2$), 3.87 (s, 3H, CH$_3$), 3.98 (s, 3H, CH$_3$), 4.60 (s, 2H, CH$_2$), 4.99 (bs, 2H, NH$_2$), 6.91 (dd, 1H, J = 1.2 Hz, J = 7.5 Hz, ArH), 7.06 (dd, 1H, J = 1.2 Hz, J = 8.1 Hz, ArH), 7.21 (d, 1H, J = 8.4 Hz, ArH), 7.26 (m, 1H, ArH), 7.31 (s, 1H, ArH), 7.52 (s, 1H, ArH), 7.87 (d, J = 8.4 Hz, 1H, ArH), 8.41 (s, 1H, ArH); $^{13}$C NMR (CDCl$_3$, δ): 13.23, 28.51, 41.26, 55.87, 56.03, 103.70, 103.92, 110.22, 115.90, 121.31, 122.56, 126.20, 126.84, 127.21, 132.30, 136.62, 137.36, 141.53, 143.45, 149.48, 152.18, 157.83, 159.98; MS-ESI m/z (% rel. int.): 374.3 ([MH]$^+$, 100); HPLC: Method A, detection UV 254 nm, RT = 3.94 min, peak area 97.1% |
| LPO 55056D | (structure) | H (b) LPO 55036C (500 mg, 0.96 mmol); 1,4-dioxane (20 mL); Pd$_2$dba$_3$ (53 mg, 0.058 mmol); BINAP (120 mg, 0.192 mmol); benzophenone imine (355 μL, 2.11 mmol); Cs$_2$CO$_3$ (626.2 mg, 1.92 mmol); overnight under reflux (115° C.). | Chromatography SiO$_2$ EtOAc:CH$_2$Cl$_2$ = 100:0 to 50:50 | 2-((6,7-dimethoxy-1-propylisoquinolin-4-yl)methyl)quinolin-8-amine (244 mg); MW: 387.47; Yield: 65%; Brown Solid; Mp (° C.): 208.8; R$_f$: 0.25 (CH$_2$Cl$_2$:EtOAc = 5:5); $^1$H-NMR (CDCl$_3$, δ): 1.08 (t, 3H, J = 7.4 Hz, CH$_3$), 1.91 (sextuplet, 2H, J = 7.5 Hz, CH$_2$), 3.18 (t, 2H, J = 7.8 Hz, CH$_2$), 3.87 (s, 3H, OMe), 3.98 (s, 3H, OMe), 4.99 (s, 2H, CH$_2$), 6.91 (dd, 1H, J = 7.5 Hz, J = 1.2 Hz, ArH), 7.1 (dd, 1H, J = 8.1 Hz, J = 1.1 Hz, ArH), 7.20-7.31 (m, 4H, 4xArH), 7.52 (s, 1H, ArH), 7.9 (d, 1H, J = 8.5 Hz, ArH), 8.41 (s, 1H, ArH); $^{13}$C-NMR (CDCl$_3$, δ): 14.4, 22.6, 37.5, 41.3, 55.9, 56.1, 103.6, 104.1, 110.2, 115.9, 121.3, 122.9, 126.2, 126.9, 127.2, 132.3, 136.6, 137.3, 141.5, 143.4, 149.4, 152.2, 157.8, 159.1; MS-ESI m/z (% rel. Int.): 388.3 ([MH]$^+$, 100); HPLC: Method A, detection UV 254 nm, RT = 4.72 min, peak area 99%. |

TABLE 6-continued

| Compound | FORMULA | General Procedure & Conditions | Work-Up & Purification | Analysis |
|---|---|---|---|---|
| ANP 53142B | [Structure: 5-((6,7-dimethoxyisoquinolin-4-yl)methyl)-2-(4-nitrophenyl)benzo[d]oxazole] | J; ANP 49184A (300 mg, 0.97 mmol); 4-nitrobenzaldehyde (146 mg, 0.97 mmol); MeOH (30 mL); 60° C. for 15 h. Then solvent was evaporated and residue was dissolved in CH$_2$Cl$_2$ (30 mL) and DDQ (241 mg, 1.06 mmol) was added; RT for 3 h. | Chromatography SiO$_2$ CH$_2$Cl$_2$:MeOH = 100:0 to 98:2 | 5-((6,7-dimethoxyisoquinolin-4-yl)methyl)-2-(4-nitrophenyl)benzo[d]oxazole (63.5 mg); MW: 441.44; Yield: 14%; Yellow Solid; Mp (° C.): 279.5–280.8; R$_f$: 0.25 (CH$_2$Cl$_2$:MeOH = 98:2); $^1$H-NMR (CDCl$_3$, δ): 3.85 (s, 3H, OCH$_3$), 4.01 (s, 3H, OCH$_3$), 4.47 (s, 2H, CH$_2$), 7.08 (s, 1H, ArH), 7.63 (s, 1H, ArH), 7.31 (dd, 1H, ArH, J = 1.61 Hz, J = 8.43 Hz), 7.53 (d, 1H, ArH, J = 8.43 Hz), 8.34–8.39 (m, 5H, 5xArH), 9.0 (s, 1H, ArH); $^{13}$C-NMR (CDCl$_3$, δ): 36.63, 55.93, 56.03, 101.89, 106.0, 110.82, 120.22, 124.20 (2xC), 124.91, 126.88, 128.13, 128.34 (2xC), 131.29, 132.71, 137.36, 142.36, 142.81, 149.41, 149.64, 149.75, 150.07, 152.94, 161.10; MS-ESI m/z (% rel. Int.): 442.3 ([MH]$^{+1}$, 100); HPLC: Method A, detection UV 254 nm, RT = 5.01 min, peak area 97.3%. |
| ANP 53192A | [Structure: methyl 3-(5-((6,7-dimethoxyisoquinolin-4-yl)methyl)benzo[d]oxazol-2-yl)benzoate] | J; ANP 49184A (200 mg, 0.64 mmol); methyl 3-formylbenzoate (105 mg, 0.64 mmol); MeOH (10 mL); 60° C. for 15 h. Then solvent was evaporated and residue was dissolved in CH$_2$Cl$_2$ (20 mL) and DDQ (161 mg, 0.71 mmol) was added; RT for 1 h. | Chromatography SiO$_2$ CH$_2$Cl$_2$:MeOH = 100:0 to 97:3 | methyl 3-(5-((6,7-dimethoxyisoquinolin-4-yl)methyl)benzo[d]oxazol-2-yl)benzoate (108.4 mg); MW: 454.47; Yield: 29%; Yellow Pale Solid; R$_f$: 0.25 (CH$_2$Cl$_2$:MeOH = 97:3); $^1$H-NMR (CDCl$_3$, δ): 3.84 (s, 3H, CH$_3$), 3.97 (s, 3H, OCH$_3$), 4.01 (s, 3H, OCH$_3$), 4.46 (s, 2H, CH$_2$), 7.08 (s, 1H, ArH), 7.22–7.27 (m, 2H, 2xArH), 7.51 (d, 1H, ArH, J = 8.44 Hz), 7.57–7.63 (m, 2H, 2xArH), 8.18–8.21 (td, 1H, ArH, J = 1.35 Hz, J = 8.02 Hz), 8.35 (s, 1H, ArH), 8.38–8.41 (dt, 1H, ArH, J = 1.29 Hz, J = 7.83 Hz), 8.87 (s, 1H, ArH), 9.0 (s, 1H, ArH); MS-ESI m/z (% rel. Int.): 455.3 ([MH]$^{+1}$, 100); HPLC: Method A, detection UV 254 nm, RT = 5.14 min, peak area 85.2%. |
| ANP 53174B | [Structure: methyl 2-(5-((6,7-dimethoxyisoquinolin-4-yl)methyl)benzo[d]oxazol-2-yl)benzoate] | J; ANP 49184A (300 mg, 0.97 mmol); methyl 2-formylbenzoate (135 μL, 0.97 mmol); MeOH (15 mL); 60° C. for 15 h. Then solvent was evaporated and residue was dissolved in CH$_2$Cl$_2$ (30 mL) and DDQ (241 mg, 0.97 mmol) was added; RT for 1 h. | Chromatography SiO$_2$ CH$_2$Cl$_2$:MeOH = 100:0 to 90:10 | methyl 2-(5-((6,7-dimethoxyisoquinolin-4-yl)methyl)benzo[d]oxazol-2-yl)benzoate (193 mg); MW: 454.47; Yield: 43%; Yellow Pale Solid; Mp (° C.): 84; R$_f$: 0.25 (EtOAc:CH$_2$Cl$_2$ = 9:1); $^1$H-NMR (CDCl$_3$, δ): 3.83 (s, 3H, CH$_3$), 3.86 (s, 3H, OCH$_3$), 4.01 (s, 3H, OCH$_3$), 4.46 (s, 2H, CH$_2$), 7.10 (s, 1H, ArH), 7.22–7.25 (m, 2H, ArH), 7.46 (d, 1H, ArH, J = 6.54 Hz), 8.02 (d, 1H, ArH, J = 5.94 Hz), 8.34 (s, 1H, ArH), 9.0 (s, 1H, ArH); $^{13}$C-NMR (CDCl$_3$, δ): 36.67, 52.65, 55.93, 56.02, 102.02, 105.99, 110.45, 120.04, 124.90, 125.87, 126.42, 128.38, 129.21, 130.00, 130.94, 131.04, 131.36, 132.62, 136.62, 142.31, 142.76, 149.54, 149.69, 150.06, 152.91, 162.49, 168.45; MS-ESI m/z (% rel. Int.): 455.3 ([MH]$^{+1}$, 100); HPLC: Method A, detection UV 254 nm, RT = 4.72 min, peak area 99.1%. |
| LPO 55012B | [Structure: 2-chloro-3-(1,3-dioxolan-2-yl)quinolin-6-ol] | L; LPO 50188A (388 mg, 1.87 mmol); PTSA (18 mg, 0.09 mmol); ethane-1,2-diol (511 μL, 9.16 mmol); toluene (8 mL); 150° C. for 3 h. | Not purified | 2-chloro-3-(1,3-dioxolan-2-yl)quinolin-6-ol (435 mg); MW: 251.67; Crude Yield: 92 %; Yellow Solid; MS-ESI m/z (% rel. Int.): 252.2/254.2 ([MH]$^{+1}$, 100/33); HPLC: Method A, detection UV 254 nm, RT = 4.32 min, peak area 61.1%. |
| TTA 46034 | [Structure: 2-(1,3-dioxolan-2-yl)quinolin-8-ol] | L; 8-Hydroxyquinoline-2-carbaldehyde (1.00 g, 5.77 mmol); PTSA (60 mg, 0.29 mmol); ethane-1,2-diol (1.8 g, 29 mmol); toluene (30 mL); 150° C. for 4 h. | Not purified | 2-(1,3-dioxolan-2-yl)quinolin-8-ol (1.17 g) MW: 217.22; Yield: 94%, Pale Pink Solid. $^1$H-NMR (CDCl$_3$, δ): 4.12–4.27 (m, 4H, 2xCH$_2$O), 5.99 (s, 1H, CH), 7.18 (dd, 1H, J = 7.5 Hz & 1.2 Hz, ArH), 7.33 (dd, 1H, J = 8.2 Hz & 1.1 Hz, ArH), 7.47 (s, 1H, J = 8.1 Hz, ArH), 7.66 (d, 1H, J = 8.5 Hz, ArH), 8.12 (signal, 1H, OH), 8.21 (s, 1H, J = 8.5 Hz, ArH); $^{13}$C-NMR (CDCl$_3$, δ): 65.81 (2xC), 104.16, 110.37, 117.73, 118.83, 128.23, 128.63, 137.16, 137.30, 152.33, 155.18; MS-ESI m/z (% rel. Int.): 218.2 ([MH]$^+$, 100); HPLC: Method A, detection UV 254 nm, RT = 4.17 min, peak area 95.9%. |

TABLE 6-continued

| Compound | FORMULA | General Procedure & Conditions | Work-Up & Purification | Analysis |
|---|---|---|---|---|
| TTA 46118A | (methyl 4-(1,3-dioxolan-2-yl)benzoate structure) | L<br>Methyl 4-formylbenzoate (4.00 g, 24.0 mmol); PTSA (300 mg, 1.2 mmol); ethane-1,2-diol (7.6 g, 120 mmol); toluene (130 mL); 160° C. for 4 h. | Not purified | methyl 4-(1,3-dioxolan-2-yl)benzoate (4.8 g) MW: 208.21; Yield: 96%; Colorless Oil; R$_f$: 0.30 (cyclohexane:EtOAc = 80:20); $^1$H-NMR (CDCl$_3$, δ): 3.92 (s, 3H, CH$_3$), 4.05-4.13 (m, 4H, 2xCH$_2$), 5.86 (s, 1H, CH), 7.55 (d, 2H, J = 8.2 Hz, ArH), 8.05 (d, 2H, J = 8.2 Hz, 2xArH); $^{13}$C-NMR (CDCl$_3$, δ): 52.11, 65.33 (2xC), 102.94, 126.44 (2xC), 129.61 (2xC), 130.76, 142.82, 166.69; MS-ESI m/z (% rel. Int.): 209.0 ([MH]$^{+1}$, 100). HPLC: Method A, detection UV 254 nm, RT = 4.71 min, peak area 82.3%. |
| LPO 50188A | (2-chloro-6-hydroxyquinoline-3-carbaldehyde structure) | M<br>2-chloro-6-methoxyquinoline-3-carbaldehyde (1.0 g, 4.5 mmol); CH$_2$Cl$_2$ (10 mL); 1M BBr$_3$ in CH$_2$Cl$_2$ (13.5 mL, 13.5 mmol); −78° C. for 10 min then RT for 2 h. | Chromatography SiO$_2$ CH$_2$Cl$_2$:MeOH = 100:0 to 98:2 | 2-chloro-6-hydroxyquinoline-3-carbaldehyde (396 mg); MW: 207.61; Yield: 42%; Yellow Solid; MS-ESI m/z (% rel. Int.): 208.1/210.0 ([MH]$^{+1}$, 100/33); HPLC: Method A, detection UV 254 nm, RT = 4.32 min, peak area 88.5%. |
| ECO 55098 | (2-chloro-3-(dimethoxymethyl)quinolin-6-ol structure) | M<br>2-chloro-6-methoxyquinoline-3-carbaldehyde (4.5 g, 20.3 mmol); CH$_2$Cl$_2$ (76 mL); 1M BBr$_3$ in CH$_2$Cl$_2$ (60 mL, 60.9 mmol); −78° C. for 2 h then RT for 3 h. Then 0.78N HCl in MeOH (26 mL); RT for 1 h. Then NH$_4$OH 7N in MeOH (3.7 mL); 0° C. for 10 min until pH = 7. | Salts were precipitated in CH$_2$Cl$_2$:MeOH = 9:1 (30 mL) and were filtered off; Filtrate was evaporated to give the title compound; Not further purified. | 2-chloro-3-(dimethoxymethyl)quinolin-6-ol (4.7g); MW: 253.05; Yield : 91%, Brown Solid. $^1$H- NMR (CD$_3$OD, δ): 3.44 (s, 6H, CH$_3$O), 5.67 (s, 1H, CHO), 7.20 (d, 1H, ArH), 7.36-7.45 (dd, 1H, ArH), 8.26 (d, 1H, ArH), 8.44 (s, 1H, ArH). MS-ESI m/z (% rel. Int.): 254.1, 256.1 ([MH]$^+$, 100/33); HPLC: Method A, detection UV 254 nm, TR = 4.72 min, peak area 99.1%. |
| LPO 50180C | (2-(1,3-dioxolan-2-yl)-5-(trifluoromethyl)quinolin-8-ol structure) | N (a)<br>TTA 46034 (500 mg, 2.30 mmol); tert-butyl hydroperoxide 70% in water (1.5 g, 16.11 mmol); sodium trifluoromethanesulfinate (1.8 g, 11.51 mmol); CH$_3$CN (5 mL); H$_2$O (2.5 mL); RT for 1.5 h. | Chromatography SiO$_2$, cyclohexane:EtOAc = 100:0 to 50:50; then chromatography RP18, CH$_3$CN:H$_2$O 100:0 to 50:50 | 2-(1,3-dioxolan-2-yl)-5-(trifluoromethyl)quinolin-8-ol (50.3 mg); MW: 285.22; Yield: 6%; White Solid; Mp (° C.): 102.7; R$_f$: 0.3 (cyclohexane:EtOAc = 5:5); $^1$H-NMR (CDCl$_3$, δ): 4.10-4.28 (m, 4H, 2xCH$_2$), 5.99 (s, 1H, CH), 7.17 (d, 1H, ArH, J = 8.1 Hz), 7.79 (d, 1H, ArH, J = 8.9 Hz), 7.85 (dd, 1H, ArH, J = 0.8 Hz, J = 8.1 Hz) 8.53 (dd, 1H, ArH, J = 1.8 Hz, J = 8.9 Hz); $^{13}$C-NMR (CDCl$_3$, δ): 103.67, 108.51, 116.60 (q, CCF$_3$, J = 31.3 Hz), 120.28, 1244 (q, CF$_3$, J = 272.2 Hz), 125.0, 127.46 (q, CH$_{Ar}$, J = 5.74 Hz), 134.34, 137.22, 155.52, 156.02; MS-ESI m/z (% rel. Int.): 286.1 ([MH]$^{+1}$, 100); HPLC: Method A, detection UV 254 nm, RT = 5.54 min, peak area 98.2%. |
| ECO 55152 | (3-(dimethoxymethyl)-5-(trifluoromethyl)quinolin-6-ol structure) | N (b)<br>ECO 55108C (609 mg); Ir(dF.ppy)$_3$ (7.3 mg, 9.56 μmol); K$_2$HPO$_4$ (250 mg, 1.44 mmol); triflyl chloride (203 μL, 1.91 mmol); CH$_3$CN (4.5 mL); 28 W compact fluorescent light bulb (1746 lumens) at 33° C. for 20 h under Ar. | Chromatography SiO$_2$, cyclohexane:EtOAc = 100:0 to 50:50 | 3-(dimethoxymethyl)-5-(trifluoromethyl)quinolin-6-ol (442 mg); MW: 287.23; Yield: 40%; Orange Solid; Mp (° C.): 154.4; 1H-NMR (CDCl$_3$, δ): 3.41 (s, 3H, CH$_3$O), 5.67 (s, 1H, CHO), 7.46 (d, 1H, J = 9.3 Hz, ArH), 8.07 (d, 1H, J = 9.3 Hz, ArH), 8.57 (s, 1H, ArH), 8.77 (s, 1H, ArH); $^{13}$C-NMR (CDCl$_3$, δ): 53.5 (2xC), 102.8, 107.9 (q, J = 29.5 Hz, CCF$_3$), 124.3, 126.5 (q, J = 274 Hz, CF$_3$), 127.4, 131.5, 134.1, 135.1, 143.7, 147.6, 157.5; MS-ESI m/z (% rel. Int.): 288.0 ([MH]$^{+1}$, 100); HPLC: Method A, detection UV 254 nm, RT = 4.37 min, peak area 99.5%. |
| SSA 48036 | (2-hydroxy-6-methoxyquinoline-3-carbaldehyde structure) | O<br>2-Chloro-6-methoxy-quinoline-3-carbaldehyde (1.5 g, 6.77 mmol); H$_2$O (30 mL); 37% HCl (60 mL); 100° C. for 6 h, then RT for 15 h. | Filtration of precipitate | 2-hydroxy-6-methoxyquinoline-3-carbaldehyde (1.15 g); MW: 239.66; Yield: 71%; Yellow Solid; Mp (° C.): 287.4; $^1$H-NMR (DMSO-d$_6$, δ): 3.79 (s, 3H, OCH$_3$), 7.31 (d, 2H, J = 8.8 Hz & 2.1 Hz, ArH), 7.46 (d, 1H, J = 2.1 Hz, ArH), 8.43 (s, 1H, ArH), 10.24 (s, 1H, CHO), 12.15 (signal, 1H, Ar- OH); MS-ESI m/z (% rel. Int.): 204.1 ([MH]$^{+1}$, 100); HPLC: Method A, detection UV 254 nm, RT = 3.69 min, peak area 98%. |

TABLE 6-continued

| Compound | FORMULA | General Procedure & Conditions | Work-Up & Purification | Analysis |
|---|---|---|---|---|
| TTA 461180 | [structure: 4-(hydroxymethyl)benzaldehyde, OHC-C6H4-CH2OH] | O<br>TTA 46118B (3.4 g, 18.9 mmol); 1.5N HCl (64 mL); MeOH (40 mL); 30° C. for 1 h. | Not purified | 4-(hydroxymethyl)benzaldehyde (2.0 g); MW: 136.15; Crude Yield: 79%; White Solid; $R_f$: 0.12 (cyclohexane:EtOAc = 80:20); $^1$H-NMR (CDCl$_3$, δ): 2.03 (t, 1H, J = 5.11 Hz, OH), 4.63 (d, 1H, J = 5.14 Hz, CH$_2$), 7.53 (d, 2H, J = 8.01 Hz, ArH), 7.87 (d, 2H, J = 8.20 Hz, ArH), 10.0 (s, 1H, CHO); $^{13}$C-NMR (CDCl$_3$, δ): 64.40, 126.95 (2xC), 130.00 (2xC), 135.53, 148.04, 192.25; MS-ESI m/z (% rel. Int.): 137.1 ([MH]$^{+1}$, 100). HPLC: Method A, detection UV 254 nm, RT = 3.08 min, peak area 94.2%. |
| LPO 55010B | [structure: quinoline-isoquinoline compound with ethoxyamine and dimethoxy groups] | P<br>LPO 50192C (58 mg, 0.10 mmol); EtOH (1 mL); hydrazine hydrate (100 pL, 2.06 mmol); 80° C. for 2 h. | Not purified | MW: 431.53; Crude Yield: quantitative; Yellow Solid; MS-ESI m/z (% rel. Int.): 432.4 ([MH]$^{+1}$, 100); HPLC: Method A, detection UV 254 nm, RT = 3.67 min, peak area 90%. | conditions in table 7) to give, after evaporation and further drying under vacuum, the tetrazole 121 or 127 (see table 7).

Procedure L for Preparation of Acetals LPO 55012B, TTA 46034 and TTA 46118a

A solution of the aldehyde (LPO 50188A, 8-hydroxyquinoline-2-carbaldehyde or methyl 4-formylbenzoate) in ethylene glycol and p-toluenesulfonic acid monohydrate (PTSA) were placed in a 250 mL round-bottom flask and toluene was added (see conditions in table 6). The mixture was heated under reflux in a Dean-Stark apparatus (according to the conditions described in table 6) until complete separation of water was effected. Toluene was evaporated then EtOAc (300 mL) and a 1 M aqueous $NaHCO_3$ solution (20 mL) were added. The separated organic layer was washed with brine (20 mL), dried over $MgSO_4$, filtered and evaporated. After further drying under vacuum, the acetal LPO 55012B, TTA 46034 or TTA 46118A (see table 6) was obtained.

Procedure M for Preparation of Compounds LPO 50188a and ECO 55098

To a solution of 2-chloro-6-methoxyquinoline-3-carbaldehyde in $CH_2Cl_2$ was added drop wise at −78° C. a 1 M $BBr_3$ solution in $CH_2Cl_2$ (see conditions in table 6). The reaction mixture was stirred at −78° C. to RT (see conditions in table 6). The reaction mixture was quenched with ice and stirred at RT for another 30 min then a saturated $NaHCO_3$ solution (400 mL) was slowly added and the aqueous layer was extracted with $CH_2Cl_2$ (3×350 mL). The combined organic layers were washed with brine (30 mL), dried over $MgSO_4$, filtered and solvent was evaporated to give crude LPO 50188A. The crude product was purified by column chromatography ($SiO_2$, see conditions in table 6) to give after evaporation and further drying under vacuum pump, LPO 50188A as a yellow solid.

Crude LPO 50188A was dissolved in a 0.78 N HCl solution in MeOH (26 mL). This reaction mixture was stirred at RT for 1 h. At 0° C., a 7 N $NH_4OH$ solution in MeOH (3.7 mL) was slowly added (until pH=7) and the solvent was evaporated. A mixture of $CH_2Cl_2$:MeOH=9:1 (30 mL) was added and the precipitate was filtered off and washed with a mixture of $CH_2Cl_2$:MeOH=9:1 (70 mL). The filtrate was evaporated and dried under vacuum to give crude ECO 55098 (see table 6).

Procedures N for Preparation of Compounds LPO 50180C and ECO 55152 a) Preparation of Compound LPO 50180C 2-(1,3-Dioxolan-2-yl)quinolin-8-ol TTA 46034 (500 mg, 2.30 mmol), tert-butyl hydroperoxide (70% solution in water, 1.5 mL, 16.11 mmol) and sodium trifluoromethanesulfinate (1.8 g, 11.51 mmol) were dissolved in $CH_3CN$ (5 mL) and $H_2O$ (2.5 mL) in a round bottom flask. This reaction mixture was stirred at RT for 1.5 h then $H_2O$ (10 mL) and a 1 M aqueous $NaHCO_3$ solution (5 mL) were added and this mixture was extracted with $CH_2Cl_2$ (3×70 mL). The combined organic layers were washed with brine (10 mL), dried over $MgSO_4$, filtered and evaporated. The crude product was purified by two successive column chromatography ($SiO_2$, eluent cyclohexane:EtOAc=100:0 to 50:50 then RP18 $CH_3CN$:$H_2O$=100:0 to 50:50) to give, after evaporation and further drying under vacuum in presence of $P_2O_5$, 2-(1,3-dioxolan-2-yl)-5-(trifluoromethyl)quinolin-8-ol LPO 50180C (see table 6).

b) Preparation of Compound ECO 55152

8 Wheaton vials were charged with Ir(dF.ppy)$_3$ (7.3 mg, 9.56 µmol) and $K_2HPO_4$ (250 mg, 1.44 mmol) and 3-(dimethoxymethyl)quinolin-6-ol ECO 55108C (105 mg, 0.48 mmol) in $CH_3CN$ (4.5 mL). This reaction mixture was cooled at −78° C. and degassed under vacuum then flushed at RT with argon (3 folds). Triflyl chloride (203 µL, 1.91 mmol) was added and the vials were sealed and exposed to light (28W compact fluorescent light bulb (1746 lumens)). The reaction mixture was stirred 20 h at 34° C. then was quenched with $H_2O$ (80 mL) and extracted with $CH_2Cl_2$ (3×70 mL). The combined organic layers were washed with brine (80 mL), dried over $MgSO_4$, filtered and evaporated. The crude product was purified by column chromatography ($SiO_2$, cyclohexane:EtOAc=100:0 to 50:50) to give, after evaporation and further drying, ECO 55152 (see table 6).

Procedure O for Preparation of Compounds SSA 48036 and TTA 46118C

2-Chloro-6-methoxy-quinoline-3-carbaldehyde or TTA 46118B was dissolved in $H_2O$ or MeOH then an HCl solution was added (see conditions table 6). The reaction mixture was stirred according to the conditions described in table 6. For the reaction involving 2-chloro-6-methoxy-quinoline-3-carbaldehyde, a precipitate appeared that was filtered and washed with a minimum amount of water, to give, after further drying under vacuum and in presence of $P_2O_5$, LPO 43136A (see table 6). For the reaction involving TTA 461188 (see table 6), the reaction mixture was evaporated. The obtained colorless oil was taken back in $CH_2Cl_2$ (180 mL) and the resulting solution was washed with $H_2O$ (2×40 mL), brine (30 mL), dried over $MgSO_4$, filtered and concentrated to dryness to give crude TTA 46118C (see table 6) that was used in the next step without further purification.

Procedure P for Preparation of Compound LPO 550108

Phthalamide derivative LPO 50192C (58 mg, 0.103 mmol) was dissolved in EtOH (1 mL) and hydrazine hydrate (100 µL, 2.06 mmol) was added. The reaction mixture was stirred under $N_2$ atmosphere at 80° C. for 2 h. Phthalhydrazine was filtered off, the filtrate was evaporated, $H_2O$ (10 mL) was added and the resulting solution was extracted with $CH_2Cl_2$ (3×30 mL). The combined organic layers were washed with brine (10 mL), dried over $MgSO_4$, evaporated to give, after further drying under vacuum and in presence of $P_2O_5$, 2-((2-((6,7-dimethoxy-1-propylisoquinolin-4-yl)methyl)quinolin-8-yl)oxy)ethanamine LPO 55010B (see table 6) as a yellow solid (50.8 mg, quantitative crude yield).

Procedure Q for Preparation of Compound 171

To a mixture of $POCl_3$ (252 µL, 2.70 mmol) and $Et_3N$ (113 µL, 0.81 mmol) in dry THF (2.5 mL) at 4° C. in a 10 mL round-bottomed flask equipped with a magnetic stirrer was added drop wise a suspension of 3-((6,7-dimethoxy-1-propylisoquinolin-4-yl)methyl)quinolin-6-ol 143 (210 mg, 0.54 mmol) in dry THF (5 mL). The mixture was stirred for 30 min at 4° C., and concentrated to dryness under vacuum. The residue was taken up in a 5 N aq. NaOH solution (1.8 mL) and stirred for 15 min at RT before concentration to a volume of around 1 mL. This residue was purified by reversed phase flash chromatography (RP18, 11.0 g, 25-40 µm, eluent $H_2O$:$CH_3CN$=100:0 to 90:10) to give, after concentration and drying under vacuum, sodium 3-((6,7-dimethoxy-1-propylisoquinolin-4-yl)methyl)quinolin-6-yl phosphate 171 (see table 7) as a white solid (87 mg, 48% yield).

TABLE 7

| Compd # | FORMULA | General Procedure | Purification | Analysis |
|---|---|---|---|---|
| 1 | (naphthalen-2-ylmethyl-6,7-dimethoxyisoquinoline · 2HCl) | A LPO 22102 (561.5 mg, 1.98 mmol); 2-naphthaldehyde (632 mg, 4.04 mmol); 37% HCl (3 mL) at 100° C. for 25 min. | Chromatography SiO$_2$, cyclohexane:acetone = 80:20 to 75:25 | 6,7-dimethoxy-4-(naphthalen-2-ylmethyl)isoquinoline hydrochloride (253 mg); MW: 365.86; Yield: 39%; Yellow Solid; Mp (° C.): 165.5; R$_f$: 0.25 (cyclohexane:acetone = 75:25, free base). $^1$H-NMR (CD$_3$OD, δ): 3.96 (s, 3H, OMe), 4.04 (s, 3H, OMe), 4.72 (s, 2H, CH$_2$), 7.42-7.47 (m, 3H, 3xArH), 7.59 (s, 1H, ArH), 7.76-7.86 (m, 3H, 5xArH), 8.24 (s, 1H, ArH), 9.31 (s, 1H, ArH). $^{13}$C-NMR (CD$_3$OD, δ): 37.1, 57.0, 57.4, 104.2, 109.0, 125.6, 127.1, 127.5, 128.0, 128.6, 128.7, 129.8, 130.4, 133.9, 135.1, 135.9, 136.6, 137.4, 142.5, 154.3, 159.7; MS-ESI m/z 330 ([MH]$^+$, 100). HPLC: Method A, detection UV 254 nm, RT = 4.97 min, peak area 99%. |
| 2 | (quinolin-3-ylmethyl-6,7-dimethoxyisoquinoline · 2HCl) | A LPO 22102 (1.08 g, 3.82 mmol); quinoline-3-carbaldehyde (600 mg, 3.82 mmol); 37% HCl (3.4 mL) at 110° C. for 30 min. | Precipitate was filtered | 3-((6,7-dimethoxyisoquinolin-4-yl)methyl)quinoline dihydrochloride (965 mg); MW: 403.3; Yield: 63%; Off-white Solid; Mp (° C.): 242.9; R$_f$: 0.25 (cyclohexane:acetone = 6:4, free base). $^1$H-NMR (CD$_3$OD, δ): 4.07 (s, 3H, OMe), 4.08 (s, 3H, OMe), 5.05 (s, 2H, CH$_2$), 7.60 (s, 1H, ArH), 7.90 (s, 1H, ArH), 7.98 (t, 1H, J = 7.3 Hz, ArH), 8.18 (t, 1H, J = 7.0 Hz, ArH), 8.28 (d, 2H, J = 8.5 Hz, ArH), 8.43 (s, 1H, ArH), 9.13 (s, 1H, ArH), 9.38 (s, 1H, ArH), 9.43 (s, 1H, ArH). $^{13}$C-NMR (CD$_3$OD, δ): 33.4, 57.2, 57.9, 103.7, 109.5, 121.5, 125.8, 130.4, 130.6, 131.5, 131.7, 132.8, 134.4, 136.3, 137.2, 138.3, 143.4, 146.8, 147.7, 154.6, 160.5; MS-ESI m/z (% rel. Int.): 331.2 ([MH]$^+$, 100). HPLC: Method A, detection UV 254 nm, RT = 3.55 min, peak area 97%. |
| 3 | (benzo[b]thiophen-5-ylmethyl-6,7-dimethoxyisoquinoline · HCl) | A LPO 22102 A (1.05 g, 3.70 mmol); benzo[b]thiophene-5-carbaldehyde (600 mg, 3.7 mmol); 37% HCl (3.4 mL) at 110° C. for 30 min. | Chromatography SiO$_2$, cyclohexane:acetone = 80:20 to 70:30 | 4-(benzo[b]thiophen-5-ylmethyl)-6,7-dimethoxyisoquinoline hydrochloride (498 mg); MW: 371.88; Yield: 36%; Brown Solid; Mp (° C.): 191.1; R$_f$: 0.25 (cyclohexane:acetone = 7:3, free base). $^1$H-NMR (CD$_3$OD, δ): 3.98 (s, 3H, OMe), 4.04 (s, 3H, OMe), 4.68 (s, 2H, CH$_2$), 7.29-7.33 (m, 2H, 2xArH), 7.56 (s, 1H, ArH), 7.57 (s, 1H, ArH), 7.79 (s, 2H, 2xArH), 7.87 (d, 1H, J = 8.3 Hz, ArH), 8.21 (s, 1H, ArH), 9.30 (s, 1H, ArH). $^{13}$C-NMR (CD$_3$OD, δ): 36.9, 57.1, 57.4, 104.2, 109.0, 124.0, 124.7, 124.9, 125.6, 126.4, 128.6, 130.4, 135.3, 136.3, 137.4, 139.9, 141.8, 142.5, 154.3, 159.8; MS-ESI m/z (% rel. Int.): 336.1 ([MH]$^+$, 100). HPLC: Method A, detection UV 254 nm, RT = 4.68 min, peak area 97%. |
| 4 | (9H-fluoren-2-ylmethyl-6,7-dimethoxyisoquinoline · HCl) | A LPO 22102 (515 mg, 1.82 mmol); 2-fluorene-carboxaldehyde (353 mg, 1.82 mmol); 37% HCl (3 mL) at 100° C. for 25 min | Chromatography SiO$_2$, cyclohexane:acetone = 80:20 to 70:30 | 4-((9H-fluoren-2-yl)methyl)-6,7-dimethoxyisoquinoline hydrochloride (231 mg); MW: 403.91; Yield: 31%; Yellow Solid; Mp (° C.): 207.5; R$_f$: 0.1 (cyclohexane:acetone = 80:20, free base). $^1$H-NMR (CD$_3$OD, δ): 3.81 (s, 2H, CH$_2$), 3.99 (s, 3H, OMe), 4.03 (s, 3H, OMe), 4.60 (s, 2H, CH$_2$), 7.25-7.36 (m, 3H, 3xArH), 7.49 (m, 2H, 2xArH), 7.55 (s, 1H, ArH), 7.72-7.77 (m, 3H, 3xArH), 8.22 (s, 1H, ArH), 9.28 (s, 1H, ArH). $^{13}$C-NMR (CD$_3$OD, δ): 37.1, 37.6, 57.0, 57.4, 104.2, 109.0, 120.8, 121.2, 125.6, 126.1, 126.7, 127.9, 128.0, 128.8, 130.4, 136.3, 137.7, 142.1, 142.4, 144.5, 145.5, 154.3, 159.7; MS-ESI m/z (% rel. Int.): 368.2 ([MH]$^+$, 100). HPLC: Method A, detection UV 254 nm, RT = 5.17 min, peak area 99%. |

TABLE 7-continued

| Compd # | FORMULA | General Procedure | Purification | Analysis |
|---|---|---|---|---|
| 5 | (structure) | A LPO 22102 (900 mg, 3.18 mmol); quinoline-2-carbaldehyde (500 mg, 3.18 mmol); 37% HCl (2.8 mL); 100° C. for 30 min. | Chromatography SiO$_2$, cyclohexane:acetone = 50:50 to 30:70 | 2-((6,7-dimethoxyisoquinolin-4-yl)methyl)quinoline dihydrochloride (384 mg); MW: 402.09; Yield: 30%; Beige Solid; Mp (° C.): 211.1. R$_f$: 0.25 (cyclohexane:acetone = 3:7, free base); $^1$H-NMR (CD$_3$OD, δ): 4.08 (s, 3H, OMe), 4.10 (s, 3H, OMe), 5.38 (s, 2H, CH$_2$), 7.65 (s, 1H, ArH), 7.82 (d, 1H, J = 8.6 Hz, ArH), 7.91 (s, 1H, ArH), 7.98 (t, 1H, ArH, J = 8.1 Hz), 8.20 (t, 1H, J = 7.2 Hz, ArH), 8.31 (d, 1H, J = 8.2 Hz, ArH), 8.46 (d, 1H, J = 8.6 Hz, ArH), 8.56 (s, 1H, ArH), 9.05 (d, 1H, J = 8.74 Hz, ArH), 9.46 (s, 1H, ArH); $^{13}$C-NMR (CD$_3$OD, δ): 35.1, 57.2, 58.2, 103.5, 109.5, 121.6, 123.5, 125.7, 129.3, 129.7, 130.4, 131.1, 132.0, 136.5, 137.3, 139.8, 143.8, 148.4, 154.6, 157.6, 160.7; MS-ESI m/z (% rel. Int.): 331.2 ([MH]$^+$, 100); HPLC: Method A, detection UV 254 nm, RT = 4.02 min, peak area 99%. |
| 6 | (structure) | A LPO 22102 (900 mg, 3.18 mmol); quinoline-6-carbaldehyde (500 mg, 3.18 mmol); 37% HCl (2.8 mL); 100° C. for 30 min. | Chromatography SiO$_2$, cyclohexane:acetone = 50:50 to 30:70 | 6-((6,7-dimethoxyisoquinolin-4-yl)methyl)quinoline dihydrochloride (664 mg); MW: 403.3; Yield: 52%; Pale Yellow Solid; Mp (° C.): 280.0; R$_f$: 0.25 (cyclohexane:acetone = 3:7, free base); $^1$H-NMR (CD$_3$OD, δ): 4.01 (s, 3H, OMe), 4.06 (s, 3H, OMe), 4.95 (s, 2H, CH$_2$), 7.54 (s, 1H, ArH), 7.87 (s, 1H, ArH), 8.08-8.13 (m, 1H, ArH), 8.25-8.30 (m, 3H, 3xArH), 8.40 (s, 1H, ArH), 9.15-9.22 (m, 2H, 2xArH), 9.40 (s, 1H, ArH). $^{13}$C-NMR (CD$_3$OD, δ): 36.4, 57.2, 57.6, 104.0, 109.4, 122.2, 123.5, 125.8, 129.9, 130.9, 131.2, 134.2, 137.3, 137.8, 138.3, 142.6, 143.1, 145.8, 148.5, 154.5, 160.2; MS-ESI m/z (% rel. Int.): 331.2 ([MH]$^+$, 100); HPLC: Method A, detection UV 254 nm, RT = 3.55 min, peak area 99%. |
| 7 | (structure) | A LPO 22102 (819 mg, 2.89 mmol); 8-hydroxyquinoline-2-carbaldehyde (500 mg, 2.89 mmol); 37% HCl (2.8 mL); 100° C. for 30 min. | Chromatography SiO$_2$, cyclohexane:acetone = 70:30 to 50:50 | 2-((6,7-dimethoxyisoquinolin-4-yl)methyl)quinolin-8-ol dihydrochloride (227 mg); MW: 419.3; Yield: 19%; Yellow Solid; Mp (° C.): 204.7; R$_f$: 0.25 (cyclohexane:acetone = 5:5, free base); $^1$H-NMR (CD$_3$OD, δ): 4.09 (s, 6H, 2xOMe), 5.34 (s, 2H, CH$_2$), 7.54 (d, 1H, J = 7.4 Hz, ArH), 7.61 (s, 1H, ArH), 7.70-7.83 (m, 3H, 3xArH), 7.93 (s, 1H, ArH), 8.41 (s, 1H, ArH), 8.99 (d, 1H, J = 8.6 Hz, ArH), 9.46 (s, 1H, ArH). $^{13}$C-NMR (CD$_3$OD, δ): 35.0, 57.2, 57.9, 103.5, 109.6, 118.0, 120.2, 124.0, 125.8, 130.3, 130.7, 131.0, 131.7, 132.0, 137.3, 143.9, 148.6, 149.5, 154.8, 156.8, 160.8; MS-ESI m/z (% rel. Int.): 347.2 ([MH]$^+$, 100); HPLC: Method A, detection UV 254 nm, RT = 4.11 min, peak area 99%. |
| 8 | (structure) | A LPO 22102 (515 mg, 1.82 mmol); 7-methoxyquinoline-3-carbaldehyde (340 mg, 1.82 mmol); 37% HCl (2 mL); 100° C. for 30 min. | Chromatography SiO$_2$, cyclohexane:acetone = 90:10 to 70:30 | 3-((6,7-dimethoxyisoquinolin-4-yl)methyl)-7-methoxyquinoline dihydrochloride (522 mg); MW: 433.33; Yield: 66%; Yellow Solid; Mp (° C.): 270.4; R$_f$: 0.25 (cyclohexane:acetone = 9:1, free base); $^1$H-NMR (CD$_3$OD, δ): 4.09 (s, 3H, OMe), 4.13 (s, 3H, OMe), 4.97 (s, 2H, CH$_2$), 7.53-7.59 (m, 3H, 3xArH), 7.86 (s, 1H, ArH), 8.16 (d, 1H, J = 9.1 Hz, ArH), 8.45 (s, 1H, ArH), 9.03 (s, 1H, ArH), 9.21 (d, 1H, J = 1.9 Hz, ArH), 9.40 (s, 1H, ArH). $^{13}$C-NMR (CD$_3$OD, δ): 32.7, 57.1 (2xC), 57.8, 99.2, 103.2, 109.1, 124.9, 125.3, 126.0, 130.9 (2xC), 131.4, 132.6, 136.7, 140.6, 142.8, 144.1, 146.8, 154.1, 160.0, 166.3; MS-ESI m/z (% rel. Int.): 361.2 ([MH]$^+$, 100); HPLC: Method A, detection UV 254 nm, RT = 3.85 min, peak area 99%. |

TABLE 7-continued

| Compd # | FORMULA | General Procedure | Purification | Analysis |
|---|---|---|---|---|
| 9 | (structure: 6-methoxynaphthalen-2-yl methyl linked to 6,7-dimethoxyisoquinoline, HCl salt) | A<br>LPO 22102 (510 mg, 1.79 mmol); 6-methoxy-2-naphthaldehyde (407 mg, 2.14 mmol); 37% HCl (3 mL); 100° C. for 30 min | Chromatography SiO$_2$, CH$_2$Cl$_2$:EtOAc = 100:0 to 60:40 | 6,7-dimethoxy-4-((6-methoxynaphthalen-2-yl)methyl)isoquinoline hydrochloride (211 mg); MW: 395.88; Yield: 30%; White Solid; Mp (° C.): 207.6; R$_f$: 0.15 (CH$_2$Cl$_2$:EtOAc = 7:3, free base); $^1$H-NMR (CD$_3$OD, δ): 3.87 (s, 3H, OMe), 3.96 (s, 3H, OMe), 4.03 (s, 3H, OMe), 4.66 (s, 2H, CH$_2$), 7.09 (d, 1H, J = 8.9 Hz, ArH), 7.18 (s, 1H, ArH), 7.37 (d, 1H, J = 8.4 Hz, ArH), 7.57 (s, 1H, ArH), 7.64-7.77 (m, 4H, 4xArH), 8.21 (s, 1H, ArH), 9.28 (s, 1H, ArH); $^{13}$C-NMR (CD$_3$OD, δ): 37.0, 55.8, 57.0, 57.3, 104.2, 106.7, 109.0, 120.3, 125.6, 128.4, 128.5, 128.7, 130.0, 130.4, 130.5, 134.2, 135.1, 136.2, 137.4, 142.5, 154.3, 159.3, 159.7; MS-ESI m/z (% rel. Int.): 360.3 ([MH]$^+$, 100); HPLC: Method A, detection UV 254 nm, RT = 5.19 min, peak area 96%. |
| 10 | (structure: dibenzo[b,d]furan-2-yl methyl linked to 6,7-dimethoxyisoquinoline, HCl salt) | A<br>LPO 22102 (355 mg, 1.25 mmol); dibenzo[b,d]furan-2-carbaldehyde (300 mg, 1.50 mmol); 37% HCl (3 mL); 100° C. for 20 min | Chromatography SiO$_2$, CH$_2$Cl$_2$:EtOAc = 100:0 to 70:30 | 4-(dibenzo[b,d]furan-2-ylmethyl)-6,7-dimethoxyisoquinoline hydrochloride (144 mg); MW: 405.87; Yield: 50%; White Solid; Mp (° C.): 347.1; R$_f$: 0.25 (CH$_2$Cl$_2$:EtOAc = 70:30, free base); $^1$H-NMR (CD$_3$OD, δ): 3.94 (s, 3H, OMe), 4.00 (s, 3H, OMe), 4.64 (s, 2H, CH$_2$), 7.32 (t, 1H, J = 7.5 Hz, ArH), 7.41-7.56 (m, 5H, 5xArH), 7.65 (s, 1H, ArH), 7.94 (d, 1H, J = 7.3 Hz, ArH), 7.97 (s, 1H, ArH), 8.21 (s, 1H, ArH), 9.16 (s, 1H, ArH); $^{13}$C-NMR (CD$_3$OD, δ): 36.9, 56.8, 57.1, 103.9, 108.5, 112.6, 112.8, 121.7, 122.0, 124.0, 125.1, 125.9, 126.0, 128.6, 129.2, 134.2, 134.6, 135.9, 144.9, 153.5, 156.5, 158.0, 158.2; MS-ESI m/z (% rel. Int.): 370.3 ([MH]$^+$, 100); HPLC: Method A, detection UV 254 nm, RT = 5.30 min, peak area 99.9%. |
| 11 | (structure: 1-methylindolin-5-yl methyl linked to 6,7-dimethoxyisoquinoline, HCl salt) | A<br>LPO 22102 (879 mg, 3.10 mmol); 1-methylindoline-5-carbaldehyde (500 mg, 3.10 mmol); 37% HCl (2.8 mL); 90° C. for 20 min. | Chromatography SiO$_2$, CH$_2$Cl$_2$:MeOH = 100:0 to 98:2 | 6,7-dimethoxy-4-((1-methylindolin-5-yl)methyl)isoquinoline hydrochloride (71 mg); MW: 370.87; Yield: 6%; Yellow Solid; Mp (° C.): 75.4; R$_f$: 0.3 (CH$_2$Cl$_2$:MeOH = 98:2, free base); $^1$H-NMR (CD$_3$OD, δ): 2.78 (s, 3H, NCH$_3$), 2.91 (t, 2H, J = 7.9 Hz, CH$_2$), 3.30-3.35 (m, 2H, NCH$_2$), 4.03 (s, 3H, OMe), 4.05 (s, 3H, OMe), 4.44 (s, 2H, CH$_2$), 6.64 (d, 1H, J = 7.9 Hz, ArH), 7.06-7.11 (m, 2H, ArH), 7.55 (s, 1H, ArH), 7.78 (s, 1H, ArH), 8.15 (s, 1H, ArH), 9.28 (s, 1H, ArH); $^{13}$C-NMR (CD$_3$OD, δ): 29.5, 36.6, 37.7, 57.1, 57.4, 57.6, 104.3, 109.0, 110.4, 121.9, 123.4, 125.6, 126.3, 129.4, 130.2, 133.5, 136.9, 137.4, 142.4, 154.3, 159.6; MS-ESI m/z (% rel. Int.): 335.4 ([MH]$^+$, 100); HPLC: Method A, detection UV 254 nm, RT = 4.07 min, peak area 98%. |
| 12 | (structure: 3,4-dihydro-4-methyl-2H-benzo[b][1,4]oxazin-7-yl methyl linked to 6,7-dimethoxyisoquinoline, HCl salt) | A<br>LPO 22102 (400 mg, 1.41 mmol); 3,4-dihydro-4-methyl-2H-benzo[b][1,4]oxazine-7-carbaldehyde (250 mg, 1.41 mmol); 37% HCl (1.4 mL); 90° C. for 20 min. | Chromatography SiO$_2$, CH$_2$Cl$_2$:MeOH = 100:0 to 98:2 | 7-((6,7-dimethoxyisoquinolin-4-yl)methyl)-4-methyl-3,4-dihydro-2H-benzo[b][1,4]oxazine hydrochloride (95 mg); MW: 386.37; Yield: 17%; Yellow Solid; Mp (° C.): 99.4; R$_f$: 0.25 (CH$_2$Cl$_2$:MeOH = 98:2, free base); $^1$H-NMR (CD$_3$OD, δ): 2.84 (s, 3H, NCH$_3$), 3.22 (t, 2H, J = 4.4 Hz, NCH$_2$), 4.03 (s, 3H, OMe), 4.05 (s, 3H, OMe), 4.22 (t, 2H, J = 3.5 Hz, OCH$_2$), 4.37 (s, 2H, CH$_2$), 6.61 (s, 1H, ArH), 6.68 (d, 1H, J = 8.2 Hz, ArH), 6.77 (d, 1H, J = 8.2 Hz, ArH), 7.56 (s, 1H, ArH), 7.76 (s, 1H, ArH), 8.14 (s, 1H, ArH), 9.25 (s, 1H, ArH); $^{13}$C-NMR (CD$_3$OD, δ): 36.4, 39.1, 50.3, 57.1, 57.4, 66.2, 104.4, 108.9, 114.3, 117.3, 122.9, 125.6, 128.8, 130.1, 136.9, 137.1, 137.5, 142.3, 146.3, 154.4, 159.7; MS-ESI m/z (% rel. Int.): 351.4 ([MH]$^+$, 100); HPLC: Method A, detection UV 254 nm, RT = 4.66 min, peak area 98%. |

TABLE 7-continued

| Compd # | FORMULA | General Procedure | Purification | Analysis |
|---|---|---|---|---|
| 13 | (structure) | A LPO 22102 (354 mg, 1.25 mmol); 2-(dimethylamino)quinoline-3-carbaldehyde (250 mg, 1.25 mmol); 37% HCl (1.4 mL); 100° C. for 30 min. | A mixture of EtOAc:EtOH = 8:2 (3 mL) was added and the precipitate was filtered | 3-((6,7-dimethoxyisoquinolin-4-yl)methyl)-N,N-dimethylquinolin-2-amine dihydrochloride (355 mg); MW: 446.37; Yield: 64%; Yellow Solid; Mp (° C.): 218.5; $^1$H-NMR (CD$_3$OD, δ): 3.50 (s, 6H, 2xNCH$_3$), 4.09 (s, 6H, 2xOMe), 4.91 (s, 2H, CH$_2$), 7.50-7.56 (m, 2H, 2xArH), 7.77-7.90 (m, 3H, 3xArH), 8.10 (d, 1H, J = 8.5 Hz, ArH), 8.17 (s, 1H, ArH), 8.30 (s, 1H, ArH), 9.42 (s, 1H, ArH); $^{13}$C-NMR (CD$_3$OD, δ): 34.3, 43.2 (2xC), 57.2, 57.7, 103.5, 109.5, 118.9, 123.6, 125.5, 125.7, 127.6, 129.5, 131.0, 133.5, 134.4, 137.1, 137.5, 143.4, 147.5, 154.7, 157.2, 160.5; MS-ESI m/z (% rel. Int.): 374.4 ([MH]$^+$, 100); HPLC: Method A, detection UV 235 nm, RT = 4.01 min, peak area 98%. |
| 14 | (structure) | A LPO 22102 (500 mg, 1.76 mmol); N-ethyl-3-carbazolecarboxaldehyde (419 mg, 1.76 mmol); 37% HCl (3 mL); 100° C. for 25 min | Chromatography SiO$_2$, cyclohexane:EtOAc = 60:40 to 30:70 | 3-((6,7-dimethoxyisoquinolin-4-yl)methyl)-9-ethyl-9H-carbazole hydrochloride (131 mg); MW: 432.94; Yield: 17%; Yellow Solid; Mp (° C.): 206.4; R$_f$: 0.30 (CH$_2$Cl$_2$:MeOH = 98:2); $^1$H-NMR (CD$_3$OD, δ): 1.34 (t, 3H, J = 7.15 Hz, CH$_3$), 3.97 (s, 3H, CH$_3$), 4.00 (s, 3H, CH$_3$), 4.31-4.38 (q, 2H, J = 7.17 Hz, CH$_2$), 4.67 (s, 2H, CH$_2$), 7.11-7.17 (m, 1H, ArH), 7.37-7.47 (m, 4H, 4xArH), 7.61 (s, 1H, ArH), 7.71 (s, 1H, ArH), 7.99 (d, 1H, J = 7.75 Hz, ArH), 8.05 (s, 1H, ArH), 8.17 (s, 1H, ArH), 9.23 (s, 1H, ArH); $^{13}$C-NMR (CD$_3$OD, δ): 14.0, 37.2, 38.4, 57.0, 57.4, 104.3, 108.9, 109.9, 110.3, 120.0, 121.2, 121.7, 123.8, 124.7, 125.5, 127.1, 127.7, 129.2, 130.1, 137.1, 137.4, 140.4, 141.7, 142.2, 154.3, 159.6; MS-ESI m/z (% rel. Int.): 397.4 ([MH]$^+$, 100); HPLC: Method A, detection UV 254 nm, RT = 5.68 min, peak area 99.9%. |
| 15 | (structure) | A LPO 22102 (970 mg, 3.42 mmol) and 1H-benzo[d]imidazole-5-carbaldehyde (500 mg, 3.42 mmol); 37% HCl (2.8 mL); 90° C. for 30 min. | Chromatography SiO$_2$, CH$_2$Cl$_2$:MeOH = 100:0 to 95:5 | 4-((1H-benzo[d]imidazol-5-yl)methyl)-6,7-dimethoxyisoquinoline dihydrochloride (394 mg); MW: 392.28; Yield: 129%; Yellow Solid; Mp (° C.): 195.2; R$_f$: 0.25 (CH$_2$Cl$_2$:MeOH = 95:5, free base); $^1$H-NMR (CD$_3$OD, δ): 4.04 (s, 3H, OMe), 4.06 (s, 3H, OMe), 4.84 (s, 2H, CH$_2$), 7.57 (s, 1H, ArH), 7.68 (d, 1H, J = 8.7 Hz, ArH), 7.86 (d, 3H, J = 8.1 Hz, ArH), 8.30 (s, 1H, ArH), 9.38 (d, 2H, J = 8.1 Hz, 2xArH); $^{13}$C-NMR (CD$_3$OD, δ): 36.7, 57.2, 57.6, 104.1, 109.3, 115.6, 115.9, 125.7, 129.3, 130.7, 131.0, 132.5, 135.3, 137.3, 138.9, 141.4, 142.9, 154.5, 160.0; MS-ESI m/z (% rel. Int.): 320.3 ([MH]$^+$, 100); HPLC: Method A, detection UV 254 nm, RT = 3.45 min, peak area 98%. |

TABLE 7-continued

| Compd # | FORMULA | General Procedure | Purification | Analysis |
|---|---|---|---|---|
| 16 | (pyrazolo[3,4-b]pyridine with Cl, linked via CH2 to 6,7-dimethoxyisoquinoline; 2HCl) | A LPO 22102 (473 mg, 1.67 mmol); SAO 33058 (350 mg, 1.67 mmol); 37% HCl (2.0 mL); 100° C. for 30 min. | Chromatography SiO$_2$, CH$_2$Cl$_2$:MeOH = 100:0 to 97:3 | 4-((4-chloro-1-ethyl-1H-pyrazolo[3,4-b]pyridin-5-yl)methyl)-6,7-dimethoxyisoquinoline dihydrochloride (27 mg); MW: 455.77; Yield: 4%; Yellow Solid; Mp (° C.): 91.6; R$_f$: 0.20 (CH$_2$Cl$_2$:MeOH = 99:1, free base); $^1$H-NMR (CD$_3$OD, δ): 1.50 (t, 3H, J = 7.2 Hz, CH$_2$CH$_3$), 4.08 (s, 3H, OMe), 4.13 (s, 3H, OMe), 4.57 (q, 2H, J = 14.5 Hz, CH$_2$CH$_3$), 4.85 (s, 2H, CH$_2$), 7.66 (s, 1H, ArH), 7.85 (s, 1H, ArH), 7.96 (s, 1H, ArH), 8.19 (s, 1H, ArH), 8.52 (s, 1H, ArH), 9.32 (s, 1H, ArH); $^{13}$C-NMR (CD$_3$OD, δ): 15.2, 31.2, 43.6, 57.1, 57.7, 103.6, 109.3, 116.9, 125.1, 125.5, 130.0, 131.5, 134.3, 137.2, 138.6, 142.8, 151.1, 152.2, 154.6, 160.3; MS-ESI m/z (% rel. Int.): 383.4, 385.4 ([MH]$^+$, 100/33); HPLC: Method A, detection UV 254 nm, RT = 4.29 min, peak area 96%. |
| 17 | (pyrazolo[3,4-b]pyridine with OEt, linked via CH2 to 6,7-dimethoxyisoquinoline; 2HCl) | | | 4-((4-ethoxy-1-ethyl-1H-pyrazolo[3,4-b]pyridin-5-yl)methyl)-6,7-dimethoxyisoquinoline dihydrochloride (63.2 mg); MW: 465.37; Yield: 8%; Yellow Solid; Mp (° C.): 144.9; R$_f$: 0.20 (CH$_2$Cl$_2$:MeOH = 97:3, free base); $^1$H-NMR (CD$_3$OD, δ): 1.41 (t, 3H, J = 6.9 Hz, CH$_2$CH$_3$), 1.55 (t, 3H, J = 7.2 Hz, CH$_2$CH$_3$), 4.08 (s, 3H, OMe), 4.17 (s, 3H, OMe), 4.58 (q, 2H, J = 14.5 Hz, CH$_2$CH$_3$), 4.70 (s, 2H, CH$_2$), 4.90 (q, 2H, J = 14.0 Hz, CH$_2$CH$_2$O), 7.70 (s, 1H, ArH), 7.86 (s, 1H, ArH), 8.17 (s, 1H, ArH), 8.61 (s, 1H, ArH), 8.64 (s, 1H, ArH), 9.33 (s, 1H, ArH); $^{13}$C-NMR (CD$_3$OD, δ): 14.6, 15.0, 28.8, 45.3, 57.2, 57.7, 72.0, 103.6, 109.3, 110.0, 116.3, 125.6, 130.5, 133.8, 135.6, 137.3, 142.6, 143.2, 146.1, 154.6, 160.2, 166.4; MS-ESI m/z (% rel. Int.): 393.4 ([MH]$^+$, 100); HPLC: Method A, detection UV 254 nm, RT = 4.07 min, peak area 97%. |
| 18 | (pyrazolo[3,4-b]pyridine with OH, linked via CH2 to 6,7-dimethoxyisoquinoline; 2HCl) | | Precipitate was filtered | 5-((6,7-dimethoxyisoquinolin-4-yl)methyl)-1-ethyl-1H-pyrazolo[3,4-b]pyridin-4-ol dihydrochloride (62.8 mg); MW: 437.32; Yield: 9%; Off-white Solid; Mp (° C.): 225.6; $^1$H-NMR (DMSO, δ): 1.37 (t, 3H, J = 7.1 Hz, CH$_2$CH$_3$), 3.98 (s, 3H, OMe), 4.12 (s, 3H, OMe), 4.44-4.46 (m, 4H, CH$_2$CH$_3$ & CH$_2$), 7.87 (s, 1H, ArH), 7.93 (s, 1H, ArH), 8.28 (s, 1H, ArH), 8.35-8.38 (m, 2H, 2xArH), 9.41 (s, 1H, ArH); $^{13}$C-NMR (DMSO, δ): 14.5, 26.3, 43.1, 56.2, 56.9, 103.1, 108.2, 110.0, 115.1, 123.4, 129.1, 133.6, 133.8, 134.9, 140.8 (2xC), 143.8, 151.8, 157.1, 166.5; MS-ESI m/z (% rel. Int.): 365.4 ([MH]$^+$, 100); HPLC: Method A, detection UV 254 nm, RT = 3.65 min, peak area 97%. |
| 19 | (2-chloroquinoline linked via CH2 to 6,7-dimethoxyisoquinoline; 2HCl) | A LPO 22102 (480 mg, 1.70 mmol) and 2-chloroquinoline-3-carbaldehyde (380 mg, 1.94 mmol); 37% HCl (3.5 mL); 100° C. for 25 min | Chromatography SiO$_2$, EtOAc:MeOH = 100:0 to 95:5 (minor compound) | 2-chloro-3-((6,7-dimethoxyisoquinolin-4-yl)methyl)quinoline dihydrochloride (63.0 mg); MW: 437.75; Yield: 9%; Pale Yellow Solid; Mp (° C.): 331.2; R$_f$: 0.5 (EtOAc:MeOH = 95:5, free base); $^1$H-NMR (CD$_3$OD, δ): 4.07 (s, 3H, OMe), 4.08 (s, 3H, OMe), 4.84 (s, 2H, CH$_2$), 7.59-7.65 (m, 2H, 2xArH), 7.78-7.88 (m, 3H, 3xArH), 7.97 (d, 1H, J = 8.41 Hz, ArH), 8.09 (s, 1H, ArH), 8.21 (s, 1H, ArH), 9.35 (s, 1H, ArH); $^{13}$C-NMR (CD$_3$OD, δ): 34.4, 57.1, 57.6, 103.6, 109.3, 125.6, 128.6, 128.8, 128.9, 128.9, 130.6, 131.0, 132.1, 133.8, 137.3, 141.1, 142.9, 148.1, 152.0, 154.6, 160.3; MS-ESI m/z (% rel. Int.): 365.3/367.3 ([MH]$^+$, 100); HPLC: Method A, detection UV 254 nm, RT = 4.48 min, peak area 96%. |

TABLE 7-continued

| Compd # | FORMULA | General Procedure | Purification | Analysis |
|---|---|---|---|---|
| 20 | (structure) | — | Chromatography SiO$_2$, EtOAc:MeOH = 100:0 to 95:5 (major compound) | 3-((6,7-dimethoxyisoquinolin-4-yl)methyl)quinolin-2-ol hydrochloride (190 mg); MW: 382.84; Yield: 30%; Yellow Solid; R$_f$: 0.25 (EtOAc:MeOH = 95:5, free base); $^1$H-NMR (DMSO d$^6$, δ): 3.98 (s, 3H, OMe), 4.06 (s, 3H, OMe), 4.64 (s, 2H, CH$_2$), 7.14 (t, 1H, J = 7.56 Hz, ArH), 7.34 (d, 1H, J = 8.12 Hz, ArH), 7.47 (t, 1H, J = 8.17 Hz, ArH), 7.56 (d, 1H, J = 7.66 Hz, ArH), 7.78 (s, 1H, ArH), 7.84 (s, 1H, ArH), 7.94 (s, 1H, ArH), 8.48 (s, 1H, ArH), 9.44 (s, 1H, ArH), 12.04 (s, 1H, OH); $^1$H-NMR (DMSO d6, δ): 29.2, 56.2, 56.7, 103.1, 108.2, 114.9, 119.1, 121.9, 123.6, 127.5, 129.8, 129.9, 130.2, 133.1, 135.1, 138.0, 138.3, 141.1, 151.8, 157.1, 161.8; MS-ESI m/z (% rel. Int.): 347.4 ([MH]$^+$, 100); HPLC: Method A, detection UV 254 nm, RT = 4.05 min, peak area 97%. |
| 21 | (structure) | B (b) Free base of 7 (350 mg, 0.83 mmol); MeI (57.2 μL, 0.92 mmol); KOH (171 mg, 2.5 mmol); H$_2$O (3.5 mL) and DME (5 mL); RT overnight. | Chromatography SiO$_2$, CH$_2$Cl$_2$:EtOAc = 50:50 to 0:100 | 2-((6,7-dimethoxyisoquinolin-4-yl)methyl)-8-methoxyquinoline dihydrochloride (128 mg); MW: 433.33; Yield: 35%; Yellow Solid: Mp (° C.): 213.6; R$_f$: 0.25 (EtOAc, free base); $^1$H-NMR (CD$_3$OD, δ): 4.07 (s, 3H, OMe), 4.09 (s, 3H, OMe), 4.22 (s, 3H, OMe), 5.25 (s, 2H, CH$_2$), 7.60 (d, 1H, J = 7.7 Hz, ArH), 7.68-.75 (m, 3H, 3xArH), 7.80 (d, 1H, J = 7.7 Hz, ArH), 7.88 (s, 1H, ArH), 8.42 (s, 1H, ArH), 8.81 (d, 1H, J = 8.6 Hz, ArH), 9.41 (s, 1H, ArH); $^{13}$C-NMR (CD$_3$OD, δ): 36.2, 57.2, 57.5, 57.9, 103.9, 109.5, 113.8, 121.3, 124.2, 125.8, 130.3, 131.1, 131.2, 131.5, 133.4, 137.4, 143.6, 146.7, 152.2, 154.7, 157.6, 160.7; MS-ESI m/z (% rel. Int.): 361.4 ([MH]$^+$, 100); HPLC: Method A, detection UV 254 nm, RT = 4.07 min, peak area 95%. |
| 22 | (structure) | A ANP 31060A (527 mg, 1.96 mmol); 2-naphthaldehyde (312 mg, 1.96 mmol); 37% HCl (3 mL) at 100° C. for 50 min | Chromatography SiO$_2$, cyclohexane:EtOAc = 50:50 to 20:80 | 6,7-dimethoxy-3-methyl-4-(naphthalen-2-ylmethyl)isoquinoline hydrochloride (49 mg); MW: 379.88; Yield: 6%; Yellow solid; Mp (° C.): 173.2; R$_f$: 0.30 (cyclohexane:EtOAc = 2:8, free base); $^1$H-NMR (CD$_3$OD, δ): 2.85 (s, 3H, CH$_3$), 3.89 (s, 3H, OMe), 4.03 (s, 3H, OMe), 4.76 (s, 2H, CH$_2$), 7.39-7.43 (m, 1H, ArH), 7.48 (s, 1H, ArH), 7.53 (s, 1H, ArH), 7.68-7.70 (m, 1H, ArH), 7.73 (s, 1H, ArH), 7.80-.82 (m, 2H, 2xArH), 9.24 (s, 1H, ArH); $^{13}$C-NMR (CD$_3$OD, δ): 17.8, 34.3, 57.0, 57.2, 104.0, 108.5, 124.7, 127.0, 127.5 (3xC), 128.5, 128.7, 129.8, 132.5, 133.8, 135.1, 136.7, 138.5, 140.9, 141.7, 153.9, 160.0; MS-ESI m/z (% rel. Int.): 344.4 ([MH]$^+$, 100); HPLC: Method A, detection UV 254 nm, RT = 4.97 min, peak area 95%. |
| 23 | (structure) | B (a) Free base of 7 (300 mg, 0.71 mmol); DMF (6 mL); Cs$_2$CO$_3$(1.17 g, 3.58 mmol); 4-picolyl chloride hydrochloride (129 mg, 0.79 mmol); 40 h at RT. | Chromatography SiO$_2$, CH$_2$Cl$_2$:MeOH = 100:0 to 98:2 | 2-((6,7-dimethoxyisoquinolin-4-yl)methyl)-8-(pyridin-4-ylmethoxy)quinoline trihydrochloride (40.5 mg); MW: 546.87; Yield: 10%; Yellow Solid; Mp (° C.): 118.1; R$_f$: 0.20 (CH$_2$Cl$_2$:MeOH = 98:2, free base); $^1$H-NMR (CD$_3$OD, δ): 4.07 (s, 6H, 2xOCH$_3$), 5.32 (s, 2H, CH$_2$), 5.91 (s, 2H, OCH$_2$), 7.61 (d, 1H, J = 7.5 Hz, ArH), 7.71-7.79 (m, 4H, 4xArH), 7.89 (s, 1H, ArH), 8.40 (d, 2H, J = 5.9 Hz, 2xArH), 9.42 (s, 1H, ArH), (s, 1H, ArH), 8.78 (d, 1H, J = 8.5 Hz, ArH), 8.94 (d, 2H, J = 6.1 Hz, 2xArH), 9.42 (s, 1H, ArH); $^{13}$C-NMR CD$_3$OD, δ): 37.1, 57.2, 58.1, 70.3, 104.3, 109.4, 115.5, 122.9, 124.4, 125.8, 126.4 (2xC), 130.3, 130.5, 131.6, 131.8, 134.8, 137.6, 142.9 (2xC), 143.5, 145.4, 150.8, 154.6, 158.5, 159.7, 160.5; MS-ESI m/z (% rel. Int.): 438.0 ([MH]$^+$, 100); HPLC: Method A, detection UV 254 nm, RT = 3.85 min, peak area 98%. |

TABLE 7-continued

| Compd # | FORMULA | General Procedure | Purification | Analysis |
|---|---|---|---|---|
| 24 | (structure) | B (b) Free base of 7 (300 mg, 0.71 mmol) and 3-picolyl chloride hydrochloride (129 mg, 0.79 mmol); KOH (236 mg, 3.57 mmol); $H_2O$ (3.5 mL) and DME (5 mL); 55 h at RT. | Chromatography $SiO_2$, $CH_2Cl_2$:MeOH = 100:0 to 95:5 | 2-((6,7-dimethoxyisoquinolin-4-yl)methyl)-8-(pyridin-3-ylmethoxy)quinoline trihydrochloride (170 mg); MW: 546.87; Yield: 43%; Yellow Solid; Mp (° C.): 200.7; $R_f$: 0.3 ($CH_2Cl_2$:MeOH = 95:5, free base); $^1$H-NMR ($CD_3OD$, δ): 4.05 (s, 3H, OMe), 4.07 (s, 3H, OMe), 5.40 (s, 2H, $CH_2$), 5.80 (s, 2H, $OCH_2$), 7.69-7.83 (m, 5H, 5xArH), 7.89 (s, 1H, ArH), 8.21 (t, 1H, J = 7.8 Hz, ArH), 8.47 (s, 1H, ArH), 8.84 (d, 1H, J = 8.6 Hz, ArH), 8.92-8.98 (m, 2H, 2xArH), 9.35 (s, 1H, ArH), 9.42 (s, 1H, ArH); $^{13}$C-NMR ($CD_3OD$, δ): 36.7, 57.2, 58.1, 68.8, 104.2, 109.4, 115.6, 122.7, 124.3, 125.8, 128.7, 130.4, 130.6, 131.5, 131.6, 134.1, 137.5, 138.5, 142.5, 142.6, 143.5, 146.0, 147.5, 150.7, 154.6, 158.4, 160.5; MS-ESI m/z (% rel. Int.): 438.4 ([MH]$^+$, 80), 93.1 (100); HPLC: Method A, detection UV 254 nm, RT = 3.88 min, peak area 98%. |
| 25 | (structure) | A TTA 24128B (500 mg, 1.68 mmol); 2-naphthaldehyde (263 mg; 1.68 mmol); 37% HCl (3 mL); 100° C. for 25 min. | Chromatography $SiO_2$, cyclohexane:EtOAc = 90:10 to 80:20 | 6,7-dimethoxy-1-methyl-4-(naphthalen-2-ylmethyl)isoquinoline hydrochloride (227 mg); MW: 379.88; Yield: 35%; Brown Solid; Mp (° C.): 152.2; $R_f$: 0.30 (cyclohexane:EtOAc = 8:2, free base); $^1$H-NMR ($CD_3OD$, δ): 3.14 (s, 3H, $CH_3$), 3.94 (s, 3H, OMe), 4.07 (s, 3H, OMe), 4.69 (s, 2H, $CH_2$), 7.43-7.47 (m, 3H, 3xArH), 7.56 (s, 1H, ArH), 7.67 (s, 1H, ArH), 7.76-7.86 (m, 4H, 4xArH), 8.12 (s, 1H, ArH); $^{13}$C-NMR ($CD_3OD$, δ): 18.1, 37.0, 57.0, 57.2, 104.8, 106.9, 124.3, 127.0, 127.5, 128.0, 128.5, 128.6, 128.7, 129.5, 129.7, 133.9, 134.1, 135.0, 136.7, 136.9, 153.9, 153.5, 153.9, 158.9; MS-ESI m/z (% rel. Int.): 344.2 ([MH]$^+$, 100); HPLC: Method A, detection UV 254 nm, RT = 5.17 min, peak area 99.9%. |
| 26 | (structure) | A TTA 24128B (500 mg, 1.68 mmol); 3-quinoline-carboxaldehyde (270 mg, 1.68 mmol); 37% HCl (3 mL); 100° C. for 25 min. | Chromatography $SiO_2$, $CH_2Cl_2$:MeOH = 100:0 to 96:4 | 3-((6,7-dimethoxy-1-methylisoquinolin-4-yl)methyl)quinoline dihydrochloride (366 mg); MW: 417.33; Yield: 52%; Grey Solid; Mp (° C.): 199.1; $R_f$: 0.25 ($CH_2Cl_2$:MeOH = 96:4, free base); $^1$H-NMR ($CD_3OD$, δ): 3.21 (s, 3H, $CH_3$), 4.06 (s, 3H, OMe), 4.12 (s, 3H, OMe), 5.01 (s, 2H, $CH_2$), 7.55 (s, 1H, ArH), 7.77 (s, 1H, ArH), 7.96 (t, 1H, J = 8.2 Hz, ArH), 8.15 (t, 1H, J = 8.55 Hz ArH), 8.26-8.30 (m, 3H, 3xArH), 9.06 (s, 1H, ArH), 9.34 (s, 1H, ArH); $^{13}$C-NMR ($CD_3OD$, δ): 18.2, 33.3, 57.2, 57.6, 104.2, 107.4, 122.0, 124.5, 130.2, 130.4, 130.6, 131.1, 131.4, 134.5, 135.9, 136.3, 139.0, 146.9, 147.1, 154.2, 154.5, 159.6; MS-ESI m/z (% rel. Int.): 345.3 ([MH]$^+$, 100); HPLC: Method A, detection UV 254 nm, RT = 4.23 min, peak area 99.9%. |
| 27 | (structure) | B (a) Free base of 7 (310 mg, 0.74 mmol); DMF (3 mL); $Cs_2CO_3$ (722 mg, 2.22 mmol); bromoethane (62 µL, 0.81 mmol); 40° C. for 7 h. | Chromatography $SiO_2$, EtOAc | 2-((6,7-dimethoxyisoquinolin-4-yl)methyl)-8-ethoxyquinoline dihydrochloride (74 mg); MW: 447.35; Yield: 26%; Pale Yellow Solid; Mp (° C.): 208.1; $R_f$: 0.17 (EtOAc); $^1$H-NMR ($CD_3OD$, δ): 1.66 (t, 3H, J = 6.89 Hz, $CH_3$), 4.10 (s, 6H, 2xOMe), 4.56 (q, 2H, J = 7.03 Hz, $OCH_2$), 5.41 (s, 2H, $CH_2$), 7.64-7.76 (m, 3H, 3xArH), 7.84-7.93 (m, 3H, 3xArH), 8.38 (s, 1H, ArH), 9.01 (d, 1H, J = 6.89 Hz, ArH), 9.46 (s, 1H, ArH); $^{13}$C-NMR ($CD_3OD$, δ): 14.7, 35.1, 57.2, 57.9, 67.1, 103.6, 109.6, 115.4, 121.2, 124.4, 125.8, 130.5, 131.6, 131.7, 131.8 (2xC), 137.3, 143.8, 148.5, 150.4, 154.8, 157.3, 160.8 ; MS-ESI m/z (% rel. Int.): 375.2 ([MH]$^+$, 100); HPLC: Method A, detection UV 254 nm, RT = 4.50 min, peak area 99%. |

TABLE 7-continued

| Compd # | FORMULA | General Procedure | Purification | Analysis |
|---|---|---|---|---|
| 28 | 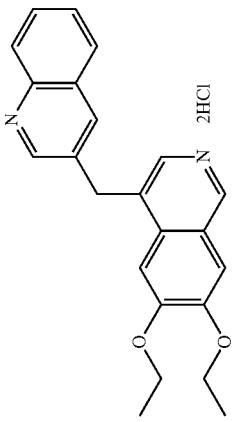 | A ECO 33100 (500 mg, 1.61 mmol); 3-quinoline carboxaldehyde (260 mg, 1.61 mmol); 37% HCl (3 mL); 100° C. for 20 min. | Chromatography SiO₂, CH₂Cl₂:MeOH = 100:0 to 95:5 | 3-((6,7-diethoxyisoquinolin-4-yl)methyl)quinoline dihydrochloride (468 mg); MW: 431.35; Yield: 67%; Off-white Solid; Mp (° C.): 214.3; $R_f$: 0.25 (CH₂Cl₂:MeOH = 95:5, free base); ¹H-NMR (CD₃OD, δ): 1.47 (t, 3H, J = 7.0 Hz, CH₃), 1.53 (t, 3H, J = 7.0 Hz CH₃), 4.28-4.38 (m, 4H, J = 7.2 Hz, 2xCH₂), 5.02 (s, 2H, CH₂), 7.54 (s, 1H, ArH), 7.85 (s, 1H, ArH), 7.95-8.01 (m, 1H, ArH), 8.15-8.21 (m, 1H, ArH), 8.27 (s, 1H, ArH), 8.30 (s, 1H, ArH), 8.42 (s, 1H, ArH), 9.12 (s, 1H, ArH), 9.39 (s, 1H, ArH); ¹³C-NMR (CD₃OD, δ): 14.6, 14.8, 33.3, 64.6, 67.2, 104.1, 110.1, 121.4, 125.7, 130.4, 130.5, 131.3, 131.8, 132.4, 134.5, 136.4, 137.0, 138.2, 143.2, 146.6, 147.8, 153.9, 159.9; MS-ESI m/z (% rel. Int.): 359.2 ([MH]⁺, 100); HPLC: Method A, detection UV 254 nm, RT = 4.59 min, peak area 99.9%. |
| 29 | 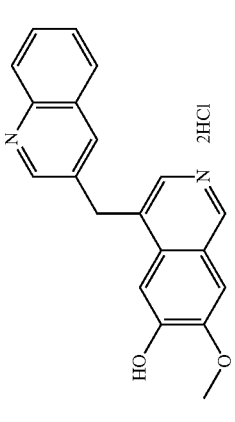 | A ECO 33118 (500 mg, 1.39 mmol); 3-quinoline carboxaldehyde (225 mg, 1.39 mmol); 37% HCl (3 mL); 100° C. for 20 min. | Chromatography SiO₂, CH₂Cl₂:MeOH = 100:0 to 96:4 | 7-methoxy-4-(quinolin-3-ylmethyl)isoquinolin-6-ol dihydrochloride (50 mg); MW: 389.28; Yield: 9%; Yellow Solid; Mp (° C.): 238.2; $R_f$: 0.25 (CH₂Cl₂:MeOH = 94:6, free base); ¹H-NMR (CD₃OD, δ): 4.13 (s, 3H, CH₃), 4.93 (s, 2H, CH₂), 7.57 (s, 1H, ArH), 7.92 (s, 1H, ArH), 7.98 (t, 1H, J = 8.1 Hz, ArH), 8.18 (t, 1H, J = 7.8 Hz ArH), 8.27 (s, 1H, ArH), 8.30 (s, 1H, ArH), 8.41 (s, 1H, ArH), 9.08 (s, 1H, ArH), 9.34 (s, 1H, ArH), 9.39 (s, 1H, ArH); ¹³C-NMR (CD₃OD,δ): 33.5, 57.2, 107.5, 110.0, 121.5, 125.1, 130.3, 130.5, 131.1, 131.6, 131.7, 134.5, 136.2, 137.4, 138.4, 143.5, 146.7, 147.5, 153.7, 159.5; MS-ESI m/z (% rel. Int.): 317.2 ([MH]⁺, 100); HPLC: Method A, detection UV 254 nm, RT = 3.75 min, peak area 99.9%. |
| 30 | 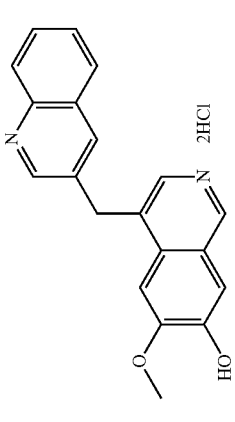 | A ECO 33124 (500 mg, 1.39 mmol); 3-quinoline carboxaldehyde (225 mg, 1.39 mmol); 37% HCl (3 mL); 100° C. for 20 min. | Chromatography SiO₂, CH₂Cl₂:MeOH = 100:0 to 95:5 | 6-methoxy-4-(quinolin-3-ylmethyl)isoquinolin-7-ol dihydrochloride (243 mg); MW: 389.28; Yield: 45%; Yellow Solid; Mp (° C.): 205.1; $R_f$: 0.25 (CH₂Cl₂:MeOH = 95:5, free base); ¹H-NMR (CD₃OD, δ): 4.12 (s, 3H, OMe), 5.03 (s, 2H, CH₂), 7.62 (s, 1H, ArH), 7.73 (s, 1H, ArH), 7.98 (t, 1H, J = 8.2 Hz, ArH), 8.15 (t, 1H, J = 8.55 Hz ArH), 8.27 (s, 1H, ArH), 8.29 (s, 1H, ArH), 8.35 (s, 1H, ArH), 9.10 (s, 1H, ArH), 9.36 (m, 2H, 2xArH); ¹³C-NMR (CD₃OD, δ): 33.3, 57.8, 103.7, 112.9, 121.5, 126.1, 130.3, 130.5, 130.6, 131.7, 132.8, 134.4, 136.2, 138.4, 143.3, 146.8, 147.6, 152.8, 159.8; MS-ESI m/z (% rel. Int.): 317.2 ([MH]⁺, 100); HPLC: Method A, detection UV 254 nm, RT = 3.85 min, peak area 99.9%. |
| 31 | 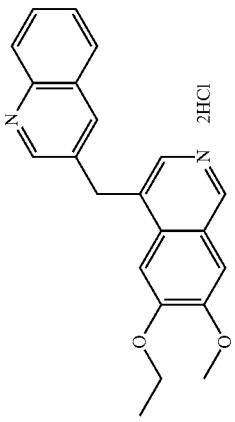 | A ECO 33138 (200 mg, 0.67 mmol); 3-quinoline carboxaldehyde (109 mg, 0.67 mmol); 37% HCl (3 mL); 100° C. for 20 min. | Chromatography SiO₂, CH₂Cl₂:MeOH = 100:0 to 95:5 | 3-((6-ethoxy-7-methoxyisoquinolin-4-yl)methyl)quinoline dihydrochloride (211 mg); MW: 417.33; Yield: 75%; Off-white Solid; Mp (° C.): 234.2; $R_f$: 0.25 (EtOAc:MeOH = 95:5, free base); ¹H-NMR (CD₃OD, δ): 1.47 (t, 3H, J = 6.95 Hz, CH₃), 4.09 (s, 3H, OMe), 4.34 (q, 2H, J = 6.95 Hz, CH₂), 5.03 (s, 2H, CH₂), 7.57 (s, 1H, ArH), 7.90 (s, 1H, ArH), 7.94-7.99 (m, 1H, ArH), 8.13-8.18 (m, 1H, ArH), 8.26-8.29 (m, 2H, 2xArH), 8.43 (s, 1H, ArH), 9.05 (s, 1H, ArH), 9.35 (s, 1H, ArH), 9.41 (s, 1H, ArH); ¹³C-NMR (CD₃OD, δ): 14.5, 33.4, 57.1, 67.1, 104.1, 109.4, 122.0, 125.6, 130.2, 130.4, 131.37, 131.4, 132.7, 134.3, 135.9, 137.2, 139.0, 143.3, 146.9, 147.2, 154.6, 159.7; MS-ESI m/z (% rel. Int.): 345.3 ([MH]⁺, 100); HPLC: Method A, detection UV 254 nm, RT = 4.30 min, peak area 99.9%. |

TABLE 7-continued

| Compd # | FORMULA | General Procedure | Purification | Analysis |
|---|---|---|---|---|
| 32 | (structure) | B (a) Free base of 7 (300 mg, 0.71 mmol); DMF (3 mL); $Cs_2CO_3$ (350 mg, 1.07 mmol); $Et_3N$ (300 µL, 2.14 mmol); 1-bromopropane (71.5 µL, 0.79 mmol); 7 min at 155° C. under microwave irradiation (150 W). | Chromatography $SiO_2$, $CH_2Cl_2$:MeOH = 100:0 to 98:2 | 2-((6,7-dimethoxyisoquinolin-4-yl)methyl)-8-propoxyquinoline dihydrochloride (116 mg); MW: 461.38; Yield: 35%; Yellow Solid; Mp (° C.): 215.5; $R_f$: 0.25 ($CH_2Cl_2$:MeOH = 98:2, free base); $^1$H-NMR ($CD_3OD$, δ): 1.18 (t, 3H, J = 7.4 Hz, $CH_3$), 2.06-2.13 (m, 2H, $CH_2$), 4.11 (s, 6H, 2xOMe), 4.45 (m, 2H, $OCH_2$), 5.42 (s, 2H, $CH_2$), 7.65 (s, 1H, ArH), 7.70-7.76 (m, 2H, 2xArH), 7.82-7.95 (m, 3H, 3xArH), 8.40 (s, 1H, ArH), 9.0 (d, 1H, J = 7.06 Hz, ArH), 9.47 (s, 1H, ArH); $^{13}$C-NMR ($CD_3OD$, δ): 10.7, 23.1, 35.3, 57.2, 57.9, 73.0, 103.6, 109.5, 1154, 121.2, 1244, 125.8, 130.5, 130.6, 131.6, 132.0, 137.4, 143.8, 148.3, 150.7, 154.7, 157.4, 160.7; MS-ESI m/z (% rel. Int.): 389.1 ([MH]$^+$, 100); HPLC: Method A, detection UV 254 nm, RT = 3.96 min, peak area 98%. |
| 33 | (structure) | A TTA 24128B (200 mg, 0.67 mmol); dibenzofuran-2-carbaldehyde (136 mg, 0.67 mmol); 37% HCl (1.2 mL); 100° C. for 20 min. | Chromatography $SiO_2$, $CH_2Cl_2$:MeOH = 100:0 to 98:2 | 4-(dibenzo[b,d]furan-2-ylmethyl)-6,7-dimethoxy-1-methylisoquinoline hydrochloride (64 mg); MW: 419.90; Yield: 22%; Yellow Solid; Mp (° C.): 130.0; $R_f$: 0.25 ($CH_2Cl_2$:MeOH = 98:2, free base); $^1$H-NMR ($CD_3OD$, δ): 3.12 (s, 3H, $CH_3$), 3.97 (s, 3H, OMe), 4.06 (s, 3H, OMe), 4.67 (s, 2H, $CH_2$), 7.30-7.35 (m, 1H, ArH), 7.44-7.49 (m, 2H, 2xArH), 7.54-7.56 (m, 3H, 3xArH), 7.65 (s, 1H, ArH), 7.95 (d, 1H, J = 7.7 Hz, ArH), 7.99 (s, 1H, ArH), 8.08 (s, 1H, ArH); $^{13}$C-NMR ($CD_3OD$, δ): 18.1, 36.7, 57.0, 57.2, 104.8, 106.9, 112.9, 112.7, 122.1, 124.3, 125.0, 126.0, 128.7, 129.2, 129.4, 134.1, 134.5, 136.6, 153.5, 153.9, 156.5, 158.0, 158.9; MS-ESI m/z (% rel. Int.): 384.1 ([MH]$^+$, 100); HPLC: Method A, detection UV 254 nm, RT = 5.01 min, peak area 99.9%. |
| 34 | (structure) | A ANP 27102 (200 mg, 0.71 mmol); 2,2-dimethylchroman-6-carbaldehyde (134 mg, 0.71 mmol); 37% HCl (1.2 mL); 100° C. for 20 min. | Chromatography $SiO_2$, $CH_2Cl_2$:MeOH = 100:0 to 97:3 | 4-((2,2-dimethylchroman-6-yl)methyl)-6,7-dimethoxyisoquinoline hydrochloride (96 mg); MW: 399.91; Yield: 34%; Yellow solid; Mp (° C.): 195.9; $R_f$: 0.3 ($CH_2Cl_2$:MeOH = 97:3, free base); $^1$H-NMR ($CD_3OD$, δ): 1.30 (s, 6H, 2xCH$_3$), 1.79 (t, 2H, J = 6.7 Hz, $CH_2$), 2.74 (t, 2H, J = 6.5 Hz, $CH_2$), 4.04 (s, 3H, OMe), 4.07 (s, 3H, OMe), 4.45 (s, 2H, CH2), 6.70 (d, 1H, J = 8.9 Hz, ArH), 7.04 (s, 2H, ArH), 7.57 (s, 1H, ArH), 7.80 (s, 1H, ArH), 8.17 (s, 1H, ArH), 9.29 (s, 1H, ArH); $^{13}$C-NMR ($CD_3OD$, δ): 23.4, 27.0 (2xC), 33.7, 36.3, 57.0, 57.4, 75.3, 104.3, 108.9, 118.6, 122.8, 125.5, 128.9, 130.0, 130.1, 131.0, 136.8, 137.4, 142.3, 154.3, 154.4, 159.6; MS-ESI m/z (% rel. Int.): 364.1 ([MH]$^+$, 100); HPLC: Method A, detection UV 254 nm, RT = 4.33 min, peak area 99%. |
| 35 | (structure) | E (a) Free base of 10 (173 mg, 0.47 mmol); DCM (20 mL) 3-chlorobenzoperoxoic acid (purity 70%, 139 mg, 0.56 mmol); RT for 24 h. | Chromatography $SiO_2$, $CH_2Cl_2$:MeOH = 100:0 to 97:3 | 4-(dibenzo[b,d]furan-2-ylmethyl)-6,7-dimethoxyisoquinoline 2-oxide (123 mg); MW: 385.41; Yield = 70%; Off- white Solid; Mp (° C.): 245.2; $R_f$ = 0.3 ($CH_2Cl_2$:MeOH = 97:3, free base); $^1$H-NMR ($CDCl_3$, δ): 3.86 (s, 3H, OMe), 4.01 (s, 3H, OMe), 4.41 (s, 2H, $CH_2$), 6.98 (s, 1H, ArH), 7.12 (s, 1H, ArH), 7.30-7.37 (m, 2H, 2xArH), 7.45 (td, 1H, J = 7.3 Hz, J = 8.2 Hz, J = 1.2 Hz, ArH), 7.54 (t, 1H, J = 8.9 Hz, J = 8.6 Hz, ArH), 7.75 (d, 1H, J = 1.4 Hz, ArH), 7.86 (d, 1H, J = 7.4 Hz, ArH), 7.97 (d, 1H, J = 1.2 Hz, ArH), 8.59 (d, 1H, J = 1.0 Hz, ArH); $^{13}$C-NMR ($CDCl_3$, δ): 36.5, 56.0, 56.2, 102.7, 103.9, 111.8, 112.0, 120.6, 120.7, 122.9, 123.7, 124.8, 125.0, 125.9, 127.5, 127.7, 132.0, 133.7, 133.9, 135.1, 151.8, 151.9, 155.2, 156.6; MS-ESI m/z (% rel. Int.): 386.1 ([MH]$^+$, 100); HPLC: Method A, detection UV 254 nm, RT = 5.01 min, peak area 98%. |

TABLE 7-continued

| Compd # | FORMULA | General Procedure | Purification | Analysis |
|---|---|---|---|---|
| 36 | 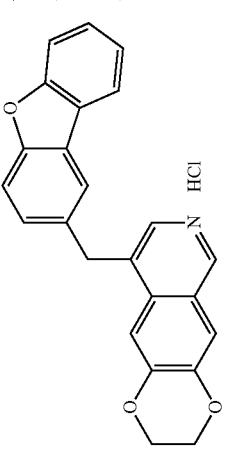 | A TTA 24150B (430 mg, 1.53 mmol); dibenzofuran-2-carbaldehyde (300 mg, 1.53 mmol); 37% HCl (2.0 mL); 90° C. for 25 min. | Chromatography SiO$_2$, cyclohexane:EtOAc = 100:0 to 50:50 | 9-(dibenzo[b,d]furan-2-ylmethyl)-2,3-dihydro-[1,4]dioxino[2,3-g]isoquinoline hydrochloride (115 mg); MW: 403.86; Yield: 19%; Yellow Solid; Mp (° C.): 278.2; R$_f$: 0.25 (cyclohexane:EtOAc = 5:5, free base); $^1$H-NMR (CD$_3$OD, δ): 4.45 (d, 2H, J = 4.8 Hz, OCH$_2$), 4.50 (d, 2H, J = 4.9 Hz, OCH$_2$), 4.64 (s, 2H, CH$_2$), 7.32-7.58 (m, 5H, 5xArH), 7.76 (s, 1H, ArH), 7.89 (s, 1H, ArH), 7.96-7.99 (m, 2H, 2xArH), 8.16 (s, 1H, ArH), 9.34 (s, 1H, ArH); $^{13}$C-NMR (CD$_3$OD, δ): 36.7, 65.6, 66.6, 111.1, 112.6, 112.9, 116.9, 121.8, 122.0, 124.1, 125.0, 125.1, 126.1, 128.7, 129.2, 129.6, 133.8, 136.2, 136.5, 144.1, 149.2, 155.2, 156.6, 158.0; MS-ESI m/z (% rel. Int.): 368.1 ([MH]$^+$, 100); HPLC: Method A, detection UV 254 nm, RT = 4.89 min, peak area 99.9%. |
| 37 | 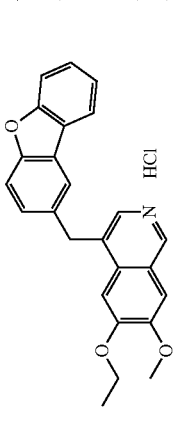 | A ECO 33138 (600 mg, 2.02 mmol); dibenzofuran-2-carbaldehyde (396 mg, 2.02 mmol); EtOH (8 mL); 37% HCl (8 mL); 100° C. under microwave irradiation (150 W) for 20 min. | Chromatography SiO$_2$, CH$_2$Cl$_2$:EtOAc = 100:0 to 50:50 | 4-(dibenzo[b,d]furan-2-ylmethyl)-6-ethoxy-7-methoxyisoquinoline hydrochloride (426 mg); MW: 419.91; Yield: 47%; Yellow Solid; Mp (° C.): 210.1; R$_f$: 0.2 (CH$_2$Cl$_2$:EtOAc = 1:1, free base); $^1$H-NMR (DMSO-d6, δ): 1.32 (t, 3H, Hz, 3H J = 6.7 Hz CH$_3$), 3.95 (s, 3H, OMe), 4.29 (q, 2H, J = 6 Hz, CH$_2$O), 4.69 (s, 2H, CH$_2$), 7.37 (m, 1H, ArH), 7.51 (m, 2H, 2xArH), 7.60 (s, 1H, ArH), 7.65 (m, 2H, 2xArH), 7.89 (s, 1H, ArH), 8.06 (d, 1H, J = 6 Hz, ArH), 8.12 (s, 1H, ArH), 8.46 (s, 1H, ArH), 9.42 (s, 1H, ArH); $^{13}$C-NMR (DMSO-d6, δ): 144, 36.9, 57.0, 66.7, 104 (ArH), 109.0, 112.6, 113.0, 121.8, 122.2, 124.1, 125.0, 125.4, 126.1, 128.7, 129.2 (ArH), 130.3, 134.0, 136.1, 137.3, 142.4, 154.4, 156.6, 158.0, 159.0; MS-ESI m/z (% rel. Int.): 384.2 ([MH]$^+$, 100); HPLC: Method A, detection UV 254 nm, RT = 5.22 min, peak area 99%. |
| 38 | 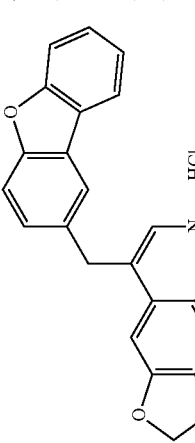 | A TTA 24156B (200 mg, 0.75 mmol); dibenzofuran-2-carbaldehyde (147 mg, 0.75 mmol); EtOH (8 mL); 37% HCl (8 mL); 100° C. under microwave irradiation (150 W) for 20 min. | Chromatography SiO$_2$, CH$_2$Cl$_2$:EtOAc = 100:0 to 50:50 | 8-(dibenzo[b,d]furan-2-ylmethyl)-[1,3]dioxolo[4,5-g]isoquinoline hydrochloride (84 mg); MW: 389.84; Yield: 29%; Yellow Solid; Mp (° C.): >310; R$_f$: 0.5 (CH$_2$Cl$_2$:EtOAc = 1:1, free base); $^1$H-NMR (MeOD, δ): 4.66 (s, 2H, CH$_2$), 6.31 (s, 2H, CH$_2$), 7.29-7.60 (m, 5H, 5xArH), 7.68 (d, 2H, J = 3 Hz, ArH), 7.96 (m, 2H, 2xArH), 8.23 (s, 1H, ArH), 9.26 (s, 1H, ArH); $^{13}$C-NMR (MeOD, δ): 36.8, 102.0, 105.5, 106.3, 112.6, 112.9, 121.3, 122.0, 124.1, 125.0, 126.1, 127.2, 128.7, 129.2, 131.4, 133.8, 136.8, 139.7, 143.1, 152.9, 156.6, 158.0, 158.5; MS-ESI m/z (% rel. Int.): 354.2 ([MH]$^+$, 100); HPLC: Method A, detection UV 254 nm, RT = 4.94 min, peak area 99%. |
| 39 | 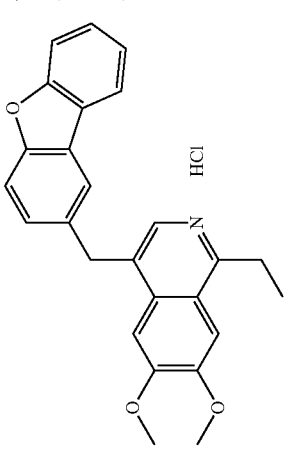 | A SSA 39098 (210 mg, 0.67 mmol); dibenzofuran-2-carbaldehyde (132 mg, 0.67 mmol); 37% HCl (1.2 mL); 100° C. for 20 min. | Chromatography SiO$_2$, CH$_2$Cl$_2$:EtOAc = 90:10 to 50:50 | 4-(dibenzo[b,d]furan-2-ylmethyl)-1-ethyl-6,7-dimethoxyisoquinoline hydrochloride (38 mg); MW: 433.93; Yield: 13%; Orange Solid; Mp (° C.): 154.4; R$_f$: 0.25 (cyclohexane:EtOAc = 5:5, free base); $^1$H-NMR (CD$_3$OD, δ): 1.12 (t, 3H, J = 7.5 Hz, CH$_3$), 3.52 (q, 2H, J = 7.48 Hz, CH$_2$), 3.98 (s, 3H, OMe), 4.06 (s, 3H, OMe), 4.67 (s, 2H, CH$_2$), 7.31-7.35 (m, 1H, ArH), 7.46-7.53 (m, 5H, 5xArH), 7.69 (s, 1H, ArH), 7.96 (d, 1H, J = 7.6 Hz, ArH), 7.97 (s, 1H, ArH), 8.09 (s, 1H, ArH); $^{13}$C-NMR (CD$_3$OD, δ): 13.8, 25.9, 36.8 (CH$_2$), 57.1, 57.3, 104.9, 106.5, 112.6, 112.9, 121.8, 122.1, 123.4, 124.1, 125.0, 126.0, 128.7, 129.3, 129.7, 134.0, 134.6, 137.1, 154.1, 156.5, 157.9 (2xC), 158.9; MS-ESI m/z (% rel. Int.): 398.0 ([MH]$^+$, 100); HPLC: Method A, detection UV 254 nm, RT = 5.22 min, peak area 99.9%. |

TABLE 7-continued

| Compd # | FORMULA | General Procedure | Purification | Analysis |
|---|---|---|---|---|
| 40 | 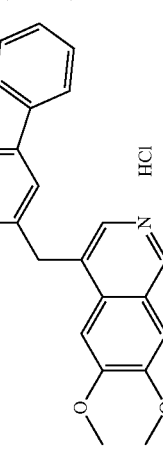 | A SSA 39102 (212 mg, 0.65 mmol); dibenzofuran-2-carbaldehyde (128 mg, 0.65 mmol); 37% HCl (1.2 mL); 100° C. for 20 min. | Chromatography SiO$_2$, CH$_2$Cl$_2$:EtOAc = 90:10 to 60:40 | 4-(dibenzo[b,d]furan-2-ylmethyl)-6,7-dimethoxy-1-propylisoquinoline hydrochloride (61 mg); MW: 447.95; Yield: 22%; Yellow Solid: Mp (° C.): 144.9; R$_f$: 0.25 (cyclohexane:EtOAc = 64, free base); $^1$H-NMR (CD$_3$OD, δ): 1.54 (t, 3H, J = 7.2 Hz, CH$_3$), 1.93-1.98 (m, 2H, CH$_2$), 3.48 (t, 2H, J = 7.1 Hz, CH$_2$), 3.99 (s, 3H, OMe), 4.07 (s, 3H, OMe), 4.68 (s, 2H, CH$_2$), 7.33-7.36 (m, 1H, ArH), 7.45-7.58 (m, 5H, 5xArH), 7.69 (s, 1H, ArH), 7.96 (d, 1H J = 7.74 Hz, ArH), 8.02 (s, 1H, ArH), 8.09 (s, 1H, ArH); $^{13}$C-NMR (CD$_3$OD, δ): 14.1, 24.1, 34.0, 36.8, 57.1, 57.3, 104.9, 106.6, 112.6, 112.9, 121.8, 122.2, 123.7, 124.1, 125.0, 126.0, 128.7, 129.3, 129.8, 134.0, 134.6, 137.1, 154.0, 156.5, 156.6, 158.0, 159.0; MS-ESI m/z (% rel. Int.): 412.0 ([MH]$^+$, 100); HPLC: Method A, detection UV 254 nm, RT = 5.40 min, peak area 98%. |
| 41 | 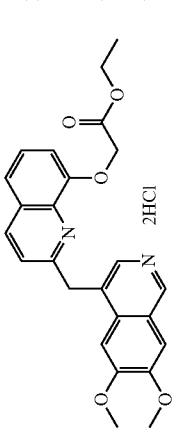 | B (a) Free base of 7 (200 mg, 0.58 mmol); DMF (3 mL); Cs$_2$CO$_3$ (564 mg, 1.73 mmol); ethyl 2-bromoacetate (91 μL, 0.81 mmol). 40° C. for 24 h. | Chromatography SiO$_2$, CH$_2$Cl$_2$:MeOH = 100:0 to 97:3 | ethyl 2-(2-((6,7-dimethoxyisoquinolin-4-yl)methyl)quinolin-8-yloxy)acetate dihydrochloride (59 mg); MW: 505.39; Yield: 20%; Yellow Solid: Mp (° C.): 122.4; R$_f$: 0.25 (CH$_2$Cl$_2$:MeOH = 99:1, free base); $^1$H-NMR (CD$_3$OD, δ): 1.35 (t, 3H, J = 7.1 Hz, CH$_3$), 4.10 (s, 3H, OMe), 4.31-4.38 (q, 2H, J = 7.1 Hz, CH$_2$), 5.28 (s, 3H, CH$_2$), 5.39 (s, 2H, CH$_2$), 7.65 (s, 1H, ArH), 7.71-7.74 (m, 1H, ArH), 7.82 (d, 1H, J = 8.6 Hz, ArH), 7.90-7.94 (m, 3H, 3xArH), 8.49 (s, 1H, ArH), 9.05 (d, 1H, J = 8.6 Hz, ArH), 9.48 (s, 1H, ArH); $^{13}$C-NMR (CD$_3$OD, δ): 14.4, 35.3, 57.22, 58.0, 63.2, 67.5, 103.51, 109.6, 116.6, 122.7, 124.5, 125.8, 130.2, 130.5, 131.4, 131.8, 137.3, 143.8, 148.4, 149.6, 154.8, 157.8, 160.8, 170.5. MS-ESI m/z (% rel. Int.): ([MH]$^+$, 100), 455.1 (30), 887.3 (4); HPLC: Method A, detection UV 254 nm, RT = 4.07 min, peak area 99.9%. |
| 42 | 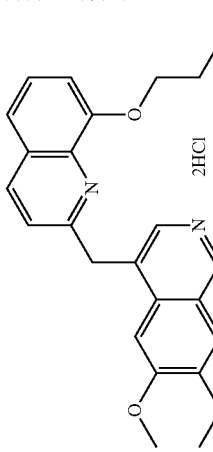 | D (a) Free base of 41 (264 mg, 0.61 mmol); t-BuOH (19 mL); MeOH (750 μL); NaBH$_4$ (25.4 mg, 0.67 mmol).140° C. for 2 h. | Chromatography SiO$_2$, CH$_2$Cl$_2$:MeOH = 100:0 to 97:3 | 2-(2-((6,7-dimethoxyisoquinolin-4-yl)methyl)quinolin-8-yloxy)ethanol dihydrochloride (86 mg); MW: 463.35; Yield: 61%; Yellow Solid: Mp (° C.): 211.9; R$_f$: 0.15 (CH$_2$Cl$_2$:MeOH = 97:3, free base); $^1$H-NMR (CD$_3$OD, δ): 4.10 (s, 3H, OMe), 4.11 (s, 3H, OMe), 4.16 (t, 2H, J = 4.4 Hz, OCH$_2$), 4.52 (t, 2H, J = 4.2 Hz, OCH$_2$), 5.49 (s, 2H, CH$_2$), 7.70-7.95 (m, 6H, 6xArH), 8.54 (s, 1H, ArH), 9.05 (d, 1H, J = 8.7 Hz, ArH), 9.49 (s, 1H, ArH); $^{13}$C-NMR (CD$_3$OD, δ): 34.9, 57.3, 58.1, 61.1, 72.7, 103.6, 109.7, 115.7, 121.6, 124.5, 125.8, 130.2, 130.5, 131.2, 131.9 (2xC), 137.4, 143.9, 148.9, 150.2, 154.8, 157.4, 160.9; MS-ESI m/z (% rel. Int.): 391.2 ([MH]$^+$, 100); HPLC: Method A, detection UV 254 nm, RT = 3.43 min, peak area 99%. |
| 43 | 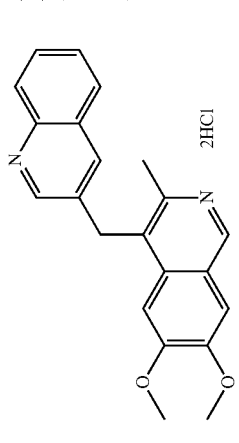 | A ANP 31060A (340 mg, 1.26 mmol); 3-quinoline-carboxaldehyde (200 mg, 1.26 mmol); 37% HCl (2.5 mL); 110° C. for 0.5 h min | Chromatography SiO$_2$, EtOAc:MeOH = 100:0 to 95:5 | 3-((6,7-dimethoxy-3-methylisoquinolin-4-yl)methyl)quinoline dihydrocloride (231 mg); MW: 417.32; Yield: 44%; Beige Solid: Mp (° C.): 237.2; R$_f$: 0.20 (EtOAc:MeOH = 95:5, free base); $^1$H-NMR (CDCl$_3$, δ): 2.85 (s, 3H, CH$_3$), 3.99 (s, 3H, CH$_3$), 4.07 (s, 3H, CH$_3$), 5.05 (s 2H, CH$_2$), 7.47 (s, 1H, ArH), 7.83 (s, 1H, ArH), 7.93 (t, 1H, J = 7 Hz, ArH), 8.11-8.28 (m, 3H, 3xArH), 8.77 (s, 1H, ArH), 9.26 (s, 1H, ArH), 9.36 (s, 1H, ArH); $^{13}$C-NMR (CDCl$_3$, δ): 17.8, 31.1, 57.1, 57.7, 103.3, 109.0, 121.6, 124.8, 128.9, 130.2, 130.5, 131.5, 134.3, 136.0, 138.4, 142.0, 142.7, 146.0, 146.7, 149.3, 154.1, 160.7; MS-ESI m/z (% rel. Int.): 345.4 ([MH]$^+$, 100); HPLC: Method A, detection UV 254 nm, RT = 3.24 min, peak area 97%. |

TABLE 7-continued

| Compd # | FORMULA | General Procedure | Purification | Analysis |
|---|---|---|---|---|
| 44 | 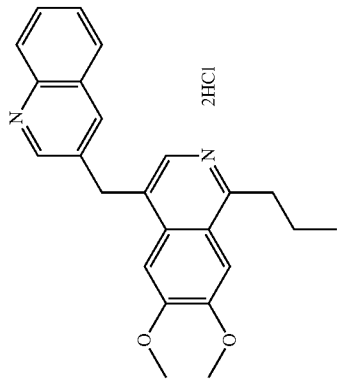 | A SSA 39102 (500 mg, 1.54 mmol); quinoline-3-carbaldehyde (241 mg, 1.54 mmol); 37% HCl (2.5 mL); 95° C. for 35 min. | Chromatography SiO$_2$, cyclohexane:EtOAc = 50:50 to 0:100 | 3-((6,7-dimethoxy-1-propylisoquinolin-4-yl)methyl)quinoline dihydrochloride (507 mg); MW: 445.38; Yield: 74%; Beige Solid; Mp (° C.): 225.4; R$_f$: 0.2 (EtOAc); $^1$H-NMR (CD$_3$OD, δ): 1.15 (t, 3H, J = 7.4 Hz, CH$_2$CH$_3$), 1.97-2.05 (m, 2H, CH$_2$CH$_3$), 3.55 (t, 2H, J = 7.6 Hz, CH$_2$CH$_3$), 4.08 (s, 3H, OMe), 4.12 (s, 3H, OMe), 5.02 (s, 2H, CH$_2$), 7.58 (s, 1H, ArH), 7.80 (s, 1H, ArH), 7.98 (t, 1H, J = 8.0 Hz, ArH), 8.18 (t, 1H, J = 7.0 Hz, ArH), 8.28-8.31 (m, 3H, 3xArH), 9.13 (s, 1H, ArH), 9.37 (d, 1H, J = 1.7 Hz, ArH); $^{13}$C-NMR (CD$_3$OD, δ): 14.1, 24.2, 33.3, 34.1, 57.2, 57.7, 104.4, 107.1, 121.7, 124.0, 130.3, 130.5, 130.8, 131.1, 131.6, 134.5, 136.1, 136.9, 138.6, 146.9, 147.5, 154.4, 157.7, 159.7; MS-ESI m/z (% rel. Int.): 373.3 ([MH]$^+$, 100); HPLC: Method A, detection UV 254 nm, RT = 3.57 min, peak area 99%. |
| 45 | 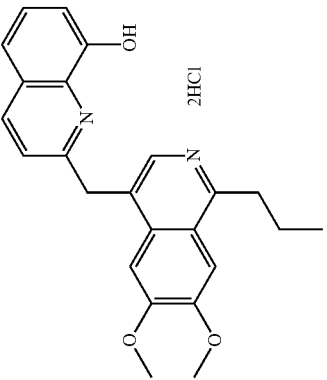 | A SSA 39102 (250 mg, 0.77 mmol); 8-hydroxyquinoline-2-carbaldehyde (133 mg, 0.77 mmol); 37% HCl (2.0 mL); 95° C. for 25 min. | Chromatography SiO$_2$, cyclohexane:EtOAc = 50:50 to 0:100 | 2-((6,7-dimethoxy-1-propylisoquinolin-4-yl)methyl)quinolin-8-ol dihydrochloride (282 mg); MW: 461.38; Yield: 79%; Yellow Solid; Mp (° C.): 219.7; R$_f$: 0.2 (EtOAc); $^1$H-NMR (CD$_3$OD, δ): 1.15 (t, 3H, J = 7.4 Hz, CH$_2$CH$_3$), 1.97-2.04 (m, 2H, CH$_2$CH$_3$), 3.56 (t, 2H, J = 7.6 Hz, CH$_2$CH$_3$), 4.08 (s, 3H, OMe), 4.13 (s, 3H, OMe), 5.29 (s, 2H, CH$_2$), 7.52 (d, 1H, J = 7.4 Hz, ArH), 7.61 (s, 1H, ArH), 7.70-7.81 (m, 4H, 4xArH), 8.33 (s, 1H, ArH), 8.92 (d, 1H, J = 9.6 Hz, ArH); $^{13}$C-NMR (CD$_3$OD, δ): 14.1, 24.2, 34.1, 35.5, 57.3, 57.8, 104.3, 107.2, 117.5, 120.1, 123.9, 124.0, 129.1, 130.5, 131.0, 131.6, 131.7, 137.1, 147.6, 149.9, 154.5, 157.1, 158.1, 159.9; MS-ESI m/z (% rel. Int.): 389.3 ([MH]$^+$, 100); HPLC: Method A, detection UV 254 nm, RT = 4.09 min, peak area 99%. |
| 46 | 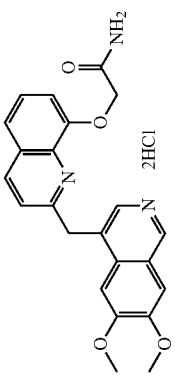 | B (a) Free base of 7 (300 mg, 0.71 mmol); DMF (8 mL); Cs$_2$CO$_3$ (564 mg, 1.73 mmol); 2-bromoacetamide (143 mg, 1.04 mmol); 80° C. for 15 h. | Chromatography SiO$_2$, CH$_2$Cl$_2$:MeOH = 100:0 to 95:5 | 2-(2-((6,7-dimethoxyisoquinolin-4-yl)methyl)quinolin-8-yl)oxy)acetamide dihydrochloride (45 mg); MW: 476.35; Yield: 13%; Yellow Solid; Mp (° C.): 166.8; R$_f$: 0.25 (CH$_2$Cl$_2$:MeOH = 95:5, free base); $^1$H-NMR (CD$_3$OD, δ): 4.07 (s, 6H, 2xOMe), 5.05 (s, 2H, CH$_2$), 5.37 (s, 2H, CH$_2$), 7.66-7.72 (m, 2H, 2xArH), 7.81 (d, 1H, J = 8.6 Hz ArH), 7.89-7.90 (m, 3H, 3xArH), 8.50 (s, 1H, ArH), 9.02 (d, 1H, J = 8.6 Hz, ArH), 9.44 (s, 1H, ArH); $^{13}$C-NMR (CD$_3$OD, δ): 35.25, 57.21, 58.04, 68.86, 103.53, 109.61, 116.54, 122.69, 124.51, 125.79, 130.26, 130.56, 131.49, 131.84 (2xC), 137.36, 143.88, 148.30, 149.64, 154.76, 157.65, 160.86, 172.40; MS-ESI m/z (% rel. Int.): 404.2 ([MH]$^+$, 100); HPLC: Method A, detection UV 254 nm, RT = 3.41 min, peak area 99.9%. |

TABLE 7-continued

| Compd # | FORMULA | General Procedure | Purification | Analysis |
|---|---|---|---|---|
| 47 | (structure) | A SSA 39102 (300 mg, 0.92 mmol) and 2-hydroxyquinoline-3-carbaldehyde (160 mg, 0.76 mmol); 37% HCl (2.0 mL); 95° C. for 25 min. | CH$_2$Cl$_2$ (10 mL) was added, precipitate was filtrated | 3-((6,7-dimethoxy-1-propylisoquinolin-4-yl)methyl)quinolin-2-ol dihydrochloride (115 mg); MW: 461.38; Yield: 27%; Pale Orange Solid; Mp (° C.): 237.4; $^1$H-NMR (CD$_3$OD, δ): 1.12 (t, 3H, J = 7.3 Hz, CH$_2$CH$_3$), 1.96 (q, 2H, J = 7.6 Hz, CH$_2$CH$_3$), 3.48 (t, 2H, J = 7.6 Hz, CH$_2$CH$_2$), 4.09 (s, 3H, OMe), 4.10 (s, 3H, OMe), 4.46 (s, 2H, CH$_2$), 7.23 (t, 1H, J = 7.4 Hz, ArH), 7.35 (d, 1H, J = 8.2 Hz, ArH), 7.52 (t, 1H, J = 8.1 Hz, ArH), 7.58 (d, 1H, J = 7.8 Hz, ArH), 7.71 (s, 1H, ArH), 7.75 (s, 1H, ArH), 7.94 (s, 1H, ArH), 8.22 (s, 1H, ArH); $^{13}$C-NMR CD$_3$OD, δ): 14.1, 24.1, 30.9, 34.0, 57.1, 57.5, 104.8, 106.7, 116.4, 121.3, 123.7, 124.0, 128.9, 130.0, 130.8, 131.7, 133.3, 137.3, 139.3, 141.2, 154.1, 156.6, 159.3, 164.3; MS-ESI m/z 389.2 ([MH]$^+$, 100); HPLC: Method A, detection UV 254 nm, RT = 4.09 min, peak area 99%. |
| 48 | (structure) | A LPO 22102 (447 mg, 1.58 mmol); 2-methylquinoline-6-carbaldehyde (270 mg, 1.58 mmol); 37% HCl (1.4 mL); 90° C. for 0.5 h. | Chromatography SiO$_2$, CH$_2$Cl$_2$:MeOH = 100:0 to 98:2 | 6-((6,7-dimethoxyisoquinolin-4-yl)methyl)-2-methylquinoline dihydrochloride (139 mg); MW: 417.33; Yield: 23%; White Solid; Mp (° C.): 165.5; R$_f$: 0.25 (CH$_2$Cl$_2$:MeOH = 98:2, free base); $^1$H-NMR (CD$_3$OD, δ): 2.77 (s, 3H, CH$_3$), 3.96 (s, 3H, OMe), 4.03 (s, 3H, OMe), 4.76 (s, 2H, CH$_2$), 7.50 (s, 1H, ArH), 7.54 (d, 1H, J = 8.5 Hz, ArH), 7.82 (d, 1H, J = 8.7 Hz, ArH), 7.91 (s, 1H, ArH), 7.98 (d, 1H, J = 8.7 Hz, ArH), 8.29 (s, 1H, ArH), 8.37 (d, 1H, J = 8.5 Hz, ArH), 9.27 (s, 1H, ArH); $^{13}$C-NMR (CD$_3$OD, δ): 23.6, 36.6, 57.0, 57.3, 103.9, 108.8, 124.2, 125.8, 127.0, 128.4, 128.8, 132.8, 133.4, 134.3, 136.5, 138.8, 140.5, 144.1, 145.0, 154.0, 159.0, 160.3; MS-ESI m/z 345.3 ([MH]$^+$, 70), 173.2 (100); HPLC: Method A, detection UV 254 nm, RT = 4.03 min, peak area 98%. |
| 49 | (structure) | A SSA 39102 (320 mg, 0.98 mmol); 2-hydroxy-6-methoxyquinoline-3-carbaldehyde (200.0 mg, 0.98 mmol); 37% HCl (2.4 mL); 95° C. for 25 min. | CH$_2$Cl$_2$ (5 mL) was added, precipitate was filtrated | 3-((6,7-dimethoxy-1-propylisoquinolin-4-yl)methyl)-6-methoxyquinolin-2-ol dihydrochloride (52 mg); MW: 491.41; Global Yield: 46%; White Solid; Mp (° C.): 262.2; $^1$H-NMR (CD$_3$OD, δ): 1.12 (t, 3H, J = 7.3 Hz, CH$_2$CH$_3$), 1.96 (q, 2H, J = 7.5 Hz, CH$_2$CH$_3$), 3.51 (t, 2H, J = 7.5 Hz, CH$_2$CH$_2$), 3.80 (s, 3H, OMe), 4.10 (s, 6H, 2xOMe), 4.46 (s, 2H, CH$_2$), 7.91 (s, 1H, ArH), 8.23 (s, 1H, ArH), 7.32 (d, 1H, J = 8.9 Hz, ArH), 7.72-7.74 (m, 2H, 2xArH), 7.11-7.17 (m, 2H, 2xArH); $^{13}$C-NMR (CD$_3$OD, δ): 14.5, 24.3, 30.9, 34.1, 56.5, 57.4, 57.9, 105.2, 106.6, 109.9, 117.9, 121.6, 122.0, 123.8, 130.0, 131.0, 133.6, 133.8, 137.4, 140.9, 154.2, 156.4, 156.9, 159.3, 163.7; MS-ESI m/z 419.3 ([MH]$^+$, 100); HPLC: Method A, detection UV 254 nm, RT = 4.11 min, peak area 99%. |

TABLE 7-continued

| Compd # | FORMULA | General Procedure | Purification | Analysis |
|---|---|---|---|---|
| 50 | (structure: 3-(1-ethyl-6,7-dimethoxyisoquinolin-4-yl)methyl)quinoline dihydrochloride) · 2HCl | A SSA 39098 (700 mg, 2.25 mmol); quinoline-3-carbaldehyde (353 mg, 2.25 mmol); 37% HCl (3.5 mL); 95° C. for 35 min. | Chromatography $SiO_2$, $CH_2Cl_2$:MeOH = 100:0 to 98:2 | 3-(1-ethyl-6,7-dimethoxyisoquinolin-4-yl)methyl)quinoline dihydrochloride (56 mg); MW: 431.35; Yield: 64%; White Solid; Mp (° C.): 119.9; $R_f$: 0.3 ($CH_2Cl_2$:MeOH = 98:2, free base); $^1$H-NMR ($CD_3OD$, δ): 1.56 (t, 3H, J = 7.6 Hz, $CH_2CH_3$), 3.58 (q, 2H, J = 7.6 Hz, $CH_2CH_3$), 4.05 (s, 3H, OMe), 4.10 (s, 3H, OMe), 4.98 (s, 2H, $CH_2$), 7.55 (s, 6H, 2xOMe), 4.45 (s, 1H, ArH), 7.79 (s, 1H, ArH), 7.93 (t, 1H, J = 7.1 Hz, ArH), 8.12 (t, 1H, J = 7.2 Hz, ArH), 8.22-8.29 (m, 3H, 3xArH), 9.02 (s, 1H, ArH), 9.31 (s, 1H, ArH); $^{13}$C-NMR ($CD_3OD$, δ): 13.9, 26.0, 33.4, 57.2, 57.6, 104.4, 106.9, 122.4, 123.6, 130.1, 130.4, 130.8, 131.2, 131.3, 134.4, 135.6, 136.9, 139.5, 146.4, 147.4, 154.4, 158.9, 159.6; MS-ESI m/z (% rel. Int.): 359.2 ([MH]$^+$, 100); HPLC: Method A, detection UV 254 nm, RT = 3.40 min, peak area 99%. |
| 51 | (structure: 3-((1-ethyl-6,7-dimethoxyisoquinolin-4-yl)methyl)-6-methoxyquinolin-2-ol dihydrochloride) · 2HCl | A SSA 39098 (200 mg, 0.64 mmol); 2-hydroxy-6-methoxyquinoline-3-carbaldehyde (130 mg, 0.64 mmol); 37% HCl (1.6 mL); 95° C. for 25 min. | Chromatography $SiO_2$, EtOAc:MeOH = 100:0 to 97:3 | 3-((1-ethyl-6,7-dimethoxyisoquinolin-4-yl)methyl)-6-methoxyquinolin-2-ol dihydrochloride (141.5 mg); MW: 477.38; Yield: 46%; Orange Solid; Mp (° C.): 268.6; $R_f$: 0.25 (EtOAc:MeOH = 95:5, free base); $^1$H-NMR ($CD_3OD$, δ): 1.54 (t, 3H, J = 7.4 Hz, $CH_2CH_3$), 3.53 (q, 2H, J = 7.6 Hz, $CH_2CH_3$), 3.81 (s, 3H, OMe), 4.09 (s, 6H, 2xOMe), 4.45 (s, 2H, $CH_2$), 7.08 (s, 1H, ArH), 7.15 (dd, 1H, J = 9.0 Hz, J = 1.9 Hz, ArH), 7.29 (d, 1H, J = 9.0 Hz, ArH), 7.72-7.73 (m, 2H, 2xArH), 7.87 (s, 1H, ArH), 8.21 (s, 1H, ArH); $^{13}$C-NMR ($CD_3OD$, δ): 13.8, 25.9, 30.9, 56.2, 57.1, 57.5, 104.9, 106.6, 109.8, 117.7, 121.3, 122.0, 123.4, 130.0, 131.1, 133.4, 133.7, 137.3, 140.8, 154.2, 157.0, 157.8, 159.3, 163.8; MS-ESI m/z (% rel. Int.): 405.3 ([MH]$^+$, 100); HPLC: Method A, detection UV 254 nm, RT = 3.90 min, peak area 99%. |
| 52 | (structure: 3-((6,7-dimethoxy-1-propylisoquinolin-4-yl)methyl)-6-ethoxyquinolin-2-ol dihydrochloride) · 2HCl | A SSA 39102 (200 mg, 0.61 mmol); 6-ethoxy-2-hydroxyquinoline-3-carbaldehyde (133 mg, 0.61 mmol); 37% HCl (1.6 mL); 95° C. for 25 min. | Chromatography $SiO_2$, $CH_2Cl_2$:MeOH = 100:0 to 96:4 | 3-((6,7-dimethoxy-1-propylisoquinolin-4-yl)methyl)-6-ethoxyquinolin-2-ol dihydrochloride (151 mg); MW: 505.43; Yield: 49%; Orange Solid; Mp (° C.): 243.7; $R_f$: 0.4 ($CH_2Cl_2$:MeOH = 96:4, free base); $^1$H-NMR ($CD_3OD$, δ): 1.12 (t, 3H, J = 7.3 Hz, $CH_2CH_3$), 1.39 (t, 3H, J = 6.9 Hz, $OCH_2CH_3$), 1.96 (s, 2H, J = 7.5 Hz, $CH_2CH_2CH_3$), 3.48 (t, 2H, J = 7.6 Hz, $CH_2CH_2CH_3$), 4.03 (q, 2H, J = 7.0 Hz, $OCH_2CH_3$), 4.09 (s, 6H, 2xOMe), 4.45 (s, 2H, $CH_2$), 7.07 (d, 1H, J = 2.6 Hz, ArH), 7.14 (dd, 1H, J = 9.0 Hz, J = 2.6 Hz, ArH), 7.29 (d, 1H, J = 9.0 Hz, ArH), 7.70 (s, 1H, ArH), 7.73 (s, 1H, ArH), 7.88 (s, 1H, ArH), 8.21 (s, 1H, ArH); $^{13}$C-NMR ($CD_3OD$, δ): 14.1, 15.1, 24.1, 30.9, 34.0, 57.1, 57.5, 65.1, 104.8, 106.7, 110.6, 117.7, 121.8, 122.1, 123.7, 129.9, 131.0, 133.4, 133.6, 137.2, 140.9, 154.2, 156.5, 159.3, 163.7; MS-ESI m/z (% rel. Int.): 433.4 ([MH]$^+$, 100); HPLC: Method A, detection UV 254 nm, RT = 4.33 min, peak area 99%. |
| 53 | (structure: 3-((6,7-dimethoxyisoquinolin-4-yl)methyl)-6-methoxyquinolin-2-ol dihydrochloride) · 2HCl | A LPO 22102 (280 mg, 0.98 mmol); SSA 48036A (HCl mg, 0.98 mmol); 37% HCl (2.4 mL); 90° C. for 25 min. | Chromatography $SiO_2$, $CH_2Cl_2$:MeOH = 100:0 to 94:6 | 3-((6,7-dimethoxyisoquinolin-4-yl)methyl)-6-methoxyquinolin-2-ol dihydrochloride (140 mg); MW: 449.33; Yield: 31%; White-off Solid; Mp (° C.): 251.5; $R_f$: 0.25 ($CH_2Cl_2$:MeOH = 94:6, free base); $^1$H-NMR ($DMSO$-$d_6$, δ): 3.71 (s, 3H, OMe), 3.97 (s, 3H, OMe), 4.04 (s, 3H, $CH_2$), 5.39 (s, 3H, OMe), 4.40 (s, 2H, $CH_2$), 7.06-7.12 (m, 2H, 2xArH), 7.26 (d, 1H, J = 8.79 Hz, ArH), 7.73 (d, 2H, J = 13.4 Hz, ArH), 7.92 (s, 1H, ArH), 8.47 (s, 1H, ArH), 9.44 (s, 1H, ArH), 11.93 (s, 1H, OH); $^{13}$C-NMR ($DMSO$-$d_6$, δ): 29.2, 55.4, 56.2, 56.7, 103.1, 108.2, 108.8, 116.2, 119.2, 119.7, 123.6, 129.9, 130.6, 132.4, 133.2, 135.2, 137.8, 141.2, 151.9, 154.2, 157.2, 161.2; MS-ESI m/z (% rel. Int.): 377.2 ([MH]$^+$, 100); HPLC: Method A, detection UV 254 nm, RT = 3.73 min, peak area 99.9%. |

TABLE 7-continued

| Compd # | FORMULA | General Procedure | Purification | Analysis |
|---|---|---|---|---|
| 54 | (structure) | A SSA 39102 (291 mg, 0.89 mmol); 2-hydroxy-6-carbaldehyde (200 mg, 0.89 mmol); 37% HCl (2.4 mL); 90° C. for 25 min. | Chromatography SiO$_2$, CH$_2$Cl$_2$:MeOH = 100:0 to 95:5 | 3-((6,7-dimethoxy-1-propylisoquinolin-4-yl)methyl)-6-methylquinolin-2-ol dihydrochloride (40 mg); MW: 475.41; Yield: 20%; Yellow Solid; Mp (° C.): 37.8; R$_f$: 0.25 (CH$_2$Cl$_2$:MeOH = 95:5, free base); $^1$H-NMR (CD$_3$OD, δ): 1.12 (t, 3H, J = 7.4 Hz, CH$_3$), 2.06 (q, 2H, J = 7.5 Hz, CH$_2$), 2.38 (s, 3H, CH$_3$), 3.48 (t, 2H, J = 7.6 Hz, CH$_2$), 4.09 (s, 3H, OMe), 4.10 (s, 3H, OMe), 4.45 (s, 2H, CH$_2$), 7.25-7.28 (m, 1H, ArH), 7.37-7.39 (m, 2H, 2xArH), 7.71 (s, 1H, ArH), 7.76 (s, 1H, ArH), 7.88 (s, 1H, ArH), 8.21 (s, 1H, ArH); $^{13}$C-NMR (CD$_3$OD, δ): 14.07, 20.82, 24.08, 30.95, 34.02, 57.07, 57.52, 104.84, 106.69, 116.29, 121.32, 123.74, 128.30, 129.92, 130.59, 133.12, 133.39, 133.96, 137.27 (2xC), 141.01, 154.17, 156.50, 159.28, 164.16; MS-ESI m/z (% rel. Int.): 403.3 ([MH]$^+$, 100); HPLC: Method A, detection UV 254 nm, RT = 4.34 min, peak area 99.9%. |
| 55 | (structure) | B (a) Free base of 49 (250 mg, 0.60 mmol); 2-chloroacetonitrile (41.7 μL, 0.66 mmol); Cs$_2$CO$_3$ (292 mg, 0.90 mmol); DMF (2.4 mL); 90° C. for 1 h. | Chromatography SiO$_2$, CH$_2$Cl$_2$:MeOH = 100:0 to 98:2 | 2-((3-((6,7-dimethoxy-1-propylisoquinolin-4-yl)methyl)-6-methoxyquinolin-2-yl)oxy)acetonitrile (58 mg); MW: 457.52; Yield: 21%; Yellow Solid; Mp (° C.): 231.6; R$_f$: 0.2 (CH$_2$Cl$_2$:MeOH = 98:2, free base); $^1$H-NMR (CDCl$_3$, δ): 1.11 (t, 3H, J = 7.3 Hz, CH$_2$CH$_3$), 1.94 (sextuplet, 2H, J = 7.3 Hz, CH$_2$CH$_2$CH$_3$), 3.23 (t, 2H, J = 7.6 Hz, CH$_2$CH$_2$CH$_3$), 3.77 (s, 3H, OMe), 3.93 (s, 3H, OMe), 4.03 (s, 3H, OMe), 4.29 (s, 2H, CH$_2$), 5.33 (s, 2H, CH$_2$CN), 6.80 (d, 1H, J = 2.6 Hz, ArH), 7.15-7.19 (m, 3H, 3xArH), 7.27-7.25 (m, 1H, ArH), 7.38 (s, 1H, ArH), 8.31 (s, 1H, ArH); $^{13}$C-NMR (CDCl$_3$, δ): 14.4, 22.5, 30.2, 30.3, 37.5, 55.7, 55.9, 56.2, 102.8, 104.4, 111.0, 114.4, 114.6, 119.2, 121.5, 122.8, 125.8, 131.3, 132.0, 132.1, 137.4, 141.8, 149.8, 152.8, 155.6, 159.1, 161.0; MS-ESI m/z (% rel. Int.): 458.5 ([MH]$^+$, 100); HPLC: Method A, UV 254 nm, RT = 4.45 min, peak area 99%. |
| 56 | (structure) | C (a) LPO 43180 (70.5 mg, 0.13 mmol), acetic anhydride (14.8 μL, 0.16 mmol); Et$_3$N (73.8 μL, 0.53 mmol); THF (3.0 mL); 4° C. for 2 h. | Chromatography SiO$_2$, CH$_2$Cl$_2$:MeOH = 100:0 to 96:4 | N-(2-((3-((6,7-dimethoxy-1-propylisoquinolin-4-yl)methyl)-6-methoxyquinolin-2-yl)oxy)ethyl)acetamide dihydrochloride (39 mg); MW: 576.51; Yield: 51%; Off-white Solid; Mp (° C.): 253.3; R$_f$: 0.15 (CH$_2$Cl$_2$:MeOH = 96:4, free base); $^1$H-NMR (CD$_3$OD, δ): 1.12 (t, 3H, J = 7.1 Hz, CH$_2$CH$_3$), 1.82 (s, 3H, COCH$_3$), 1.96 (sextuplet, 2H, J = 7.1 Hz, CH$_2$CH$_2$CH$_3$), 3.49 (t, 2H, J = 7.1 Hz, CH$_2$CH$_2$CH$_3$), 3.56 (t, 2H, J = 6.5 Hz, CH$_2$N), 3.82 (s, 3H, OMe), 4.09 (s, 3H, OMe), 4.12 (s, 3H, OMe), 4.46-4.49 (m, 4H, CH$_2$ & CH$_2$O), 7.14 (s, 1H, ArH), 7.23 (d, 1H, J = 8.8 Hz, ArH), 7.67-7.72 (m, 3H, 3xArH), 7.88 (s, 1H, ArH), 8.19 (s, 1H, ArH); $^{13}$C-NMR (CD$_3$OD, δ): 14.1, 22.3, 24.2, 31.8, 34.0, 38.5, 43.2, 56.3, 57.2, 57.6, 104.8, 106.7, 111.3, 117.2, 120.8, 122.9, 123.7, 129.9, 130.4, 133.2, 134.7, 137.3, 140.2, 154.1, 156.4, 156.7, 159.2, 163.2, 174.1; MS-ESI m/z (% rel. Int.): 504.4 ([MH]$^+$, 100); HPLC: Method A, detection UV 254 nm, RT = 4.04 min, peak area 99%. |

TABLE 7-continued

| Compd # | FORMULA | General Procedure | Purification | Analysis |
|---|---|---|---|---|
| 57 | (structure) | A SSA 39102 (300 mg, 0.92 mmol); 2-methylquinoline-6-carbaldehyde (158 mg, 0.92 mmol); 37% HCl (1.4 mL); 95° C. for 0.5 h. | Chromatography SiO$_2$, CH$_2$Cl$_2$:MeOH = 99:1 to 98:2 | 6-((6,7-dimethoxy-1-propylisoquinolin-4-yl)methyl)-2-methylquinoline dihydrochloride (93 mg); MW: 459.41; Yield: 22%; Brown Solid; Mp (° C.): 200.5; R$_f$: 0.15 (CH$_2$Cl$_2$:MeOH = 98:2, free base); $^1$H-NMR (CD$_3$OD, δ): 1.14 (t, 3H, J = 7.4 Hz, CH$_2$CH$_2$CH$_3$), 1.98 (sextuplet, 2H, J = 7.5 Hz CH$_2$CH$_2$CH$_3$), 3.02 (s, 3H, CH$_3$), 3.54 (t, 2H, J = 7.5 Hz, CH$_2$CH$_2$CH$_3$), 4.00 (s, 3H, OMe), 4.10, (s, 3H, OMe), 4.86 (m, 2H, CH$_2$), 7.51 (s, 1H, ArH), 7.76 (s, 1H, ArH), 7.93 (d, 1H, J = 8.5 Hz, ArH), 8.15-8.27 (m, 4H, 4xArH), 8.96 (d, 1H, J = 8.7 Hz, ArH); $^{13}$C-NMR (CD$_3$OD, δ): 14.1, 20.9, 24.2, 34.1, 36.3, 57.2, 57.4, 104.7, 107.0, 121.6, 123.9, 125.2, 128.9, 129.6, 130.4, 132.6, 137.1 (2xC), 138.2, 141.8, 147.3, 154.3, 157.4, 159.3, 159.4; MS-ESI m/z (% rel. Int.): 387.3 ([MH]$^+$, 100); HPLC: Method A, detection UV 254 nm, RT = 3.52 min, peak area 99%. |
| 58 | (structure) | A SSA 39098 (300 mg, 0.96 mmol); 2-methylquinoline-6-carbaldehyde (165 mg, 0.96 mmol); 37% HCl (1.4 mL); 95° C. for 0.5 h. | Chromatography SiO$_2$, CH$_2$Cl$_2$:MeOH = 99:1 to 98:2 | 6-((1-ethyl-6,7-dimethoxyisoquinolin-4-yl)methyl)-2-methylquinoline dihydrochloride (90 mg); MW: 445.38; Yield: 21%; Off-white Solid; Mp (° C.): 234.6; R$_f$: 0.15 (CH$_2$Cl$_2$:MeOH = 98:2, free base); $^1$H-NMR (CD$_3$OD, δ): 1.57 (t, 3H, J = 7.7 Hz, CH$_2$CH$_3$), 3.03 (s, 3H, CH$_3$), 3.59 (q, 2H, J = 7.7 Hz, CH$_2$CH$_3$), 4.00 (s, 3H, OMe), 4.10 (s, 3H, OMe), 4.87-4.88 (m, 2H, CH$_2$), 7.51 (s, 1H, ArH), 7.78 (s, 1H, ArH), 7.93 (d, 1H, J = 8.2 Hz, ArH), 8.16-8.27 (m, 4H, 4xArH), 8.96 (d, 1H, J = 8.8 Hz, ArH); $^{13}$C-NMR (CD3OD, δ): 13.9, 20.9, 25.9, 36.3, 57.2, 57.4, 104.8, 106.8, 121.5, 123.6, 125.2, 128.9, 129.6, 130.5, 132.6, 137.1 (2xC), 138.1, 141.8, 147.3, 154.3, 158.6, 159.3, 159.4; MS-ESI m/z (% rel. Int.): 373.4 ([MH]$^+$, 20), 187.2 (100); HPLC: Method A, detection UV 254 nm, RT = 3.27 min, peak area 97%. |
| 59 | (structure) | A SSA 48060 (300 mg, 0.84 mmol); 2-methylquinoline-6-carbaldehyde (143 mg, 0.84 mmol); 37% HCl (1.4 mL); 95° C. for 0.5 h. | Chromatography SiO$_2$, cyclohexane:EtOAc = 50:50 to 20:80 | 6-((6,7-dimethoxy-1-phenylisoquinolin-4-yl)methyl)-2-methylquinoline dihydrochloride (192 mg); MW: 493.42; Yield: 47%; Yellow Solid; Mp (° C.): 231.5; R$_f$: 0.15 (cyclohexane:EtOAc = 5:5, free base); $^1$H-NMR (CD$_3$OD, δ): 3.04 (s, 3H, CH$_3$), 3.88 (s, 3H, O—Me), 4.02 (s, 3H, OMe), 4.98 (s, 2H, CH$_2$), 7.48 (s, 1H, ArH), 7.59 (s, 1H, ArH), 7.79-7.90 (m, 5H, 5xArH), 7.95 (d, 1H, J = 8.8 Hz, ArH), 8.25 (s, 2H, ArH), 8.31 (s, 1H, ArH), 8.44 (s, 1H, ArH), 8.99 (d, 1H, J = 8.5 Hz, ArH); $^{13}$C-NMR (CD$_3$OD, δ): 20.9, 36.5, 56.8, 57.6, 104.7, 108.4, 121.6, 124.1, 125.2, 129.0, 129.7, 130.7 (2xC), 131.2 (2xC), 132.2, 133.1, 133.4, 137.2 (2xC), 137.9, 138.2, 141.8, 147.4, 154.0, 154.4, 159.3, 159.5; MS-ESI m/z (% rel. Int.): 421.3 ([MH]$^+$, 100); HPLC: Method A, detection UV 254 nm, RT = 3.63 min, peak area 98%. |

TABLE 7-continued

| Compd # | FORMULA | General Procedure | Purification | Analysis |
|---|---|---|---|---|
| 60 | (structure: 6-((1-cyclohexyl-6,7-dimethoxyisoquinolin-4-yl)methyl)-2-methylquinoline dihydrochloride) · 2HCl | A SSA 48072 (300 mg, 0.82 mmol); 2-methylquinoline-6-carbaldehyde (140 mg, 0.82 mmol); 37% HCl (1.4 mL); 95° C. for 0.5 h. | Chromatography $SiO_2$, cyclohexane:EtOAc = 100:100 to 50:50 | 6-((1-cyclohexyl-6,7-dimethoxyisoquinolin-4-yl)methyl)-2-methylquinoline dihydrochloride (91 mg); MW: 499.47; Yield: 22%; Yellow Solid; Mp (° C.): 225.7; $R_f$: 0.25 (cyclohexane:EtOAc = 5:5, free base); $^1$H-NMR ($CD_3OD$, δ), 1.48-2.16 (m, 10H, 5x$CH_2$), 3.03 (s, 3H, $CH_3$), 3.94-4.02 (m, 4H, OMe & $CHCH_2$), 4.12 (s, 3H, OMe), 4.88 (s, 2H, $CH_2$), 7.51 (s, 1H, ArH), 7.85 (s, 1H, ArH), 7.93 (d, 1H, J = 8.4 Hz, ArH), 8.16-8.25 (m, 4H, 4xArH), 8.96 (d, 1H, J = 8.9 Hz, ArH); $^{13}$C-NMR ($CD_3OD$, δ): 20.9, 26.7, 27.1 (2xC), 32.7 (2xC), 36.4, 40.8, 57.2, 57.4, 104.9, 106.6, 121.5, 123.2, 125.2, 128.9, 129.6, 130.6, 132.4, 137.1, 137.3, 138.1, 141.8, 147.3, 154.3, 159.3, 159.4, 160.7; MS-ESI m/z (% rel. Int.): 427.4 ([MH]$^+$, 100); HPLC: Method A, detection UV 254 nm, RT = 3.88 min, peak area 98%. |
| 61 | (structure: 3-((1-isobutyl-6,7-dimethoxyisoquinolin-4-yl)methyl)quinoline) · 2HCl | A SSA 48066 (300 mg, 0.88 mmol); 3-quinoline carboxaldehyde (140 mg, 0.88 mmol); 37% HCl (2.5 mL); 90° C. for 25 min. | Chromatography $SiO_2$, $CH_2Cl_2$:MeOH = 100:0 to 98:2 | 3-((1-isobutyl-6,7-dimethoxyisoquinolin-4-yl)methyl)quinoline dihydrochloride (135 mg); MW: 459.41; Yield: 33%; Orange Pale Solid; Mp (° C.): 151.0; $R_f$: 0.25 ($CH_2Cl_2$:MeOH = 98:2, free base); $^1$H-NMR ($CD_3OD$, δ): 1.10 (d, 6H, J = 6.6 Hz, 2x$CH_3$), 2.32-2.37 (m, 1H, CH), 3.46 (d, 2H, J = 7.41 Hz $CH_2$), 4.09 (s, 3H, OMe), 4.12 (s, 3H, OMe), 5.05 (s, 2H, $CH_2$), 7.60 (s, 1H, ArH), 7.79 (s, 1H, ArH), 7.99 (t, 1H, J = 7.68 Hz, ArH), 8.19 (t, 1H, J = 7.12 Hz, ArH), 8.31-8.34 (m, 3H, 3xArH), 9.20 (s, 1H, ArH), 9.41 (s, 1H, ArH); $^{13}$C-NMR ($CD_3OD$, δ): 22.83 (2xC), 31.62, 33.36, 40.72, 57.23, 57.79, 104.43, 107.42, 121.37, 124.36, 130.37, 130.57, 130.80, 131.22, 131.71, 134.47, 136.34, 136.92, 138.18, 146.67, 147.98, 154.27, 156.95, 159.74; MS-ESI m/z (% rel. Int.): 387.4 ([MH]$^+$, 90); HPLC: Method A, detection UV 254 nm, RT = 3.78 min, peak area 99.9%. |
| 62 | (structure: 3-((1-cyclopropyl-6,7-dimethoxyisoquinolin-4-yl)methyl)quinoline) · 2HCl | A SSA 48084 (300 mg, 0.93 mmol); 3-quinoline carboxaldehyde (146 mg, 0.93 mmol); 37% HCl (2.5 mL); 95° C. for 0.5 h. | Chromatography $SiO_2$, $CH_2Cl_2$:MeOH = 100:0 to 97:3 | 3-((1-cyclopropyl-6,7-dimethoxyisoquinolin-4-yl)methyl)quinoline dihydrochloride (91 mg); MW: 443.37; Yield: 22%; Beige Solid; Mp (° C.): 212.6; $R_f$: 0.25 ($CH_2Cl_2$:MeOH = 97:3, free base); $^1$H-NMR ($CD_3OD$, δ): 1.38-1.42 (m, 2H, $CH_2$), 1.56-1.60 (m, 2H, $CH_2$), 3.04 (m, 1H, CH), 4.06 (s, 3H, OMe), 4.13 (s, 3H, OMe), 5.00 (s, 2H, $CH_2$), 7.53 (s, 1H, ArH), 7.95-8.00 (m, 1H, ArH), 8.08 (s, 1H, ArH), 8.15-8.21 (m, 2H, 2xArH), 8.27-8.30 (m, 2H, 2xArH), 9.09 (s, 1H, ArH), 9.35 (s, 1H, ArH); $^{13}$C-NMR ($CD_3OD$, δ): 9.57 (2xC), 13.71, 33.30, 57.17, 57.66, 104.29, 107.59, 121.65, 125.49, 130.26, 130.50, 130.62, 130.70, 131.62, 134.60, 136.15, 136.29, 138.53, 146.79, 147.35, 154.32, 157.89, 159.66; MS-ESI m/z (% rel. Int.): 371.3 ([MH]$^+$, 100); HPLC: Method A, detection UV 254 nm, RT = 3.73 min, peak area 99.9%. |

TABLE 7-continued

| Compd # | FORMULA | General Procedure | Purification | Analysis |
|---|---|---|---|---|
| 63 | (structure) | A SSA 48060 (300 mg, 0.83 mmol); 3-quinoline carboxaldehyde (131 mg, 0.83 mmol); 37% HCl (2.5 mL); 90° C. for 0.5 h. | Chromatography SiO$_2$, CH$_2$Cl$_2$:MeOH = 100:0 to 98:2 | 3-((6,7-dimethoxy-1-phenylisoquinolin-4-yl)methyl)quinoline dihydrochloride (141.5 mg); MW: 479.40; Yield: 35%; Yellow Pale Solid; Mp (° C.): 219.8; R$_f$: 0.25 (CH$_2$Cl$_2$:MeOH = 98:2, free base); $^1$H-NMR (CD$_3$OD, δ): 3.89 (s, 3H, OMe), 4.09 (s, 3H, OMe), 5.12 (s, 2H, CH$_2$), 7.51 (s, 1H, ArH), 7.65 (s, 1H, ArH), 7.79-7.83 (m, 3H, 3xArH), 7.88-7.99 (m, 2H, 2xArH), 8.00-8.03 (m, 1H, ArH), 8.17-8.23 (m, 1H, ArH), 8.31-8.35 (m, 2H, 2xArH), 9.49 (s, 1H, ArH), 9.22 (s, 1H, ArH), 9.45 (s, 1H, ArH); $^{13}$C-NMR (CD$_3$OD, δ): 33.42, 56,76, 57.82, 104.31, 108.61, 121.37, 124.14, 130.36, 130.58, 130.71 (2xC), 130.94, 131.19 (2xC), 131.71, 131.73, 132.20, 133.11, 134.58, 136.36, 137.76, 138.18, 146.67, 147.84, 154.37, 154.50, 159.86; MS-ESI m/z (% rel. Int.): 407.3 ([MH]$^+$, 65), 204.2 (100); HPLC: Method A, detection UV 254 nm, RT = 3.72 min, peak area 99.9%. |
| 64 | (structure) | A SSA 481000 (300 mg, 0.88 mmol); 3-quinoline carboxaldehyde (139 mg, 0.88 mmol); 37% HCl (2.5 mL); 90° C. for 0.5 h. | Chromatography SiO$_2$, CH$_2$Cl$_2$:MeOH = 100:0 to 98:2 | 3-((1-butyl-6,7-dimethoxyisoquinolin-4-yl)methyl)quinoline dihydrochloride (235 mg); MW: 459.41; Yield: 58%; Beige Solid; Mp (° C.): 204.7; R$_f$: 0.25 (CH$_2$Cl$_2$:MeOH = 98:2, free base); $^1$H-NMR (CD$_3$OD, δ): 1.03 (t, 3H, J = 7.3 Hz, CH3) 1.52-1.59 (m, 2H, CH$_2$), 1.88-1.94 (m, 2H, CH$_2$), 3.55 (t, 2H, J = 7.80 Hz, CH$_2$), 4.05 (s, 3H, OMe), 4.09 (s, 3H, OMe), 4.99 (s, 2H, CH$_2$), 7.55 (s, 1H, ArH), 7.76 (s, 1H, ArH), 7.97 (t, 1H, J = 8.1 Hz, ArH); 8.17 (t, 1H, J = 6.99 Hz, ArH), 8.27-8.30 (m, 3H, 3xArH), 9.13 (s, 1H, ArH), 9.36 (s, 1H, ArH); $^{13}$C-NMR (CD$_3$OD, δ): 14.06, 23.65, 32.20, 32.87, 33.30, 57.18, 57.69, 104.40, 107.09, 121.36, 123.90, 130.34, 130.56, 130.85, 131.02, 131.72, 134.53, 136.34, 136.91, 138.18, 146.63, 147.87, 154.36, 157.94, 159.72; MS-ESI m/z (% rel. Int.): 387.3 ([MH]$^+$, 100); HPLC: Method A, detection UV 254 nm, RT = 3.89 min, peak area 99.9%. |
| 65 | (structure) | A SSA 39102 (207 mg, 0.64 mmol); isoquinoline-3-carbaldehyde TTA 46014B (100 mg, 0.64 mmol); 37% HCl (1.6 mL); 90° C. for 0.5 h. | Chromatography SiO$_2$, CH$_2$Cl$_2$:MeOH = 100:0 to 96:4 | 4-(isoquinolin-3-ylmethyl)-6,7-dimethoxy-1-propylisoquinoline dihydrochloride (77 mg); MW: 445.38; Yield: 27%; Brown Solid; Mp (° C.): 216.9; R$_f$: 0.25 (CH$_2$Cl$_2$:MeOH = 96:4, free base); $^1$H-NMR (CD$_3$OD, δ): 1.16 (t, 3H, J = 7.3 Hz, CH$_3$), 1.98-2.05 (m, 2H, CH$_2$), 3.56 (t, 2H, J = 7.5 Hz, CH$_2$), 4.05 (s, 3H, OMe), 4.13 (s, 3H, OMe), 5.16 (s, 2H, CH$_2$), 7.56 (s, 1H, ArH), 7.83 (s, 1H, ArH), 8.03-8.06 (m, 1H, ArH), 8.19-8.22 (m, 2H, 2xArH), 8.27-8.31 (m, 2H, 2xArH), 8.55 (d, 1H, J = 8.3 Hz, ArH), 9.84 (s, 1H, ArH); $^{13}$C-NMR (CD$_3$OD, δ): 14.15, 24.24, 33.92, 34.15, 57.24, 57.74, 104.24, 107.18, 124.03, 126.15, 127.93, 128.53, 128.98, 131.16, 131.67, 132.16, 137.03, 138.58, 140.87, 143.29, 149.36, 154.47, 158.13, 159.90; MS-ESI m/z (% rel. Int.): 373.3 ([MH]$^+$, 100); HPLC: Method A, detection UV 254 nm, RT = 3.72 min, peak area 99.9%. |

TABLE 7-continued

| Compd # | FORMULA | General Procedure | Purification | Analysis |
|---|---|---|---|---|
| 66 | (structure) 2HCl | A LPO 22102 (198 mg, 0.70 mmol); TTA 46014B (100 mg, 0.64 mmol); 37% HCl (284 µL); 95° C. for 25 min | Chromatography SiO$_2$, CH$_2$Cl$_2$:MeOH = 100:0 to 97:3 | 4-(isoquinolin-3-ylmethyl)-6,7-dimethoxyisoquinoline dihydrochloride (36 mg); MW: 403.31; Yield: 14%; Pale Yellow Solid; Mp (° C.): 217.7; R$_f$: 0.18 (CH$_2$Cl$_2$:MeOH = 98:2, free base); $^1$H-NMR (CDCl$_3$, δ): 4.07 (d, 6H, J = 6 Hz, 2xOMe), 5.19 (s, 2H, CH$_2$), 7.61 (s, 1H, ArH), 7.92 (s, 1H, ArH), 8.00-8.05 (m, 1H, ArH), 8.18 (d, 2H, J = 1 Hz, 2xArH), 8.26 (s, 1H, ArH), 8.42 (s, 1H, ArH), 8.53 (d, 1H, J = 8 Hz, ArH), 9.46 (s, 1H, ArH), 9.84 (s, 1H, ArH); $^{13}$C-NMR (CDCl$_3$, δ): 33.9, 57.2, 57.9, 103.6, 109.6, 125.8, 126.3, 127.9, 128.6, 130.7, 131.7, 132.2, 137.3, 138.6, 140.9, 143.0, 143.7, 149.3, 154.7, 160.7; MS-ESI m/z (% rel. Int.): 331.3 ([MH]$^+$, 100), 166.1 (52); HPLC: Method A, detection UV 254 nm, RT = 3.33 min, peak area 99%. |
| 67 | (structure) 2HCl | A SSA 48100 (300 mg, 0.88 mmol); 2-methylquinoline-6-carbaldehyde (151 mg, 0.88 mmol); 37% HCl (1.4 mL); 95° C. for 0.5 h. | Chromatography SiO$_2$, CH$_2$Cl$_2$:MeOH = 100:0 to 98:2 | 6-((1-butyl-6,7-dimethoxyisoquinolin-4-yl)methyl)-2-methylquinoline dihydrochloride (166 mg); MW: 473.43; Yield: 40%; Yellow Solid; Mp (° C.): 166.5; R$_f$: 0.25 (CH$_2$Cl$_2$:MeOH = 98:2, free base); $^1$H-NMR (CD$_3$OD, δ): 1.06 (t, 3H, J = 7.3 Hz, CH$_2$CH$_3$), 1.57 (sext., 2H, J = 7.3 Hz, CH$_2$CH$_3$), 1.93 (sext., 2H, J = 7.9 Hz, CH$_2$CH$_2$CH$_3$), 3.03 (s, 3H, CH$_3$), 3.56 (t, 2H, J = 7.9 Hz, CH$_2$C$_3$H$_7$), 3.99 (s, 3H, OMe), 4.10 (s, 3H, OMe), 4.87 (s, 2H, CH$_2$), 7.51 (s, 1H, ArH), 7.75 (s, 1H, ArH), 7.93 (d, 1H, J = 8.6 Hz, ArH), 8.15-8.26 (m, 4H, 4xArH), 8.96 (d, 1H, J = 8.4 Hz, ArH); $^{13}$C-NMR (CD$_3$OD, δ): 14.1, 20.9, 23.6, 32.2, 32.8, 36.3, 57.2, 57.5, 104.8, 106.9, 121.6, 123.9, 125.2, 128.9, 129.6, 130.4, 132.6, 137.0, 137.1, 138.2, 141.8, 147.3, 154.2, 157.6, 159.3 (2xC); MS-ESI m/z (% rel. Int.): 401.4 ([MH]$^+$, 20); HPLC: Method A, detection UV 254 nm, RT = 3.51 min, peak area 98%. |
| 68 | (structure) 2HCl | A SSA 48066 (300 mg, 0.88 mmol); 2-methylquinoline-6-carbaldehyde (151 mg, 0.88 mmol); 37% HCl (1.4 mL); 95° C. for 0.5 h. | Chromatography SiO$_2$, cyclohexane:EtOAc = 50:50 to 30:70 | 6-((1-isobutyl-6,7-dimethoxyisoquinolin-4-yl)methyl)-2-methylquinoline dihydrochloride (301 mg); MW: 473.43; Yield: 72%; Yellow Solid; Mp (° C.): 71; R$_f$: 0.15 (cyclohexane:EtOAc = 5:5, free base); $^1$H-NMR (CD$_3$OD, δ): 1.08 (s, 3H, CH$_3$), 1.11 (s, 3H, CH$_3$), 2.29-2.38 (sextuplet, 1H, J = 6.8 Hz, CH$_3$CHCH$_3$), 3.03 (s, 3H, CH$_3$), 3.44 (t, 2H, J = 7.4 Hz, CH$_2$CH), 4.00 (s, 3H, OMe), 4.10 (s, 3H, OMe), 4.89 (s, 2H, CH$_2$), 7.53 (s, 1H, ArH), 7.75 (s, 1H, ArH), 7.94 (d, 1H, J = 8.6 Hz, ArH), 8.16-8.27 (m, 4H, 4xArH), 8.96 (d, 1H, J = 8.6 Hz, ArH); $^{13}$C-NMR (CD$_3$OD, δ): 20.9, 22.8 (2xC), 31.6, 36.4, 40.7, 57.2, 57.5, 104.7, 107.2, 121.6, 124.3, 125.2, 128.9, 129.7, 130.4, 132.7, 137.1 (2xC), 138.2, 141.7, 147.3, 154.2, 156.6, 159.3, 159.4; MS-ESI m/z (% rel. Int.): 401.5 ([MH]$^+$, 20), 201.3 (100); HPLC: Method A, detection UV 254 nm, RT = 3.42 min, peak area 98%. |

TABLE 7-continued

| Compd # | FORMULA | General Procedure | Purification | Analysis |
|---|---|---|---|---|
| 69 | (structure: 7-methylquinoline linked via CH₂ to 6,7-dimethoxy-1-propylisoquinoline, 2HCl) | A SSA 48070 (215 mg, 0.66 mmol); 3-(1,3-dioxolan-2-yl)-7-methylquinoline SSA 48104 (142 mg, 0.66 mmol); 37% HCl (1.2 mL); 95° C. for 0.5 h. | Chromatography SiO₂, cyclohexane:EtOAc = 50:50 to 30:70 | 3-((6,7-dimethoxy-1-propylisoquinolin-4-yl)methyl)-7-methylquinoline dihydrochloride (151.5 mg); MW: 459.41; Yield: 50%; Grey Solid; Mp (° C.): 166.6; R$_f$: 0.15 (cyclohexane:EtOAc = 50:50, free base); $^1$H-NMR (CD₃OD, δ): 1.15 (t, 3H, J = 7.3 Hz, CH₃), 1.94-2.04 (sextuplet, 2H, J = 7.6 Hz, CH₂CH₂CH₃), 2.72 (s, 3H, CH₃), 3.55 (t, 2H, J = 7.6 Hz, CH₂CH₂CH₃), 4.07 (s, 3H, OMe), 4.12 (s, 3H, OMe), 4.98 (s, 2H, CH₂), 7.57 (s, 1H, ArH), 7.79 (s, 1H, ArH), 7.84 (dd, 1H, J = 1.2 Hz, J = 8.6 Hz, ArH), 8.06 (s, 1H, ArH), 8.18 (d, 1H, J = 8.6 Hz, ArH), 8.29 (s, 1H, ArH), 9.08 (s, 1H, ArH), 9.28 (d, 1H, J = 1.9 Hz, ArH); $^{13}$C-NMR (CD₃OD, δ): 14.1, 22.4, 24.2, 33.2, 34.1, 57.2, 57.7, 104.4, 107.1, 120.1, 124.0, 129.0, 129.9, 130.8, 131.2, 133.5, 134.0, 136.9, 138.8, 146.0, 147.3, 148.8, 154.4, 157.7, 159.7; MS-ESI m/z (% rel. Int.): 387.4 ([MH]$^+$, 40), 194.2 (100); HPLC: Method A, detection UV 254 nm, RT = 3.47 min, peak area 98%. |
| 70 | (structure: 7-methylquinoline linked via CH₂ to 1-butyl-6,7-dimethoxyisoquinoline) | A SSA 48100 (200 mg, 0.59 mmol); 3-(1,3-dioxolan-2-yl)-7-methylquinoline SSA 48104 (132 mg, 0.62 mmol); | Chromatography SiO₂, cyclohexane:EtOAc = 100:0 to 50:50 | 3-((1-butyl-6,7-dimethoxyisoquinolin-4-yl)methyl)-7-methylquinoline (119 mg); MW: 400.51; Yield: 50%; White Solid; Mp (° C.): 142.6; R$_f$: 0.2 (cyclohexane:EtOAc = 50:50; $^1$H-NMR (CDCl₃, δ): 1.02 (t, 3H, J = 7.3 Hz, CH₃), 1.46-1.58 (sext., 2H, J = 7.4 Hz, CH₂CH₂CH₃), 1.83-1.94 (sext., 2H, J = 7.8 Hz, CH₂CH₂CH₂CH₃), 2.52 (s, 3H, CH₃), 3.23 (t, 2H, J = 7.8 Hz, CH₂CH₂CH₂CH₃), 3.81 (s, 3H, OMe), 4.01 (s, 3H, OMe), 4.43 (s, 2H, CH₂), 7.04 (s, 1H, ArH), 7.29 (d, 1H, J = 9.3 Hz, ArH), 7.37 (s, 1H, ArH), 7.51 (d, 1H, J = 8.3 Hz, ArH), 7.74 (s, 1H, ArH), 7.83 (s, 1H, ArH), 8.31 (s, 1H, ArH), 8.90 (d, 1H, J = 2.2 Hz, ArH); $^{13}$C-NMR (CD₃OD, δ): 14.1, 22.4, 23.6, 32.2, 32.9, 33.2, 57.2, 57.7, 104.4, 107.1, 120.0, 123.9, 129.0, 129.9, 130.8, 131.2, 133.5, 133.9, 136.9, 138.6, 145.9, 147.5, 149.0, 154.4, 157.9, 159.7; MS-ESI m/z (% rel. Int.): 401.4 ([MH]$^+$, 40), 201.3 (100); HPLC: Method A, detection UV 254 nm, RT = 3.87 min, peak area 98%. |
| 71 | (structure: quinoline linked via CH₂ to 1-cyclohexyl-6,7-dimethoxyisoquinoline, 2HCl) | A SSA 48072 (300 mg, 0.82 mmol); 3-quinoline carboxaldehyde (130 mg, 0.82 mmol); 37% HCl (2.5 mL); 95° C. for 0.5 h. | Chromatography SiO₂, cyclohexane:EtOAc = 100:0 to 97:3 | 3-((1-cyclohexyl-6,7-dimethoxyisoquinolin-4-yl)methyl)quinoline dihydrochloride (131 mg); MW: 485.45; Yield: 33%; Orange Solid; Mp (° C.): 105.7° C.; R$_f$: 0.25 (cyclohexane:EtOAc = 97:3, free base); $^1$H-NMR (CD₃OD, δ): 1.51-2.16 (m, 10H, 5xCH2), 3.98-4.02 (m, 1H, 5xCH₂), 4.05 (s, 3H, OMe), 4.12 (s, 3H, OMe), 5.02 (s, 2H, CH₂), 7.55 (s, 1H, ArH), 7.87 (s, 1H, ArH), 7.98 (t, 1H, J = 8.11 Hz, ArH), 8.19 (t, 1H, J = 7.06 Hz, ArH), 8.28-8.31 (m, 3H, 3xArH), 9.14 (s, 1H, ArH), 9.37 (s, 1H, ArH); $^{13}$C-NMR (CD₃OD, δ): 26.67, 27.11 (2xC), 32.72 (2xC), 33.36, 40.84, 57.21, 57.70, 104.54, 106.85, 121.37, 123.32, 130.33, 130.55, 130.73, 131.04, 131.73, 134.55, 136.35, 137.14, 138.17, 146.62, 147.84, 154.43, 159.76, 161.06; MS-ESI m/z (% rel. Int.): 413.4 ([MH]$^+$, 84); HPLC: Method A, detection UV 254 nm, RT = 4.14 min, peak area 99.9%. |

TABLE 7-continued

| Compd # | FORMULA | General Procedure | Purification | Analysis |
|---|---|---|---|---|
| 72 | (structure with isoquinoline, dimethoxyisoquinoline, 2HCl) | A SSA 39098 (198 mg, 0.64 mmol); isoquinoline-3-carbaldehyde TTA 46014B (100 mg, 0.64 mmol); 37% HCl (1.6 mL); 90° C. for 0.5 h. | Chromatography SiO$_2$, EtOAc:MeOH = 100:0 to 96:4 | 1-ethyl-4-(isoquinolin-3-ylmethyl)-6,7-dimethoxyisoquinoline dihydrochloride (29.3 mg); MW: 431.35; Yield: 11%; Yellow Solid; Mp (° C.): 213.1; Rf: 0.25 (CH$_2$Cl$_2$:MeOH = 98:2, free base); $^1$H-NMR (CD$_3$OD, δ): 1.57 (t, 3H, J = 7.6 Hz, CH$_3$), 3.60 (q, 2H, J = 7.6 Hz, CH$_2$), 4.02 (s, 3H, OMe), 4.11 (s, 3H, OMe), 5.11 (s, 2H, CH$_2$), 7.54 (s, 1H, ArH), 7.82 (s, 1H, ArH), 8.01 (m, 1H, ArH), 8.16-8.22 (m, 3H, 3xArH), 8.28 (s, 1H, ArH), 8.50 (d, 1H, J = 8.3 Hz ArH), 9.80 (s, 1H, ArH); $^{13}$C-NMR (CD$_3$OD, δ): 13.91, 26.02, 34.11, 57.24, 57.68, 104.27, 107.0, 123.70, 125.87, 127.96, 128.46, 129.08, 131.18, 131.54, 132.04, 137.05, 138.35, 140.74, 143.72, 149.55, 154.52, 159.33, 159.87; MS-ESI m/z (% rel. Int): 359.3 ([MH]$^+$, 100), HPLC: Method A, detection UV 254 nm, RT = 3.56 min, peak area 99.9%. |
| 73 | (structure with quinoline-OCH$_2$C(O)NH$_2$, dimethoxyisoquinoline, 2HCl) | B (a) SSA 48106 (330 mg, 0.85 mmol); DMF (9 mL); Cs$_2$CO$_3$ (830 mg, 2.55 mmol); 2-bromoacetamide (188 mg, 1.36 mmol); 80° C. overnight. | Chromatography SiO$_2$, CH$_2$Cl$_2$:MeOH = 100:0 to 95:5 | 2-(2-((6,7-dimethoxy-1-propylisoquinolin-4-yl)methyl)quinolin-8-yl)oxy)acetamide dihydrochloride (105 mg); MW: 518.43; Yield: 24%; Grey Solid; Mp (° C.): 188.2; Rf: 0.25 (CH$_2$Cl$_2$:MeOH = 95:5, free base); $^1$H-NMR (CD$_3$OD, δ): 1.11 (t, 3H, J = 7.3 Hz, CH$_3$), 1.97 (m, 2H, J = 7.5 Hz, CH$_2$), 3.53 (t, 2H, J = 7.5 Hz, CH$_2$), 4.05 (s, 3H, OMe), 4.09 (s, 3H, OMe), 5.05 (s, 2H, CH$_2$), 5.32 (s, 2H, CH$_2$), 7.60 (s, 1H, ArH), 7.67-7.71 (m, 1H, ArH), 7.78-7.82 (m, 2H, 2xArH), 7.88-7.90 (m, 2H, 2xArH), 8.38 (s, 1H, ArH), 9.0 (d, 1H, J = 8.7 Hz, ArH); $^{13}$C-NMR (CD$_3$OD, δ): 14.10, 24.21, 34.13, 35.18, 57.25, 57.90, 68.85, 104.18, 107.23, 116.54, 122.70, 124.0, 124.45, 128.61, 130.54, 131.26, 131.48, 131.73, 137.04, 148.28, 149.63, 154.50, 157.84, 158.29, 160.07, 172.40; MS-ESI m/z (% rel. Int.): 446.4 ([MH]$^+$, 31); HPLC: Method A, detection UV 254 nm, RT = 3.67 min, peak area 99.9%. |
| 74 | (structure with 7-methylquinoline, dimethoxyisoquinoline) | A ANP 27102 (200 mg, 0.71 mmol); 3-[1,3]dioxolan-2-yl-7-methyl-quinoline (152 mg, 0.71 mmol); | Chromatography SiO$_2$, CH$_2$Cl$_2$:MeOH = 100:0 to 98:2 | 3-((6,7-dimethoxy-1-propylisoquinolin-4-yl)methyl)-7-methylquinoline (76 mg); MW: 344.4; Yield: 31%; White Solid; Mp (° C.): 168.4; Rf: 0.25 (CH$_2$Cl$_2$:MeOH = 98:2); $^1$H-NMR (CD$_3$OD, δ): 2.53 (s, 3H, CH$_3$), 3.83 (s, 3H, OMe), 4.00 (s, 3H, OMe), 4.47 (s, 2H, CH$_2$), 7.04 (s, 1H, ArH), 7.23 (s, 1H, ArH), 7.30 (d, 1H, J = 8.3 Hz, ArH), 7.52 (d, 1H, J = 8.3 Hz, ArH), 7.74 (s, 1H, ArH), 7.84 (s, 1H, ArH), 8.36 (s, 1H, ArH), 8.89 (s, 1H, ArH), 9.01 (s, 1H, ArH); $^{13}$C-NMR (CD$_3$OD, δ): 21.76, 33.93, 55.92, 56.01, 101.67, 106.09, 124.89, 126.04, 127.02, 127.35, 128.16, 129.11, 131.15, 131.65, 134.33, 139.34, 142.79, 147.32, 149.76, 150.16, 151.36, 153.10; MS-ESI m/z (% rel. Int.): 345.4 ([MH]$^+$, 44); HPLC: Method A, detection UV 254 nm, RT = 3.28 min, peak area 99.9%. |
| 75 | (structure with quinoline-OCH$_2$CH$_2$OH, dimethoxyisoquinoline, 2HCl) | D (a) ANP 49102A (200 mg, 0.42 mmol); tBuOH (19 mL); NaBH$_4$ (20 mg, 0.51 mmol); 140° C. (reflux) for 2 h. | Chromatography SiO$_2$, CH$_2$Cl$_2$:MeOH = 100:0 to 97:3 | 2-((2-((6,7-dimethoxy-1-propylisoquinolin-4-yl)methyl)quinolin-8-yl)oxy)ethanol (52 mg); MW: 505.39; Yield: 24%; Yellow Solid; Rf: 0.25 (CH$_2$Cl$_2$:MeOH 97:3, free base); $^1$H-NMR (CD$_3$OD, δ): 1.13 (t, 3H, J = 7.3 Hz, CH$_3$), 1.98 (m, 2H, J = 7.6 Hz, CH$_2$), 3.55 (t, 2H, J = 7.5 Hz, CH$_2$), 4.06 (s, 3H, OMe), 4.10 (s, 3H, OMe), 4.14 (t, 2H, J = 4.5 Hz, CH$_2$), 4.49 (t, 2H, J = 4.2 Hz, CH$_2$), 5.36 (s, 2H, CH$_2$), 7.63 (s, 1H, ArH), 7.69-7.88 (m, 5H, 5xArH), 8.39 (s, 1H, ArH), 8.98 (d, 1H, J = 8.7 Hz, ArH); $^{13}$C-NMR (CD$_3$OD, δ): 14.11, 24.33, 34.14, 35.22, 57.27, 57.95, 61.11, 72.59, 104.30, 107.24, 115.41, 121.60, 124.01, 124.33, 128.74, 130.46, 131.27, 131.65, 131.73, 137.06, 148.18, 150.53, 154.49, 157.68, 158.27, 160.04; MS-ESI m/z (% rel. Int.): 433.1 ([MH]$^+$, 100). HPLC: Method A, detection UV 254 nm, RT = 3.75 min, peak area 99.9% |

TABLE 7-continued

| Compd # | FORMULA | General Procedure | Purification | Analysis |
|---|---|---|---|---|
| 76 | | C (a) LPO 50016B (131 mg, 0.28 mmol); acetic anhydride (32 μL, 0.34 mmol); Et₃N (79.4 μL, 0.57 mmol); anhydrous THF (2 mL); 4° C. for 2 h. | Chromatography SiO₂, CH₂Cl₂:MeOH = 98:2 to 95:5 | N-(2-((3-((6,7-dimethoxy-1-propylisoquinolin-4-yl)methyl)-6-methoxyquinolin-2-yl)amino)ethyl)acetamide dihydrochloride (38 mg); MW: 575.53; Yield: 23%; Beige Solid; R$_f$: 0.2 (CH₂Cl₂:MeOH = 96:4, free base); ¹H-NMR (CD₃OD, δ): 1.17 (t, 3H, J = 7.3 Hz, CH₃), 1.99-2.06 (m, 5H, COCH₃ & CH₂CH₂CH₃), 3.57 (t, 4H, J = 7.5 Hz, 2xNCH₂), 3.80-3.84 (m, 5H, OMe & CH₂CH₂CH₃), 4.08 (s, 3H, OMe), 4.15 (s, 3H, OMe), 4.60 (s, 2H, CH₂), 7.22 (d, 1H, J = 2.7 Hz, ArH), 7.43 (dd, 1H, J = 2.7 Hz, J = 9.2 Hz, ArH), 7.52 (s, 1H, ArH), 7.83 (s, 1H, ArH), 8.08 (d, 1H, J = 9.2 Hz, ArH), 8.13 (s, 1H, ArH); ¹³C-NMR CD₃OD, δ): 14.2, 22.4, 24.2, 31.5, 34.1, 38.9, 43.5, 56.4, 57.2, 57.7, 104.5, 107.0, 109.5, 120.1, 123.8, 123.9, 124.0, 124.1, 129.9, 130.1, 131.7, 137.5, 142.3, 152.6, 154.5, 157.7, 159.0, 159.7, 175.7; MS-ESI m/z (% rel. Int.): 503.4 ([MH]⁺, 20), 252.3 (100); HPLC: Method A, detection UV 254 nm, RT = 3.72 min, peak area 99%. |
| 77 | | H (a) LPO 50012 (120 mg, 0.27 mmol); 2-(di-tert-butylphosphino)biphenyl (0.8 mg, 2.75 μmol); 2N EtNH₂ in THF (206 μL, 0.41 mmol), Pd(OAc)₂ (0.6 mg, 2.75 μmol); tBuOK (43 mg, 0.38 mmol); toluene (1.5 mL); 100° C. for 6 h. | Chromatography SiO₂, CH₂Cl₂:MeOH = 100:0 to 98:2 | 3-((6,7-dimethoxy-1-propylisoquinolin-4-yl)methyl)-N-ethyl-6-methoxyquinolin-2-amine dihydrochloride (19 mg); MW: 518.48; Yield: 14%; Beige Solid; Mp (° C.): 82; R$_f$: 0.3 (CH₂Cl₂:MeOH = 98:2, free base); ¹H-NMR (CD₃OD, δ): 1.16 (t, 3H, J = 7.2 Hz, CH₂CH₂CH₃), 1.47 (t, 3H, J = 7.2 Hz, NCH₂CH₃), 1.96-2.06 (sext, 2H, J = 7.5 Hz, CH₂CH₂CH₃), 3.57 (t, 2H, J = 7.3 Hz, NCH₂), 3.76-3.83 (m, 5H, OMe & CH₂CH₂CH₃), 4.08 (s, 3H, OMe), 4.15 (s, 3H, OMe), 4.64 (s, 2H, CH₂), 7.21 (d, 1H, J = 2.8 Hz, ArH), 7.40 (dd, 1H, J = 2.8 Hz, J = 9.2 Hz, ArH), 7.49 (s, 1H, ArH), 7.81-7.82 (m, 2H, 2xArH), 8.00 (d, 1H, J = 9.2 Hz, ArH), 8.12 (s, 1H, ArH); ¹³C-NMR (CD₃OD, δ): 13.9, 14.2, 24.2, 31.5, 34.1, 39.0, 56.4, 57.2, 57.6, 104.4, 107.0, 109.6, 119.8, 123.8 (3xC), 123.9, 130.0, 130.1, 131.6, 137.4, 142.3, 152.3, 154.4, 157.7, 158.9, 159.7; MS-ESI m/z (% rel. Int.): 446.5 ([MH]⁺, 20), 223.8 (100); HPLC: Method A, detection UV 254 nm, RT = 3.68 min, peak area 99%. |
| 78 | 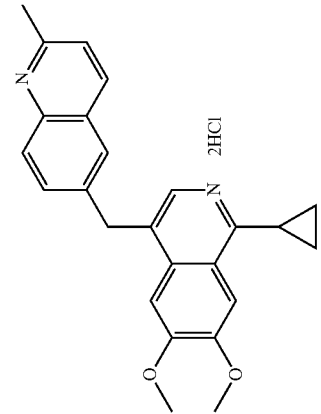 | A SSA 48084 (300 mg, 0.93 mmol); 2-methylquinoline-6-carbaldehyde (159 mg, 0.93 mmol); 37% HCl (1.4 mL); 95° C. for 0.5 h. | Chromatography SiO₂, cyclohexane:EtOAc = 50:50 to 30:70 | 6-((1-cyclopropyl-6,7-dimethoxyisoquinolin-4-yl)methyl)-2-methylquinoline dihydrochloride (84 mg); MW: 457.39; Yield: 20%; White Solid; Mp (° C.): 204.9; R$_f$: 0.15 (cyclohexane:EtOAc = 50:50, free base); ¹H-NMR (CD₃OD, δ): 1.35-1.41 (m, 2H, CH₂CH₂), 1.54-1.61 (m, 2H, CH₂CH₂), 3.00-3.05 (m, 4H, CHCH & CH₂), 3.98 (s, 3H, OMe), 4.11 (s, 3H, OMe), 4.87 (s, 2H, CH₂), 7.48 (s, 1H, ArH), 7.93 (d, 1H, J = 8.6 Hz, ArH), 8.04 (s, 1H, ArH), 8.15-8.22 (m, 4H, 4xArH), 8.95 (d, 1H, J = 8.6 Hz, ArH); ¹³C-NMR (CD₃OD, δ): 9.5 (2xC), 13.6, 20.9, 36.3, 57.1, 57.4, 104.6, 107.4, 121.5, 125.2, 125.4, 128.9, 129.6, 130.2, 132.3, 136.4, 137.0, 138.2, 141.9, 147.3, 154.2, 157.5, 159.2, 159.3; MS-ESI m/z (% rel. Int.): 385.3 ([MH]⁺, 20), 193.2 (100). HPLC: Method A, detection UV 254 nm, RT = 3.27 min, peak area 98%. |

TABLE 7-continued

| Compd # | FORMULA | General Procedure | Purification | Analysis |
|---|---|---|---|---|
| 79 | 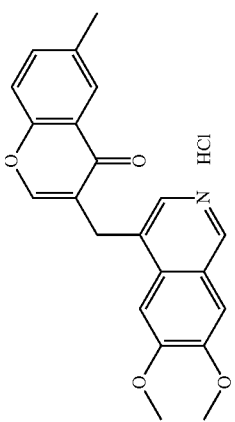 | A ANP 27102 (300 mg, 1.06 mmol); 3-formyl-6-methylchromone (199 mg, 1.06 mmol); 37% HCl (2.5 mL); 90° C. for 25 min. | Chromatography $SiO_2$, $CH_2Cl_2$:MeOH = 100:0 to 97:3 | 3-((6,7-dimethoxyisoquinolin-4-yl)methyl)-6-methyl-4H-chromen-4-one hydrochloride (82 mg); MW: 397.85; Yield: 19%; Yellow Pale Solid; Mp (° C.): 206.6; $R_f$: 0.25 ($CH_2Cl_2$:MeOH = 97:3, free base); $^1$H-NMR ($CD_3OD$, δ): 2.45 (s, 3H, $CH_3$), 4.05 (s, 3H, OMe), 4.14 (s, 3H, OMe), 4.36 (s, 2H, $CH_2$), 7.46 (d, 1H, J = 8.6 Hz, ArH), 7.60 (d, 1H, J = 8.7 Hz, ArH), 7.77 (s, 2H, 2×ArH), 7.93 (s, 1H, ArH), 8.32 (s, 2H, 2×ArH), 9.25 (s, 1H, ArH); $^{13}$C-NMR ($CD_3OD$, δ): 21.16, 26.63, 57.22, 57.82, 104.06, 109.10, 119.43, 122.04, 124.44, 125.57, 125.68, 130.50, 134.76, 136.91, 137.25, 137.34, 142.28, 154.46, 156.40, 157.39, 160.03, 179.06; MS-ESI m/z (% rel. Int.): 362.2 ([MH]$^+$, 100); HPLC: Method A, detection UV 254 nm, RT = 4.13 min, peak area 99.9%. |
| 80 | 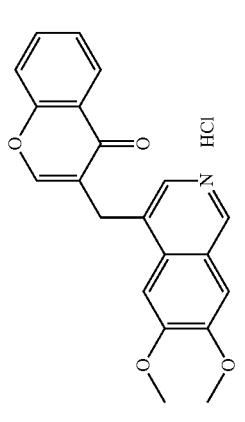 | A ANP 27102 (300 mg, 1.06 mmol); chromone-3-carboxaldehyde (184 mg, 1.06 mmol); 37% HCl (2.5 mL); 90° C. for 25 min. | Chromatography $SiO_2$, $CH_2Cl_2$:MeOH = 100:0 to 97:3 | 3-((6,7-dimethoxyisoquinolin-4-yl)methyl)-4H-chromen-4-one hydrochloride (58 mg); MW: 383.82; Yield: 14%; Yellow Pale Solid; Mp (° C.): 208.3; $R_f$: 0.25 ($CH_2Cl_2$:MeOH = 97:3, free base); $^1$H-NMR ($CD_3OD$, δ): 4.04 (s, 3H, OMe), 4.13 (s, 3H, OMe), 4.37 (s, 2H, $CH_2$), 7.47 (t, 1H, J = 8.1 Hz ArH), 7.58 (d, 1H, J = 8.0 Hz ArH), 7.75-7.78 (m, 3H, 3×ArH), 7.92 (d, 1H, ArH), 8.14 (dd, 1H, J =1.5 Hz, J = 6.5 Hz, ArH), 8.30 (s, 1H, ArH), 8.34 (s, 1H, ArH), 9.25 (s, 1H, ArH); $^{13}$C-NMR ($CD_3OD$, δ): 26.58, 57.06, 57.65, 103.93, 109.04, 119.60, 122.23, 124.72, 125.51, 126.42, 126.85, 130.45, 134.59, 165.66, 137.28, 142.32, 154.45, 157.51, 158.10, 160.03, 179.03; MS-ESI m/z (% rel. Int.): 348.3 ([MH]$^+$, 100); HPLC: Method A, detection UV 254 nm, RT = 3.85 min, peak area 99.9% |
| 81 | 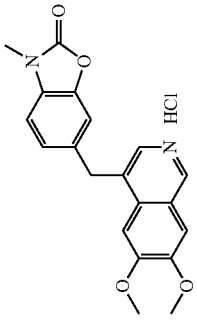 | A ANP 27102 (300 mg, 1.06 mmol); 3-methyl-2-oxo-2,3-dihydrobenzo[d]oxazole-6-carbaldehyde (188 mg, 1.06 mmol); 37% HCl (2.5 mL); 90° C. for 25 min. | Chromatography $SiO_2$, $CH_2Cl_2$:MeOH = 100:0 to 97:3 | 6-((6,7-dimethoxyisoquinolin-4-yl)methyl)-3-methylbenzo[d]oxazol-2(3H)-one hydrochloride (103.5 mg); MW: 386.83; Yield: 25%; Yellow Solid; Mp (° C.): 172.4; $R_f$: 0.25 ($CH_2Cl_2$:MeOH = 97:3, free base); $^1$H-NMR ($CD_3OD$, δ): 3.37 (s, 3H, $CH_3$), 4.02 (s, 3H, OMe), 4.05 (s, 3H, OMe), 4.60 (s, 2H, $CH_2$), 7.15 (d, 1H, J = 8.0 Hz ArH), 7.22-7.25 (m, 2H, 2×ArH), 7.53 (s, 1H, ArH), 7.79 (s, 1H, ArH), 8.21 (s, 1H, ArH), 9.29 (s, 1H, ArH); $^{13}$C-NMR ($CD_3OD$, δ): 28.47, 36.69, 57.07, 57.46, 104.10, 109.08, 110.06, 111.26, 125.61, 125.86, 130.49, 132.30, 134.09, 135.83, 137.29, 142.69, 144.53, 154.38, 156.55, 159.84; MS-ESI m/z (% rel. Int.): 351.2 ([MH]$^+$, 100); HPLC: Method A, detection UV 254 nm, RT = 3.63 min, peak area 99.9%. |

TABLE 7-continued

| Compd # | FORMULA | General Procedure | Purification | Analysis |
|---|---|---|---|---|
| 82 | (structure: 6-((6,7-dimethoxy-1-propylisoquinolin-4-yl)methyl)-3-methylbenzo[d]oxazol-2(3H)-one dihydrochloride) · 2HCl | A SSA 39102 (200 mg, 0.61 mmol); 3-methyl-2-oxo-2,3-dihydrobenzo[o]oxazole-6-carbaldehyde (113 mg, 0.64 mmol); 37% HCl (1.2 mL); 95° C. for 0.5 h. | Chromatography SiO$_2$, CH$_2$Cl$_2$:MeOH = 100:0 to 98:2 | 6-((6,7-dimethoxy-1-propylisoquinolin-4-yl)methyl)-3-methylbenzo[d]oxazol-2(3H)-one dihydrochloride (63.0 mg); MW: 428.91; Yield: 24%; Yellow Solid; Mp (° C.): 207.9; R$_f$: 0.2 (CH$_2$Cl$_2$:MeOH = 98:2, free base); $^1$H-NMR (CD$_3$OD, δ): 1.12 (t, 3H, J = 7.2 Hz, CH$_2$CH$_2$CH$_3$), 1.94-2.01 (sextuplet, 2H, J = 7.4 Hz, CH$_2$CH$_2$CH$_3$), 3.39 (s, 3H, NCH$_3$), 3.50 (t, 2H, J = 7.4 Hz, CH$_2$CH$_2$CH$_3$), 4.02 (s, 3H, OMe), 4.09 (s, 3H, OMe), 4.59 (s, 2H, CH$_2$), 7.15-7.29 (m, 3H, 3xArH), 7.53 (s, 1H, ArH), 7.73 (s, 1H, ArH), 8.10 (s, 1H, ArH); $^{13}$C-NMR (CD$_3$OD, δ): 14.1, 24.1, 28.5, 34.0, 36.7, 57.1, 57.4, 104.9, 106.8, 110.0, 111.2, 123.8, 125.8, 129.8, 132.3, 134.1, 134.2, 137.1, 144.5, 154.1, 156.5, 156.9, 159.1; MS-ESI m/z (% rel. Int.): 393.3 ([MH]$^+$, 100); HPLC: Method A, detection UV 254 nm, RT = 4.11 min, peak area 98%. |
| 83 | (structure: 2-((1-ethyl-6,7-dimethoxyisoquinolin-4-yl)methyl)quinolin-8-ol) | A SSA 39098 (6.3 g, 20.23 mmol); 8-hydroxyquinoline-2-carbaldehyde (3.5 g, 20.2 mmol); 37% HCl (30 mL); 100° C. for 30 min | Chromatography SiO$_2$, CH$_2$Cl$_2$:MeOH = 100:0 to 90:10 | 2-((1-ethyl-6,7-dimethoxyisoquinolin-4-yl)methyl)quinolin-8-ol (6.31 g); MW: 374.43; Yield: 83%; Pale Yellow Solid; Mp (° C.): 147.3-150.2; $^1$H NMR (CDCl$_3$, δ): 1.46 (t, J = 7.5 Hz, 3H, CH$_3$), 1.95 (bs, 1H, OH), 3.25 (q, J = 7.8 Hz, 2H, CH$_2$), 3.84 (s, 3H, CH$_3$), 3.99 (s, 3H, CH$_3$), 4.62 (s, 2H, CH$_2$), 7.16 (dd, J = 1.2 Hz, J = 7.5Hz, 1H, ArH), 7.22-7.44 (m, 5H, 5xArH), 7.97 (d, J = 8.4Hz, 1H, ArH), 8.41 (s, 1H, ArH); MS-ESI m/z (% rel. int.): 375.2 ([MH]$^+$, 97); HPLC: Method A, Detection UV 254 nm, RT = 3.81 min, peak area 91%. |
| 84 | (structure: N-(2-((1-ethyl-6,7-dimethoxyisoquinolin-4-yl)methyl)quinolin-8-yl)sulfamide) | I RBO 51118B (336 mg, 0.90 mmol); 1,4-dioxane (20 mL); sulfamide (865 mg, 9.0 mmol); reflux for 16 h | Chromatography SiO$_2$, eluent CH$_2$Cl$_2$:MeOH = 100:0 to 98:2 | N-(2-((1-ethyl-6,7-dimethoxyisoquinolin-4-yl)methyl)quinolin-8-yl)sulfamide (108 mg); MW: 452.53; Last step yield: 27% after recrystallisation in CH$_3$CN; Crystalline White Solid; Mp (° C.): 209.6-210.9; $^1$H NMR (CDCl$_3$, δ): 1.45 (t, J = 7.5 Hz, 3H, CH$_3$), 3.25 (q, J = 7.8 Hz, 2H, CH$_2$), 3.89 (s, 3H, CH$_3$), 3.99 (s, 3H, CH$_3$), 4.62 (s, 2H, CH$_2$), 4.78 (bs, 2H, NH$_2$), 7.34 (m, 3H, ArH), 7.48 (m, 2H, 2xArH), 7.78 (m, 1H, ArH), 8.00 (d, 1H, J = 8.5 Hz, ArH), 8.37 (s, 1H, ArH), 9.06 (bs, 1H, NH); $^{13}$C NMR (DMSO-d$_6$, δ): 12.9, 27.4, 54.9, 55.6, 55.7, 103.0, 104.1, 113.2, 120.3, 121.85, 122.4, 125.8, 126.2, 126.4, 131.1, 134.3, 136.4, 137.2, 141.0, 149.3, 152.0, 159.0, 159.5; MS-ESI m/z (% rel. int.): 453.3 ([MH]$^+$, 100); HPLC: Method A, Detection UV 254 nm, RT = 4.31 min, peak area 98.8%. |

TABLE 7-continued

| Compd # | FORMULA | General Procedure | Purification | Analysis |
|---|---|---|---|---|
| 85 | (structure) | I LPO 55056D (208 mg, 0.54 mmol); 1,4-dioxane (13 mL); sulfamide (516 mg, 5.368 mmol); 15 h at 110° C. | Chromatography SiO$_2$, eluent CH$_2$Cl$_2$:MeOH = 100:0 to 98:2 | N-(2-((1-propyl-6,7-dimethoxyisoquinolin-4-yl)methyl)quinolin-8-yl)sulfamide (132 mg); MW: 466.55; Last step yield: 53%; White Solid; Mp (° C.): 221.9; R$_f$: 0.20 (CH$_2$Cl$_2$:MeOH = 98:2); $^1$H-NMR (DMSO-d$_6$, δ): 0.99 (t, 3H, J = 7.4 Hz, CH$_2$CH$_3$), 1.78-1.85 (sextuplet, 2H, J = 7.4 Hz, CH$_2$CH$_3$), 3.14 (t, 2H, J = 7.1 Hz, CH$_2$CH$_2$), 3.85 (s, 3H, OMe), 3.90 (s, 3H, OMe), 4.67 (s, 2H, CH$_2$), 7.41 (s, 1H, ArH), 7.48-7.56 (m, 4H, 4xArH), 7.63-7.68 (m, 1H, ArH), (s, 1H, ArH), $^{13}$C-NMR DMSO-d$_6$, δ): 14.1, 21.7, 36.2, 39.8, 55.6, 55.7, 103.0, 104.3, 113.2, 120.3, 122.2, 124.4, 125.7, 126.2, 126.3, 131.1, 134.3, 136.4, 137.2, 141.1, 149.3, 152.0, 158.1, 159.5; MS-ESI m/z (% rel. Int.): 467.4 ([MH]$^{+1}$, 100); HPLC: Method A, detection UV 254 nm, peak area 99%. |
| 86 | (structure) | C (d) RBO 51118B (100 mg, 0.27 mmol); CH$_2$Cl$_2$ (10 mL); pyridine (43 µL, 0.53 mmol); methanesulfonyl chloride (21 µL, 0.27 mmol); 70° C. for 30 min (microwave). | Chromatography SiO$_2$, EtOAc:MeOH = 100:0 to 90:10 | N-(2-((1-ethyl-6,7-dimethoxyisoquinolin-4-yl)methyl)quinolin-8-yl)methanesulfonamide (100 mg); MW: 451.54; Yield: 83%; White Solid; Mp (° C.): 160.1-162.4; R$_f$: 0.25 (EtOAc:MeOH=90:10); $^1$H NMR (CDCl$_3$, δ): 1.56 (t, 3H, CH$_3$, J = 7.5 Hz), 3.09 (s, 3H, CH$_3$), 3.50 (q, 2H, CH$_2$, J = 7.5 Hz) 3.99 (s, 3H, OCH$_3$), 4.05 (s, 3H, OCH$_3$), 4.70 (s, 2H, CH$_2$), 7.37-7.40 (m, 2H, 2xArH), 7.51-7.543(m, 3H, 3xArH), 7.78-7.82 (m, 1H, ArH), 8.10 (d, 1H, ArH, J = 8.5 Hz) 8.41 (s, 1H, ArH), 8.80 (br s, 1H, NH), $^{13}$C NMR (CDCl$_3$, δ): 14.0, 25.3, 39.6, 40.2, 56.3, 56.8, 103.6, 104.5, 114.5, 122.0, 122.1, 122.2, 127.1 (2xC), 128.9, 132.3, 133.6, 135.1, 137.3, 137.8, 151.9, 156.2, 157.5, 157.5; MS-ESI m/z (% rel. Int.): 452 ([MH]$^+$, 100); HPLC: Method A, detection UV 254 nm, RT = 4.35 min, peak area 97.6%. |
| 87 | (structure) | C (a) RBO 51118B (100 mg, 0.27 mmol); AcOH (10 mL); potassium cyanate (21.9 mg, 0.27 mmol); H$_2$O (1 mL); 40° C. for 3 h. | Precipitate was filtered | 1-(2-((1-ethyl-6,7-dimethoxyisoquinolin-4-yl)methyl)quinolin-8-yl)urea (48 mg); MW: 416.47; Yield: 43%; White Solid; Mp (° C.): 259.7-261.2; $^1$H NMR (DMSO-d$_6$ δ): 1.33 (t, 3H, CH$_3$, J = 7.5 Hz), 3.19 (q, 2H, CH$_2$, J = 7.5 Hz) 3.82 (s, 3H, CH$_3$), 3.88 (s, 3H, CH$_3$), 4.69 (s, 2H, CH$_2$), 6.62 (br s, 2H, NH$_2$), 7.35-7.42 (m, 4H, 4xArH), 7.68 (s, 1H, ArH), 8.14 (d, 1H, ArH, J = 8.4 Hz), 8.44 (s, 1H, ArH), 8.50 (dd, 1H, ArH, J = 1.5 Hz & J = 8.4 Hz) 9.44 (br s, 1H, NH); $^{13}$C NMR (DMSO-d$_6$, δ): 12.8, 27.4, 39.0, 55.4, 55.5, 103.0, 107.1, 114.2, 118.7, 121.6, 121.9, 125.8, 126.1, 126.6, 131.1, 136.1, 136.4, 136.9, 141.0, 149.2, 151.9, 155.8, 158.4, 159.1; MS-ESI m/z (% rel. int.): 417 ([MH]$^+$, 100); HPLC: Method A, detection UV 254 nm, RT = 3.88 min, peak area 97.9 %. |

TABLE 7-continued

| Compd # | FORMULA | General Procedure | Purification | Analysis |
|---|---|---|---|---|
| 88 | (structure) | C (a) RBO 51118B (120 mg, 0.32 mmol); THF (5 mL); NMP (71 µL, 0.64 mmol); pyridine (26 µL, 0.32 mmol); acetic anhydride (152 µL, 1.61 mmol); RT overnight. | Chromatography SiO$_2$, CH$_2$Cl$_2$:EtOAc = 100:0 to 0:100 | N-(2-((1-ethyl-6,7-dimethoxyisoquinolin-4-yl)methyl)quinolin-8-yl)acetamide (78 mg); MW: 415.48; Yield: 60%; White Solid; Mp (° C.): 210-212.7; R$_f$: 0.25 (EtOAc); $^1$H NMR (CDCl$_3$, δ): 1.47 (t, 3H, CH$_3$, J = 7.5 Hz), 2.22 (s, 3H, CH$_3$), 3.26 (q, 2H, CH$_2$, J = 7.5 Hz), 3.80 (s, 3H, OCH$_3$), 4.00 (s, 3H, OCH$_3$), 4.65 (s, 2H, CH$_2$), 7.29 (s, 1H, ArH), 7.31 (d, 1H, ArH, J = 8.5 Hz), 7.36 (s, 1H, ArH), 7.40-7.51 (m, 2H, 2xArH), 8.00 (d, 1H, ArH, J = 8.5 Hz), 8.37 (s, 1H, ArH), 8.71 (dd, 1H, ArH, J = 1.7 Hz, J = 7.1 Hz), 9.66 (br s, 1H, NH); $^{13}$C NMR (CDCl$_3$, δ): 13.2, 24.7, 28.5, 40.4, 55.7, 55.9, 103.2, 104.1, 116.6, 121.2, 121.5, 122.5, 125.5, 126.3, 126.9, 132.2, 134.0, 137.0, 137.3, 141.8, 149.6, 152.2, 158.6, 160.1, 168.3; MS-ESI m/z (% rel. int.): 416 ([MH]$^+$, 100); HPLC: Method A, detection UV 254 nm, RT = 4.13 min, peak area 96.5%. |
| 89 | (structure) | C (d) RBO 51118B (120 mg, 0.32 mmol); CH$_2$Cl$_2$ (10 mL); pyridine (52 µL, 0.64 mmol); ethanesulfonyl chloride (30 µL, 0.32 mmol); 70° C. for 3 h (microwave). | Chromatography SiO$_2$, EtOAc:MeOH = 100:0 to 90:10 | N-(2-((1-ethyl-6,7-dimethoxyisoquinolin-4-yl)methyl)quinolin-8-yl)ethanesulfonamide (60 mg); MW: 465.56; Yield: 40%; White Solid; Mp (° C.): 197.2-198.7; R$_f$: 0.25 (EtOAc:MeOH = 90:10); $^1$H NMR (CDCl$_3$, δ): 1.26 (t, 3H, CH$_3$, J = 7.4 Hz), 1.46 (t, 3H, CH$_3$, J = 7.5 Hz), 3.16 (q, 2H, CH$_2$, J = 7.4 Hz), 3.25 (q, 2H, CH$_2$, J = 7.5 Hz), 3.88 (s, 3H, OCH$_3$), 4.00 (s, 3H, OCH$_3$), 4.63 (s, 2H, CH$_2$), 7.31-7.35 (m, 3H, 3xArH), 7.45-7.47 (m, 2H, 2xArH), 7.82 (dd, 1H, ArH, J = 3.5 Hz & J = 5.4 Hz), 8.01 (d, 1H, ArH, J = 8.5 Hz), 8.36 (s, 1H, ArH), 8.92 (br s, 1H, NH); $^{13}$C NMR (CDCl$_3$, δ): 8.1, 13.2, 28.5, 29.6, 40.6, 45.8, 55.9, 56.0, 102.9, 104.1, 114.6, 121.9, 122.2, 122.5, 125.3, 126.6, 126.8, 132.0, 133.7, 137.1, 137.3, 141.6, 149.6, 152.5, 159.8, 160.2; MS-ESI m/z (% rel. int.): 466 ([MH]$^+$, 100); HPLC: Method A, detection UV 254 nm, RT = 4.58 min, peak area 97.2%. |
| 90 | (structure) | H (d) RBO 51116 (3 g, 5.92 mmol); DMF (20 mL); Zn(CN)$_2$ (800 mg, 6.81 mmol); Pd(PPh$_3$)$_4$ (684 mg, 0.60 mmol); 180° C. for 10 min (microwave). | Chromatography SiO$_2$, CH$_2$Cl$_2$:EtOAc = 100:0 to 0:100 | 2-((1-ethyl-6,7-dimethoxyisoquinolin-4-yl)methyl)quinoline-8-carbonitrile (1.0 g); MW: 383.44; Yield: 44%; White Solid; Mp (° C.): 191.6-193.9; R$_f$: 0.3 (EtOAc); $^1$H NMR (CDCl$_3$, δ): 1.44 (t, 3H, CH$_3$, J = 7.5 Hz), 3.23 (q, 2H, CH$_2$, J = 7.5 Hz), 3.97 (s, 3H, OCH$_3$), 4.05 (s, 3H, OCH$_3$), 4.70 (s, 2H, CH$_2$), 7.30 (s, 1H, ArH), 7.47 (d, 1H, ArH, J = 9.0 Hz), 7.53-7.59 (m, 1H, ArH), 7.76 (s, 1H, ArH), 7.97 (dd, 1H, ArH, J = 9.0 Hz & J = 1.4 Hz), 8.03 (d, 1H, ArH, J = 9.0 Hz), 8.12 (dd, 1H, ArH, J = 9.0 Hz & J = 1.4 Hz), 8.48 (s, 1H, ArH); $^{13}$C NMR (CDCl$_3$, δ): 13.2, 28.5, 41.5, 55.8, 56.7, 103.6, 103.8, 122.5, 123.1, 125.4 (2xC), 125.6, 126.7, 132.2, 132.6 (2xC), 135.6, 136.7 (2xC), 141.2, 149.6, 152.5, 160.3, 163.5; MS-ESI m/z (% rel. int.): 384 ([MH]$^+$, 100); HPLC: Method A, detection UV 254 nm, RT = 4.51 min, peak area 98.2%. |

TABLE 7-continued

| Compd # | FORMULA | General Procedure | Purification | Analysis |
|---|---|---|---|---|
| 91 | (structure) | E (b) 90 (300 mg, 0.78 mmol); EtOH (10 mL); H$_2$O$_2$ 35% (236 µL, 2.74 mmol); NaOH (1.57 mL, 0.78 mmol); reflux for 3 h. | Chromatography SiO$_2$, CH$_2$Cl$_2$:MeOH = 100:0 to 98:2 | 2-(1-ethyl-6,7-dimethoxyisoquindin-4-yl)methyl)quinoline-8-carboxamide (147.6 mg); MW: 401.46; Yield: 47%; White Solid; Mp (° C.): 246.3-248.7; R$_f$: 0.25 (CH$_2$Cl$_2$:MeOH = 98:2); $^1$H NMR (CDCl$_3$, δ): 1.47 (t, 3H, CH$_3$, J = 7.5 Hz), 3.27 (q, 2H, CH$_2$, J = 7.5 Hz), 3.76 (s, 3H, OCH$_3$), 4.00 (s, 3H, OCH$_3$), 4.68 (s, 2H, CH$_2$), 5.80 (br s, 1H, NH), 7.14 (s, 1H, ArH), 7.35 (s, 1H, ArH), 7.42 (d, 1H, ArH, J = 8.5 Hz), 7.63 (t, 1H, ArH, J = 7.5 Hz), 7.93 (dd, 1H, ArH, J = 1.5 Hz, J = 8.0 Hz), 8.15 (d, 1H, ArH, J = 8.5 Hz), 8.40 (s, 1H, ArH), 8.80 (dd, 1H, ArH, J = 1.5 Hz J = 7.5 Hz), 10.74 (br s, 1H, NH); $^{13}$C NMR (CDCl$_3$, δ): 13.3, 28.5, 40.7, 55.9, 55.9, 102.7, 104.1, 120.9, 122.5, 124.9, 126.0, 127.0, 127.9, 131.9, 132.2, 134.3, 138.2, 142.0, 144.9, 149.6, 152.4, 160.4, 160.6, 167.6; MS-ESI m/z (% rel. int.): 402 ([MH]$^+$, 100); HPLC: Method A, detection UV 254 nm, RT = 3.85 min, peak area 99.4%. |
| 92 | (structure) | H (c) RBO 51116 (300 mg, 0.59 mmol); 1,4-dioxane (20 mL); Pd$_2$(dba)$_3$ (11.22 mg, 0.036 mmol); Xantphos (68.5 mg, 0.12 mmol); ethyl oxamate (83 mg, 0.71 mmol); Cs$_2$CO$_3$ (386 mg, 1.19 mmol); reflux for 4 h. | Chromatography SiO$_2$, CH$_2$Cl$_2$:EtOAc = 100:0 to 50:50 | ethyl 2-(2-((1-ethyl-6,7-dimethoxyisoquinolin-4-yl)methyl)quinolin-8-yl)amino)-2-oxoacetate (170 mg); MW: 473.52; Yield: 61%; White Solid; Mp (° C.): 209.7-212.0; R$_f$: 0.30 (CH$_2$Cl$_2$:EtOAc = 50:50); $^1$H NMR (CDCl$_3$, δ): 1.40-1.57 (m, 6H, 2xCH$_3$), 3.25 (q, 2H, CH$_2$, J = 7.5 Hz), 3.80 (s, 3H, OCH$_3$), 3.98 (s, 3H, OCH$_3$), 4.48 (s, 2H, CH$_2$), 4.68 (s, 2H, CH$_2$), 7.33-7.37 (m, 2H, 2xArH), 7.43 (s, 1H, ArH), 7.52-7.54 (m, 2H, 2xArH), 8.01 (d, 1H, ArH, J = 9.0 Hz), 8.44 (s, 1H, ArH), 8.78-8.81 (m, 1H, ArH), 11.49 (br s, 1H, NH); $^{13}$C NMR (CDCl$_3$, δ): 13.1, 14.1, 28.5, 41.1, 55.7, 55.9, 63.6, 103.0, 104.0, 117.6, 122.0, 122.5, 123.1, 125.5, 126.4, 126.6, 132.0, 132.4, 136.9, 137.7, 141.6, 149.5, 152.3, 154.1, 159.8, 160.2, 160.8; MSS-ESI m/z (% rel. int.): 474 ([MH]$^+$, 100); HPLC: Method A, detection UV 254 nm, RT = 4.94 min, peak area 95.0% |
| 93 | (structure) | C (b) RBO 51118B (500 mg, 1.34 mmol);Et$_3$N (0.37 mL, 2.66 mmol); RBO 56082 (158 mg, 1.47 mmol); RT overnight. | Chromatography SiO$_2$, CH$_2$Cl$_2$:EtOAc = 100:0 to 0:100 | N$^1$-(2-((1-ethyl-6,7-dimethoxyisoquinolin-4-yl)methyl)quinolin-8-yl)oxalamide (500 mg); MW: 444.48; Yield: 30%; White Solid; Mp (° C.): 292.7-295.1; R$_f$: 0.2 (EtOAc); $^1$H NMR (DMSO-d$_6$ δ): 1.34 (t, 3H, CH$_3$, J = 7.4 Hz), 3.20 (q, 2H, CH$_2$, J = 7.4 Hz), 3.77 (s, 3H, OCH$_3$), 3.89 (s, 3H, OCH$_3$), 4.67 (s, 2H, CH$_2$), 7.42 (s, 1H, ArH), 7.53-7.62 (m, 3H, 3xArH), 7.69 (d, 1H, ArH, J = 9.0 Hz), 8.23 (br s, 1H, NH), 8.29 (d, 1H, ArH, J = 8.5 Hz), 8.42 (s, 1H, ArH), 8.54 (br s, 1H, NH), 8.69 (d, 1H, ArH, J = 7.5 Hz), 11.57 (br s, 1H, NH); $^{13}$C NMR (DMSO-d$_6$, δ): 12.8, 27.4, 39.5, 55.3, 55.6, 102.5, 104.2, 116.20, 121.8, 122.5, 122.9, 125.5, 126.3, 126.4, 131.0, 132.2, 137.0, 137.3, 141.1, 149.2, 151.9, 157.9, 159.1, 159.9, 161.7; MS-ESI m/z (% rel. int.): 445 ([MH]$^+$, 100); HPLC: Method A, detection UV 254 nm, RT = 4.37 min, peak area 98.8%. |

TABLE 7-continued

| Compd # | FORMULA | General Procedure | Purification | Analysis |
|---|---|---|---|---|
| 94 | (structure) | I RBO 51194 (350 mg, 0.90 mmol); 1,4-dioxane (10 mL); sulfamide (100 mg, 1.04 mmol); reflux for 2 h. | Chromatography SiO$_2$, CH$_2$Cl$_2$:EtOAc = 100:0 to 0:100 | N-(2-(1-ethyl-6,7-dimethoxyisoquinolin-4-yl)methyl)quinolin-8-yl)methyl)sulfamide (30 mg); MW: 466.55; Yield: 7%; White Solid; Mp (° C.): 217.0-219.6; R$_f$: 0.30 (EtOAc); $^1$H NMR (DMSO-d$_6$, δ): 1.33 (t, 3H, CH$_3$, J = 7.5 Hz), 3.20 (q, 2H, CH$_2$, J = 7.5 Hz), 3.81 (s, 3H, OCH$_3$), 3.90 (s, 3H, OCH$_3$), 4.64 (s, 2H, CH$_2$), 4.81 (s, 2H, CH$_2$), 6.74 (br s, 2H, NH$_2$), 7.08 (br s, 1H, NH), 7.41-7.44 (m, 2H, 2xArH), 7.50 (s, 1H, ArH), 7.54 (d, 1H, ArH, J = 9.0 Hz), 7.78-7.85 (m, 2H, 2xArH), 8.21 (d, 1H, ArH, J = 9.0 Hz), 8.38 (s, 1H, ArH); $^{13}$C NMR (DMSO-d$_6$, δ): 12.8, 27.4, 42.5, 55.5, 55.6, 59.7, 102.9, 104.1, 121.2, 121.8, 125.7, 125.9, 126.0, 126.5, 127.5, 131.0, 135.5, 137.0, 141.2, 144.6, 149.2, 151.9, 158.9, 160.0; MS-ESI m/z (% rel. int.): 467 ([MH]$^+$, 100); HPLC: Method A, detection UV 254 nm, RT = 4.13 min, peak area 99.0%. |
| 95 | (structure) | A LPO 55016B (793 mg, 3.62 mmol); 37% HCl (15 mL); SSA 39098 (1.14 g, 3.65 mmol); 100° C. for 1 h. | Precipitate was filtered | 3-((1-ethyl-6,7-dimethoxyisoquinolin-4-yl)methyl)quinolin-6-ol (1.10 g); MW: 374.43; Yield: 81%; Pale Beige Solid; Mp (° C.): 225.3-229.0; $^1$H NMR (CD$_3$OD, δ): 1.41 (t, 3H, CH$_3$, J = 7.6 Hz), 3.25 (q, 2H, CH$_2$, J = 7.6 Hz), 3.83 (s, 3H, OCH$_3$), 3.97 (s, 3H, OCH$_3$), 4.49 (s, 2H, CH$_2$), 6.94 (d, 1H, ArH, J = 2.5 Hz), 7.23-7.27 (m, 2H, 2xArH), 7.48 (s, 1H, ArH), 7.78 (d, 1H, ArH, J = 9.0 Hz), 7.85 (s, 1H, ArH), 8.14 (s, 1H, ArH), 8.52 (d, 1H, ArH, J = 2.0 Hz); $^{13}$C NMR (CD$_3$OD, δ): 14.3, 29.1, 34.5, 56.3, 56.4, 103.9, 105.7, 109.4, 123.8, 124.2, 128.5, 129.9, 131.4, 133.4, 134.5, 134.9, 141.3, 142.3, 148.2, 151.5, 154.5, 159.7, 161.6; MS-ESI m/z (% rel. int.): 375 ([MH]$^+$, 100); HPLC: Method A, detection UV 254 nm, RT = 3.59 min, peak area 96.7%. |
| 96 | (structure) | H (c) RBO 56020 (1.00 g, 1.97 mmol); THF (15 mL); Pd$_2$(dba)$_3$ (37 mg, 0.12 mmol); Xantphos (228 mg, 0.39 mmol); tert-butyl carbamate (463 mg, 3.95 mmol); Cs$_2$CO$_3$ (1.29 g, 3.96 mmol); 140° C. for 25 min (microwave). | Chromatography SiO$_2$, EtOAc:MeOH = 100:0 to 90:10 | 3-((1-ethyl-6,7-dimethoxyisoquinolin-4-yl)methyl)quinolin-6-amine (627 mg); MW: 373.45; Yield: 85%; Pale Yellow Solid. Mp (° C.): 207-208.7; R$_f$: 0.5 (EtOAc: MeOH = 90:10, free base); $^1$H NMR (CDCl$_3$, δ): 1.47 (t, 3H, CH$_3$, J = 7.5 Hz), 3.27 (q, 2H, CH$_2$, J = 7.5 Hz), 3.82 (s, 3H, OCH$_3$), 3.90 (br s, 2H, NH$_2$), 4.01 (s, 3H, OCH$_3$), 4. 40 (s, 2H, CH$_2$), 6.70 (d, 1H, ArH, J = 2.5 Hz), 7.05-7.10 (m, 2H, 2xArH), 7.37 (s, 1H, ArH), 7.52 (d, 1H, ArH, J = 1.2 Hz), 7.84 (d, 1H, ArH, J = 8.9 Hz), 8.31 (s, 1H, ArH), 8.68 (d, 1H, ArH, J = 2.2 Hz); $^{13}$C NMR (CDCl$_3$, δ): 13.2, 28.5, 34.1, 55.8, 55.9, 102.6, 104.2, 107.0, 121.0, 122.5, 125.8, 129.5, 130.3, 131.5, 132.3, 133.1, 141.8, 142.2, 144.8, 147.8, 149.5, 152.3, 160.0; MS-ESI m/z (% rel. int.): 374 ([MH]$^+$, 100); HPLC: Method A, detection UV 254 nm, RT = 3.67 min, peak area 95.1%. |

TABLE 7-continued

| Compd # | FORMULA | General Procedure | Purification | Analysis |
|---|---|---|---|---|
| 97 | (structure) | H (c) RBO 56020 (200 mg, 0.39 mmol); 1,4-dioxane (15 mL); Pd₂(dba)₃ (7.48 mg, 0.024 mmol); Xantphos (45.7 mg, 0.079 mmol); pyrrolidinone (60 μL, 0.80 mmol); Cs₂CO₃ (257 mg, 0.79 mmol); 160° C for 5 min (microwave). | Chromatography SiO₂, CH₂Cl₂:gEtOAc = 100:0 to 0:100 | 1-(3-(0-ethyl-6,7-dimethoxyisoquinolin-4-yl)methyl)quinolin-6-yl)pyrrolidin-2-one (123 mg); MW: 441.52; Yield: 71%; Pale Yellow Solid; Mp (° C.): 198.4-199.5; R$_f$: 0.1 (EtOAc); $^1$H NMR (CDCl₃, δ): 1.48 (t, 3H, CH₃, J = 7.5 Hz), 2.17-2.24 (m, 2H, CH₂), 2.64 (t, 2H, CH₂, J = 16.2 Hz), 3.28 (q, 2H, CH₂, J = 7.5 Hz), 3.81 (s, 3H, OCH₃), 3.93 (t, 2H, CH₂, J = 7.0 Hz), 4.02 (s, 3H, OCH₃), 4.46 (s, 2H, CH₂), 7.02 (s, 1H, ArH), 7.39 (s, 1H, ArH), 7.71 (d, 1H, ArH, J = 1.8 Hz), 7.80 (s, 1H, ArH), 8.04-8.06 (m, 2H, 2xArH), 8.32 (s, 1H, ArH), 8.88 (d, 1H, ArH, J = 2.2 Hz); $^{13}$C NMR (CDCl₃, δ): 13.2, 17.8, 28.5, 32.7, 33.9, 48.7, 55.8, 55.9, 104.2, 104.2, 115.9, 122.3, 125.4, 128.1, 129.6, 131.4, 133.3, 134.2, 137.7, 141.8, 144.1, 149.5, 150.7, 152.4, 160.2, 174.4; MS-ESI m/z (% rel. int.): 442 ([MH]⁺, 100); HPLC: Method A, detection UV 254 nm, RT = 3.66 min, peak area 96.4%. |
| 98 | (structure) | C (b) 96 (567 mg, 1.52 mmol); THF (10 mL); Et₃N (0.41 mL, 2.95 mmol); RBO 56082 (180 mg, 1.67 mmol); RT overnight. | Chromatography SiO₂, CH₂Cl₂:MeOH = 100:0 to 95:5 | N¹-(3-((1-ethyl-6,7-dimethoxyisoquinolin-4-yl)methyl)quinolin-6-yl)oxalamide (306 mg); MW: 444.48; Yield: 45%; White Solid; Mp (° C.): 234.1-237.4; R$_f$: 0.3 (CH₂Cl₂:MeOH = 95:5); $^1$H NMR (DMSO-d₆ δ): 1.34 (t, 3H, CH₃, J = 7.5 Hz), 3.21 (q, 2H, CH₂, J = 7.5 Hz), 3.85 (s, 3H, OCH₃), 3.92 (s, 3H, OCH₃), 4.52 (s, 2H, CH₂), 7.37 (s, 1H, ArH), 7.44 (s, 1H, ArH), 7.92 (d, 1H, ArH, J = 9.0 Hz), 8.04-8.09 (m, 2H, 2xArH), 8.15 (br s, 1H, NH), 8.28 (s, 1H, ArH), 8.34 (br s, 1H, NH), 8.38 (d, 1H, ArH, J = 2.1 Hz), 8.83 (d, 1H, ArH, J = 2.1 Hz), 10.87 (br s, 1H, NH); $^{13}$C NMR (DMSO-d₆, δ): 11.7, 26.3, 31.5, 54.5, 54.5, 101.6, 103.2, 115.0, 120.7, 122.2, 125.3, 126.5, 128.0, 129.4, 132.8, 132.9, 134.7, 139.8, 142.5, 148.2, 149.7, 150.9, 157.8, 158.0, 160.8; MS-ESI m/z (% rel. int.): 445 ([MH]⁺, 100); HPLC: Method A, detection UV 254 nm, RT = 3.43 min, peak area 99.3%. |
| 99 | (structure) | C (d) 96 (200 mg, 0.54 mmol); CH₂Cl₂ (15 mL); pyridine (86 μL, 1.07 mmol); methanesulfonyl chloride (41 μL, 0.53 mmol); 70° C. for 1 h 10 (microwave). | Chromatography SiO₂, CH₂Cl₂:MeOH = 100:0 to 80:20 | N-(3-((1-ethyl-6,7-dimethoxyisoquinolin-4-yl)methyl)quinolin-6-yl)methanesulfonamide (113 mg); MW: 451.54; Yield: 47%; White Solid; Mp (° C.): 219.7-222.4; R$_f$: 0.5 (CH₂Cl₂:MeOH = 90:10); $^1$H NMR (CDCl₃, δ): 1.49 (t, 3H, CH₃, J = 7.5 Hz), 3.04 (s, 3H, CH₃), 3.29 (q, 2H, CH₂, J = 7.5 Hz), 3.83 (s, 3H, OCH₃), 4.03 (s, 3H, OCH₃), 4.47 (s, 2H, CH₂), 6.67 (br s, 1H, NH), 7.01 (s, 1H, ArH), 7.38-7.42 (m, 2H, 2xArH), 7.50 (d, 1H, ArH, J = 2.4 Hz), 7.68 (d, 1H, ArH, J = 1.1 Hz), 8.05 (d, 1H, ArH, J = 9.0 Hz), 8.29 (s, 1H, ArH), 8.92 (d, 1H, ArH, J = 2.1 Hz); $^{13}$C NMR (DMSO-d₆, δ): 12.6, 27.3, 32.5, 39.0, 55.2, 55.3, 102.4, 104.1, 114.2, 121.8, 122.8, 126.3, 128.0, 129.6, 130.6, 133.7, 134.0, 136.5, 140.7, 143.3, 149.3, 150.3, 152.1, 159.1; MS-ESI m/z (% rel. int.): 452 ([MH]⁺, 100). HPLC: Method A, detection UV 254 nm, RT = 3.67 min, peak area 97.8%. |
| 100 | (structure) | I 96 (350 mg, 0.94 mmol); 1,4-dioxane (15 mL); sulfamide (901 mg, 9.37 mmol); reflux overnight. | Chromatography SiO₂, CH₂Cl₂:MeOH = 100:0 to 90:10 | N-(3-((1-ethyl-6,7-dimethoxyisoquinolin-4-yl)methyl)quinolin-6-yl)sulfamide (10.6 mg); MW: 452.53; Yield: 2.5%; White Solid; Mp (° C.): 227.0-230.8; R$_f$: 0.4 (CH₂Cl₂:MeOH = 90:10); $^1$H NMR (DMSO-d₆): 1.34 (t, 3H, CH₃, J = 7.5 Hz), 3.22 (q, 2H, CH₂, J = 7.5 Hz), 3.82 (s, 3H, OCH₃), 3.92 (s, 3H, OCH₃), 4.51 (s, 2H, CH₂), 7.23 (br s, 2H, NH₂), 7.32 (s, 1H, ArH), 7.42-7.45 (m, 3H, 3xArH), 7.85-7.88 (m, 2H, 2xArH), 8.28 (s, 1H, ArH), 8.82 (br s, 1H, NH), 9.88 (s,1H, ArH); $^{13}$C NMR (DMSO-d₆, δ): 12.8, 27.4, 32.5, 55.6 (2xC), 102.5, 104.3, 111.5, 121.9, 126.4, 128.1, 129.3, 130.6, 133.1, 133.9, 137.6, 141.1, 142.6, 149.3, 149.6, 152.0, 158.9 (1xC not seen); MS-ESI m/z (% rel. int.): 453 ([MH]⁺, 100); HPLC: Method A, detection UV 254 nm, RT = 3.76 min, peak area 97.2%. |

TABLE 7-continued

| Compd # | FORMULA | General Procedure | Purification | Analysis |
|---|---|---|---|---|
| 101 | *structure* | B (a) 99 (83 mg, 0.18 mmol); CH₃CN (15 mL); Cs₂CO₃ (66 mg, 0.20 mmol); CH₃I (12 µL, 0.19 mmol); 80° C. for 11 min (microwave). | Chromatography SiO₂, CH₂Cl₂:MeOH = 100:0 to 98:2 | N-(3-((1-ethyl-6,7-dimethoxyisoquinolin-4-yl)methyl)quinolin-6-yl)-N-methylmethanesulfonamide (30 mg); MW: 465.56; Yield: 35%; Off-White Solid; Mp (° C.)178.0-178.5; R$_f$: 0.8 (CH₂Cl₂:MeOH = 90:10); ¹H NMR (CDCl₃, δ): 1.48 (t, 3H, CH₃, J = 7.5 Hz), 2.84 (s, 3H, CH₃), 3.29 (q, 2H, CH₂, J = 7.9 Hz), 3.38 (s, 3H, CH₃), 3.84 (s, 3H, OCH₃), 4.03 (s, 3H, OCH₃), 4.48 (s, 2H, CH₂), 7.02 (s, 1H, ArH), 7.40 (s, 1H, ArH), 7.60 (d, 1H, ArH, J = 2.3 Hz), 7.63-7.74 (m, 2H, 2xArH), 8.08 (d, 1H, ArH, J = 9.0 Hz), 8.30 (s, 1H, ArH), 8.98 (d, 1H, ArH, J = 2.1 Hz); ¹³C NMR (CDCl₃, δ): 13.2, 28.5, 33.9, 35.6, 38.0, 55.9, 56.0, 102.3, 104.3, 122.6, 123.5, 125.2, 127.1, 128.1, 130.5, 131.4, 133.8, 134.4, 139.6, 141.8, 145.6, 149.6, 152.0, 152.5, 160.3; MS-ESI m/z (% rel. int.): 466 ([MH]⁺, 100); HPLC: Method A, detection UV 254 nm, RT = 3.78 min, peak area 98.9%. |
| 102 | *structure* | A LPO 22102 (200 mg, 0.71 mmol); 6-fluoro-3-formylchromone (141 mg, 0.73 mmol); 37% HCl (1.2 mL); EtOH (1.2 mL); 90° C. for 25 min | Chromatography SiO₂, CH₂Cl₂:MeOH = 100:0 to 98:2 | 3-((6,7-dimethoxyisoquinolin-4-yl)methyl)-6-fluoro-4H-chromen-4-one hydrochloride (119 mg); MW: 401.82; Yield: 42%; Off-White Solid; Mp (° C.): 240.8; R$_f$: 0.25 (CH₂Cl₂:MeOH = 98:2, free base); ¹H-NMR (CD₃OD, δ): 4.07 (s, 3H, OCH₃), 4.16 (s, 3H, OCH₃), 4.39 (s, 2H, CH₂), 7.55-7.69 (m, 2H, 2xArH), 7.75- 7.80 (m, 3H, 3xArH), 8.35 (s, 1H, ArH), 8.40 (s, 1H, ArH), 9.28 (s, 1H, ArH); ¹³C-NMR (CD₃OD, δ): 26.50, 57.04, 57.65, 103.92, 109.02, 110.70, 111.02, 121.68, 122.19, 122.30, 123.57, 123.91, 125.53, 130.51, 134.42, 154.45, 157.64, 161.46 (d, CF, J = 206.4 Hz), 178.26; MS-ESI m/z (% rel. Int.): 366.2 ([MH]⁺, 100), peak area 99.9%. HPLC: Method A, detection UV 254 nm, RT = 4.04 min, peak area 99.9%. |
| 103 | *structure* | A LPO 22102 (300 mg, 1.06 mmol); 6-chloro-3-formylchromone (221 mg, 1.06 mmol); 37% HCl (2.5 mL); EtOH (2.5 mL); 90° C. for 25 min. | Chromatography SiO₂, CH₂Cl₂:MeOH = 100:0 to 98:2 | 6-chloro-3-((6,7-dimethoxyisoquinolin-4-yl)methyl)-4H-chromen-4-one hydrochloride (39.7 mg); MW: 418.27; Yield: 9%; Yellow Pale Solid; Mp (° C.): 203.7-207.2; R$_f$: 0.25 (CH₂Cl₂:MeOH = 98:2, free base); ¹H-NMR (CDCl₃, δ): 4.07 (s, 3H, OCH₃), 4.15 (s, 3H, OCH₃), 4.33 (s, 2H, CH₂), 7.47 (d, 1H, ArH, J = 8.95 Hz), 7.63- 7.67 (m, 2H, 2xArH), 7.75 (s, 1H, ArH), 8.14-8.15 (m, 2H, ArH), 8.35 (s, 1H, ArH), 9.22 (s, 1H, ArH); ¹³C-NMR (CDCl₃, δ): 28.88, 60.50, 61.06, 106.99, 111.66, 124.13, 125.07, 127.96, 128.29, 128.92, 132.97, 135.57, 137.23, 138.40, 139.79, 144.62, 156.92, 158.73, 160.00, 162.35, 180.15; MS-ESI m/z (% rel. Int.): 382.2 ([MH]⁺, 100); HPLC: Method A, detection UV 254 nm, RT = 4.37 min, peak area 99.9%. |
| 104 | *structure* | A LPO 22102 (300 mg, 1.06 mmol); 6,8-dichloro-3-formylchromone (257 mg, 1.06 mmol); 37% HCl (2.5 mL); EtOH (2.5 mL); 90° C. for 25 min. | Chromatography SiO₂, CH₂Cl₂:MeOH = 100:0 to 98:2 | 6,8-dichloro-3-((6,7-dimethoxyisoquinolin-4-yl)methyl)-4H-chromen-4-one hydrochloride (179.7 mg); MW: 452.72; Yield: 37%; Yellow Solid; Mp (° C.): 207.8; R$_f$: 0.25 (CH₂Cl₂:MeOH = 98:2, free base); ¹H-NMR (CDCl₃, δ): 4.09 (s, 3H, OCH₃), 4.18 (s, 3H, OCH₃), 5.34 (s, 2H, CH₂), 7.69-7.80 (m, 3H, 3xArH), 8.06 (s, 1H, ArH), 8.35 (m, 2H, 2xArH), 9.24 (s, 1H, ArH); ¹³C-NMR (CDCl₃, δ): 28.0, 59.39, 59.98, 105.79, 110.74, 124.48, 126.63, 127.09, 127.67, 128.18, 132.17, 134.25, 135.81, 137.20, 138.84, 143.76, 153.82, 156.01, 158.84, 161.54, 178.72; MS-ESI m/z (% rel. Int.): 416.1 ([MH]⁺, 100); HPLC: Method A, detection UV 254 nm, RT = 4.74 min, peak area 99.9%. |

TABLE 7-continued

| Compd # | FORMULA | General Procedure | Purification | Analysis |
|---|---|---|---|---|
| 105 | (structure shown: 6-((6,7-dimethoxy-1-methylisoquinolin-4-yl)methyl)-2-methylquinoline dihydrochloride, 2HCl) | A TTA 241258B (300 mg, 1.01 mmol); 2-methylquinoline-6-carbaldehyde (172.7 mg, 1.01 mmol); 37% HCl (1.4 mL); EtOH (1.4 mL); 90° C. for 25 min | Chromatography $SiO_2$, $CH_2Cl_2$:MeOH = 100:0 to 98:2 | 6-((6,7-dimethoxy-1-methylisoquinolin-4-yl)methyl)-2-methylquinoline dihydrochloride (78.4 mg); MW: 431.35; Yield: 18%; Green Solid; Mp (°C.): 70.8; $R_f$: 0.20 ($CH_2Cl_2$:MeOH = 98:2, free base); $^1$H-NMR ($CD_3OD$, δ): 3.02 (s, 3H, $CH_3$), 3.19 (s, 3H, $CH_3$), 3.98 (s, 3H, $OCH_3$), 4.09 (s, 3H, $OCH_3$), 4.89 (s, 2H, $CH_2$), 7.49 (s, 1H, ArH), 7.73 (s, 1H, ArH), 7.94 (d, 1H, ArH, J = 8.64 Hz), 8.15-8.26 (m, 4H, ArH), 8.96 (d, 1H, ArH, J = 8.64 Hz); $^{13}$C NMR ($CD_3OD$, δ): 18.17, 20.86, 36.27, 57.15, 57.42, 104.57, 107.24, 121.50, 124.51, 125.19, 128.91, 129.56, 130.20, 132.53, 136.47, 137.05, 138.12, 41.89, 147.30, 154.10, 154.18, 159.24, 159.28; MS-ESI m/z (% rel. Int.): 359.3 ([MH]$^{+1}$, 100); HPLC: Method A, detection UV 254 nm, RT = 3.17 min, peak area 99.9%. |
| 106 | (structure shown, 2HCl) | C (c) ANP 49184A (200 mg, 0.58 mmol); $Et_3N$ (88 μL, 0.63 mmol); CDI (108 mg, 0.66 mmol); $CH_2Cl_2$ (7 mL); 0° C. to RT for 5 h. | Precipitate was filtered | 5-((6,7-dimethoxyisoquinolin-4-yl)methyl)benzo[d]oxazol-2(3H)-one hydrochloride (39 mg); MW: 372.80; Yield: 63%; White Solid; Mp (°C.): 200.5-214.7; $^1$H-NMR ($CD_3OD$, δ): 4.05 (s, 3H, $OCH_3$), 4.07 (s, 3H, $OCH_3$), 4.59 (s, 2H, $CH_2$), 7.06-7.11 (m, 2H, 2xArH), 7.19 (m, 1H, ArH), 7.55 (s, 1H, ArH), 7.80 (s, 1H, ArH), 8.19 (s, 1H, ArH), 9.31 (s, 1H, ArH); $^{13}$C-NMR ($CD_3OD$, δ): 36.85, 57.18, 57.56, 104.13, 109.08, 111.03, 111.42, 124.03, 125.63, 130.47, 132.37, 135.22, 135.93, 137.34, 142.61, 144.49, 154.42 (2xC), 159.86; MS-ESI m/z (% rel. Int.): 337.2 ([MH]$^{+1}$, 100); HPLC: Method A, detection UV 254 nm, RT = 3.59 min, peak area 99.9%. |
| 107 | (structure shown, HCl) | B (a) 106 (65.7 mg, 0.19 mmol); $K_2CO_3$ (30 mg, 0.21 mmol); bromoethane (17 μL, 0.234 mmol); acetone (3 mL); 60°C overnight. | Chromatography $SiO_2$, $CH_2Cl_2$:MeOH = 100:0 to 98:2 | 5-((6,7-dimethoxyisoquinolin-4-yl)methyl)-3-ethylbenzo[d]oxazol-2(3H)-one hydrochloride (40.8 mg); MW: 400.86; Yield: 52%; White Solid; Mp (°C.): 191.8; $R_f$: 0.25 ($CH_2Cl_2$:MeOH = 98:2, free base); $^1$H-NMR ($CD_3OD$, δ): 1.13 (t, 3H, $CH_3$, J = 7.2 Hz), 3.88 (q, 2H, $CH_2$, J = 7.2 Hz), 4.05 (s, 3H, $OCH_3$), 4.07 (s, 3H, $OCH_3$), 4.64 (s, 2H, $CH_2$), 7.12-7.16 (m, 1H, ArH), 7.23-7.26 (m, 2H, 2xArH), 7.57 (s, 1H, ArH), 7.82 (s, 1H, ArH), 8.22 (s, 1H, ArH), 9.32 (s, 1H, ArH); $^{13}$C-NMR ($CD_3OD$, δ): 13.12, 36.82, 38.17, 57.05, 57.45, 104.08, 109.05, 110.48, 111.08, 124.20, 125.60, 130.46, 132.89, 135.52, 135.88, 137.35, 142.61, 143.20, 154.43, 156.15, 159.91; MS- ESI m/z (% rel. Int.): 365.3 ([MH]$^{+1}$, 100); HPLC: Method A, detection UV 254 nm, RT = 3.97 min, peak area 99.9%. |

TABLE 7-continued

| Compd # | FORMULA | General Procedure | Purification | Analysis |
|---|---|---|---|---|
| 108 | 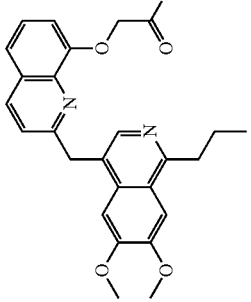 | F (a) ANP 49102A (56 mg, 0.117 mmol) in MeOH (2.5 mL); KOH 85% (262.6 mg, 3.98 mmol) in MeOH/H$_2$O (0.8 mL/0.8 mL); 100° C. overnight. | Chromatography SiO$_2$, CH$_2$Cl$_2$:MeOH = 100:0 to 98:2 | 2-((2-((6,7-dimethoxy-1-propylisoquinolin-4-yl)methyl)quinolin-8-yl)oxy)acetic acid dihydrochloride (47.3 mg); MW: 519.42; Yield: 78%; Yellow Solid; Mp (° C.): 192.5; R$_f$: 0.15 (CH$_2$Cl$_2$:MeOH = 98:2); $^1$H-NMR (CD$_3$OD, δ): 1.14 (t, 3H, CH$_3$, J = 7.33 Hz), 2.00 (q, 2H, CH$_2$, J = 7.56 Hz), 3.55 (t, 2H, CH$_2$, J = 7.59 Hz), 4.09 (s, 3H, OCH$_3$), 4.12 (s, 3H, OCH$_3$), 5.20 (s, 2H, OCH$_2$), 5.28 (s, 2H, CH$_2$), 7.62-7.69 (m, 2H, 2xArH), 7.77-7.89 (m, 4H, 4xArH), 8.40 (s, 1H, ArH), 8.95 (d, 1H, ArH, J = 8.63 Hz); $^{13}$C-NMR (CD$_3$OD, δ): 14.11, 24.21, 34.12 (2xC), 57.25, 57.86, 67.30, 104.20, 107.22, 116.28, 122.57, 123.99, 124.38, 128.74, 130.47, 131.20, 131.28, 132.13, 137.05, 145.96, 147.93, 149.77, 154.49, 158.26, 160.03, 172.20; MS-ESI m/z (% rel. Int.): 447.3 ([MH]$^{+1}$, 100); HPLC: Method A, detection UV 254 nm, RT = 3.73 min, peak area 99.9%. |
| 109 | 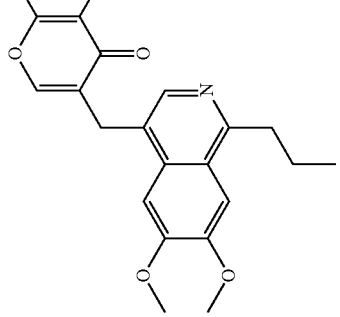 | A SSA 39102 (200 mg, 0.61 mmol); 6-fluoro-3-formylchromone (122.8 mg, 0.64 mmol); 37% HCl (1.2 mL); EtOH (1.2 mL); 90° C. for 30 min. | Chromatography SiO$_2$, CH$_2$Cl$_2$:MeOH = 100:0 to 98:2 | 3-((6,7-dimethoxy-1-propylisoquinolin-4-yl)methyl)-6-fluoro-4H-chromen-4-one hydrochloride (26.8 mg); MW: 443.90; Yield: 10%; White Solid; Mp (° C.): 189.5; R$_f$: 0.20 (CH$_2$Cl$_2$:MeOH = 98:2); $^1$H-NMR (CDCl$_3$, δ): 1.11 (t, 3H, CH$_3$, J = 7.26 Hz), 1.99 (q, 3H, CH$_2$, J = 7.3 Hz), 3.58 (t, 2H, CH$_2$, J = 7.32 Hz), 4.08 (s, 3H, OCH$_3$), 4.15 (s, 3H, OCH$_3$), 4.28 (s, 2H, CH$_2$), 7.40-7.52 (m, 3H, 3xArH), 7.85 (dd, 1H, ArH, J = 2.79 Hz; J = 8.07 Hz), 8.00 (s, 1H, ArH), 8.28 (s, 1H, ArH); $^{13}$C-NMR (CDCl$_3$, δ) 23.45, 24.83, 32.55, 56.40, 57.11, 103.99, 104.72, 110.48, 110.79, 120.53, 120.65, 122.32, 122.66, 124.64, 124.74, 128.85, 131.32, 135.34, 152.40, 152.68, 155.24, 155.49, 157.19, 159.72 (d, CF, J = 248.3 Hz), 176.27, 176.30; MS-ESI m/z (% rel. Int.): 408.3 ([MH]$^{+1}$, 100); HPLC: Method A, detection UV 254 nm, RT = 4.49 min, peak area 99.9%. |
| 110 | 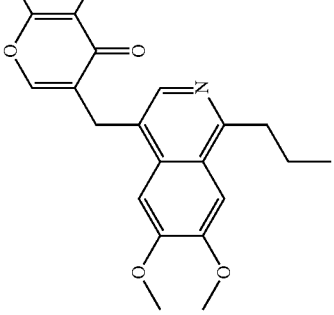 | A SSA 39102 (300 mg, 0.92 mmol); 6-formyl-6-methylchromone (173 mg, 0.92 mmol); 37% HCl (2.5 mL); EtOH (2.5 mL); 90° C. for 25 min. | Chromatography SiO$_2$, CH$_2$Cl$_2$:MeOH = 100:0 to 98:1 | 3-((6,7-dimethoxy-1-propylisoquinolin-4-yl)methyl)-6-methyl-4H-chromen-4-one hydrochloride (90 mg); MW: 439.93; Yield: 22%; Orange Solid; Mp (° C.): 177-191.1; R$_f$: 0.25 (CH$_2$Cl$_2$:MeOH = 99:1); $^1$H-NMR (CD$_3$OD, δ): 1.07 (t, 3H, CH$_3$, J = 7.49 Hz), 1.88-1.96 (m, 2H, CH$_2$), 2.44 (s, 3H, CH$_3$), 3.44 (t, 3H, CH$_3$, J = 7.45 Hz), 4.06 (s, 3H, OCH$_3$), 4.10 (s, 3H, OCH$_3$), 4.32 (s, 2H, OCH$_2$), 7.46 (d, 1H, ArH, J = 8.64 Hz), 7.60 (d, 1H, ArH, J = 8.64 Hz), 7.68 (s, 1H, ArH), 7.74 (s, 1H, ArH), 7.93 (s, 1H, ArH), 8.15 (s, 1H, ArH), 8.29 (s, 1H, ArH); $^{13}$C-NMR (CD$^3$OD, δ): 14.07, 20.96, 24.11, 26.43, 34.01, 57.12, 57.58, 104.68, 106.72, 119.39, 122.11, 123.68, 124.40, 125.58, 129.73, 133.01, 136.86, 137.07, 137.24, 154.18, 156.39, 156.51, 157.44, 159.31, 179.01; MS-ESI m/z (% rel. Int.): 404.2 ([MH]$^{+1}$, 100); HPLC: Method A, detection UV 254 nm, RT = 4.69 min, peak area 99.9%. |

TABLE 7-continued

| Compd # | FORMULA | General Procedure | Purification | Analysis |
|---|---|---|---|---|
| 111 | (structure) HCl | C (C) ANP 49184A (311 mg, 0.90 mmol); Et₃N (137 µL, 0.99 mmol); CDI (167 mg, 1.03 mmol); CH₂Cl₂ (9 mL); 0° C. for 5 h. | Chromatography SiO₂, CH₂Cl₂:MeOH = 100:0 to 96:4 | 6-((6,7-dimethoxyisoquinolin-4-yl)methyl)benzo[d]oxazol-2(3H)-one hydrochloride (41.9 mg); MW: 372.80; Yield: 34%; White Solid; Mp (° C.): 191.8; R_f: 0.25 (CH₂Cl₂:MeOH = 96:4, free base); ¹H-NMR (CDCl₃, δ): 3.80 (s, 3H, OCH₃), 3.85 (s, 3H, OCH₃), 4.28 (s, 2H, CH₂), 6.82-6.84 (m, 3H, 3xArH), 7.15 (s, 1H, ArH), 7.51 (s, 1H, ArH), 7.88 (s, 1H, ArH), 9.06 (s, 1H, ArH); ¹³C-NMR (CDCl₃, δ): 39.97, 60.40, 60.60, 106.49, 111.89, 113.92, 114.21, 128.16, 128.27, 132.94, 133.42, 135.37, 138.04, 139.88, 145.06, 148.43, 156.87, 159.73, 162.26; MS-ESI m/z (% rel. Int.): 337.2 ([MH]⁺¹, 100), peak area 99.9%. detection UV 254 nm, RT = 3.51 min, peak area 99.9%. |
| 112 | (structure) HCl | B (a) 111 (50 mg, 0.15 mmol); K₂CO₃ (23 mg, 0.16 mmol); bromoethane (14 µL, 0.18 mmol); acetone (3 mL); 60° C. overnight. | Chromatography SiO₂, CH₂Cl₂:MeOH = 100:0 to 98:2 | 6-((6,7-dimethoxyisoquinolin-4-yl)methyl)-3-ethylbenzo[d]oxazol-2(3H)-one hydrochloride (30 mg); MW: 400.86; Yield: 50%; White Solid; Mp (° C.): 188.9; R_f: 0.3 (CH₂Cl₂:MeOH = 98:2, free base); ¹H-NMR (CD₃OD, δ): 1.33 (t, 3H, CH₃, J = 7.2 Hz), 3.89 (q, 2H, CH₂, J = 7.2 Hz), 4.05 (s, 3H, OCH₃), 4.06 (s, 3H, OCH₃), 4.61 (s, 2H, CH₂), 7.17-7.28 (m, 3H, 3xArH), 7.54 (s, 1H, ArH), 7.80 (s, 1H, ArH), 8.21 (s, 1H, ArH), 9.32 (s, 1H, ArH); ¹³C-NMR (CD₃OD, δ): 13.31, 36.77, 38.33, 57.21, 57.60, 104.12, 109.17, 110.22, 111.51, 125.65, 125.90, 130.42, 131.28, 133.94, 135.85, 137.36, 142.63, 144.61, 154.43, 156.06, 159.90; MS-ESI m/z (% rel. Int.): 365.2 ([MH]⁺¹, 100); HPLC: Method A, detection UV 254 nm, RT = 3.95 min, peak area 99.9%. |
| 113 | (structure) 2HCl | H (a) LPO 50042C (141 mg, 0.36 mmol); 2-(di-tert-butyl)phosphinobiphenyl (1.1 mg, 0.0036 mmol); 2M EtNH₂ in THF (269 µL, 0.54 mmol); tBuOK (56.2 mg, 0.5 mmol); Toluene (2.5 mL); 170° C. for 5.5 h (microwave). | Chromatography SiO₂, CH₂Cl₂:MeOH = 100:0 to 98:2 and EtOAc:MeOH = 100:0 to 98:2 | 3-((6,7-dimethoxyisoquinolin-4-yl)methyl)-N-ethyl-6-methoxyquinolin-2-amine dihydrochloride (13.9 mg); MW: 476.44; Yield: 8%; Yellow Solid; R_f: 0.25 (EtOAc:MeOH = 98:2); ¹H-NMR (CD₃OD, δ): 1.47 (t, 3H, CH₃, J = 7.20 Hz), 3.78 (q, 2H, CH₂, J = 7.20 Hz), 3.83 (s, 3H, CH₃), 4.10 (s, 3H, OCH₃), 4.12 (s, 3H, OCH₃), 4.67 (s, 2H, CH₂), 7.21 (d, 1H, ArH, J = 2.65 Hz), 7.41 (dd, 1H, ArH, J = 9.14 Hz), 7.53 (s, 1H, ArH), 7.80 (s, 1H, ArH), 7.94 (s, 1H, ArH), 7.98 (d, 1H, ArH, J = 9.16 Hz), 8.27 (s, 1H, ArH), 9.45 (s, 1H, ArH); ¹³C-NMR (CD₃OD, δ): 13.88, 31.51, 38.99, 56.34, 57.19, 57.74, 103.69, 109.41, 109.62, 119.76, 123.71, 123.78, 123.86, 125.70, 130.68, 131.61, 131.75, 137.75, 142.34, 143.44, 152.29, 154.72, 158.88, 160.49; MS-ESI m/z (% rel. Int.): 404.3 ([MH]⁺¹, 100); HPLC: Method A, detection UV 254 nm, RT = 3.37 min, peak area 99.9%. |
| 114 | (structure) | ANP 49184A (200 mg, 0.64 mmol); benzaldehyde (65 µL, 0.64 mmol) in MeOH (20 mL); 60° C. overnight; DDQ (16, mg, 0.71 mmol) in CH₂Cl₂ (20 mL); RT for 30 min. | Chromatography SiO₂, CH₂Cl₂:MeOH = 100:0 to 98:2 | 5-((6,7-dimethoxyisoquinolin-4-yl)methyl)-2-phenylbenzo[d]oxazole (112 mg); MW: 396.44; Yield: 44%; Off- White Solid; Mp (° C.): 172.3-172.8; R_f: 0.25 (CH₂Cl₂:MeOH = 98:2); 1H-NMR (CDCl₃, δ): 3.84 (s, 3H, OCH₃), 4.00 (s, 3H, OCH₃), 4.45 (s, 2H, CH₂), 7.08 (s, 1H, ArH), 7.21-7.26 (m, 2H, 2xArH), 7.46-7.59 (m, 5H, 5xArH), 8.20-8.22 (m 2H, 2xArH), 8.34 (s 1H ArH), 8.99 (s 1H ArH); ¹³C-NMR (CDCl₃, δ): 36.70, 55.92, 56.0, 102.06, 105.95, 110.44, 119.65, 124.90, 125.56, 127.13, 127.58 (2C), 128.37, 128.89 (2xC), 131.36, 131.53, 136.62, 142.56, 142.83, 149.49, 149.55, 150.03, 152.87, 163.52; MS-ESI m/z (% rel. Int.): 397.3 ([MH]⁺¹, 100); HPLC: Method A, detection UV 254 nm, RT = 4.70 min, peak area 99.9%. |

TABLE 7-continued

| Compd # | FORMULA | General Procedure | Purification | Analysis |
|---|---|---|---|---|
| 115 | 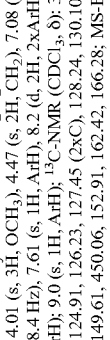 | J ANP 49184A (200 mg, 0.64 mmol); methyl 4-formylbenzoate (106 mg, 0.64 mmol) in MeOH (20 mL); 60° C. overnight; DDQ (161.mg, 0.71 mmol) ) in CH$_2$Cl$_2$ (20 mL); RT for 30 min. | Chromatography SiO$_2$, EtOAc: CH$_2$Cl$_2$ = 0:100 to 85:15 | methyl 4-(5-((6,7-dimethoxyisoquinolin-4-yl)methyl)benzo[o]oxazol-2-yl)benzoate (77.5 mg); MW: 454.47; Yield: 26%; White Solid; Mp (° C.): 233-233.6; R$_f$: 0.25 (EtOAc:CH$_2$Cl$_2$ = 85:15); $^1$H-NMR (CDCl$_3$, δ): 3.84 (s, 3H, CH$_3$), 3.96 (s, 3H, CH$_3$), 4.01 (s, 3H, OCH$_3$), 4.47 (s, 2H, CH$_2$), 7.08 (s, 1H, ArH), 7.22-7.26 (m, 2H, 2xArH), 7.50 (d, 1H, ArH, J = 8.4 Hz), 7.61 (s, 1H, ArH), 8.2 (d, 2H, 2xArH, J = 8.5 Hz), 8.29 (d, 2H, 2xArH, J = 8.5 Hz), 8.34 (s, 1H, ArH); 9.0 (s, 1H, ArH); $^{13}$C-NMR (CDCl$_3$, δ): 36.67, 52.37, 55.92, 56.01, 101.99, 105.98, 110.63, 119.94, 124.91, 126.23, 127.45 (2xC), 128.24, 130.10 (2xC), 130.97, 131.33, 132.57, 136.97 (2xC), 142.46, 142.83, 149.61, 450.06, 152.91, 162.42, 166.28; MS-ESI m/z (% rel. Int.): 455.3 ([MH]$^{+1}$, 100); HPLC: Method A, detection UV 254 nm, RT = 4.74 min, peak area 99.9%. |
| 116 | 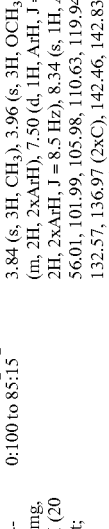 | B (a) Free base of 83 (83.7 mg, 0.22 mmol); acetone (3 mL); Cs$_2$CO$_3$(80.3 mg, 0.25 mmol); 2-bromoacetamide (61.7 mg, 0.45 mmol); 70° C. overnight. | Chromatography SiO$_2$, CH$_2$Cl$_2$:MeOH = 98:2 to 95:5 | 2-(2-((1-ethyl-6,7-dimethoxyisoquinolin-4-yl)methyl)quinolin-8-yl)oxy)acetamide (45.3 mg); MW: 431.48; Yield: 47%; White Solid; R$_f$: 0.25 (CH$_2$Cl$_2$:MeOH = 95:5); $^1$H-NMR (DMSO-d$_6$, δ): 1.32 (t, 3H, CH$_3$, J = 7.47 Hz), 3.19 (q, 2H, CH$_2$, J = 7.47 Hz), 3.86 (s, 3H, OCH$_3$), 3.89 (s, 3H, OCH$_3$), 4.61 (s, 2H, CH$_2$), 4.70 (s, 2H, CH$_2$), 7.19 (dd, 1H, ArH, J = 1.92 Hz, J = 7.02 Hz), 7.39-7.50 (m, 5H, 3xArH + NH$_2$), 7.72 (s, 1H, ArH), 7.83 (s, 1H, NH$_2$), 8.19 (d, 1H, ArH, J = 8.53 Hz), 8.39 (s, 1H, ArH); $^{13}$C-NMR (DMSO-d$_6$, δ): 12.88, 27.43, 39.50, 55.54, 55.57, 68.54, 103.39, 104.08, 111.91, 120.59, 121.84, 122.01, 125.92, 126.22, 127.51, 131.14, 136.64, 138.83, 140.97, 149.25, 151.90, 153.51, 159.03, 159.62, 170.13; MS-ESI m/z (% rel. Int.): 432.3 ([MH]$^{+1}$, 100); HPLC: Method A, detection UV 254 nm, RT = 3.50 min, peak area 99.9%. |
| 117 | 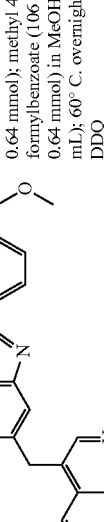 | A TTA 24128B (164 mg, 0.55 mmol); SSA 48104 (119 mg, 0.55 mmol); 37% HCl (1.5 mL); EtOH (1.5 mL); 90° C. for 20 min. | Chromatography SiO$_2$, CH$_2$Cl$_2$:MeOH = 100:0 to 95:5 | 3-((6,7-dimethoxyisoquinolin-4-yl)methyl)-7-methylquinoline (58.4 mg); MW: 358.43; Yield: 30%; Yellow Solid; Mp (° C.): 169.4-173.0; R$_f$: 0.25 (CH$_2$Cl$_2$: MeOH = 95:5); $^1$H-NMR (CDCl$_3$, δ): 2.53 (s, 3H, CH$_3$), 2.92 (s, 3H, CH$_3$), 3.82 (s, 3H, OCH$_3$), 4.02 (s, 3H, OCH$_3$), 4.45 (s, 2H, CH$_2$), 7.03 (s, 1H, ArH), 7.28-7.32 (m, 2H, 2xArH), 7.51 (d, 1H, ArH, J = 8.34 Hz), 7.71 (s, 1H, ArH), 7.83 (s, 1H, NH$_2$), 8.28 (s, 1H, NH$_2$), 8.90 (s, 1H, ArH); $^{13}$C-NMR (CDCl$_3$, δ): 21.76, 22.56, 34.0, 55.83, 55.95, 102.42, 104.66, 123.40, 125.87, 126.06, 127.01, 128.17, 129.05, 131.24, 131.99, 134.24, 139.24, 141.78, 147.32, 149.57, 151.38, 152.49, 155.66; MS-ESI m/z (% rel. Int.): 359.3 ([MH]$^{+1}$, 70); HPLC: Method A, detection UV 254 nm, RT = 3.37 min, peak area 99.9%. |
| 118 | 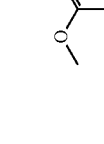 | F (a) LPO 50156C (144 mg, 0.29 mmol) in MeOH (3 mL); NaOH (117.9 mg, 2.95 mmol) in MeOH/H$_2$O (1 mL/1 mL); RT for 20 min. | Chromatography RP 18, eluent: water: 100% to water: CH$_3$CN = 7:3 | sodium 3-(2-((6,7-dimethoxyisoquinolin-4-yl)methyl)quinolin-8-yl)oxy)propanoate (41.9 mg); MW: 482.5; Yield: 31%; Yellow Solid; Mp (° C.): 169.4-173.0; R$_f$: 0.25 (CH$_2$Cl$_2$:MeOH = 95:5); $^1$H-NMR (CD$_3$OD, δ): 1.04 (t, 3H, CH$_3$, J = 7.4 Hz), 1.85 (q, 2H, CH$_2$, J = 7.6 Hz), 2.27-2.34 (m, 2H, OCH$_2$), 2.63-2.69 (m, 1H, CH$_2$), 2.86-2.99 (m, 1H, CH$_2$), 3.17 (t, 2H, CH$_2$, J = 7.5 Hz), 3.86 (s, 3H, OCH$_3$), 3.93 (s, 3H, OCH$_3$), 4.96-5.01 (m, 2H, CH$_2$), 7.11 (dd, 1H, ArH, J = 1.1 Hz, J = 7.6 Hz), 7.24 (dd, 1H, ArH, J = 1.1 Hz, J = 8.2 Hz), 7.29 (d, 1H, ArH, J = 8.58 Hz), 7.36 (d, 1H, ArH, J = 7.8 Hz), 7.39 (d, 1H, ArH), 7.74 (s, 1H, ArH), 8.03 (d, 1H, ArH, J = 8.58 Hz), 8.34 (s, 1H, ArH); $^{13}$C-NMR (CD$_3$OD, δ): 14.51, 24.19, 31.33, 37.30, 37.87, 48.16, 56.33, 56.66, 104.61, 105.61, 112.08, 118.60, 122.70, 124.20, 128.25, 128.89, 131.97, 133.74, 137.91, 138.91, 139.58, 151.18, 154.19, 154.44, 159.97, 162.90, 182.32; MS-ESI m/z (% rel. Int.): 461.2 ([MH]$^{+1}$, 100); HPLC: Method A, detection UV 254 nm, RT = 4.36 min, peak area 99.9%. |

TABLE 7-continued

| Compd # | FORMULA | General Procedure | Purification | Analysis |
|---|---|---|---|---|
| 119 | (structure) | 167 (206 mg, 0.53 mmol); 1,4-dioxane (10 mL); sulfamide (203 mg, 2.12 mmol); reflux overnight. | Chromatography SiO$_2$, CH$_2$Cl$_2$:MeOH = 95:5 then solid was precipitated in acetone (5 mL) and filtered. | N-(2-((1-(methoxymethyl)-6,7-dimethoxyisoquinolin-4-yl)methyl)quinolin-8-yl)sulfamide (26 mg); MW: 468.53; Yield: 10 %; White Solid; Mp (° C.): 218.7; $^1$H-NMR (DMSO-d$_6$, δ): 3.33 (s, 3H, OCH$_3$), 3.87 (s, 6H, 2xOCH$_3$), 4.72 (s, 2H, CH$_2$), 4.89 (s, 2H, CH$_2$), 7.51-7.55 (m, 6H, 4xArH & NH$_2$), 7.59 (s, 1H, ArH), 7.66 (m, 1H, ArH), 8.26 (d, 1H, J = 8.5 Hz, ArH), 8.42 (s, 1H, ArH), 8.94 (s, 1H, NH); $^{13}$C-NMR (DMSO-d$_6$, δ): 39.5, 55.5, 55.7, 57.7, 74.7, 102.8, 104.4, 113.2, 120.3, 122.4, 122.7, 126.3, 126.4, 127.9, 131.5, 134.3, 136.4, 137.2, 140.9, 149.4, 152.2, 153.6, 159.2; MS-ESI m/z (% rel. Int.): 469.3 ([MH]$^{+1}$, 100); HPLC: Method A, detection UV 254 nm, RT = 4.05 min, peak area 96.8%. |
| 120 | (structure) | B (a) 131 (89.8 mg, 0.25 mmol); acetone (4 mL); Cs$_2$CO$_3$ (243 mg, 0.75 mmol); 2-bromoacetamide (55 mg, 0.40 mmol); 60° C. overnight. | Chromatography SiO$_2$, CH$_2$Cl$_2$:MeOH = 100:0 to 97:3 | 2-(2-((6,7-dimethoxy-1-methylisoquinolin-4-yl)methyl)quinolin-8-yloxy)acetamide (17.8 mg); MW: 417.46; Yield: 137.%; Yellow Solid; Mp (° C.): 212.8-217.6; R$_f$: 0.25 (CH$_2$Cl$_2$:MeOH = 97:3); $^1$H-NMR (CDCl$_3$, δ): 2.89 (s, 3H, CH$_3$) 3 86 (s, 3H, OCH$_3$), 3.99 (s, 3H, OCH$_3$), 4.63 (s, 2H, CH$_2$), 4.74 (s, 2H, CH$_2$), 7.16-7.19 (m, 1H, ArH), 7.25 (s, 1H, ArH), 7.34 (d, 1H, ArH, J = 8.50 Hz), 7.40 (s, 1H, ArH), 7.43-7.45 (m, 2H, 2xArH), 8.02 (d, 1H, ArH, J = 8.52 Hz), 8.36 (s, 1H, ArH); $^{13}$C-NMR (CDCl$_3$, δ): 22.46, 40.99, 55.91, 55.95, 70.63, 103.18, 104.37, 113.90, 121.90, 122.01, 123.31, 125.78, 126.36, 128.11, 131.77, 136.85, 140.02, 141.48, 149.60, 152.49, 154.03, 155.61, 160.12, 171.66; MS-ESI m/z (% rel. Int.): 418 ([MH]$^{+1}$, 100); HPLC: Method A, detection UV 254 nm, RT = 3.39 min, peak area 99.9%. |
| 121 | (structure) | K LPO 50040C (100 mg, 0.23 mmol); sodium azide (76.1 mg, 1.17 mmol); ammonium chloride (62.6 mg, 1.17 mmol) in DMF (5 mL); 100° C. for 2 h. | Chromatography SiO$_2$, CH$_2$Cl$_2$:MeOH = 100:0 to 95:5 | 8-((1H-tetrazol-5-yl)methoxy)-2-((6,7-dimethoxy-1-propylisoquinolin-4-yl)methyl)quinoline (32.2 mg); MW: 470.52; Yield: 29%; Off-White Solid; Mp (° C.): 169.4-173.0; R$_f$: 0.25 (CH$_2$Cl$_2$:MeOH = 95:5); $^1$H-NMR (DMSO-d$_6$, δ): 0.96 (t, 3H, CH$_3$, J = 7.29 Hz), 1.79 (q, 2H, CH$_2$, J = 7.45 Hz), 3.14 (t, 2H, CH$_2$, J = 6.16 Hz), 3.73 (s, 3H, OCH$_3$), 3.88 (s, 3H, OCH$_3$), 4.60 (s, 2H, CH$_2$), 5.61 (s, 2H, OCH$_2$), 7.39-7.49 (m, 5H, 5xArH), 7.71 (s, 1H, ArH), 8.18 (d, 1H, ArH, J = 8.49 Hz), 8.38 (s, 1H, ArH); $^{13}$C-NMR (DMSO-d$_6$, δ): 14.0, 21.74, 35.85, 38.66, 55.57, 55.64, 60.91, 103.45, 104.35, 111.50, 120.60, 121.97, 122.11, 126.18, 126.31, 127.58, 131.55, 136.68, 138.72, 139.86, 149.43, 152.29, 153.09, 154.74, 157.85, 159.38; MS-ESI m/z (% rel. Int.): 471.3 ([MH]$^{+1}$, 100); HPLC: Method A, detection UV 254 nm, RT = 4.02 min, peak area 99.9%. |
| 122 | (structure) | F (a) LPO 50164C (199.2 mg, 0.42 mmol) in MeOH (3 mL); NaOH (168 mg, 4.19 mmol) in MeOH/H$_2$O (1 mL/1 mL); RT for 20 min. | Chromatography RP 18, eluent: water = 100% to water: CH$_3$CN = 7:3 | sodium 3-(2-((1-ethyl-6,7-dimethoxyisoquinolin-4-yl)methyl)quinolin-8-yloxy)propanoate (68 mg); MW: 468.48; Yield: 36%; Pale Yellow Solid; Mp (° C.): 215.8; R$_f$: 0.25 (CH$_3$CN:H$_2$O = 3:7); $^1$H-NMR (CD$_3$OD, δ): 1.38 (t, 3H, CH$_3$, J = 7.56 Hz), 2.28-2.34 (m, 2H, CH$_2$), 2.63-2.69 (m, 1H, CH$_2$, J = 6.57 Hz), 2.90-2.97 (m, 1H, CH$_2$, J = 6.57 Hz), 3.22 (q, 2H, CH$_2$, J = 7.56 Hz), 3.87 (s, 3H, OCH$_3$), 3.93 (s, 3H, OCH$_3$), 4.96-5.01 (m, 2H, CH$_2$), 7.11 (dd, 1H, ArH, J = 0.88 Hz, J = 7.54 Hz), 7.21-7.29 (m, 2H, 2xArH), 7.34-7.41 (m, 2H, 2xArH), 7.74 (s, 1H, ArH), 8.03 (d, 1H, ArH, J = 8.61 Hz), 8.34 (s, 1H, ArH); $^{13}$C-NMR (CD$_3$OD, δ): 14.28, 29.07, 31.34, 37.30, 48.16, 56.35, 56.66, 104.68, 105.46, 112.13, 118.49, 122.67, 123.82, 128.26, 128.92, 131.97, 133.76, 137.90, 139.00, 139.67, 151.24, 154.18, 154.62, 161.15, 162.89, 182.32; MS-ESI m/z (% rel. Int.): 447.2 ([MH]$^{+1}$, 100); HPLC: Method A, detection UV 254 nm, RT = 4.18 min, peak area 99.9%. |

TABLE 7-continued

| Compd # | FORMULA | General Procedure | Purification | Analysis |
|---|---|---|---|---|
| 123 | (structure: 2-(1-cyclopropyl-6,7-dimethoxyisoquinolin-4-yl)methyl)quinolin-8-ol) | A SSA 48084 (300 mg, 0.93 mmol); 8-hydroxyquinoline-2-carbaldehyde (167 mg, 0.93 mmol); 37% HCl (1.2 mL); EtOH (1.2 mL); 90° C. for 25 min. | Chromatography SiO$_2$, cyclohexane:EtOAc = 100:0 to 50:50 then CH$_2$Cl$_2$:MeOH = 100:0 to 98:2 | 2-(1-cyclopropyl-6,7-dimethoxyisoquinolin-4-yl)methyl)quinolin-8-ol (104.7 mg); MW: 386.44; Yield: 29%; Yellow Solid; Mp (° C.): 190.5; R$_f$: 0.3 (CH$_2$Cl$_2$:MeOH = 98:2); $^1$H-NMR (CDCl$_3$, δ): 1.07-1.13 (m, 2H, CH$_2$), 1.21-1.34 (m, 2H, CH$_2$), 2.52-2.61 (m, 1H, CH), 3.84 (s, 3H, OCH$_3$), 4.01 (s, 3H, OCH$_3$), 4.59 (s, 2H, CH$_2$), 7.16 (dd, 1H, ArH, J = 1.2 Hz, J = 7.57 Hz), 7.23-7.27 (m, 2H, 2xArH), 7.36-7.42 (m, 2H, 2xArH), 7.61 (s, 1H, ArH), 7.96 (d, 1H, ArH, J = 8.52 Hz), 8.32 (s, 1H, ArH), $^{13}$C-NMR (CDCl$_3$, δ): 8.61 (2xC), 13.72, 40.82, 55.86, 55.89, 103.06, 104.08, 110.17, 117.74, 121.93, 123.68, 124.85, 126.91, 127.21, 131.78, 136.76, 137.25, 141.63, 149.57, 151.67, 152.31, 158.82, 158.87. MS-ESI m/z (% rel. Int.): 387.3 ([MH]$^{+1}$, 100). HPLC: Method A, detection UV 254 nm, RT = 3.94 min, peak area 99.0%. |
| 124 | (structure: 2-((6,7-dimethoxy-3-methylisoquinolin-4-yl)methyl)quinolin-8-ol) | A ANP 31060A (1.14 g, 4.23 mmol); 8-hydroxyquinoline-2-carbaldehyde (733 mg, 4.23 mmol); 37% HCl (4 mL); EtOH (4 mL); 90° C. for 25 min. | Chromatography SiO$_2$, CH$_2$Cl$_2$:MeOH = 100:0 to 94:6 | 2-((6,7-dimethoxy-3-methylisoquinolin-4-yl)methyl)quinolin-8-ol (318 mg); MW: 360.41; Yield: 21%; Yellow Pale Solid; Mp (° C.): 194.6; R$_f$: 0.25 (CH$_2$Cl$_2$:MeOH = 94:6); $^1$H-NMR (CDCl$_3$, δ): 2.82 (s, 3H, CH$_3$), 3.85 (s, 3H, OCH$_3$), 3.98 (s, 3H, OCH$_3$), 4.72 (s, 2H, CH$_2$), 7.10-7.17 (m, 3H, 3xArH), 7.23-7.27 (m, 1H, ArH), 7.30 (s, 1H, ArH), 7.39 (t, 1H, ArH, J = 8.04 Hz), 7.97 (d, 1H, ArH, J = 8.49Hz), 8.94 (s, 1H, ArH); $^{13}$C-NMR (CDCl$_3$, δ): 22.89, 37.97, 55.94 (2xC), 102.03, 105.81, 110.18, 117.68, 121.35, 123.61, 123.94, 126.95, 127.20, 132.61, 136.94, 137.51, 148.54, 148.88, 149.45, 151.66, 153.12, 158.35; MS-ESI m/z (% rel. Int.): 361.2 ([MH]$^{+1}$, 100); HPLC: Method A, detection UV 254 nm, RT = 3.70 min, peak area 99.9%. |
| 125 | (structure: 2-(2-((6,7-dimethoxy-1-propylisoquinolin-4-yl)methyl)quinolin-8-yl)oxy)-N-methylacetamide) | B (a) Free base of 45 (100 mg, 0.26 mmol); acetone (4 mL); Cs$_2$CO$_3$ (168 mg, 0.51 mmol); 2-chloro-N-methylacetamide (55 mg, 0.51 mmol); 60° C. overnight. | Chromatography SiO$_2$, CH$_2$Cl$_2$:MeOH = 100:0 to 95:5 | 2-(2-((6,7-dimethoxy-1-propylisoquinolin-4-yl)methyl)quinolin-8-yl)oxy)-N-methylacetamide (61 mg); MW: 459.54; Yield: 51%; White Solid; Mp (° C.): 214.7-216.0; R$_f$: 0.25 (CH$_2$Cl$_2$: MeOH = 95:5); $^1$H-NMR (CDCl$_3$, δ): 1.08 (t, 3H, CH$_3$, J = 7.35 Hz), 1.92 (m, 2H, CH$_2$, J = 7.45 Hz), 2.89 (d, 3H, CH$_3$, J = 4.86 Hz), 3.18 (t, 2H, CH$_2$, J = 7.63 Hz), 3.86 (s, 3H, OCH$_3$), 3.99 (s, 3H, OCH$_3$), 4.66 (s, 2H, CH$_2$), 4.79 (s, 2H, CH$_2$), 7.17-7.22 (m, 1H, ArH), 7.29-7.34 (m, 2H, 2xArH), 7.40-7.49 (m, 3H, 3xArH), 8.01 (d, 1H, ArH, J = 8.52 Hz), 8.38 (s, 1H, ArH), 8.51 (s, 1H, NH); $^{13}$C-NMR (CDCl$_3$, δ): 14.35, 22.53, 25.65, 37.48, 41.36, 55.89 (2C), 71.02, 103.25, 104.25, 113.99, 121.91, 122.03, 122.87, 125.41, 126.41, 128.16, 132.11, 136.92, 139.95, 141.57, 149.56, 152.40, 154.07, 159.35, 160.12, 169.43. MS-ESI m/z (% rel. Int.): 460.4 ([MH]$^{+1}$, 100). HPLC: Method A, detection UV 254 nm, RT = 3.77 min, peak area 99.9%. |

TABLE 7-continued

| Compd # | FORMULA | General Procedure | Purification | Analysis |
|---|---|---|---|---|
| 126 | (structure) | B (a) Free base of 45 (100 mg, 0.26 mmol); acetone (4 mL); Cs$_2$CO$_3$ (168 mg, 0.51 mmol); 2-chloro-N-cyclopropylacetamide (55 mg, 0.51 mmol); 60° C. overnight. | Chromatography SiO$_2$, EtOAc:MeOH = 100:0 to 95:5 | N-cyclopropyl-2-(2-((6,7-dimethoxy-1-propylisoquinolin-4-yl)methyl)quinolin-8-yl)oxy)acetamide (37.4 mg); MW: 485.57; Yield: 37%; White Solid; Mp (° C.): 193.4; R$_f$: 0.25 (EtOAc:MeOH = 95:5); $^1$H-NMR (CDCl$_3$, δ): 0.57-0.61 (m, 2H, CH$_2$), 0.77-0.82 (m, 2H, CH$_2$), 1.08 (t, 3H, CH$_3$, J = 7.35 Hz), 1.88-2.04 (m, 2H, CH$_2$, J = 7.56 Hz), 2.79-2.81 (m, 1H, CH), 3.19 (t, 2H, CH$_2$, J = 7.62 Hz), 3.85 (s, 3H, OCH$_3$), 3.99 (s, 3H, OCH$_3$), 4.68 (s, 2H, CH$_2$), 4.79 (s, 2H, CH$_2$), 7.17-7.20 (m, 1H, ArH), 7.28 (d, 1H, ArH, J = 8.52 Hz), 7.33 (s, 1H, ArH), 7.43-7.45 (m, 2H, 2xArH), 7.52 (s, 1H, ArH), 7.99 (d, 1H, ArH, J = 8.52 Hz), 8.39 (s, 1H, ArH), 8.52 (s, 1H, NH); $^{13}$C-NMR (CDCl$_3$, δ): 6.35 (2xC), 14.34, 22.11, 22.54, 37.48, 41.45, 55.89 (2xC), 71.17, 103.29, 104.26, 114.09, 121.96, 122.03, 122.88, 125.40, 126.39, 128.14, 132.16, 136.90, 139.93, 141.51, 149.57, 152.42, 154.08, 159.39, 160.27, 170.3; MS-ESI m/z (% rel. Int.): 486.4 ([MH]$^+$, 100); HPLC: Method A, detection UV 254 nm, RT = 3.96 min, peak area 99.9%. |
| 127 | (structure) | K LPO 50172C (80 mg, 0.19 mmol); sodium azide (63 mg, 0.97 mmol); ammonium chloride (51.7 mg, 0.97 mmol) in DMF (4 mL); 100° C. for 2.5 h. | Chromatography SiO$_2$, CH$_2$Cl$_2$:MeOH = 100:0 to 9:1 | 8-((1H-tetrazol-5-yl)methoxy)-2-((1-ethyl-6,7-dimethoxyisoquinolin-4-yl)methyl)quinoline (44 mg); MW: 456.5; Yield: 50%; Off-White Solid; Mp (° C.): 240.5; R$_f$: 0.3 (CH$_2$Cl$_2$:MeOH = 9:1); $^1$H-NMR (DMSO-d$_6$, δ): 1.32 (t, 3H, CH$_3$, J = 7.44 Hz), 3.19 (q, 2H, CH$_2$, J = 7.45 Hz), 3.75 (s, 3H, OCH$_3$), 3.89 (s, 3H, OCH$_3$), 4.58 (s, 2H, CH$_2$), 5.61 (s, 2H, OCH$_2$), 7.39-7.48 (m, 5H, 5xArH), 7.73 (s, 1H, ArH), 8.17 (d, 1H, ArH, J = 8.52 Hz), 8.38 (s, 1H, ArH); $^{13}$C-NMR (DMSO-d$_6$, δ): 12.90, 27.25, 38.71, 55.60 (2C), 60.94, 103.49, 104.10, 111.37, 120.45, 121.79, 121.92, 126.12, 126.20, 127.54, 131.35, 136.55, 138.79, 140.27, 149.36, 152.09, 153.25, 154.92, 158.83, 159.36; MS-ESI m/z (% rel. Int.): 457.2 ([MH]$^+$, 100); HPLC: Method A, detection UV 254 nm, RT = 3.87 min, peak area 99.9%. |
| 128 | (structure) | B (a) 83 (200 mg, 0.53 mmol); DMF (4 mL); Cs$_2$CO$_3$ (261 mg, 0.80 mmol); Et$_3$N (82.2 µL, 0.59 mmol); ethyl-2-bromoacetate (65 µL, 0.59 mmol); 120° C. for 15 min (microwave). | Chromatography SiO$_2$, cyclohexane:EtOAc = 50:50 to 0:100 | ethyl 2-((2-((1-ethyl-6,7-dimethoxyisoquinolin-4-yl)methyl)quinolin-8-yl)oxy)acetate (198.1 mg); MW: 460.52; Yield: 81%; Yellow Solid; Mp (° C.): 140.9; R$_f$: 0.25 (EtOAc); $^1$H-NMR (CDCl$_3$, δ): 1.31 (t, 3H, CH$_3$, J = 7.14 Hz), 1.45 (t, 3H, CH$_3$, J = 7.54 Hz), 3.24 (q, 2H, CH$_2$, J = 7.53 Hz), 3.92 (s, 3H, OCH$_3$), 3.97 (s, 3H, OCH$_3$), 4.30 (q, 2H, CH$_2$, J = 7.14 Hz) 4.70 (s, 2H, CH$_2$) 4.97 (s 2H, CH$_2$) 6.96-6.99 (m, 1H, ArH) 7.24-7.30 (m 2H, 2xArH) 7.33-7.37 (m, 2H, 2xArH), 7.67 (s, 1H, ArH), 7.92 (d, 1H, ArH, J = 8.52 Hz), 8.43 (s, 1H, ArH); $^{13}$C-NMR (CDCl$_3$, δ): 13.23, 14.19, 28.51, 41.59, 55.85, 56.26, 61.32, 66.53, 103.84, 103.95, 110.46, 120.95, 121.82, 122.50, 125.83, 126.07, 128.14, 132.32, 136.51, 139.33, 141.43, 149.53, 152.32, 153.41, 160.07, 168.74; MS-ESI m/z (% rel. Int.): 461.3 ([MH]$^+$, 60); HPLC: Method A, detection UV 254 nm, RT = 4.18 min, peak area 99.0%. |

TABLE 7-continued

| Compd # | FORMULA | General Procedure | Purification | Analysis |
|---|---|---|---|---|
| 129 | (structure) | H (a) LPO 50012C (125 mg, 0.24 mmol); 2-dicyclohexylphosphino-2′,6′-dimethoxybiphenyl) (1 mg, 0.0025 mmol); 2M methylamine in THF (1.2 mL, 2.45 mmol); tBuOK (82.5 mg, 0.50 mmol); 145° C. for 25 min (microwave) | Chromatography SiO$_2$, cyclohexane:EtOAc = 50:50 to 0:100 | 3-((6,7-dimethoxy-1-propylisoquinolin-4-yl)methyl)-6-methoxy-N-methylquinolin-2-amine (46 mg); MW: 431.53; Yield: 44%; Yellow Solid; R$_f$: 0.25 (EtOAc); $^1$H-NMR (CDCl$_3$, δ): 1.11 (t, 3H, CH$_3$, J = 7.33 Hz), 1.95 (q, 2H, CH$_2$, J = 7.57 Hz), 3.15 (d, 3H, CH$_3$, J = 4.8 Hz), 3.23 (t, 3H, CH$_3$, J = 7.62 Hz), 3.77 (s, 3H, OCH$_3$), 3.81 (s, 3H, OCH$_3$), 4.05 (s, 3H, OCH$_3$), 4.12 (s, 2H, CH$_2$), 4.61 (d, 1H, NH, J = 4.56 Hz), 6.72 (d, 1H, ArH, J = 2.77 Hz), 7.00 (s, 1H, ArH), 7.16 (dd, 1H, ArH, J = 2.82 Hz, J = 9.09 Hz), 7.20 (s, 1H, ArH), 7.41 (s, 1H, ArH), 7.69 (d, 1H, ArH, J = 9.09 Hz), 8.20 (s, 1H, ArH); $^{13}$C-NMR (CDCl$_3$, δ): 14.38, 22.49, 28.85, 31.83, 37.53, 55.42, 55.95, 102.34, 104.44, 106.16, 120.20, 121.62, 122.76, 123.75, 124.02, 127.52, 132.0, 134.81, 141.79, 142.52, 149.67, 152.57, 154.62, 154.83, 159.40; MS-ESI m/z (% rel. Int.): 432.3 ([MH]$^{+1}$, 50); HPLC: Method A, detection UV 254 nm, RT = 4.18 min, peak area 99.0%. |
| 130 | (structure) | B (a) 123 (50 mg, 0.13 mmol); acetone (3 mL); Cs$_2$CO$_3$ (46.4 mg, 0.14 mmol); 2-bromoacetamide (36 mg, 0.26 mmol); 70° C. overnight. | Chromatography SiO$_2$, CH$_2$Cl$_2$:MeOH = 100:0 to 96:4 | 2-((2-((1-cyclopropyl-6,7-dimethoxyisoquinolin-4-yl)methyl)quinolin-8-yl)oxy)acetamide (40.5 mg); MW: 443.49; Yield: 71%; Off-White Solid; Mp (° C.): 217.9; R$_f$: 0.3 (CH$_2$Cl$_2$:MeOH = 96:4); $^1$H-NMR (CDCl$_3$, δ): 1.08-1.14 (m, 2H, CH$_2$), 1.21-1.26 (m, 2H, CH$_2$), 2.54-2.59 (m, 1H, CH), 3.87 (s, 3H, OCH$_3$), 4.02 (s, 3H, OCH$_3$), 4.61 (s, 2H, CH$_2$), 4.74 (s, 2H, CH$_2$), 7.15-7.18 (m, 1H, ArH), 7.33-7.45 (m, 4H, 4xArH), 7.62 (s, 1H, ArH), 7.01 (d, 1H, ArH, J = 8.49 Hz), 8.29 (s, 1H, ArH); $^{13}$C-NMR (CDCl$_3$, δ): 8.71 (2xC), 13.69, 40.98, 55.90 (2xC), 70.69, 103.15, 104.06, 113.93, 121.90, 122.09, 123.60, 124.78, 126.32, 128.11, 131.72, 136.80, 140.07, 141.75, 149.63, 152.39, 154.07, 158.86, 160.23, 171.60; MS-ESI m/z (% rel. Int.): 444.3 ([MH]$^{+1}$, 60); HPLC: Method A, detection UV 254 nm, RT = 3.58 min, peak area 99.0%. |
| 131 | (structure) | A TTA 24128B (2.0 g, 7.43 mmol); 8-hydroxyquinoline-2-carbaldehyde (1.30 g, 7.43 mmol); 37% HCl (7 mL); EtOH (7 mL); 95° C. for 25 min. | Chromatography SiO$_2$, EtOAc:MeOH = 100:0 to 96:4 | 2-((6,7-dimethoxy-1-methylisoquinolin-4-yl)methyl)quinolin-8-ol (88 mg); MW: 360.41; Yield: 3%; Yellow Solid; Mp (° C.): 199.4-200.3; R$_f$: 0.2 (EtOAc:MeOH = 96:4); $^1$H-NMR (CDCl$_3$, δ): 2.89 (s, 3H, CH$_3$), 3.84 (s, 3H, OCH$_3$), 3.98 (s, 3H, OCH$_3$), 4.61 (s 2H, CH$_2$), 7.16 (d, 1H J = 7.56 Hz, ArH), 7.23-7.27 (m, 3H, 3xArH), 7.36-7.42 (m, 2H, 2xArH), 7.96 (d, 1H, J = 8.52 Hz, ArH), 8.36 (s, 1H, ArH); $^{13}$C-NMR (CDCl$_3$, δ): 22.48, 40.78, 55.87, 55.90, 103.10, 104.41, 110.22, 117.74, 121.85, 123.38, 125.78, 126.92, 127.23, 131.80, 136.80, 137.27, 141.50, 149.56, 151.69, 152.42, 155.67, 158.73; MS-ESI m/z (% rel. Int.): 361.3 ([MH]$^{+1}$, 100); HPLC: Method A, detection UV 254 nm, RT = 3.70 min, peak area 99.0%. |

TABLE 7-continued

| Compd # | FORMULA | General Procedure | Purification | Analysis |
|---|---|---|---|---|
| 132 | (structure: 4-CF₃ quinolin-8-ol with 2-((6,7-dimethoxy-1-propylisoquinolin-4-yl)methyl) substituent) | A SSA 39102 (63.1 mg, 0.19 mmol); LPO 50180C (50 mg, 0.18 mmol); HCl 37% (0.5 mL); EtOH (0.5 mL); 95° C. for 25 min. | Chromatography SiO₂, cyclohexane:EtOAc = 100:0 to 50:50 | 2-((6,7-dimethoxy-1-propylisoquinolin-4-yl)methyl)-5-(trifluoromethyl)quinolin-8-ol (48.3 mg); MW: 456.46; Yield: 60%; White Solid; Mp (° C.): 182.9; R$_f$: 0.3 (cyclohexane: EtOAc = 5: 5); $^1$H-NMR (CDCl$_3$, δ): 1.09 (t, 3H, CH$_2$CH$_3$, J = 7.3 Hz), 1.92 (sextuplet, 2H, CH$_2$CH$_3$, J = 7.7 Hz), 3.20 (t, 2H, CH$_2$CH$_2$, J = 7.9 Hz), 3.85 (s, 3H, OCH$_3$), 4.00 (s, 3H, OCH$_3$), 4.63 (s, 2H, CH$_2$), 7.15 (d, 1H, ArH, J = 8.1 Hz), 7.27-7.34 (m, 2H, 2xArH), 7.42 (d, 1H, ArH, J = 8.1 Hz), 7.78 (d, 1H, ArH, J = 8.1 Hz), 8.31 (dd, 1H, ArH, J = 8.9 Hz, J = 1.7 Hz), 8.40 (s, 1H, ArH); $^{13}$C-NMR (CDCl$_3$, δ): 14.4, 22.7, 37.5, 40.4, 55.9, 56.0, 102.8, 104.4, 108.4, 116.7 (q, CCF$_3$, J = 31.4 Hz), 122.6, 122.9, 124.4 (q, CF$_3$, J = 272.2 Hz), 124.9, 126.4 (q, CHCCF$_3$, J = 5.6 Hz), 132.0, 133.9, 134.0, 137.3, 141.8, 149.6, 152.4, 154.9, 159.6 (2xC); MS-ESI m/z (% rel. Int.): 457.3 ([MH]⁺¹, 100); HPLC: Method A, detection UV 254 nm, RT = 5.22 min, peak area 98.0%. |
| 133 | (structure: 4-CF₃ quinoline-8-yloxy acetamide with 2-((6,7-dimethoxy-1-propylisoquinolin-4-yl)methyl) substituent) | B (a) 132 (36 mg, 0.08 mmol); acetone (2 mL); Cs$_2$CO$_3$ (28.3 mg, 0.087 mmol); 2-bromoacetamide (22 mg, 0.16 mmol); 80° C. overnight. | Chromatography SiO₂, CH$_2$Cl$_2$:MeOH = 100:0 to 97:3 | 2-((2-((6,7-dimethoxy-1-propylisoquinolin-4-yl)methyl)-5-(trifluoromethyl)quinolin-8-yl)oxy)acetamide (18.3 mg); MW: 513.51; Yield: 45%; White Solid; Mp (° C.): 236.7; R$_f$: 0.3 (CH$_2$Cl$_2$:MeOH = 97: 3); $^1$H-NMR (CDCl$_3$, δ): 1.09 (t, 3H, CH$_3$, J = 7.4 Hz), 1.92 (sextuplet, 2H, CH$_2$, J = 7.5 Hz), 3.20 (t, 2H, CH$_2$, J = 7.8 Hz), 3.86 (s, 3H, OCH$_3$), 4.00 (s, 3H, OCH$_3$), 4.66 (s, 2H, CH$_2$), 4.74 (s, 2H, OCH$_2$), 7.10 (d, 1H, ArH, J = 8.1 Hz), 7.34 (s, 2H, 2xArH), 7.51 (d, 1H, ArH, J = 8.9 Hz), 7.83 (d, 1H, ArH, J = 8.1 Hz), 8.39 (s, 2H, 2xArH); $^{13}$C-NMR (CDCl$_3$, δ): 14.4, 22.6, 37.5, 40.7, 55.9, 56.0, 69.4, 102.9, 104.2, 110.1, 120.0 (q, CCF$_3$, J = 5.7 Hz), 122.8, 123.3, 124.4, 124.6 (q, CF$_3$, J = 272.8 Hz), 125.1, 125.3 (q, CH—CCF$_3$, J = 31.3 Hz), 132.0, 133.4, 140.0, 141.7, 149.6, 152.4, 156.4, 159.4, 160.8, 170.5; MS-ESI m/z (% rel. Int.): 514.2 ([MH]⁺¹, 100); HPLC: Method A, detection UV 254 nm, RT = 4.46 min, peak area 98.0%. |
| 134 | (structure: 4-CF₃ quinoline-8-yloxy 2-methylpropanamide with 2-((6,7-dimethoxy-1-propylisoquinolin-4-yl)methyl) substituent) | B (a) Free base of 45 (90 mg, 0.23 mmol); acetone (4 mL); Cs$_2$CO$_3$ (113 mg, 0.35 mmol); 2-bromo-2-methylpropionamide (77 mg, 0.46 mmol); 80° C. for 4 h. | Chromatography SiO₂, cyclohexane:EtOAc = 50:50 to 0:100 | 2-((2-((6,7-dimethoxy-1-propylisoquinolin-4-yl)methyl)quinolin-8-yl)oxy)-2-methylpropanamide (65.4 mg); MW: 473.56; Yield: 60%; Off-White Solid; Mp (° C.): 183.0; R$_f$: 0.15 (EtOAc); $^1$H-NMR (CDCl$_3$, δ): 1.09 (t, 3H, CH$_3$, J = 7.4 Hz) 1.56 (s, 6H, 2xCH$_3$), 1.93 (sextuplet, 2H, CH$_2$, J = 7.6 Hz), 3.19 (t, 2H, CH$_2$, J = 7.7 Hz), 3.79 (s, 3H, OCH$_3$), 3.9,7 (s, 3H, OCH$_3$), 4.56 (s, 2H, CH$_2$), 5.77 (s, 1H, 0.5xNH$_2$), 7.21-7.52 (m, 6H, 6xArH), 8.01 (d, 1H, ArH, J = 8.5 Hz), 8.38 (s, 1H, ArH), 10.08 (s, 1H, 0.5xNH$_2$); $^{13}$C-NMR (CDCl$_3$, δ): 14.4, 22.5, 25.3 (2xC), 37.5, 41.1, 55.9, 56.1, 83.8, 102.9, 104.2, 121.6, 121.7, 122.8, 123.0, 125.2, 126.0, 128.3, 132.0, 137.2, 141.8, 143.0, 149.5, 150.6, 152.4, 159.5, 160.2, 178.9; MS-ESI m/z (% rel. Int.): 474.4 ([MH]⁺¹, 100); HPLC: Method A, detection UV 254 nm, RT = 4.33 min, peak area 99.0%. |

TABLE 7-continued

| Compd # | FORMULA | General Procedure | Purification | Analysis |
|---|---|---|---|---|
| 135 | (structure) | B (a) 83 (100 mg, 0.27 mmol); DMF (3 mL); Cs$_2$CO$_3$ (174 mg, 0.53 mmol); bromoethanol (38 µL, 0.53 mmol); KI (22 mg, 0.13 mmol) in DMF (3 mL); 90° C. overnight. | Chromatography SiO$_2$, CH$_2$Cl$_2$:MeOH = 100:0 to 94:6 | 2-(2-((1-ethyl-6,7-dimethoxyisoquinolin-4-yl)methyl)quinolin-8-yl)oxy)ethanol (11.6 mg); MW: 418.48; Yield: 10% Yellow Solid; Mp (° C.): 234.9-237; R$_f$: 0.2 (CH$_2$Cl$_2$:MeOH = 94.6); $^1$H-NMR (CDCl$_3$, δ): 1.44 (t, 3H, CH$_3$, J = 7.5 Hz), 3 23 (q, 2H, CH$_2$, J = 7.53 Hz), 3.90 (s, 3H, OCH$_3$), 3.97 (s, 3H, OCH$_3$), 4.01 (m, 2H, CH$_2$), 4.30 (t, 2H, CH$_2$, J = 4.08 Hz), 4.61 (s, 2H, CH$_2$), 7.17-7.23 (m, 2H, 2xArH), 7.28 (s, 1H, ArH), 7.35-7.45 (m, 3H, 3xArH), 7.95 (d, 1H, ArH, J = 8.53 Hz), 8.34 (s, 1H, ArH); $^{13}$C-NMR (CDCl$_3$, δ): 13.22, 28.50, 40.45, 55.87, 56.24, 61.00, 73.07, 103.40, 103.88, 113.32, 121.00, 121.85, 122.49, 125.53, 126.55, 128.12, 132.08, 137.21, 139.76, 141.52, 149.54, 152.4, 154.10, 159.9, 160.21; MS-ESI m/z peak Int.): 419.3 ([MH]$^{+1}$, 100); HPLC: Method A, detection UV 254 nm, RT = 3.82 min, peak area 99.0%. |
| 136 | (structure) | C (a) LPO 55010B (51 mg, 0.12 mmol); CH$_2$Cl$_2$ (5 mL); pyridine (19 µL, 0.24 mmol); acetic anhydride (22.1 µL, 0.24 mmol); RT for 2 h. | Chromatography SiO$_2$, CH$_2$Cl$_2$:MeOH = 100:0 to 98:2 | N-(2-((2-((6,7-dimethoxy-1-propylisoquinolin-4-yl)methyl)quinolin-8-yl)oxy)ethyl)acetamide (25.3 mg); MW: 346.38; Yield: 34%; White Solid; Mp (° C.): 218.8; R$_f$: 0.20 (CH$_2$Cl$_2$:MeOH = 96:4); $^1$H-NMR (CDCl$_3$ + CD$_3$OD, δ): 3.87 (s, 3H, OCH$_3$), 4.02 (s, 3H, OCH$_3$), 4.47 (s, 2H, CH$_2$), 6.95 (d, 1H, ArH, J = 2.5 Hz), 7.08 (s, 1H, ArH), 7.28-7.35 (m, 3H, 3xArH), 7.67 (s, 1H, ArH), 7.89 (d, 1H, ArH, J = 9.1 Hz), 8.26 (s, 1H, ArH), 8.65 (d, 1H, ArH, J = 1.9 Hz), 8.96 (s, 1H, ArH); $^{13}$C-NMR (CDCl$_3$ + CD$_3$OD, δ): 34.0, 56.1, 56.2, 101.8, 106.4, 108.4, 122.1, 125.1, 128.2, 129.7, 129.8, 131.7, 132.7, 133.9, 141.6, 142.1, 148.0, 149.2, 150.6, 153.7, 156.0; MS-ESI m/z (% rel. Int.): 347.4 ([MH]$^{+1}$, 100); HPLC: Method A, detection UV 254 nm, RT = 3.18 min, peak area 99.0%. |
| 137 | (structure) | A LPO 22102 (357 mg, 1.26 mmol); LPO 55016B (249 mg, 1.15 mmol); 37% HCl (2.5 mL); EtOH (2.5 mL); 95° C. for 25 min. | Chromatography SiO$_2$, CH$_2$Cl$_2$:MeOH = 100:0 to 96:4 | 3-((6,7-dimethoxyisoquinolin-4-yl)methyl)quinolin-6-ol (134.3 mg); MW: 218.80; Yield: 34%; White Solid; Mp (° C.): 218.8; R$_f$: 0.20 (CH$_2$Cl$_2$:MeOH = 96:4); $^1$H-NMR (CD$_3$OD, δ): 3.87 (s, 3H, OCH$_3$), 4.02 (s, 3H, OCH$_3$), 4.47 (s, 2H, CH2), 6.95 (d, 1H, J = 2.46 Hz, ArH), 7.08 (s, 1H, ArH), 7.28-7.35 (m, 2H, 2xArH), 7.67 (s, 1H, ArH), 7.89 (d, 1H, J = 9.1 Hz, ArH), 8.26 (s, 1H, ArH), 8.65 (d, 1H, J = 1.86 Hz, ArH), 8.96 (s, 1H, ArH); $^{13}$C-NMR (CD$_3$OD, δ): 34.0, 56.1, 56.2, 101.8, 106.4, 108.4, 122.1, 125.1, 128.2, 129.7, 129.8, 131.7, 132.7, 133.9, 141.6, 142.1, 148.0, 149.2, 150.6, 153.7, 156.0; MS-ESI m/z (% rel. Int.): 347.4 ([MH]$^{+1}$, 100); HPLC: Method A, detection UV 254 nm, RT = 3.18 min, peak area 99.0%. |
| 138 | (structure) | B (a) 137 (50 mg, 0.14 mmol); acetone (2 mL); Cs$_2$CO$_3$ (51.6 mg, 0.16 mmol); 2-bromoacetamide (39.8 mg, 0.29 mmol); 80° C. for 1 h. | Chromatography SiO$_2$, CH$_2$Cl$_2$:MeOH = 100:0 to 95:5 | 2-((3-((6,7-dimethoxyisoquinolin-4-yl)methyl)quinolin-6-yl)oxy)acetamide (25.7 mg); MW: 403.43; Yield: 44%; White Solid; Mp (° C.): 218.7; R$_f$: 0.35 (CH$_2$Cl$_2$:MeOH = 95:5); $^1$H-NMR (DMSO-d$_6$, δ): 3.86 (s, 3H, OCH$_3$), 3.90 (s, 3H, OCH$_3$), 4.51 (s, 4H, 2xCH$_2$), 7.21 (s, 1H, ArH), 7.36-7.42 (m, 3H, 3xArH), 7.52-7.59 (m, 2H, 2xArH), 7.88-7.98 (m, 2H, 2xArH), 8.35 (s, 1H, ArH), 8.92 (d, 2H, NH$_2$, J = 57.9 Hz); $^{13}$C-NMR (DMSO-d$_6$, δ): 32.5, 55.7, 55.8, 66.9, 101.9, 106.4, 106.6, 121.6, 124.5, 128.3, 128.5, 130.0, 130.5, 133.3, 133.6, 141.8, 142.5, 148.9, 149.4, 149.9, 152.8, 155.8, 169.5; MS-ESI m/z (% rel. Int.): 404.2 ([MH]$^{+1}$, 100); HPLC: Method A, detection UV 254 nm, RT = 3.05 min, peak area 99.0%. |

TABLE 7-continued

| Compd # | FORMULA | Purification | General Procedure | Analysis |
|---|---|---|---|---|
| 139 | (structure) | Chromatography SiO$_2$, CH$_2$Cl$_2$:MeOH = 100:0 to 96:4 | B (a) Free base of 45 (700 mg, 1.80 mmol); DMF (9 mL); Cs$_2$CO$_3$ (1.76 g, 5.41 mmol); 2-bromoacetamide (398 mg, 2.58 mmol); 80° C. overnight. | 2-((2-((6,7-dimethoxy-1-propylisoquinolin-4-yl)methyl)quinolin-8-yl)oxy)acetamide (146 mg); MW: 445.51; Yield: 25%; White Solid; Mp (° C.): 226.9; R$_f$: 0.25 (CH$_2$Cl$_2$:MeOH = 96:4); $^1$H-NMR (CDCl$_3$, δ): 1.08 (t, 3H, CH$_3$, J = 7.35 Hz), 1.92 (m, 2H, CH$_2$, J = 7.68 Hz), 3.18 (t, 2H, CH$_2$, J = 7.66 Hz), 3.86 (s, 3H, OCH$_3$), 3.99 (s, 3H, OCH$_3$), 4.63 (s, 2H, CH$_2$), 4.75 (s, 2H, CH$_2$), 5.58 (s, 1H, NH$_2$), 7.16-7.19 (dd, 1H, ArH, J = 2.76 Hz, J = 6.12 Hz), 7.32-7.37 (m, 2H, 2xArH), 7.40-7.45 (m, 3H, 3xArH), 8.02 (d, 1H, ArH, J = 8.49 Hz), 8.22 (s, 1H, NH$_2$), 8.39 (s, 1H, ArH); $^{13}$C-NMR (CDCl$_3$, δ): 14.38, 22.57, 37.51, 41.08, 55.89, 55.92, 70.71, 103.25, 104.20, 113.98, 121.93, 122.08, 122.82, 125.47, 126.34, 128.11, 132.07, 136.84, 140.08, 141.77, 149.53, 152.34, 154.07, 159.30, 160.18, 171.62; MS-ESI m/z (% rel. Int.): 446.3 ([MH]$^{+1}$, 100); HPLC: Method A, detection UV 254 nm, RT = 3.63 min, peak area 99.9%. |
| 140 | (structure) | Chromatography SiO$_2$, cyclohexane:EtOAc = 100:0 to 50:50 | C (a) Free base of 45 (100 mg, 0.257 mmol); CH$_2$Cl$_2$ (5 mL); DMAP (6.3 mg, 0.051 mmol); acetic anhydride (96.7 μL, 1.03 mmol); RT overnight. | 2-((6,7-dimethoxy-1-propylisoquinolin-4-yl)methyl)quinolin-8-yl acetate (64.9 mg); MW: 430.5; Yield: 59%; Yellow Solid; Mp (° C.): 187.3; R$_f$: 0.20 (cyclohexane:EtOAc = 50:50); $^1$H-NMR (CDCl$_3$, δ): 1.08 (t, 3H, CH$_3$, J = 7.3 Hz), 1.92 (q, 2H, CH$_2$, J = 7.6 Hz), 2.44 (s, 3H, COCH$_3$), 3.19 (t, 2H, CH$_2$, J = 7.8 Hz), 3.84 (s, 3H, OCH$_3$), 3.98 (s, 3H, OCH$_3$), 4.60 (s, 2H, CH$_2$), 7.22-7.49 (m, 6H, 6xArH), 7.63 (dd, 1H, ArH, J = 8.0 Hz, J = 1.4 Hz), 7.97 (d, 1H, ArH, J = 8.5 Hz) 8.41 (s, 1H, ArH); $^{13}$C-NMR (CDCl$_3$, δ): 14.4, 20.8, 22.6, 37.5, 41.6, 55.9, 56.1, 103.5, 104.1, 121.5, 121.6, 122.8, 125.6 (2xC), 125.7, 128.0, 132.3, 136.5, 140.4, 141.8, 147.2, 149.5, 152.3, 159.2, 161.0, 169.6; MS-ESI m/z (% rel. Int.): 431.3 ([MH]$^{+1}$, 100); HPLC: Method A, detection UV 254 nm, RT = 4.69 min, peak area 99.0%. |
| 141 | (structure) | Chromatography SiO$_2$, cyclohexane:EtOAc = 100:0 to 50:50 | C (a) 83 (60 mg, 0.267 mmol); acetic anhydride (2 mL); 130° C. overnight. | 2-((1-ethyl-6,7-dimethoxyisoquinolin-4-yl)methyl)quinolin-8-yl acetate (45.7 mg); MW: 416.47; Yield: 41%; Yellow Solid; Mp (° C.): 200.8; R$_f$: 0.15 (cyclohexane:EtOAc = 50:50); $^1$H-NMR (CDCl$_3$, δ): 1.46 (t, 3H, CH$_3$, J = 7.5 Hz), 2.44 (s, 3H, COCH$_3$), 3.25 (q, 2H, CH$_2$, J = 7.6 Hz), 3.84 (s, 3H, OCH$_3$), 3.98 (s, 3H, OCH$_3$), 4.61 (s, 2H, CH$_2$), 7.23-7.49 (m, 6H, 6xArH), 7.63 (dd, 1H, ArH, J = 8.0 Hz, J = 1.5 Hz), 7.97 (d, 1H, ArH, J = 8.6 Hz), 8.42 (s, 1H, ArH); $^{13}$C-NMR (CDCl$_3$, δ): 13.3, 20.8, 28.6, 41.6, 55.9, 56.1, 103.5, 103.9, 121.5, 121.6, 122.5, 125.6, 125.7, 125.8, 128.0, 132.3, 136.5, 140.4, 141.8, 147.2, 149.5, 152.3, 160.1, 161.0, 169.6; MS-ESI m/z (% rel. Int.): 417.3 ([MH]$^{+1}$, 100); HPLC: Method A, detection UV 254 nm, RT = 4.35 min, peak area 99.0%. |

TABLE 7-continued

| Compd # | FORMULA | General Procedure | Purification | Analysis |
|---|---|---|---|---|
| 142 | (structure) | D (a) 115 (50 mg, 0.11 mmol); tBuOH (4 mL); MeOH (0.2 mL); NaBH$_4$ (46 mg, 0.12 mmol); 100° C. for 4 h. | Chromatography SiO$_2$, CH$_2$Cl$_2$:MeOH = 100:0 to 95:5 | (4-(5-((6,7-dimethoxyisoquinolin-4-yl)methyl)benzo[d]oxazol-2-yl)phenyl)methanol (11.6 mg); MW: 426.46; Yield: 24%; White Solid; Mp (° C.): 204.2-205.9; R$_f$: 0.25 (CH$_2$Cl$_2$:MeOH = 95:5); $^1$H-NMR (CDCl$_3$, δ): 3.85 (s, 3H, OCH$_3$), 4.00 (s, 3H, OCH$_3$), 4.45 (s, 2H, CH$_2$), 4.72 (s, 2H, CH$_2$), 7.11 (s, 1H, ArH), 7.19-7.24 (m, 2H, 2xArH), 7.47-7.56 (m, 4H, 4xArH), 8.15-8.22 (m, 2H, 2xArH), 8.91 (s, 1H, ArH); $^{13}$C-NMR (CDCl$_3$, δ): 36.50, 55.86, 55.93, 63.88, 101.93, 105.98, 110.51, 119.25, 124.85, 125.56, 125.63, 127.07 (2xC), 127.59 (2xC), 129.0, 131.63, 136.45, 141.48, 142.09, 145.38, 148.79, 149.31, 150.16, 153.16, 163.64; MS-ESI m/z (% rel. Int.): 427.3 ([MH]$^{+1}$, 100); HPLC: Method A, detection UV 254 nm, RT = 4.11 min, peak area 98.0%. |
| 143 | (structure) | A SSA 39102 (8A56.5 mg, 2.63 mmol); LPO 55016B (519.7 mg, 2.39 mmol); 37% HCl (5 mL); EtOH (5 mL); 95° C. for 20 min. | Chromatography SiO$_2$, CH$_2$Cl$_2$:MeOH = 100:0 to 95:5 | 3-((6,7-dimethoxyisoquinolin-4-yl)methyl)quinolin-6-ol (143.7 mg); MW: 388.46; Yield: 15%; Off-White Solid; Mp (° C.): 216.9; R$_f$: 0.2 (CH$_2$Cl$_2$:MeOH = 98:2); $^1$H-NMR (CD$_3$OD, δ): 1.07 (t, 3H, CH$_3$, J = 7.4 Hz), 1.87 (sextuplet, 2H, CH$_2$, J = 7.5 Hz), 3.21 (t, 2H, CH$_2$, 3.84 (s, 3H, OCH$_3$), 3.97 (s, 3H, OCH$_3$), 4.51 (s, 2H, CH$_2$), 7.0 (d, 1H, ArH, J = 2.7 Hz), 7.24 (s, 1H, ArH), 7.28 (dd, 1H, ArH, J = 9.1 Hz, J = 2.7 Hz), 7.47 (s, 1H, ArH), 7.83 (d, 1H, ArH, J = 9.2 Hz), 7.90 (d, 1H, ArH, J = 1.3 Hz), 8.14 (s, 1H, ArH), 8.60 (d, 1H, ArH, J = 2.1 Hz); $^{13}$C-NMR (CD$_3$OD, δ): 14.5, 24.2, 34.5, 37.9, 56.4, 56.4, 103.8, 105.9, 109.3, 123.1, 124.2, 128.4, 130.2, 131.1, 133.4, 134.9, 135.2, 141.3, 142.8, 149.1, 151.5, 154.6, 157.7, 160.5; MS-ESI m/z (% rel. Int.): 389.4 ([MH]$^{+1}$, 70), 195.2 (100); HPLC: Method A, detection UV 254 nm, RT = 3.46 min, peak area 99.0%. |
| 144 | (structure) | B (a) 143 (84 mg, 0.22 mmol); acetone (4 mL); Cs$_2$CO$_3$ (77.4 mg, 0.24 mmol); 2-bromoacetamide (59.7 mg, 0.43 mmol); 80° C. for 1 h. | Chromatography SiO$_2$, CH$_2$Cl$_2$:MeOH = 100:0 to 95:5 | 2-((3-((6,7-dimethoxy-1-propylisoquinolin-4-yl)methyl)quinolin-6-yl)oxy)acetamide (69.9 mg); MW: 445.51; Yield: 73%; White Solid; Mp (° C.): 231.2; R$_f$: 0.2 (CH$_2$Cl$_2$:MeOH = 98:2); $^1$H-NMR (DMSO-d$_6$, δ): 1.00 (t, 3H, CH$_3$, J = 7.3 Hz), 1.83 (sextuplet, 2H, CH$_2$, J = 7.3 Hz), 3.16 (t, 2H, CH$_2$, J = 7.5 Hz), 3.83 (s, 3H, OCH$_3$), 3.92 (s, 3H, OCH$_3$), 4.51 (s, 4H, 2xCH$_2$), 7.21 (d, 1H, ArH, J = 2.6 Hz), 7.32 (s, 1H, ArH), 7.38-7.44 (m, 3H, 2xArH + 0.5xNH$_2$), 7.59 (s, 1H, 0.5xNH$_2$), 7.89 (d, 1H, ArH, J = 9.2 Hz), 7.97 (s, 1H, ArH), 8.26 (s, 1H, ArH), 8.81 (d, 1H, ArH, J = 1.9 Hz); $^{13}$C-NMR (DMSO-d$_6$, δ): 14.1, 21.6, 32.6, 36.2, 55.6 (2xC), 66.9, 102.7, 104.4, 106.6, 121.5, 122.2, 126.4, 128.5, 130.0, 130.7, 133.2, 133.9, 141.1, 142.5, 149.3, 149.4, 152.0, 155.8, 158.0, 169.5; MS-ESI m/z (% rel. Int.): 446.5 ([MH]$^{+1}$, 100); HPLC: Method A, detection UV 254 nm, RT = 3.43 min, peak area 99.0%. |
| 145 | (structure) | F (a) 115 (103 mg, 0.23 mmol); 85% KOH (150 mg, 0.33 mmol) in MeOH/H$_2$O (1 mL/1 mL); 70° C. for 30 min. | Chromatography RP 18, eluent: water: 100% to water: CH$_3$CN = 73 | potassium 4-(5-((6,7-dimethoxyisoquinolin-4-yl)methyl)benzo[d]oxazol-2-yl)benzoate (19.8 mg); MW: 478.54; Yield: 18%; Beige Solid; R$_f$: 0.25 (water: CH$_3$CN = 7:3); 1H-NMR (CDCl$_3$, δ): 3.84 (s, 3H, OCH$_3$), 3.96 (s, 3H, OCH$_3$), 4.50 (s, 2H, CH$_2$), 7.23 (s, 1H, ArH), 7.32 (dd, 1H, ArH, J = 8.41 Hz, J = 8.41 Hz), 7.40 (s, 1H, ArH), 7.55-7.59 (m, 2H, 2xArH), 8.06-8.09 (m, 2H, 2xArH), 8.15-8.21 (m, 3H, 3xArH), 8.91 (s, 1H, ArH); $^{13}$C-NMR (CDCl$_3$, δ): 39.84, 59.19 (2xC), 105.91, 110.04, 114.35, 123.01, 129.05, 130.02, 130.66, 131.63, 133.42, 133.63, 135.66, 141.05, 144.69, 145.33, 145.85, 152.47, 153.38, 154.45, 157.50, 167.52, 176.60; MS-ESI m/z (% rel. Int.): 441.2 ([MH]$^{+1}$, 100); HPLC: Method A, detection UV 254 nm, RT = 4.10 min, peak area 99.9%. |

TABLE 7-continued

| Compd # | FORMULA | General Procedure | Purification | Analysis |
|---|---|---|---|---|
| 146 | 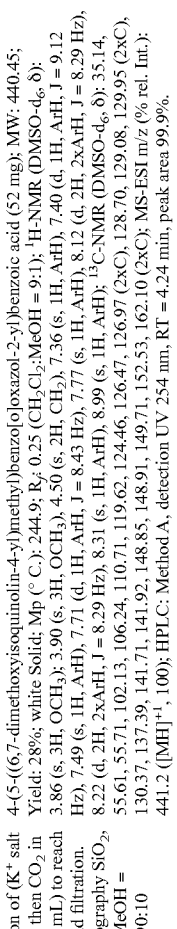 | F (a) 115 (179 mg, 0.39 mmol); KOH 85% (520 mg, 7.88 mmol) in MeOH/water (7 mL/2 mL); 70° C. for 30 min. | Purification of (K+ salt (see 145), then $CO_2$ in water (30 mL) to reach pH = 5 and filtration. Chromatography $SiO_2$, $CH_2Cl_2$:MeOH = 100:0 to 90:10 | 4-(5-((6,7-dimethoxyisoquinolin-4-yl)methyl)benzo[o]oxazol-2-yl)benzoic acid (52 mg); MW: 440.45; Yield: 28%; white Solid; Mp (° C.): 244.9; $R_f$: 0.25 ($CH_2Cl_2$:MeOH = 9:1); $^1$H-NMR (DMSO-$d_6$, δ): 3.86 (s, 3H, $OCH_3$), 3.90 (s, 3H, $OCH_3$), 4.50 (s, 2H, $CH_2$), 7.36 (s, 1H, ArH), 7.40 (d, 1H, ArH, J = 9.12 Hz), 7.49 (s, 1H, ArH), 7.71 (d, 1H, ArH, J = 8.43 Hz), 7.77 (s, 1H, ArH), 8.12 (d, 2H, 2xArH, J = 8.29 Hz), 8.22 (d, 2H, 2xArH, J = 8.29 Hz), 8.31 (s, 1H, ArH), 8.99 (s, 1H, ArH); $^{13}$C-NMR (DMSO-$d_6$, δ): 35.14, 55.61, 55.71, 102.13, 106.24, 110.71, 119.62, 124.46, 126.47, 126.97 (2xC), 128.70, 129.08, 129.95 (2xC), 130.37, 137.39, 141.71, 141.92, 148.85, 148.91, 149.71, 152.53, 162.10 (2xC); MS-ESI m/z (% rel. Int.): 441.2 ([MH]$^{+1}$, 100); HPLC: Method A, detection UV 254 nm, RT = 4.24 min, peak area 99.9%. |
| 147 | 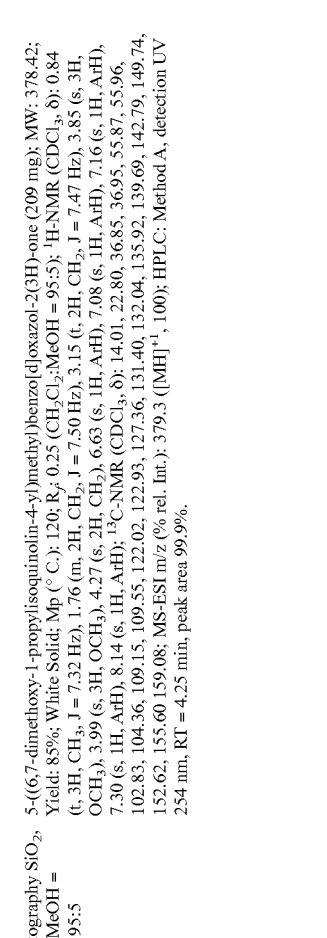 | C (c) ANP 53156A (612 mg, 1.73 mmol); Et3N (266 μL, 1.91 mmol); CDI (324 mg, 1.99 mmol); $CH_2Cl_2$ (15 mL); 4° C. to RT overnight. | Chromatography $SiO_2$, $CH_2Cl_2$:MeOH = 100:0 to 95:5 | 5-((6,7-dimethoxy-1-propylisoquinolin-4-yl)methyl)benzo[d]oxazol-2(3H)-one (209 mg); MW: 378.42; Yield: 85%; White Solid; Mp (° C.): 120; $R_f$: 0.25 ($CH_2Cl_2$:MeOH = 95:5); $^1$H-NMR (CDCl$_3$, δ): 0.84 (t, 3H, $CH_3$, J = 7.32 Hz), 1.76 (m, 2H, $CH_2$, J = 7.50 Hz), 3.15 (t, 2H, $CH_2$, J = 7.47 Hz), 3.85 (s, 3H, $OCH_3$), 3.99 (s, 3H, $OCH_3$), 4.27 (s, 2H, $CH_2$), 6.63 (s, 1H, ArH), 7.08 (s, 1H, ArH), 7.16 (s, 1H, ArH), 7.30 (s, 1H, ArH), 8.14 (s, 1H, ArH); $^{13}$C-NMR (CDCl$_3$, δ): 14.01, 22.80, 36.85, 36.95, 55.87, 55.96, 102.83, 104.36, 109.15, 109.55, 122.02, 122.93, 127.36, 131.40, 132.04, 135.92, 139.69, 142.79, 149.74, 152.62, 155.60 159.08; MS-ESI m/z (% rel. Int.): 379.3 ([MH]$^{+1}$, 100); HPLC: Method A, detection UV 254 nm, RT = 4.25 min, peak area 99.9%. |
| 148 | 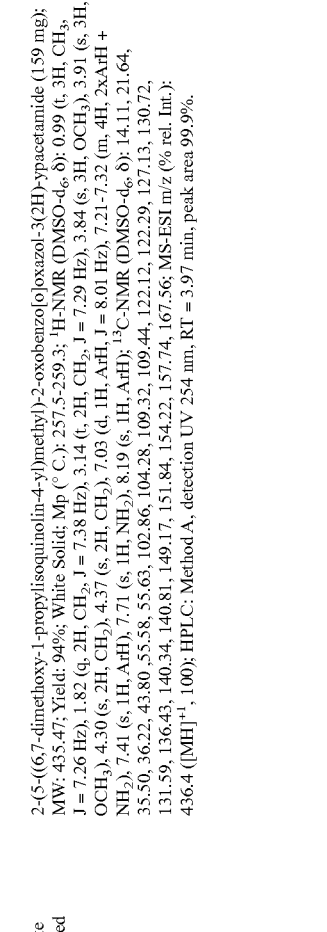 | B (a) 147 (150 mg, 0.39 mmol); acetone (6 mL); $K_2CO_3$ (60 mg, 0.44 mmol); 2-bromoacetamide (93 mg, 0.67 mmol); 60° C. overnight. | Precipitate was filtered | 2-(5-((6,7-dimethoxy-1-propylisoquinolin-4-yl)methyl)-2-oxobenzo[o]oxazol-3(2H)-yl)acetamide (159 mg); MW: 435.47; Yield: 94%; White Solid; Mp (° C.): 257.5-259.3; $^1$H-NMR (DMSO-$d_6$, δ): 0.99 (t, 3H, $CH_3$, J = 7.26 Hz), 1.82 (q, 2H, $CH_2$, J = 7.38 Hz), 3.14 (t, 2H, $CH_2$, J = 7.29 Hz), 3.84 (s, 3H, $OCH_3$), 3.91 (s, 3H, $OCH_3$), 4.30 (s, 2H, $CH_2$), 4.37 (s, 2H, $CH_2$), 7.03 (d, 1H, ArH, J = 8.01 Hz), 7.21-7.32 (m, 4H, 2xArH + $NH_2$), 7.41 (s, 1H, ArH), 7.71 (s, 1H, $NH_2$), 8.19 (s, 1H, ArH); $^{13}$C-NMR (DMSO-$d_6$, δ): 14.11, 21.64, 35.50, 36.22, 43.80 ,55.58, 55.63, 102.86, 104.28, 109.32, 109.44, 122.12, 122.29, 127.13, 130.72, 131.59, 136.43, 140.34, 140.81, 149.17, 151.84, 154.22, 157.74, 167.56; MS-ESI m/z (% rel. Int.): 436.4 ([MH]$^{+1}$, 100); HPLC: Method A, detection UV 254 nm, RT = 3.97 min, peak area 99.9%. |

TABLE 7-continued

| Compd # | FORMULA | General Procedure | Purification | Analysis |
|---|---|---|---|---|
| 149 | [structure] | D (b) ANP 53142B (151 mg, 0.34 mmol); MeOH (35 mL); Pd/C (45 mg); hydrogen; RT overnight. | Chromatography SiO$_2$, CH$_2$Cl$_2$:MeOH = 100:0 to 98:2 | 4-(5-((6,7-dimethoxyisoquinolin-4-yl)methyl)benzo[d]oxazol-2-yl)aniline (29.7 mg); MW: 411.45; Yield: 20%; White Solid; Mp (° C.): 211.7; R$_f$: 0.25 (CH$_2$Cl$_2$:MeOH = 98:2); $^1$H-NMR (DMSO-d$_6$ δ): 3.85 (s, 3H, OCH$_3$), 3.89 (s, 3H, OCH$_3$), 4.45 (s, 2H, CH$_2$), 5.97 (s, 2H, NH$_2$), 6.67 (d, 1H, ArH, J = 8.70 Hz), 6.86 (d, 1H, ArH, J = 8.79 Hz), 7.22-7.28 (d, 1H, ArH, J = 6.66 Hz), 7.35 (s, 1H, ArH), 7.49-7.61 (m, 4H, 4xArH), 7.82 (d, 1H, ArH, J = 8.64 Hz), 7.92 (d, 1H, ArH, J = 8.70 Hz), 8.29 (s, 1H, ArH), 8.98 (s, 1H, ArH); $^{13}$C-NMR (acetone d6, δ): 36.77, 54.21, 56.10 (2xC), 103.13, 106.93, 110.58, 114.17, 114.74 (2xC), 116.21, 119.75, 125.53, 125.94, 129.28, 129.71, 129.92 (2xC), 131.87, 137.79, 143.37, 150.06, 151.34, 153.05, 154.0; MS-ESI m/z (% rel. Int.): 412.3 ([MH]$^{+1}$, 44); HPLC: Method A, detection UV 254 nm, RT = 4.28 min, peak area 99.5%. |
| 150 | [structure] | F (b) LPO 55070A (120 mg, 0.28 mmol); 37% HCl (1 mL); AcOH (1 ml); 110° C. for 4 h. | Chromatography SiO$_2$, CH$_2$Cl$_2$:MeOH = 100:0 to 7:3 | 2-((3-((6,7-dimethoxyisoquinolin-4-yl)methyl)quinolin-6-yl)oxy)acetic acid (14.1 mg); MW: 404.42; Yield: 13%; White Solid; Mp (° C.): 253.5; R$_f$: 0.25 (CH$_2$Cl$_2$:MeOH = 7:3); $^1$H-NMR (CDCl$_3$, δ): 3.88 (s, 3H, OCH$_3$), 4.01 (s, 3H, OCH$_3$), 4.45 (s, 4H, 2xCH$_2$), 6.98 (s, 1H, ArH), 7.10 (s, 1H, ArH), 7.29 (s, 1H, ArH), 7.40-7.44 (m, 1H, ArH), 7.79 (s, 1H, ArH), 7.90 (d, 1H, ArH, J = 9.19 Hz), 8.19 (s, 1H, ArH), 8.65 (s, 1H, ArH), 8.93 (s, 1H, ArH); $^{13}$C- NMR (CDCl$_3$, δ): 36.76, 59.08, 59.12, 70.52, 104.67, 109.42 (2C), 125.62, 128.08, 131.21, 132.40, 132.63, 134.67, 135.94, 137.62, 144.46, 145.62, 151.55, 152.15, 153.57, 156.73, 160.08, 178.30; MS-ESI m/z (% rel. Int.): 405.2 ([MH]$^{+1}$, 100); HPLC: Method A, detection UV 254 nm, RT = 3.47 min, peak area 99.0%. |
| 151 | [structure] | D (a) ANP 53192A (100 mg, 0.22 mmol); THF (4 mL); LiAlH$_4$, THF (484 µL, 0.48 mmol); 4° C. to RT for 3.5 h. | Chromatography SiO$_2$, EtOAc:MeOH = 100:0 to 98:2 | (3-(5-((6,7-dimethoxyisoquinolin-4-yl)methyl)benzo[d]oxazol-2-yl)phenyl)methanol (21.1 mg); MW: 426.46; Yield: 22%; White Solid; Mp (° C.): 202.5-204.1; R$_f$: 0.25 (EtOAc:MeOH = 98:2); $^1$H-NMR (CDCl$_3$, δ): 3.83 (s, 3H, OCH$_3$), 3.99 (s, 3H, OCH$_3$), 4.43 (s, 2H, CH$_2$), 4.80 (s, 2H, CH$_2$), 7.08 (s, 1H, ArH), 7.20-7.27 (m, 2H, 2xArH), 7.43-7.56 (m, 4H, 4xArH), 8.10-8.12 (m, 1H, ArH), 8.22-8.30 (m, 2H, 2xArH), 8.98 (s, 1H, ArH); $^{13}$C-NMR (CDCl$_3$, δ): 36.66, 55.95, 56.02, 64.64, 102.02, 105.99, 110.49, 119.62, 124.91, 125.63, 125.91, 126.64, 127.21, 128.64, 129.14, 130.01, 131.50, 136.52, 142.11, 142.27, 142.45, 124.91, 125.63, 125.91, 149.46, 150.12, 153.03, 163.43; MS-ESI m/z (% rel. Int.): 427.3 ([MH]$^{+1}$, 100); HPLC: Method A, detection UV 254 nm, RT = 4.44 min, peak area 99.0%. |
| 152 | [structure] | H (b) ANP 53184A (768 mg, 1.56 mmol) in toluene (30 mL); benzophenone imine (576 µL, 3.43 mmol); Pd$_2$dba$_3$ (86 mg, 0.09 mmol); BINAP (194 mg, 0.31 mmol); Cs$_2$CO$_3$ (1.00 g, 3.12 mmol); Toluene (30 mL); 115° C. overnight. | 3N HCl (25 mL); THF (25 mL); RT for 15 min; neutralisation with 1M NaHCO$_3$. Chromatography SiO$_2$, CH$_2$Cl$_2$:MeOH = 100:0 to 96:4 | 2-((6,7-dimethoxy-1-methylisoquinolin-4-yl)methyl)quinolin-8-amine (75 mg); MW: 359.42; Yield: 41%; Yellow Solid; Mp (° C.): 238.3-240.5; R$_f$: 0.25 (CH$_2$Cl$_2$:MeOH = 96:4); $^1$H-NMR (CDCl$_3$, δ): 2.88 (s, 3H, CH$_3$), 3.87 (s, 3H, OCH$_3$), 3.98 (s, 3H, OCH$_3$), 4.60 (s, 2H, CH$_2$), 4.99 (s, 2H, NH$_2$), 6.91 (dd, 1H, ArH, J = 1.11 Hz, J = 7.50 Hz), 7.06 (dd, 1H, ArH, J = 0.99 Hz, J = 8.10 Hz), 7.20 (d, 1H, ArH, J = 8.50 Hz), 8.38 (s, 1H, ArH); $^{13}$C-NMR (CDCl$_3$, δ): 22.55, 41.23, 55.89, 56.05, 103.57, 104.23, 110.23, 115.89, 123.36, 126.40, 126.85, 127.19, 131.96, 136.63, 137.33, 141.41, 143.44, 149.45, 152.24, 155.44, 157.84; MS-ESI m/z (% rel. Int.): 360.3 ([MH]$^{+1}$, 100); HPLC: Method A, detection UV 254 nm, RT = 4.20 min, peak area 99.9%. |

TABLE 7-continued

| Compd # | FORMULA | General Procedure | Purification | Analysis |
|---|---|---|---|---|
| 153 | (structure: 4-cyanophenyl benzoxazole linked via CH2 to 6,7-dimethoxyisoquinoline) | J<br>ANP 49184A (400 mg, 1.28 mmol); 4-cyanobenzaldehyde (169 mg, 1.28 mmol) in MeOH (20 mL) 60° C. overnight; DDQ (332 mg, 1.42 mmol) in CH$_2$Cl$_2$ (40 mL); RT for 30 min. | Chromatography SiO$_2$, CH$_2$Cl$_2$:EtOAc = 100:0 to 15:85 | 4-(5-(6,7-dimethoxyisoquinolin-4-yl)methyl)benzo[d]oxazol-2-yl)benzonitrile (66 mg); MW: 482.53; Yield: 12%; Beige Solid; Mp (° C.): 253.9-256.1; R$_f$: 0.25 (EtOAc:CH$_2$Cl$_2$ = 85:15); $^1$H-NMR (CDCl$_3$, δ): 3.85 (s, 3H, OCH$_3$), 4.02 (s, 3H, OCH$_3$), 4.47 (s, 2H, CH$_2$), 7.09 (s, 1H, ArH), 7.24-7.30 (m, 2H, 2xArH), 7.52 (d, 1H, ArH, J = 8.40 Hz), 7.61 (s, 1H, ArH), 7.81 (d, 2H, 2xArH, J = 8.32 Hz), 8.31-8.33 (m, 3H, 3xArH), 9.01 (s, 1H, ArH); $^{13}$C-NMR (CDCl$_3$, δ): 36.63, 55.97, 56.07, 101.92, 106.06, 110.81, 114.80, 118.11, 120.15, 124.85, 126.69, 127.93 (2xC), 128.46, 131.05, 131.53, 132.68 (2C), 137.06, 142.09, 142.34, 149.12, 149.67, 150.22, 153.19, 161.42; MS-ESI m/z (% rel. Int.): 422.2 ([MH]$^{+1}$, 100); HPLC: Method A, detection UV 254 nm, RT = 4.85 min, peak area 99.9%. |
| 154 | (structure: 2-hydroxymethylphenyl benzoxazole linked to 6,7-dimethoxyisoquinoline) | D (a)<br>ANP 53174 B (90 mg, 0.22 mmol); THF (3.5 mL); LiAlH$_4$ in THF (435 µL, 0.44 mmol); 4° C. to RT for 3 h. | Chromatography SiO$_2$, CH$_2$Cl$_2$:MeOH = 100:0 to 96:4 | (2-(5-((6,7-dimethoxyisoquinolin-4-yl)methyl)benzo[d]oxazol-2-yl)phenyl)methanol (18.9 mg); MW: 426.46; Yield: 22%; White Solid; Mp (° C.): 203.3-204.6; R$_f$: 0.25 (CH$_2$Cl$_2$:MeOH = 96:4); $^1$H-NMR (CDCl$_3$, δ): 3.88 (s, 3H, OCH$_3$), 4.03 (s, 3H, OCH$_3$), 4.48 (s, 2H, CH$_2$), 4.82 (s, 2H, CH$_2$), 7.11 (s, 1H, ArH), 7.25-7.29 (m, 2H, 2xArH), 7.48-7.58 (m, 5H, 5xArH), 8.20-8.22 (m, 1H, ArH), 8.33 (m, 1H, ArH), 9.03 (s, 1H, ArH); $^{13}$C-NMR (CDCl$_3$, δ): 36.59, 55.99, 56.06, 64.64, 101.95, 106.15, 110.67, 119.65, 124.86, 125.73, 126.20, 128.23, 128.61, 129.73, 130.99, 131.62, 131.84, 136.75, 141.63, 141.80, 141.90, 148.96 (2xC), 150.31, 153.33, 162.94; MS-ESI m/z (% rel. Int.): 427.2 ([MH]$^{+1}$, 100); HPLC: Method A, detection UV 254 nm, RT = 4.60 min, peak area 99.0%. |
| 155 | (structure: 6-hydroxyquinoline linked via CH2 to 1-methyl-6,7-dimethoxyisoquinoline) | A<br>TTA 24128B (407 mg, 1.37 mmol); ECO 55108C (300 mg, 1.37 mmol); 37% HCl (3 mL); EtOH (3 mL); 90° C. for 25 min. | Chromatography SiO$_2$, CH$_2$Cl$_2$:MeOH = 100:0 to 94:6 | 3-((6,7-dimethoxy-1-methylisoquinolin-4-yl)methyl)quinolin-6-ol (116 mg); MW: 360.41; Yield: 24%; Off-White Solid; Mp (° C.): 269.2-272.9; R$_f$: 0.2 (CH$_2$Cl$_2$:MeOH = 94:6); $^1$H-NMR (CDCl$_3$, δ): 2.90 (s, 3H, CH$_3$), 3.84 (s, 3H, OCH$_3$), 4.02 (s, 3H, OCH$_3$), 4.42 (s, 2H, CH$_2$), 6.94 (d, 1H, ArH, J = 2.52 Hz), 7.05 (s, 1H, ArH), 7.28-7.32 (m, 2H, 2xArH), 7.59 (s, 1H, ArH), 7.90 (d, 1H, ArH, J = 9.10 Hz), 8.17 (s, 1H, ArH), 8.68 (s, 1H, ArH); $^{13}$C-NMR (CDCl$_3$, δ): 21.51, 33.66, 55.65, 55.75, 102.15, 104.42, 107.95, 121.79, 123.27, 126.29, 129.35, 129.59, 131.31, 132.57, 133.29, 140.19, 141.78, 147.60, 149.62, 152.68, 155.23, 155.73; MS-ESI m/z (% rel. Int.): 361.3 ([MH]$^{+1}$, 100); HPLC: Method A, detection UV 254 nm, RT = 3.74 min, peak area 99.0%. |
| 156 | (structure: 8-sulfamoylamino-quinoline linked via CH2 to 1-methyl-6,7-dimethoxyisoquinoline) | I<br>152 (227 mg, 0.63 mmol); sulfamide (243 mg, 2.53 mmol); 1,4-dioxane (20 mL); 110° C. overnight. | Chromatography SiO$_2$, CH$_2$Cl$_2$:MeOH = 100:0 to 96:4 | (2-(6,7-dimethoxy-1-methyl-isoquinolin-4-ylmethyl)-quinolin-8-yl)-sulfamide (61.9 mg); MW: 438.50; Yield: 22%; Yellow Solid; Mp (° C.): 232.0-236.0; R$_f$: 0.25 (CH$_2$Cl$_2$:MeOH = 96:4); $^1$H-NMR (DMSO-d$_6$, δ): 2.80 (s, 3H, CH$_3$), 3.85 (s, 3H, OCH$_3$), 4.91 (s, 3H, OCH$_3$), 4.67 (s, 2H, CH$_2$), 7.36 (s, 1H, ArH), 7.52 (m, 6H, 4xArH + NH$_2$), 7.66 (s, 1H, ArH), 8.250 (d, 1H, ArH, J = 8.10 Hz), 8.33 (s, 1H, ArH), 8.96 (s, 1H, NH); $^{13}$C-NMR (DMSO-d$_6$, δ): 22.24, 39.51, 55.57, 55.67, 102.87, 104.68, 113.21, 120.28, 122.34, 122.58, 125.96, 126.23, 126.34, 130.82, 134.32, 136.37, 137.14, 141.05, 149.24, 152.07, 154.86, 159.48; MS-ESI m/z (% rel. Int.): 439.2 ([MH]$^{+1}$, 100); HPLC: Method A, detection UV 254 nm, RT = 4.57 min, peak area 99.9%. |

TABLE 7-continued

| Compd # | FORMULA | General Procedure | Purification | Analysis |
|---|---|---|---|---|
| 157 | 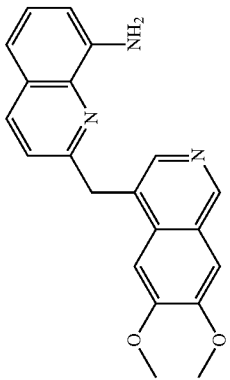 | H (b) ANP 57032A (840 mg, 1.75 mmol); benzophenoneimine (678 μL, 3.86 mmol); Pd₂dba₃ (96 mg, 0.11 mmol); BINAP (218 mg, 0.35 mmol); Cs₂CO₃ (1.14 g, 3.51 mmol); toluene (30 mL); 115° C. overnight. | 3N HCl (25 mL); THF (25 mL); RT for 15 min; neutralisation with 1M NaHCO₃. Chromatography SiO₂, EtOAc:MeOH = 100:0 to 98:2 | 2-((6,7-dimethoxyisoquinolin-4-yl)methyl)quinolin-8-amine (98.5 mg); MW: 345.39; Yield: 60%; Yellow Solid; Mp (° C.):168.0-171.4; R$_f$: 0.25 (EtOAc:MeOH = 98:2); ¹H-NMR (CDCl₃, δ): 3.88 (s, 3H, OCH₃), 3.98 (s, 3H, OCH₃), 4.62 (s, 2H, CH₂), 6.91 (d, 1H, ArH, J = 7.44 Hz), 7.07 (d, 1H, ArH, J = 7.98 Hz), 7.17-7.22 (m, 2H, 2xArH), 7.24-7.30 (m, 2H, 2xArH), 7.50 (s, 1H, ArH), 7.89 (d, 1H, ArH, J = 8.41 Hz), 8.47 (s, 1H, ArH), 8.98 (s, 1H, ArH); ¹³C-NMR (CDCl₃, δ): 41.14, 55.98, 56.14, 102.84, 105.68, 110.26, 115.89, 121.30, 124.90, 126.93, 127.20, 127.85, 131.92, 136.69, 137.35, 142.39, 143.44, 149.59, 150.06, 152.88, 157.37; MS-ESI m/z (% rel. Int.): 346.1 ([MH]⁺¹, 100); HPLC: Method A, detection UV 254 nm, RT = 4.08 min, peak area 99.9%. |
| 158 | 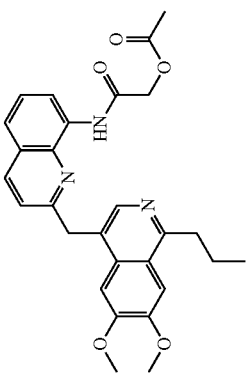 | C (a) LPO 55056D (113 mg, 0.29 mmol); pyridine (75.3 μL, 0.93 mmol); acetoxyacetylchloride (47 μL, 0.44 mmol); THF (1.1 mL); RT for 1 h. | Chromatography SiO₂, cyclohexane:EtOAc = 100:0 to 50:50 | 2-(2-((6,7-dimethoxy-1-propylisoquinolin-4-yl)methyl)quinolin-8-yl)amino)-2-oxoethyl acetate (124 mg); MW: 487.55; Yield: 95%; Off-white Solid; Mp (° C.): 164.8; R$_f$: 0.25 (EtOAc:MeOH = 98:2); ¹H-NMR (DMSO-d₆, δ): 1.09 (t, 3H, CH₃, J = 7.4 Hz), 2.34 (s, 3H, CH₃), 3.20 (t, 2H, J = 7.65 Hz), 3.75 (s, 3H, OCH₃), 4.00 (s, 3H, OCH₃), 4.63 (s, 2H, CH₂), 4.83 (s, 2H, CH₂), 7.28 (m, 1H, ArH), 7.35 (s, 1H, ArH), 7.50 (m, 2H, 2xArH)i 8.00 (d, 1H, ArH, J = 8.5 Hz), 8.39 (s, 1H, ArH), 8.76 (dd, 1H, ArH, J = 6.4 Hz, J = 2.5 Hz), 10.6 (s, 1H, NH); ¹³C-NMR (DMSO-d6, δ): 14.4, 20.8, 22.6, 29.7, 37.5, 41.3, 55.7, 55.9, 63.4, 102.8, 104.3, 117.1, 121.7, 122.2, 125.2, 126.5, 126.9, 132.1, 132.9, 137.2, 137.6, 141.8, 149.5, 152.4, 159.3, 159.5, 165.2, 169.3; MS-ESI m/z (% rel. Int.): 488.1 ([MH]⁺¹, 100); HPLC: Method A, detection UV 254 nm, RT = 4.95 min, peak area 98.0%. |
| 159 | 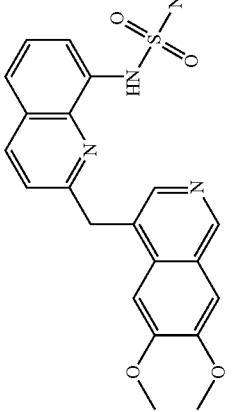 | I 157 (300 mg, 0.87 mmol); sulfamide (334 mg, 3.47 mmol); 1,4-dioxane (25 mL); 110° C. overnight. | Chromatography SiO₂, CH₂Cl₂:EtOAc = 100:0 to 85:15 | (2-(6,7-dimethoxy-1-methyl-isoquinolin-4-ylmethyl)-quinolin-8-yl)-sulfamide (8 mg); MW: 424.47; Yield: 2%; White Solid; Mp (° C.): 197.9-199.5; R$_f$: 0.25 (EtOAc:CH₂Cl₂ = 85:15); 1H-NMR (THF-d8, δ): 2.13 (s, 3H, OCH₃), 2.15 (s, 3H, OCH₃), 2.94 (s, 2H, CH₂), 4.89 (s, 1H, ArH), 5.56 (s, 1H, ArH), 5.66-5.79 (m, 4H, 4xArH), 6.03 (dd, 1H, ArH, J = 1.99 Hz, J = 6.79 Hz), 6.36 (d, 1H, ArH, J = 8.5 Hz), 6.69 (s, 1H, NH); 7.24 (s, 1H, ArH); ¹³C-NMR (THF-d8, δ): 38.34, 53.10, 53.55, 100.13, 103.69, 111.74, 118.15, 120.04, 123.10, 124.37, 124.94, 125.14, 129.39, 133.36, 134.96, 135.36, 140.62, 147.53, 148.75, 151.52, 157.54; MS-ESI m/z (% rel. Int.): 425.2 ([MH]⁺¹, 100); HPLC: Method A, detection UV 254 nm, RT = 3.93 min, peak area 99.9%. |

TABLE 7-continued

| Compd # | FORMULA | General Procedure | Purification | Analysis |
|---|---|---|---|---|
| 160 | (structure) | F (a) 158 (110 mg, 0.23 mmol); 2M LiOH (226 µL, 0.45 mmol); THF (5 mL); 70° C. for 2 h. | Chromatography SiO$_2$, CH$_2$Cl$_2$:MeOH = 100:0 to 98:2 | N-(2-((6,7-dimethoxy-1-propylisoquinolin-4-yl)methyl)quinolin-8-yl)-2-hydroxyacetamide (80 mg); MW: 445.51; Yield: 73%; Off-white Solid; Mp (° C.): 234.6; R$_f$: 0.25 (CH$_2$Cl$_2$:MeOH = 98:2); $^1$H-NMR (CDCl$_3$, δ): 1.03 (t, 3H, CH$_3$, J = 7.4 Hz), 1.87 (m, 2H, CH$_2$, J = 7.7 Hz), 3.13 (t, 2H, CH$_2$, J = 7.7 Hz), 3.79 (s, 3H, OCH$_3$), 3.96 (s, 3H, OCH$_3$), 4.39 (s, 2H, CH$_2$), 4.54 (s, 2H, CH$_2$), 7.24 (m, 3H, 3xArH), 7.44 (m, 2H, 2xArH), 7.50 (m, 2H, 2xArH), 7.85 (d, 1H, ArH, J = 8.5 Hz), 8.43 (s, 1H, ArH), 8.75 (dd, 1H, ArH, J = 7.4 Hz, J = 1.3 Hz), 10.9 (s, 1H, NH); $^{13}$C-NMR (DMSO-d$_6$, δ): 14.4, 22.7, 37.4, 40.5, 55.8, 55.9, 62.9, 102.9, 104.1, 116.8, 121.4, 121.8, 122.8, 125.8, 126.4, 126.8, 132.2, 133.3, 136.9, 137.8, 141.3, 149.5, 158.6, 159.0; MS-ESI m/z (% rel. Int.): 446.2 ([MH]$^{+1}$, 100); HPLC: Method A, detection UV 254 nm, RT = 4.93 min, peak area 96.0%. |
| 161 | (structure) | A LPO 22102 (151 mg, 0.53 mmol); ECO 55152 (139 mg, 0.48 mmol); 37% HCl (1.4 mL); EtOH (1.4 mL); 95° C. for 25 min. | Chromatography SiO$_2$, CH$_2$Cl$_2$:MeOH = 100:0 to 90:10 | 3-((6,7-dimethoxyisoquinolin-4-yl)methyl)-5-(trifluoromethyl)quinolin-6-ol (18.9 mg); MW: 414.38; Yield: 9.5%; White Solid; Mp (° C.): 304.8-310.5° C.; R$_f$: 0.25 (CH$_2$Cl$_2$:MeOH = 90:10); $^1$H-NMR (DMSO-d$_6$, δ): 3.86 (s, 3H, OCH$_3$), 3.90 (s, 3H, OCH$_3$), 4.60 (s, 2H, CH$_2$), 7.30-7.43 (m, 2H, 2xArH), 7.50 (s, 2H, 2xArH), 8.03 (d, 1H, ArH, J = 9.3 Hz), 8.31 (s, 1H, ArH), 8.38 (s, 1H, ArH), 8.76 (s, 1H, ArH), 9.00 (s, 1H, ArH); $^{13}$C-NMR (DMSO-d$_6$, δ): 32.8, 55.6, 101.9, 104.5, 106.3, 122.0, 123.2 (q, CF$_3$, J = 275.8 Hz), 124.4, 125.6, 127.0, 128.1, 129.4, 130.3, 134.9, 141.1, 142.0, 148.8, 149.2, 149.8, 152.7, 156.0; MS-ESI m/z (% rel. Int.): 415.2 ([MH]$^{+1}$, 100); HPLC: Method A, detection UV 254 nm RT = 4.02 min, peak area 97.0%. |
| 162 | (structure) | A SSA 39102 (157 mg, 0.48 mmol); ECO 55152 (125 mg, 0.44 mmol); 37% HCl (1.4 mL); EtOH (1.4 mL); 95° C. for 25 min. | Chromatography SiO$_2$, CH$_2$Cl$_2$:MeOH = 100:0 to 90:10 | 3-((6,7-dimethoxy-1-propylisoquinolin-4-yl)methyl)-5-(trifluoromethyl)quinolin-6-ol (95 mg); MW: 456.46; Yield: 48%; Off-White Solid; Mp (° C.): 209.3; R$_f$: 0.25 (CH$_2$Cl$_2$:MeOH = 90:10); $^1$H-NMR (CDCl$_3$, δ): 1.05 (t, 3H, CH$_3$, J = 7.4 Hz), 1.88 (m, 2H, CH$_2$, J = 7.6 Hz), 3.21 (t, 2H, CH$_2$, J = 7.7 Hz), 3.87 (s, 3H, OCH$_3$), 4.02 (s, 3H, OCH$_3$), 4.47 (s, 2H, CH$_2$), 7.10 (s, 1H, ArH), 7.27-7.37 (m, 2H, 2xArH, J = 9.3 Hz), 8.03 (d, 1H, ArH, J = 9.3 Hz), 8.25 (s, 1H, ArH), 8.30 (s, 1H, ArH), 8.65 (s, 1H, ArH); $^{13}$C-NMR (DMSO-d$_6$, δ): 14.3, 22.8, 34.8, 37.1, 55.8, 55.9, 102.2, 106.1 (q, CCF$_3$, J = 28.6 Hz), 122.6, 122.8 (q, CF$_3$, J = 275 Hz), 123.6, 126.0, 130.1, 131.8, 134.0, 134.8, 140.6, 142.0, 148.7, 148.7, 149.7, 152.8, 155.1, 159.3; MS-ESI m/z (% rel. Int.): 457.1 ([MH]$^+$, 100); HPLC: Method A, detection UV 254 nm, RT = 4.39 min, peak area 98.0%. |

TABLE 7-continued

| Compd # | FORMULA | General Procedure | Purification | Analysis |
|---|---|---|---|---|
| 163 | (structure: 8-hydroxyquinoline linked via CH2 to 6,7-dimethoxy-1-(methoxymethyl)isoquinoline) | A TTA 46082 (1.1 g, 3.36 mmol); 8-hydroxyquinoline-2-carbaldehyde (581 mg, 3.36 mmol); 37% HCl (3.5 mL); EtOH (3.5 mL); 95° C. for 30 min. | Chromatography SiO$_2$, cyclohexane:EtOAc = 100:0 to 0:100 | 2-((6,7-dimethoxy-1-(methoxymethyl)isoquinolin-4-yl)methyl)quinolin-8-ol (640 mg); MW: 390.43; Yield: 49%; Brown solid; Mp (° C.): 157.7; R$_f$: 0.25 (EtOAc); $^1$H-NMR (CDCl$_3$, δ), 3.46 (s, 3H, OCH$_3$), 3.84 (s, 3H, OCH$_3$), 3.99 (s, 3H, OCH$_3$), 4.65 (s, 2H, CH$_2$), 5.00 (s, 2H, CH$_2$), 7.17 (dd, 1H, ArH, J = 7.6 Hz, J = 1.05 Hz), 7.24-7.27 (m, 2H, 2xArH), 7.55 (s, 1H, ArH), 7.98 (d, 1H, ArH, J = 8.5 Hz), 8.20 (br s, 1H, ArH), 8.44 (s, 1H, ArH); $^{13}$C-NMR (DMSO-d$_6$, δ): 40.8, 55.9 (2xC), 58.3, 75.5, 102.9, 104.2, 110.3, 117.8, 121.9, 123.4, 126.9, 127.3, 127.6, 132.5, 136.9, 137.3, 141.3, 149.8, 151.7, 152.6, 154.2, 158.4; MS-ESI m/z (% rel. Int.): 391.2 ([MH]$^{+1}$, 98); HPLC: Method A, detection UV 254 nm, RT = 3.84 min, peak area 99.9%. |
| 164 | (structure: quinoline-8-yloxyacetamide linked via CH2 to 6,7-dimethoxy-1-(methoxymethyl)isoquinoline) | B (a) 163 (130 mg, 0.33 mmol); DMF (3.5 mL); Cs$_2$CO$_3$ (193 mg, 0.59 mmol); 2-bromoacetamide (91 mg, 0.66 mmol); 80° C. for 7 h. | Chromatography SiO$_2$, CH$_2$Cl$_2$:MeOH = 100:0 to 95:5 | 2-(2-((6,7-dimethoxy-1-(methoxymethyl)isoquinolin-4-yl)methyl)quinolin-8-yloxy)acetamide (106 mg); MW: 447.48; Yield: 72%; Pale Yellow Solid; Mp (° C.): 196.9; R$_f$: 0.45 (CH$_2$Cl$_2$:MeOH = 95:5); $^1$H-NMR (CDCl$_3$, δ): 3.46 (s, 3H, OCH$_3$), 3.84 (s, 3H, OCH$_3$), 3.99 (s, 2H, CH$_2$), 4.65 (s, 2H, CH$_2$), 5.00 (s, 2H, CH$_2$), 5.50 (br s, 1H, NH), 7.14 (dd, 1H, ArH, J = 6.0 Hz, J = 2.9 Hz), 7.35 (m, 2H, 2xArH), 7.45 (m, 2H, 2xArH), 7.55 (s, 1H, ArH), 7.93 (br s, 1H, NH), 8.03 (d, 1H, ArH, J = 8.5 Hz), 8.42 (s, 1H, ArH); $^{13}$C-NMR (DMSO-d$_6$, δ): 40.9, 55.9 (2xC), 58.5, 70.3, 75.5, 102.9, 104.2, 113.5, 121.8, 122.0, 123.3, 126.4, 127.6, 128.1, 132.5, 136.9, 140.0, 141.6, 149.8, 152.6, 153.9, 154.1, 159.7, 171.4; MS-ESI m/z (% rel. Int.): 448.2 ([MH]$^{+1}$, 54); HPLC: Method A, detection UV 254 nm, RT = 3.84 min, peak area 99.9%. |
| 165 | (structure: ethyl quinolin-8-yloxyacetate linked via CH2 to 6,7-dimethoxy-1-(methoxymethyl)isoquinoline) | B (a) 163 (310 mg, 0.79 mmol); acetone (10 mL); Cs$_2$CO$_3$ (388 mg, 1.19 mmol); ethyl 2-bromoacetate (123 μL, 1.11 mmol); 65° C. overnight. | Chromatography SiO$_2$, Cyclohexane:EtOAc = 100:0 to 0:100 | ethyl 2-((2-((6,7-dimethoxy-1-(methoxymethyl)isoquinolin-4-yl)methyl)quinolin-8-yl)oxy)acetate (303 mg); MW: 476.52; Yield: 80%; Pale Brown Solid; Mp (° C.): 118.5; R$_f$: 0.2 (EtOAc); $^1$H-NMR (CDCl$_3$, δ): 1.31 (t, 3H, CH$_3$), 3.45 (s, 3H, OCH$_3$), 3.92 (s, 3H, OCH$_3$), 3.98 (s, 2H, CH$_2$), 4.32 (q, 2H, CH$_2$, J = 7.1 Hz), 4.73 (s, 2H, CH$_2$), 4.98 (s, 2H, CH$_2$), 6.98 (dd, 1H, ArH, J = 5.7 Hz, J = 3.2 Hz), 7.22 (d, 1H, ArH, J = 9.4 Hz), 7.37 (m, 2H, 2xArH), 7.53 (s, 1H, ArH), 7.68 (s, 1H, ArH), 7.92 (d, 1H, ArH, J = 8.5 Hz), 8.46 (s, 1H, ArH); $^{13}$C-NMR (DMSO-d$_6$, δ): 41.62, 55.9, 56.3, 58.3, 61.4, 66.4, 75.5, 103.6, 103.9, 110.4, 120.9, 121.8, 123.3, 125.9, 127.8, 128.1 (2xC), 132.7, 136.6, 139.3, 141.1, 149.8, 152.6, 153.4, 154.0, 159.7, 168.7; MS-ESI m/z (% rel. Int.): 477.3 ([MH]$^{+1}$, 26); HPLC: Method A, detection UV 254 nm, RT = 4.18 min, peak area 99.9%. |

TABLE 7-continued

| Compd # | FORMULA | General Procedure | Purification | Analysis |
|---|---|---|---|---|
| 166 | (structure) | D (a) 165 (273 mg, 0.57 mmol); t-BuOH (20 mL); MeOH (0.5 mL); NaBH$_4$ (24 mg, 0.63 mmol); 100° C. for 2 h. | Chromatography SiO$_2$, CH$_2$Cl$_2$:MeOH = 99:1 to 95:5 | 2-(2-((6,7-dimethoxy-1-(methoxymethyl)isoquinolin-4-yl)methyl)quinolin-8-yloxy)ethanol (137 mg); MW: 434.48; Yield: 55%; Yellow Solid; Mp (° C.): 157.7. R$_f$: 0.2 (CH$_2$Cl$_2$:MeOH = 95:5); $^1$H-NMR (CDCl$_3$, δ): 3.46 (s, 3H, OCH$_3$), 3.92-3.98 (m, 8H, CH$_2$ + 2×OCH$_3$), 4.35 (q, 2H, CH$_2$, J = 4.3 Hz), 4.66 (s, 2H, CH$_2$), 4.99 (s, 2H, CH$_2$), 7.20 (d, 1H, ArH, J = 8.5 Hz), 7.29 (m, 2H, 2×ArH), 7.44 (m, 2H, 2×ArH), 7.52 (d, 2H, 2×ArH, J = 7.3 Hz), 7.96 (d, 1H, ArH, J = 8.6 Hz), 8.42 (s, 1H, ArH); $^{13}$C-NMR (DMSO-d$_6$, δ): 40.7, 55.9, 56.3 58.4, 61.1, 74.4, 75.5, 103.1, 104.1, 115.8, 121.7, 121.8, 123.3, 126.6, 127.5, 128.2, 132.5, 137.2, 140.4, 141.3, 149.8, 152.7, 154.2, 154.3, 159.7; MS-ESI m/z (% rel. Int.): 435.2 ([MH]$^+$, 56); HPLC: Method A, detection UV 254 nm, RT = 3.58 min, peak area 99.9%. |
| 167 | (structure) | H (b) ECO 59060 (380 mg, 0.73 mmol); benzophenoneimine (389 μL, 2.39 mmol); Pd$_2$dba$_3$ (40 mg, 0.044 mmol); BINAP (96 mg, 0.145 mmol); Cs$_2$CO$_3$ (474 mg, 1.45 mmol); toluene (15 mL); 115° C. overnight. 3N HCl (25 mL); THF (25 mL); RT for 15 min; neutralisation with 1M NaHCO$_3$. | Chromatography SiO$_2$, CH$_2$Cl$_2$:MeOH = 100:0 to 95:5 | 2-((6,7-dimethoxy-1-(methoxymethyl)isoquinolin-4-yl)methyl)quinolin-8-amine (71 mg); MW: 389.45; Yield: 20%; Orange Solid; Mp (° C.): 196.9; R$_f$: 0.45 (CH$_2$Cl$_2$:MeOH = 95:5); $^1$H-NMR (CDCl$_3$, δ): 3.48 (s, 3H, OCH$_3$), 3.86 (s, 3H, OCH$_3$), 4.00 (s, 3H, OCH$_3$), 4.68 (s, 2H, CH$_2$), 4.70 (s, 2H, CH$_2$), 5.00 (s, 2H, CH$_2$), 6.90 (dd, 1H, ArH, J = 6.4 Hz), 6.93 (d, 1H, ArH, J = 8.1 Hz), 7.17 (d, 1H, ArH, J = 8.5 Hz), 7.26 (m, 1H, ArH), 7.52 (s, 1H, ArH), 7.54 (s, 1H, ArH), 7.88 (d, 1H, ArH, J = 8.5 Hz) 8.44 (s, 1H, ArH); $^{13}$C-NMR (DMSO-d$_6$, δ): 41.3, 55.9, 56.1 58.3, 75.5, 103.3, 104.0, 110.3, 115.9, 121.3, 123.3, 126.9, 127.2, 128.2, 132.7, 136.7, 137.3, 141.2, 143.4, 149.7, 152.5, 153.9, 157.5; MS-ESI m/z (% rel. Int.): 390.1 ([MH]$^+$, 100); HPLC: Method A, detection UV 254 nm, RT = 3.78 min, peak area 97.0%. |
| 168 | (structure) | A TTA 46082 (210 mg, 0.64 mmol); ECO 55114C (140 mg, 0.64 mmol); 37% HCl (1 mL); EtOH (1 mL); 95° C. for 0.5 h. | Chromatography SiO$_2$, CH$_2$Cl$_2$:MeOH = 100:0 to 95:5 | 3-((6,7-dimethoxy-1-(methoxymethyl)isoquinolin-4-yl)methyl)quinolin-6-ol (67 mg); MW: 390.43; Yield: 27%; White Solid; Mp (° C.): 256.3; R$_f$: 0.3 (CH$_2$Cl$_2$:MeOH = 95:5); $^1$H-NMR (CDCl$_3$, δ): 3.42 (s, 3H, OCH$_3$), 3.80 (s, 3H, CH$_3$O), 3.98 (s, 3H, OCH$_3$), 4.42 (s, 2H, CH$_2$), 5.01 (s, 2H, CH$_2$), 6.90 (d, 1H, ArH, J = 2.6 Hz), 6.99 (s, 1H, ArH), 7.28 (s, 1H, ArH), 7.38 (dd, 1H, ArH, J = 2.6 Hz, J = 9.1 Hz), 7.58 (s, 1H, ArH), 8.01 (d, 1H, ArH, J = 9.2 Hz), 8.33 (s, 1H, ArH), 8.87 (d, 1H, ArH, J = 2.0 Hz); $^{13}$C-NMR (CDCl$_3$, δ): 34.1, 55.9, 56.0, 58.7, 74.4, 102.3, 104.6, 107.7, 122.7, 123.7, 129.0, 129.5, 130.6, 132.5, 132.7, 139.7, 142.6, 147.8, 150.3, 153.3, 153.9, 156.9; MS-ESI m/z (% rel. Int.): 391.1 ([MH]$^+$, 100); HPLC: Method A, detection UV 254 nm, RT = 3.30 min, peak area 99%. |

TABLE 7-continued

| Compd # | FORMULA | General Procedure | Purification | Analysis |
|---|---|---|---|---|
| 169 | (structure) | A TTA 46082B (224 mg, 0.69 mmol); ECO 55152C (179 mg, 0.62 mmol); 37% HCl (1.8 mL); EtOH (1.8 mL); 95° C. for 0.5 h. | Chromatography SiO$_2$, CH$_2$Cl$_2$:MeOH = 100:0 to 95:5 | 3-((6,7-dimethoxy-1-(methoxymethyl)isoquinolin-4-yl)methyl)-5-(trifluoromethyl)quinolin-6-ol (40.9 mg); MW: 458.43; Yield 29%; White Solid; Mp (° C.): 201.1; R$_f$: 0.3 (CH$_2$Cl$_2$:MeOH = 95:5); $^1$H-NMR (DMSO-d$_6$, δ): 3.35 (s, 3H, OCH$_3$), 3.86 (s, 3H, OCH$_3$), 3.90 (s, 3H, OCH$_3$), 4.60 (s, 2H, CH$_2$),4.90 (s, 2H, CH$_2$), 7.40 (m, 2H, 2xArH), 7.56 (s, 1H, ArH), 8.05 (d, 1H, J = 9.3 Hz, ArH), 8.30 (s, 1H, ArH), 8.34 (s, 1H, ArH), 8.75 (s, 1H, ArH); $^{13}$C-NMR (DMSO-d$_6$, δ): 32.9, 55.5, 57.6, 74.6, 102.5, 103.9 (q, J = 30.0 Hz, CCF$_3$, weak), 104.5, 122.0, 122.7, 125.2 (q, J = 273 Hz, CF$_3$), 125.6, 128.5, 129.4, 131.1, 134.8, 135.1, 140.7, 141.1, 148.7, 149.4, 152.3, 153.6, 156.1; MS-ESI m/z (% rel. Int.): 459.1 ([MH]$^+$, 100); HPLC: Method A, detection UV 254 nm, RT = 3.95 min, peak area 99%. |
| 170 | (structure) | J ANP 53010A (117 mg, 0.38 mmol); TTA 46118C (51.5 mg, 0.38 mmol); MeOH (3.5 mL); 60° C. overnight; DDQ (332 mg, 1.42 mmol) in CH$_2$Cl$_2$ (6 mL); RT for 0.5h. | Chromatography SiO$_2$, EtOAc to EtOAc:MeOH = 98:2 | (4-(6-((6,7-dimethoxyisoquinolin-4-yl)methyl)benzo[d]oxazol-2-yl)phenyl)methanol (7 mg); MW: 426.46; Yield 4%; Beige Solid; $^1$H-NMR (CDCl$_3$, δ): 3.84 (s, 3H, OCH$_3$), 4.01 (s, 3H, OCH$_3$), 4.47 (s, 2H, CH$_2$), 4.79 (s, 2H, CH$_2$), 6.82 (d, 1H, J = 8.3 Hz, ArH), 7.08 (s, 1H, ArH), 7.13 (d, 1H, J = 7.7 Hz, ArH), 7.23-7.32 (m, 1H, ArH), 7.50 (d, 2H, J = 8.1 Hz, 2xArH), 7.70 (d, 1H, J = 8.6 Hz, ArH), 8.17 (d, 2H, J = 8.1 Hz, 2xArH), 8.17 (s, 1H, ArH), 9.01 (s, 1H, ArH); $^{13}$C-NMR (CDCl$_3$, δ): 36.9, 55.9, 56.0, 64.8, 102.1, 106.0, 110.4, 113.9, 119.7, 124.9, 125.3, 126.3, 127.7 (2xC), 128.2, 131.4, 137.7, 140.8, 142.7, 144.5, 149.6, 150.1, 151.2, 152.9. MS-ESI m/z (% rel. Int.): 427.2 ([MH]$^+$, 100); HPLC: Method A, detection UV 254 nm, RT = 3.94 min, peak area 99.0%. |
| 171 | (structure) | Q 143 (210 mg, 0.54 mmol); POCl$_3$ (252 µL, 2.70 mmol); NEt$_3$ (113 µL, 0.81 mmol) in dry THF (2.5 mL) at 4° C. Then 5N aq. NaOH (1.8 mL) for 15 min at RT. | Chromatography RP18, H$_2$O:CH$_3$CN = 100:0 to 90:10 | sodium 3-((6,7-dimethoxy-1-propylisoquinolin-4-yl)methyl)quinolin-6-yl phosphate (87 mg); MW: 512.4; Yield: 48%; White solid; Mp (° C.): 197.1; $^1$H-NMR (CD$_3$OD, δ): 1.07 (t, 3H, J = 7.4 Hz, CH$_2$CH$_3$), 1.88 (m, 2H, J = 5.7 Hz, CH$_2$), 3.22 (t, 2H, J = 7.7 Hz, CH$_2$), 3.73 (s, 3H, OCH$_3$), 3.98 (s, 3H, OCH$_3$), 4.54 (s, 2H, CH$_2$), 7.22 (s, 1H, ArH), 7.48 (s, 1H, ArH), 7.61 (dd, 1H, J = 3.8 Hz, J = 9.3 Hz, ArH), 7.72 (d, 1H, J = 2.1 Hz, ArH), 7.83 (d, 1H, J = 9.1 Hz, ArH), 7.94 (s, 1H, ArH), 8.17 (s, 1H, ArH), 8.63 (s, 1H, ArH). $^{13}$C-NMR (CD$_3$OD, δ): 14.5, 24.3, 34.5, 37.9, 56.4, 103.9, 105.8, 115.1 (J = 4.4 Hz), 124.2, 126.9 (J = 6.6 Hz), 128.4, 129.0, 130.7, 133.4, 134.4, 136.0, 141.4, 143.4, 149.4, 151.5, 154.5, 155.5 (J = 5.8 Hz), 160.5. MS-ESI m/z (rel. int.): 469.3 ([MH]$^+$, 98); HPLC: Method A, detection UV 254 nm, RT = 3.16 min, peak area 97.0%. |

Scottish Biomedical Phosphodiesterase Assay (PDEs1-3, PDEs5-9 and PDE11)

The assay utilizes the IMAP technology, which is based on the high affinity binding of phosphate by immobilized metal coordination complexes on nanoparticles. The binding reagent complexes with phosphate groups on nucleotide monophosphate generated from cyclic nucleotides (cAMP/cGMP) through phosphodiesterases. With fluorescence polarization detection, binding causes a change in the rate of the molecular motion of the phosphate bearing molecule, and results in an increase in the fluorescence polarization value observed for the fluorescent label attached to the substrate.

Previously prepared stocks of the compounds in 100% DMSO were used at a concentration of 30 mM and all assays were performed in 3% DMSO (final). The compounds were tested at a concentration of 10 µM in duplicate against each phosphodiesterase. The percentage inhibition values were calculated based on the two data points.

Diaxonhit Phosphodiesterase Assay (PDE10A and PDE4D3)

The PDE assay is based on the homogenous time-resolved fluorescence resonance energy transfer (TR-FRET) technology (LANCE® from Perkin Elmer). This competition based assay is formatted using a cAMP specific antibody labeled with the dye, Alexa Fluor® 647, biotin-cAMP and streptavidin labeled with Europium (Eu-SA). As the complex of Eu-SA/biotin-cAMP/Alexa Fluor 647 labeled antibody is formed, an increase in signal is generated. When there is PDE activity, resulting in the degradation of the cyclic nucleotide, the complex is not formed and a decrease in signal is observed.

The phosphodiesterase assay was developed using the LANCE® cAMP kit (PerkinElmer). The assay buffer contained HBSS with 5 mM HEPES, 0.1% BSA, and 1.5 mM $MgCl_2$, pH 7.4. PDE10A (BPS Bioscience) was used at 200 pg/well (with a specific activity of 3200 pmole/min/µg with assay conditions: 10 mM Tris-HCl, pH 7.4, 10 mM $MgCl_2$, 1 mM $MnCl_2$, 200 µM cAMP, 2.5 kU 5' nucleotidase, 37° C., 20 min) and PDE4D3 (BPS Bioscience) was used at 100 pg/well (with a specific activity of 32713 pmole/min/µg with assay conditions: 10 mM Tris-HCl, pH 7.4, 10 mM $MgCl_2$, 1 mM $MnCl_2$, 200 µM cAMP, 2.5 kU 5' nucleotidase, 37° C., 20 min). The Biotin-cAMP tracer, supplied in 10 mmol/L Tris-HCl buffered (pH 8.0) salt solution with 1 mmol/L ethylenediaminetetraacetic acid (EDTA), 0.1% bovine serum albumin (BSA), and 0.05% sodium azide, is used at a dilution of 1/375. The assay detection mixture contained the LANCE Eu-W8044 labeled streptavidin 1/2250 (supplied in 50 mmol/L Tris-HCl buffered (pH 7.8) salt solution with 0.9% sodium chloride (NaCl), 0.1% BSA, and 0.05% sodium azide) and the Alexa Fluor® 647-anti cAMP antibody 1/200 (supplied in 50 mmol/L Tris-HCl buffered (pH 7.8) salt solution with 0.9% NaCl, 0.1% BSA, and 0.05% sodium azide). Chemical compounds were dissolved in DMSO (final concentration 2% (v/v)).

In a 384-well plate, 2 µL of the inhibitor and 3 µL PDE were added to the well, followed by the addition of 5 µl substrate biotinylated cAMP (1:5). After 60 min incubation at room temperature, 10 µL of assay detection mixture was added to the assay plate. After 1 h at room temperature, the signal was measured on EnVision™ (Perkin Elmer).

The compounds of the present invention have PDE10A inhibitory activities generally less than 10,000 nM (<10,000 nM). In one embodiment, they have activities less than 1000 nM (<1000 nM); in another embodiment less than 500 nM (<500 nM); in another embodiment less than 100 nM (<100 nM); in another embodiment less than 50 nM (<50 nM); and in another embodiment less than 20 nM (<20 nM)

The activities of specific compounds are shown in Table 8 below.

TABLE 8

| Compound N° | PDE10A $IC_{50}$ |
|---|---|
| 1 | 105 nM |
| 2 | 13 nM |
| 3 | 100 nM |
| 4 | 110 nM |
| 5 | 208 nM |
| 6 | 54 nM |
| 7 | 23 nM |
| 8 | 18 nM |
| 9 | 54 nM |
| 10 | 7.6 nM |
| 11 | 132 nM |
| 12 | 70 nM |
| 13 | 142 nM |
| 14 | 26 nM |
| 15 | 74 nM |
| 16 | 330 nM |
| 17 | 3556 nM |
| 18 | 238 nM |
| 19 | 95 nM |
| 20 | — |
| 21 | 46 nM |
| 22 | 1069 nM |
| 23 | 213 nM |
| 24 | 90 nM |
| 25 | 194 nM |
| 26 | 49 nM |
| 27 | 49 nM |
| 28 | 168 nM |
| 29 | >10000 nM |
| 30 | >10000 nM |
| 31 | 92 nM |
| 32 | 315 nM |
| 33 | 184 nM |
| 34 | 81 nM |
| 35 | 31 nM |
| 36 | 7558 nM |
| 37 | 287 nM |
| 38 | 3174 nM |
| 39 | 339 nM |
| 40 | 278 nM |
| 41 | 51 nM |
| 42 | 42 nM |
| 43 | 39 nM |
| 44 | 11 nM |
| 45 | 20 nM |
| 46 | 21 nM |
| 47 | 36 nM |
| 48 | 6.5 nM |
| 49 | 63 nM |
| 50 | 19 nM |
| 51 | 44 nM |
| 52 | 99 nM |
| 53 | 25 nM |
| 54 | 151 nM |
| 55 | 158 nM |
| 56 | 65 nM |
| 57 | 20 nM |
| 58 | 28 nM |
| 59 | 148 nM |
| 60 | 368 nM |
| 61 | 20 nM |
| 62 | 42 nM |
| 63 | — |
| 64 | 92 nM |
| 65 | 159 nM |
| 66 | 30 nM |
| 67 | 154 nM |
| 68 | 31 nM |
| 69 | 5.2 nM |
| 70 | 946 nM |
| 71 | >10000 nM |
| 72 | 32 nM |
| 73 | 1.4 nM |

TABLE 8-continued

| Compound N° | PDE10A IC$_{50}$ |
|---|---|
| 74 | 1.2 nM |
| 75 | 6.6 nM |
| 76 | 11 nM |
| 77 | 9.7 nM |
| 78 | 25 nM |
| 79 | 5.1 nM |
| 80 | 41 nM |
| 81 | 3.6 nM |
| 82 | 4.4 nM |
| 83 | 11 nM |
| 84 | 0.53 nM |
| 85 | 0.82 nM |
| 86 | 8.3 nM |
| 87 | 58 nM |
| 88 | 17 nM |
| 89 | 3.5 nM |
| 90 | 46 nM |
| 91 | 77 nM |
| 92 | 495 nM |
| 93 | 17 nM |
| 94 | 13 nM |
| 95 | 28 nM |
| 96 | 13 nM |
| 97 | 15 nM |
| 98 | 3.5 nM |
| 99 | 16 nM |
| 100 | 4.6 nM |
| 101 | 43 nM |
| 102 | 38 nM |
| 103 | 20 nM |
| 104 | 27 nM |
| 105 | 4.3 nM |
| 106 | 28 nM |
| 107 | 7.8 nM |
| 108 | 4.9 nM |
| 109 | 54 nM |
| 110 | 31 nM |
| 111 | 34 nM |
| 112 | 32 nM |
| 113 | 32 nM |
| 114 | 189 nM |
| 115 | 61 nM |
| 116 | 20 nM |
| 117 | 7.1 nM |
| 118 | 2.3 nM |
| 119 | 0.18 nM |
| 120 | 64 nM |
| 121 | 4.7 nM |
| 122 | 5.0 nM |
| 123 | 151 nM |
| 124 | 41 nM |
| 125 | 51 nM |
| 126 | 71 nM |
| 127 | 31 nM |
| 128 | 59 nM |
| 129 | 9.5 nM |
| 130 | 67 nM |
| 131 | 42 nM |
| 132 | 491 nM |
| 133 | 102 nM |
| 134 | 59 nM |
| 135 | 192 nM |
| 136 | 58 nM |
| 137 | 2.9 nM |
| 138 | 2.5 nM |
| 139 | 5.3 nM |
| 140 | 109 nM |
| 141 | 3107 nM |
| 142 | 19 nM |
| 143 | 9.4 nM |
| 144 | 6.5 nM |
| 145 | 1.6 nM |
| 146 | 4.7 nM |
| 147 | 64 nM |
| 148 | 87 nM |
| 149 | 49 nM |
| 150 | 7.9 nM |
| 151 | 28 nM |
| 152 | 13 nM |
| 153 | 148 nM |
| 154 | 95 nM |
| 155 | 18 nM |
| 156 | 0.71 nM |
| 157 | 13 nM |
| 158 | 204 nM |
| 159 | 0.42 nM |
| 160 | 15 nM |
| 161 | 6.0 nM |
| 162 | 13 nM |
| 163 | 19 nM |
| 164 | 21 nM |
| 165 | 71 nM |
| 166 | 28 nM |
| 167 | 8.6 nM |
| 168 | 5.6 nM |
| 169 | 4.5 nM |
| 170 | 20 nM |
| 171 | 62 nM |

The compounds have also been tested for their activities on PDEs1-9 and PDE11. The most active PDE10A inhibitors (<20 nM) are all selective (at least 120 to 10000-fold) vs PDEs1-3, PDEs5-9 and PDE11. They are also selective (at least 55 to 3000-fold) for PDE10A vs PDE4D3 (excepted the compound 162 that inhibits PDE4D3 with an IC$_{50}$ of 232 nM, compound 93 that inhibits PDE4D3 with an IC$_{50}$ of 398 nM, compound 83 that inhibits PDE4D3 with an IC$_{50}$ of 439 nM) and compound 169 that inhibits PDE4D3 with an IC$_{50}$ of 194 nM.

Each and every reference (whether patent publication or a scientific/journal publication) disclosed herein is incorporated by reference herein for all purposes.

The details of specific embodiments described in this invention are not be construed as limitations. Various equivalents and modifications may be made without departure from the essence and scope of this invention, and it is understood that such equivalent embodiments are part of this invention.

What is claimed is:

1. A compound of Formula (I)

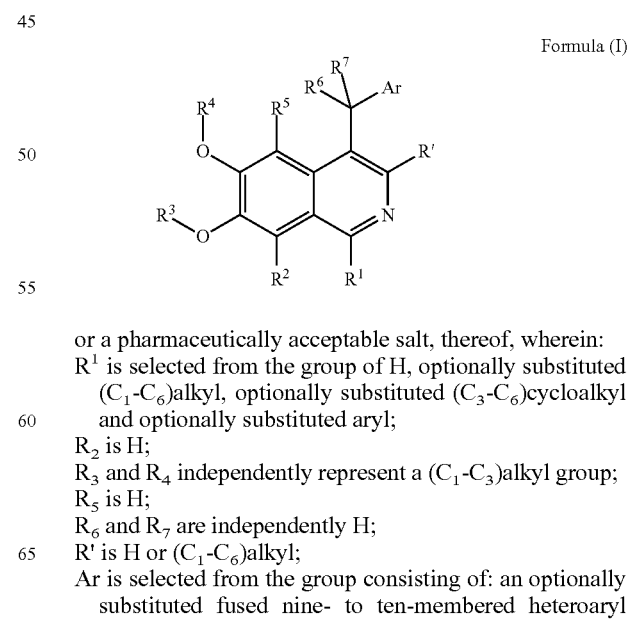

Formula (I)

or a pharmaceutically acceptable salt, thereof, wherein:
$R^1$ is selected from the group of H, optionally substituted $(C_1-C_6)$alkyl, optionally substituted $(C_3-C_6)$cycloalkyl and optionally substituted aryl;
$R_2$ is H;
$R_3$ and $R_4$ independently represent a $(C_1-C_3)$alkyl group;
$R_5$ is H;
$R_6$ and $R_7$ are independently H;
R' is H or $(C_1-C_6)$alkyl;
Ar is selected from the group consisting of: an optionally substituted fused nine- to ten-membered heteroaryl selected from the group consisting of: optionally substituted benzo-fused aryl, optionally substituted benzo-fused heteroaryl, optionally substituted benzo-fused heterocyclyl which is attached to the carbon bearing the $R^6$ and $R^7$ groups through a carbon atom of the benzene ring of said benzo-fused heterocyclyl, an optionally substituted pyrazolo-pyridyl, and optionally substituted benzo-fused cycloalkyl, wherein two optional substituents at adjacent positions of each of said optionally substituted fused nine- to ten-membered heteroaryl, optionally substituted benzo-fused aryl, optionally substituted benzo-fused heteroaryl, optionally substituted benzo-fused heterocyclyl, and optionally substituted benzo-fused cycloalkyl can be taken together with the atoms to which they are attached to form an aryl;

wherein said benzo-fused heterocyclyl is selected from the group consisting of indolinyl, chromanyl, and dihydro-2H-benzo[b][1,4]oxazinyl, each of which is unsubstituted or substituted at a nitrogen or carbon atom with at least one —($C_1$-$C_6$)alkyl.

2. The compound according to claim 1, wherein $R^3$ and $R^4$ are both methyl.

3. The compound according to claim 1, wherein the optionally substituted ($C_1$-$C_6$)alkyl of $R_1$ is selected from the group consisting of ethyl, n-propyl, n-butyl, and isobutyl; the optionally substituted aryl is optionally substituted phenyl; and the optionally substituted ($C_3$-$C_6$)cycloalkyl is selected from the group consisting of cyclopropyl and cyclohexyl.

4. The compound according to claim 1, wherein R' is selected from the group consisting of H and methyl.

5. The compound according to claim 1, wherein Ar is an optionally substituted pyrazolo-pyridyl that is attached to the carbon bearing the $R^6$ and $R^7$ groups through a carbon atom of the pyridine ring of said pyrazolo-pyridyl.

6. The compound according to claim 1, wherein Ar is an optionally substituted benzo-fused aryl and is napthyl, wherein said naphthyl is unsubstituted or substituted with a ($C_1$-$C_6$)alkoxy.

7. The compound according to claim 1, wherein Ar is an optionally substituted benzo-fused heteroaryl, which is attached to the carbon bearing the $R^6$ and $R^7$ groups either through a carbon atom of the benzene ring or through a carbon atom of the heteroaryl ring, and wherein two optional substituents at adjacent positions of said benzofused heteroaryl can be taken together with the atoms to which they are attached to form an aryl.

8. The compound according to claim 7, wherein said benzo-fused heteroaryl is selected from the group consisting of quinolinyl, benzofuranyl, benzopyrrolyl, benzothiophenyl, benzimidazolyl, dibenzofuranyl, carbazolyl, 4H-chromen-4-onyl, benzo[d]oxazolyl, and benzo[d]oxazol-2(3H)-onyl, each of which is unsubstituted or substituted with at least one substituent selected from the group consisting of halogen, haloalkyl, cyano, optionally substituted aryl, -aryl-($C_1$-$C_6$)alkyl-OH, -aryl-C(=O)—OH, -aryl-CN, -aryl-OH, —$NH_2$, —NH($C_1$-$C_6$)alkyl, N(($C_1$-$C_6$)alkyl))$_2$, hydroxy, hydroxy-($C_1$-$C_6$)alkyl, —O—($C_1$-$C_6$)alkyl-tetrazole, —O—($C_1$-$C_6$)alkyl-NH—C(=O)—($C_1$-$C_6$)alkyl, —O—($C_1$-$C_6$)alkyl-N(($C_1$-$C_6$)alkyl)-C(=O)—($C_1$-$C_6$)alkyl, —C(=O)—($C_1$-$C_6$)alkyl ($C_1$-$C_6$)alkoxy, ($C_1$-$C_6$)alkyl, —O—($C_1$-$C_6$)alkyl-pyridyl, —O—($C_1$-$C_6$)alkyl-C(=O)—O—($C_1$-$C_6$)alkyl, —O—($C_1$-$C_6$)alkyl-OH, —O—($C_1$-$C_6$)alkyl-C(=O)—$NH_2$, —O—($C_1$-$C_6$)alkyl-C(=O)—OH, —O—($C_1$-$C_6$)alkyl-C(=O)—NH—(($C_1$-$C_6$)alkyl), —O—($C_1$-$C_6$)alkyl-C(=O)—NH—(($C_1$-$C_6$)cycloalkyl), —NH—($C_1$-$C_6$)alkyl, —NHS(=O)$_2$$NH_2$, —NHS(=O)$_2$NH—($C_1$-$C_6$)alkyl, —NHS(=O)$_2$—($C_1$-$C_6$)alkyl, —N(($C_1$-$C_6$)alkyl)-S(=O)$_2$—($C_1$-$C_6$)alkyl, —NH—C(=O)—($C_1$-$C_6$)alkyl-OH, —NH—C(=O)—C(=O)—O—($C_1$-$C_6$)alkyl, —NH—C(=O)—C(=O)—$NH_2$, —NH—C(=O)—$NH_2$, —NH—C(=O)—($C_1$-$C_6$)alkyl-O—C(=O)—($C_1$-$C_6$)alkyl, —NH—C(=O)—($C_1$-$C_6$)alkyl, —P(=O)(OH)$_2$, —N-pyrrolidin-2-one, and —NH—($C_1$-$C_6$)alkyl-NH—C(=O)—($C_1$-$C_6$)alkyl.

9. The compound according to claim 1, wherein Ar is a benzo-fused cycloalkyl, which is attached to the carbon bearing the $R^6$ and $R^7$ groups through a carbon atom of the benzene ring of said benzo-fused cycloalkyl.

10. The compound according to claim 9, wherein said benzo-fused cycloalkyl is fluorenyl.

11. A compound selected from the group consisting of:
6,7-dimethoxy-4-(naphthalen-2-ylmethyl)isoquinoline hydrochloride 1,
3-((6,7-dimethoxyisoquinolin-4-yl)methyl)quinoline dihydrochloride 2,
4-(benzo[b]thiophen-5-ylmethyl)-6,7-dimethoxyisoquinoline hydrochloride 3,
4-((9H-fluoren-2-yl)methyl)-6,7-dimethoxyisoquinoline hydrochloride 4,
2-((6,7-dimethoxyisoquinolin-4-yl)methyl)quinoline dihydrochloride 5,
6-((6,7-dimethoxyisoquinolin-4-yl)methyl)quinoline dihydrochloride 6,
2-((6,7-dimethoxyisoquinolin-4-yl)methyl)quinolin-8-ol dihydrochloride 7,
3-((6,7-dimethoxyisoquinolin-4-yl)methyl)-7-methoxyquinoline dihydrochloride 8,
6,7-dimethoxy-4-((6-methoxynaphthalen-2-yl)methyl)isoquinoline hydrochloride 9,
4-(dibenzo[b,d]furan-2-ylmethyl)-6,7-dimethoxyisoquinoline hydrochloride 10,
6,7-dimethoxy-4-((1-methylindolin-5-yl)methyl)isoquinoline hydrochloride 11,
7-((6,7-dimethoxyisoquinolin-4-yl)methyl)-4-methyl-3,4-dihydro-2H-benzo[b][1,4]oxazine hydrochloride 12,
3-((6,7-dimethoxyisoquinolin-4-yl)methyl)-N,N-dimethylquinolin-2-amine dihydrochloride 13,
3-((6,7-dimethoxyisoquinolin-4-yl)methyl)-9-ethyl-9H-carbazole hydrochloride 14,
4-((1H-benzo[d]imidazol-5-yl)methyl)-6,7-dimethoxyisoquinoline dihydrochloride 15,
4-((4-chloro-1-ethyl-1H-pyrazolo[3,4-b]pyridin-5-yl)methyl)-6,7-dimethoxyisoquinoline dihydrochloride 16,
4-((4-ethoxy-1-ethyl-1H-pyrazolo[3,4-b]pyridin-5-yl)methyl)-6,7-dimethoxyisoquinoline dihydrochloride 17,
5-((6,7-dimethoxyisoquinolin-4-yl)methyl)-1-ethyl-1H-pyrazolo[3,4-b]pyridin-4-ol dihydrochloride 18,
2-chloro-3-((6,7-dimethoxyisoquinolin-4-yl)methyl)quinoline dihydrochloride 19,
3-((6,7-dimethoxyisoquinolin-4-yl)methyl)quinolin-2-ol hydrochloride 20,
2-((6,7-dimethoxyisoquinolin-4-yl)methyl)-8-methoxyquinoline dihydrochloride 21,
6,7-dimethoxy-3-methyl-4-(naphthalen-2-ylmethyl)isoquinoline hydrochloride 22,
2-((6,7-dimethoxyisoquinolin-4-yl)methyl)-8-(pyridin-4-ylmethoxy)quinoline trihydrochloride 23,
2-((6,7-dimethoxyisoquinolin-4-yl)methyl)-8-(pyridin-3-ylmethoxy)quinoline trihydrochloride 24,
6,7-dimethoxy-1-methyl-4-(naphthalen-2-ylmethyl)isoquinoline hydrochloride 25,
3-((6,7-dimethoxy-1-methylisoquinolin-4-yl)methyl)quinoline dihydrochloride 26, 2-((6,7-dimethoxyisoquinolin-4-yl)methyl)-8-ethoxyquinoline dihydrochloride 27,
3-((6,7-diethoxyisoquinolin-4-yl)methyl)quinoline dihydrochloride 28,
3-((6-ethoxy-7-methoxyisoquinolin-4-yl)methyl)quinoline dihydrochloride 31,
2-((6,7-dimethoxyisoquinolin-4-yl)methyl)-8-propoxyquinoline dihydrochloride 32,
4-(dibenzo[b,d]furan-2-ylmethyl)-6,7-dimethoxy-1-methylisoquinoline hydrochloride 33,
4-((2,2-dimethylchroman-6-yl)methyl)-6,7-dimethoxyisoquinoline hydrochloride 34,
4-(dibenzo[b,d]furan-2-ylmethyl)-6,7-dimethoxyisoquinoline 2-oxide 35,
4-(dibenzo[b,d]furan-2-ylmethyl)-6-ethoxy-7-methoxyisoquinoline hydrochloride 37,
4-(dibenzo[b,d]furan-2-ylmethyl)-1-ethyl-6,7-dimethoxyisoquinoline hydrochloride 39,
4-(dibenzo[b,d]furan-2-ylmethyl)-6,7-dimethoxy-1-propylisoquinoline hydrochloride 40,
ethyl 2-((2-((6,7-dimethoxyisoquinolin-4-yl)methyl)quinolin-8-yl)oxy)acetate dihydrochloride 41,
2-((2-((6,7-dimethoxyisoquinolin-4-yl)methyl)quinolin-8-yl)oxy)ethanol dihydrochloride 42,
3-((6,7-dimethoxy-3-methylisoquinolin-4-yl)methyl)quinoline dihydrocloride 43,
3-((6,7-dimethoxy-1-propylisoquinolin-4-yl)methyl)quinoline dihydrochloride 44,
2-((6,7-dimethoxy-1-propylisoquinolin-4-yl)methyl)quinolin-8-ol dihydrochloride 45,
2-((2-((6,7-dimethoxyisoquinolin-4-yl)methyl)quinolin-8-yl)oxy)acetamide 46,
3-((6,7-dimethoxy-1-propylisoquinolin-4-yl)methyl)quinolin-2-ol dihydrochloride 47,
6-((6,7-dimethoxyisoquinolin-4-yl)methyl)-2-methylquinoline dihydrochloride 48,
3-((6,7-dimethoxy-1-propylisoquinolin-4-yl)methyl)-6-methoxyquinolin-2-ol dihydrochloride 49,
3-((1-ethyl-6,7-dimethoxyisoquinolin-4-yl)methyl)quinoline dihydrochloride 50,
3-((1-ethyl-6,7-dimethoxyisoquinolin-4-yl)methyl)-6-methoxyquinolin-2-ol dihydrochloride 51,
3-((6,7-dimethoxy-1-propylisoquinolin-4-yl)methyl)-6-ethoxyquinolin-2-ol dihydrochloride 52,
3-((6,7-dimethoxyisoquinolin-4-yl)methyl)-6-methoxyquinolin-2-ol dihydrochloride 53,
3-((6,7-dimethoxy-1-propylisoquinolin-4-yl)methyl)-6-methylquinolin-2-ol dihydrochloride 54,
2-((3-((6,7-dimethoxy-1-propylisoquinolin-4-yl)methyl)-6-methoxyquinolin-2-yl)oxy)acetonitrile 55,
N-(2-((3-((6,7-dimethoxy-1-propylisoquinolin-4-yl)methyl)-6-methoxyquinolin-2-yl)oxy)ethyl)acetamide dihydrochloride 56,
6-((6,7-dimethoxy-1-propylisoquinolin-4-yl)methyl)-2-methylquinoline dihydrochloride 57,
6-((1-ethyl-6,7-dimethoxyisoquinolin-4-yl)methyl)-2-methylquinoline dihydrochloride 58,
6-((6,7-dimethoxy-1-phenylisoquinolin-4-yl)methyl)-2-methylquinoline dihydrochloride 59,
6-(1-cyclohexyl-6,7-dimethoxyisoquinolin-4-yl)methyl)-2-methylquinoline dihydrochloride 60,
3-((1-isobutyl-6,7-dimethoxyisoquinolin-4-yl)methyl)quinoline dihydrochloride 61,
3-((1-cyclopropyl-6,7-dimethoxyisoquinolin-4-yl)methyl)quinoline dihydrochloride 62,
3-((6,7-dimethoxy-1-phenylisoquinolin-4-yl)methyl)quinoline dihydrochloride 63,
3-((1-butyl-6,7-dimethoxyisoquinolin-4-yl)methyl)quinoline dihydrochloride 64,
4-(isoquinolin-3-ylmethyl)-6,7-dimethoxy-1-propylisoquinoline dihydrochloride 65,
4-(isoquinolin-3-ylmethyl)-6,7-dimethoxyisoquinoline dihydrochloride 66,
6-((1-butyl-6,7-dimethoxyisoquinolin-4-yl)methyl)-2-methylquinoline dihydrochloride 67,
6-((1-isobutyl-6,7-dimethoxyisoquinolin-4-yl)methyl)-2-methylquinoline dihydrochloride 68,
3-((6,7-dimethoxy-1-propylisoquinolin-4-yl)methyl)-7-methylquinoline dihydrochloride 69,
3-((1-butyl-6,7-dimethoxyisoquinolin-4-yl)methyl)-7-methylquinoline 70,
1-ethyl-4-(isoquinolin-3-ylmethyl)-6,7-dimethoxyisoquinoline dihydrochloride 72,
2-((2-((6,7-dimethoxy-1-propylisoquinolin-4-yl)methyl)quinolin-8-yl)oxy)acetamide dihydrochloride 73,
3-((6,7-dimethoxyisoquinolin-4-yl)methyl)-7-methylquinoline 74,
2-((2-((6,7-dimethoxy-1-propylisoquinolin-4-yl)methyl)quinolin-8-yl)oxy)ethanol 75,
N-(2-((3-((6,7-dimethoxy-1-propylisoquinolin-4-yl)methyl)-6-methoxyquinolin-2-yl)amino)ethyl)acetamide dihydrochloride 76,
3-((6,7-dimethoxy-1-propylisoquinolin-4-yl)methyl)-N-ethyl-6-methoxyquinolin-2-amine dihydrochloride 77,
6-((1-cyclopropyl-6,7-dimethoxyisoquinolin-4-yl)methyl)-2-methylquinoline dihydrochloride 78,
3-((6,7-dimethoxyisoquinolin-4-yl)methyl)-6-methyl-4H-chromen-4-one hydrochloride 79,
3-((6,7-dimethoxyisoquinolin-4-yl)methyl)-4H-chromen-4-one hydrochloride 80,
6-((6,7-dimethoxyisoquinolin-4-yl)methyl)-3-methylbenzo[d]oxazol-2(3H)-one hydrochloride 81, and
6-((6,7-dimethoxy-1-propylisoquinolin-4-yl)methyl)-3-methylbenzo[d]oxazol-2(3H)-one dihydrochloride 82,
2-((1-ethyl-6,7-dimethoxyisoquinolin-4-yl)methyl)quinolin-8-ol 83,
N-(2-((1-ethyl-6,7-dimethoxyisoquinolin-4-yl)methyl)quinolin-8-yl)sulfamide 84,
N-(2-((1-propyl-6,7-dimethoxyisoquinolin-4-yl)methyl)quinolin-8-yl)sulfamide 85,
N-(2-((1-ethyl-6,7-dimethoxyisoquinolin-4-yl)methyl)quinolin-8-yl)methanesulfonamide 86,
1-(2-((1-ethyl-6,7-dimethoxyisoquinolin-4-yl)methyl)quinolin-8-yl)urea 87,
N-(2-((1-ethyl-6,7-dimethoxyisoquinolin-4-yl)methyl)quinolin-8-yl)acetamide 88,
N-(2-((1-ethyl-6,7-dimethoxyisoquinolin-4-yl)methyl)quinolin-8-yl)ethanesulfonamide 89,
2-((1-ethyl-6,7-dimethoxyisoquinolin-4-yl)methyl)quinoline-8-carbonitrile 90,
2-((1-ethyl-6,7-dimethoxyisoquinolin-4-yl)methyl)quinoline-8-carboxamide 91,
ethyl 2-((2-((1-ethyl-6,7-dimethoxyisoquinolin-4-yl)methyl)quinolin-8-yl)amino)-2-oxoacetate 92,
$N^1$-(2-((1-ethyl-6,7-dimethoxyisoquinolin-4-yl)methyl)quinolin-8-yl)oxalamide 93,
N-((2-((1-ethyl-6,7-dimethoxyisoquinolin-4-yl)methyl)quinolin-8-yl)methyl)sulfamide 94,
3-((1-ethyl-6,7-dimethoxyisoquinolin-4-yl)methyl)quinolin-6-ol 95,
3-((1-ethyl-6,7-dimethoxyisoquinolin-4-yl)methyl)quinolin-6-amine 96,
1-(3-((1-ethyl-6,7-dimethoxyisoquinolin-4-yl)methyl)quinolin-6-yl)pyrrolidin-2-one 97, $N^1$-(3-((1-ethyl-6,7-dimethoxyisoquinolin-4-yl)methyl)
quinolin-6-yl)oxalamide 98,
N-(3-((1-ethyl-6,7-dimethoxyisoquinolin-4-yl)methyl)
quinolin-6-yl)methanesulfonamide 99,
N-(3-((1-ethyl-6,7-dimethoxyisoquinolin-4-yl)methyl)
quinolin-6-yl)sulfamide 100,
N-(3-((1-ethyl-6,7-dimethoxyisoquinolin-4-yl)methyl)
quinolin-6-yl)-N-ethylmethanesulfonamide 101,
3-((6,7-dimethoxyisoquinolin-4-yl)methyl)-6-fluoro-4H-chromen-4-one hydrochloride 102,
6-chloro-3-((6,7-dimethoxyisoquinolin-4-yl)methyl)-4H-chromen-4-one hydrochloride 103,
6,8-dichloro-3-((6,7-dimethoxyisoquinolin-4-yl)methyl)-4H-chromen-4-one hydrochloride 104,
6-((6,7-dimethoxy-1-methylisoquinolin-4-yl)methyl)-2-methylquinoline dihydrochloride 105,
5-((6,7-dimethoxyisoquinolin-4-yl)methyl)benzo[d]oxazol-2(3H)-one hydrochloride 106,
5-((6,7-dimethoxyisoquinolin-4-yl)methyl)-3-ethylbenzo[d]oxazol-2(3H)-one hydrochloride 107,
2-((2-((6,7-dimethoxy-1-propylisoquinolin-4-yl)methyl)quinolin-8-yl)oxy)acetic acid dihydrochloride 108,
3-((6,7-dimethoxy-1-propylisoquinolin-4-yl)methyl)-6-fluoro-4H-chromen-4-one hydrochloride 109,
3-((6,7-dimethoxy-1-propylisoquinolin-4-yl)methyl)-6-methyl-4H-chromen-4-one hydrochloride 110,
6-((6,7-dimethoxyisoquinolin-4-yl)methyl)benzo[d]oxazol-2(3H)-one hydrochloride 111,
6-((6,7-dimethoxyisoquinolin-4-yl)methyl)-3-ethylbenzo[d]oxazol-2(3H)-one hydrochloride 112,
3-((6,7-dimethoxyisoquinolin-4-yl)methyl)-N-ethyl-6-methoxyquinolin-2-amine dihydrochloride 113,
5-((6,7-dimethoxyisoquinolin-4-yl)methyl)-2-phenyl-benzo[d]oxazole 114,
methyl 4-(5-((6,7-dimethoxyisoquinolin-4-yl)methyl)benzo[d]oxazol-2-yl)benzoate 115,
2-((2-((1-ethyl-6,7-dimethoxyisoquinolin-4-yl)methyl)quinolin-8-yl)oxy)acetamide 116,
3-((6,7-dimethoxy-1-methylisoquinolin-4-yl)methyl)-7-methylquinoline 117,
sodium 3-((2-((6,7-dimethoxy-1-propylisoquinolin-4-yl)methyl)quinolin-8-yl)oxy)propanoate 118,
N-(2-((1-(methoxymethyl)-6,7-dimethoxyisoquinolin-4-yl)methyl)quinolin-8-yl)sulfamide 119,
2-((2-((6,7-dimethoxy-1-methylisoquinolin-4-yl)methyl)quinolin-8-yl)oxy)acetamide 120,
8-((1H-tetrazol-5-yl)methoxy)-2-((6,7-dimethoxy-1-propylisoquinolin-4-yl)methyl)quinoline 121,
sodium 3-((2-((1-ethyl-6,7-dimethoxyisoquinolin-4-yl)methyl)quinolin-8-yl)oxy)propanoate 122,
2-((1-cyclopropyl-6,7-dimethoxyisoquinolin-4-yl)methyl)quinolin-8-ol 123,
2-((6,7-dimethoxy-3-methylisoquinolin-4-yl)methyl)quinolin-8-ol 124,
2-((2-((6,7-dimethoxy-1-propylisoquinolin-4-yl)methyl)quinolin-8-yl)oxy)-N-methylacetamide 125,
N-cyclopropyl-2-((2-((6,7-dimethoxy-1-propylisoquinolin-4-yl)methyl)quinolin-8-yl)oxy)acetamide 126,
8-((1H-tetrazol-5-yl)methoxy)-2-((1-ethyl-6,7-dimethoxyisoquinolin-4-yl)methyl)quinoline 127,
ethyl 2-((2-((1-ethyl-6,7-dimethoxyisoquinolin-4-yl)methyl)quinolin-8-yl)oxy)acetate 128,
3-((6,7-dimethoxy-1-propylisoquinolin-4-yl)methyl)-6-methoxy-N-methylquinolin-2-amine 129,
2-((2-((1-cyclopropyl-6,7-dimethoxyisoquinolin-4-yl)methyl)quinolin-8-yl)oxy)acetamide 130,
2-((6,7-dimethoxy-1-methylisoquinolin-4-yl)methyl)quinolin-8-ol 131,
2-((6,7-dimethoxy-1-propylisoquinolin-4-yl)methyl)-5-(trifluoromethyl)quinolin-8-ol 132,
2-((2-((6,7-dimethoxy-1-propylisoquinolin-4-yl)methyl)-5-(trifluoromethyl)quinolin-8-yl)oxy)acetamide 133,
2-((2-((6,7-dimethoxy-1-propylisoquinolin-4-yl)methyl)quinolin-8-yl)oxy)-2-methylpropanamide 134,
2-((2-((1-ethyl-6,7-dimethoxyisoquinolin-4-yl)methyl)quinolin-8-yl)oxy)ethanol 135,
N-(2-((2-((6,7-dimethoxy-1-propylisoquinolin-4-yl)methyl)quinolin-8-yl)oxy)ethyl)acetamide 136,
3-((6,7-dimethoxyisoquinolin-4-yl)methyl)quinolin-6-ol 137,
2-((3-((6,7-dimethoxyisoquinolin-4-yl)methyl)quinolin-6-yl)oxy)acetamide 138,
2-((2-((6,7-dimethoxy-1-propylisoquinolin-4-yl)methyl)quinolin-8-yl)oxy)acetamide 139,
2-((6,7-dimethoxy-1-propylisoquinolin-4-yl)methyl)quinolin-8-yl acetate 140,
(4-(5-((6,7-dimethoxyisoquinolin-4-yl)methyl)benzo[d]oxazol-2-yl)phenyl)methanol 141,
(4-(5-((6,7-dimethoxyisoquinolin-4-yl)methyl)benzo[d]oxazol-2-yl)phenyl)methanol 142,
3-((6,7-dimethoxy-1-propylisoquinolin-4-yl)methyl)quinolin-6-ol 143,
2-((3-((6,7-dimethoxy-1-propylisoquinolin-4-yl)methyl)quinolin-6-yl)oxy)acetamide 144,
potassium 4-(5-((6,7-dimethoxyisoquinolin-4-yl)methyl)benzo[d]oxazol-2-yl)benzoate 145,
4-(5-((6,7-dimethoxyisoquinolin-4-yl)methyl)benzo[d]oxazol-2-yl)benzoic acid 146,
5-((6,7-dimethoxy-1-propylisoquinolin-4-yl)methyl)benzo[d]oxazol-2(3H)-one 147,
2-(5-((6,7-dimethoxy-1-propylisoquinolin-4-yl)methyl)-2-oxobenzo[d]oxazol-3(2H)-yl)acetamide 148,
4-(5-((6,7-dimethoxyisoquinolin-4-yl)methyl)benzo[d]oxazol-2-yl)aniline 149,
2-((3-((6,7-dimethoxyisoquinolin-4-yl)methyl)quinolin-6-yl)oxy)acetic acid 150,
(3-(5-((6,7-dimethoxyisoquinolin-4-yl)methyl)benzo[d]oxazol-2-yl)phenyl)methanol 151,
2-((6,7-dimethoxy-1-methylisoquinolin-4-yl)methyl)quinolin-8-amine 152,
4-(5-((6,7-dimethoxyisoquinolin-4-yl)methyl)benzo[d]oxazol-2-yl)benzonitrile 153,
(2-(5-((6,7-dimethoxyisoquinolin-4-yl)methyl)benzo[d]oxazol-2-yl)phenyl)methanol 154,
3-((6,7-dimethoxy-1-methylisoquinolin-4-yl)methyl)quinolin-6-ol 155,
(2-(6,7-dimethoxy-1-methyl-isoquinolin-4-ylmethyl)-quinolin-8-yl)-sulfamide 156,
2-((6,7-dimethoxyisoquinolin-4-yl)methyl)quinolin-8-amine 157,
2-((2-((6,7-dimethoxy-1-propylisoquinolin-4-yl)methyl)quinolin-8-yl)amino)-2-oxoethyl acetate 158,
(2-(6,7-dimethoxy-1-methyl-isoquinolin-4-ylmethyl)-quinolin-8-yl)-sulfamide 159,
N-(2-((6,7-dimethoxy-1-propylisoquinolin-4-yl)methyl)quinolin-8-yl)-2-hydroxyacetamide 160,
3-((6,7-dimethoxyisoquinolin-4-yl)methyl)-5-(trifluoromethyl)quinolin-6-ol 161,
3-((6,7-dimethoxyisoquinolin-4-yl)methyl)-5-(trifluoromethyl)quinolin-6-ol 162,
2-((6,7-dimethoxy-1-(methoxymethyl)isoquinolin-4-yl)methyl)quinolin-8-ol 163, 2-((2-((6,7-dimethoxy-1-(methoxymethyl)isoquinolin-4-yl)methyl)quinolin-8-yl)oxy)acetamide 164, Ethyl 2-((2-((6,7-dimethoxy-1-(methoxymethyl)isoquinolin-4-yl)methyl)quinolin-8-yl)oxy)acetate 165, 2-((2-((6,7-dimethoxy-1-(methoxymethyl)isoquinolin-4-yl)methyl)quinolin-8-yl)oxy)ethanol 166, 2-((6,7-dimethoxy-1-(methoxymethyl)isoquinolin-4-yl)methyl)quinolin-8-amine 167, 3-((6,7-dimethoxy-1-(methoxymethyl)isoquinolin-4-yl)methyl)quinolin-6-ol 168, 3-((6,7-dimethoxy-1-(methoxymethyl)isoquinolin-4-yl)methyl)-5-(trifluoromethyl)quinolin-6-ol 169, (4-(6-((6,7-dimethoxyisoquinolin-4-yl)methyl)benzo[d]oxazol-2-yl)phenyl)methanol 170, and sodium 3-((6,7-dimethoxy-1-propylisoquinolin-4-yl)methyl)quinolin-6-yl phosphate 171; or a pharmaceutically acceptable salt thereof.

12. A pharmaceutical composition comprising at least one compound of claim 1, or a pharmaceutically acceptable salt thereof, and at least one pharmaceutically acceptable carrier.

13. A method for inhibiting PDE10A in a mammal, comprising administering to said mammal in need thereof, a therapeutically effective amount of at least one compound of claim 1 or a pharmaceutically acceptable salt thereof.

* * * * *

UNITED STATES PATENT AND TRADEMARK OFFICE
CERTIFICATE OF CORRECTION

PATENT NO. : 9,200,016 B2
APPLICATION NO. : 14/097808
DATED : December 1, 2015
INVENTOR(S) : Bertrand Leblond et al.

It is certified that error appears in the above-identified patent and that said Letters Patent is hereby corrected as shown below:

On the title page

Item 54 in column 1, in "Title", lines 1-2, delete "6, 7-DIALKOXY-3-ISOQUINOLINE" and insert -- 6,7-DIALKOXY-3-ISOQUINOLINE --, therefor.

Item 56, in column 2, under "Other Publications", line 44, delete "3-formyl-2quinolones" and insert -- 3-formyl-2-quinolones --, therefor.

In the specification

In column 1, lines 1-2, delete "6, 7-DIALKOXY-3-ISOQUINOLINE" and insert -- 6,7-DIALKOXY-3-ISOQUINOLINE --, therefor.

In column 7, line 37, delete "hetorocyclyl," and insert -- heterocyclyl, --, therefor.

In column 7, line 42, delete "hetorocyclyl," and insert -- heterocyclyl, --, therefor.

In column 8, line 5, delete "hetorocyclyl," and insert -- heterocyclyl, --, therefor.

In column 8, line 10, delete "hetorocyclyl," and insert -- heterocyclyl, --, therefor.

In column 8, line 36, delete "24126B." and insert -- 24128B, --, therefor.

In column 8, line 36, delete "39008," and insert -- 39098, --, therefor.

In column 8, line 40, delete "31060A" and insert -- 31060A. --, therefor.

In column 9, line 44, delete "antracenyl," and insert -- anthracenyl, --, therefor.

In column 9, line 48, delete "a-naphthyl," and insert -- α-naphthyl, --, therefor.

In column 9, line 49, delete "antracenyl." and insert -- anthracenyl. --, therefor.

In column 11, line 15, delete "napthyl," and insert -- naphthyl, --, therefor.

In column 11, line 22, delete "benzofused" and insert -- benzo-fused --, therefor.

In column 11, line 29, delete "4-only" and insert -- 4-onyl --, therefor.

In column 11, line 49, delete "2(3H)-only" and insert -- 2(3H)-onyl --, therefor.

Signed and Sealed this
Twenty-sixth Day of April, 2016

Michelle K. Lee
*Director of the United States Patent and Trademark Office*

CERTIFICATE OF CORRECTION (continued)
U.S. Pat. No. 9,200,016 B2

In column 11, line 67, delete "—C(=O)—($C_1$-$C_6$)alkyl" and insert -- —C(=O)—($C_1$-$C_6$)alkyl, --, therefor.

In column 12, line 50, delete "hetorocyclyl," and insert -- heterocyclyl, --, therefor.

In column 12, line 54, delete "hetorocyclyl," and insert -- heterocyclyl, --, therefor.

In column 12, lines 62-66, delete " " and insert -- , --, therefor.
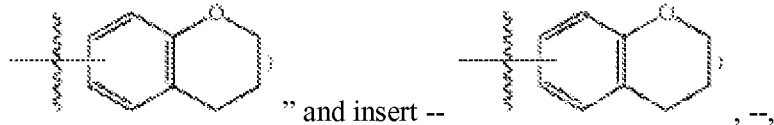

In column 14, line 49, delete "dihydrocloride" and insert -- dihydrochloride --, therefor.

In column 17, line 22, delete "2((2-" and insert -- 2-((2- --, therefor.

In column 18, line 59, delete "1)." and insert -- 1; see FIG. 1). --, therefor.

In column 22, line 54, delete "($R_1$=H)" and insert -- ($R_1$ = H) --, therefor.

In columns 25-26, line 6, delete "MeOH, MeOH," and insert -- MeOH, --, therefor.

In column 27, line 60, delete "MeOH, MeOH," and insert -- MeOH, --, therefor.

In column 29, line 31, delete "60&" and insert -- 60% --, therefor.

In columns 37-38, line 3 (Structures), delete "ii" and insert -- iii --, therefor.

In columns 37-38, line 4 (Structures), delete "xii" and insert -- xiii --, therefor.

In columns 37-38, line 4 (Structures), delete "xii" and insert -- xiv --, therefor.

In columns 37-38, line 4 (Structures), delete "xii" and insert -- xv --, therefor.

In columns 37-38, line 6 (Structures), delete "10 min." and insert -- 10 min, --, therefor.

In columns 37-38, line 9 (Structures), delete "ro" and insert -- to --, therefor.

In column 44, line 37, delete "1-1'-Carbonyldiimidazole," and insert -- 1,1'-Carbonyldiimidazole, --, therefor.

In column 44, line 45, delete "Et: 50%" and insert -- Et: 127 50% --, therefor.

In columns 45-46, line 10 (Structures), delete "iii)" and insert -- vi) --, therefor.

In columns 45-46, line 10 (Structures), delete "iii)" and insert -- vii) --, therefor.

In column 53, line 65, delete "fonic" and insert -- folic --, therefor.

In column 55, line 54, delete "excipinent)" and insert -- excipient) --, therefor.

In column 57, line 29, delete "occlusive" and insert -- occlusive. --, therefor.

In column 59, line 48, delete "human" and insert -- human. --, therefor.

In column 60, line 26, delete "temperal" and insert -- temporal --, therefor.

In column 61, line 16, delete "temperal" and insert -- temporal --, therefor.

In column 62, line 26, delete "Stargard's" and insert -- Stargardt's --, therefor.

In column 62, line 59, delete "Stargard's" and insert -- Stargardt's --, therefor.

CERTIFICATE OF CORRECTION (continued)
U.S. Pat. No. 9,200,016 B2

In column 63, line 25, delete "Stargard's" and insert -- Stargardt's --, therefor.

In column 64, line 17, delete "24178a," and insert -- 24178A, --, therefor.

In columns 65-66, line 7 (TABLE 1), delete "([MHr]$^+$" and insert -- ([MH]$^+$, --, therefor.

In columns 65-66, line 9 (TABLE 1), delete "AlCl3" and insert -- AlCl$_3$ --, therefor.

In columns 65-66, line 12 (TABLE 1), delete "7.54," and insert -- 7.54 --, therefor.

In columns 67-68, line 18 (TABLE 1-continued), delete "FOMRULA" and insert -- FORMULA --, therefor.

In columns 67-68, line 24 (TABLE 1-continued), delete "(CDCl$_3$,δ):" and insert -- (CDCl$_3$, δ): --, therefor.

In columns 69-70, line 14 (TABLE 1-continued), delete "(cyclopropy1" and insert -- (cyclopropyl --, therefor.

In columns 69-70, line 19 (TABLE 1-continued), delete "337.46:" and insert -- 337.46; --, therefor.

In columns 69-70, line 20 (TABLE 1-continued), delete "Yield;" and insert -- Yield: --, therefor.

In columns 71-72, line 8 (TABLE 1-continued), delete "3,4-diethoxybenzaehyde" and insert -- 3,4-diethoxybenzaldehyde --, therefor.

In columns 71-72, line 28 (TABLE 1-continued), delete "Oi1;" and insert -- Oil; --, therefor.

In columns 73-74, line 12 (TABLE 1-continued), delete "6h.." and insert -- 6h. --, therefor.

In columns 73-74, line 12 (TABLE 1-continued), delete "ArH)" and insert -- ArH). --, therefor.

In columns 75-76, line 9 (TABLE 2), delete "CH3)," and insert -- CH$_3$), --, therefor.

In columns 75-76, line 12 (TABLE 2), delete "N-(1-(3,4-dimethoxyphenypethyl)" and insert -- N-(1-(3,4-dimethoxyphenyl)ethyl) --, therefor.

In columns 75-76, line 14 (TABLE 2), delete "2xOCH2" and insert -- 2xOCH$_2$ --, therefor.

In columns 77-78, line 16 (TABLE 2-continued), delete "(3,4-dimethoxypheny1)" and insert -- (3,4-dimethoxyphenyl) --, therefor.

In columns 77-78, line 19 (TABLE 2-continued), delete "CH2)," and insert -- CH$_2$), --, therefor.

In columns 77-78, line 19 (TABLE 2-continued), delete "CH2)," and insert -- CH$_2$), --, therefor.

In columns 77-78, line 22 (TABLE 2-continued), delete "(5,33 g);" and insert -- (5.33 g); --, therefor.

In columns 79-80, line 16 (TABLE 2-continued), delete "98% ;" and insert -- 98%; --, therefor.

In columns 79-80, line 16 (TABLE 2-continued), delete "Oil ;" and insert -- Oil; --, therefor.

In columns 81-82, line 10 (TABLE 2-continued), delete "( q," and insert -- (q, --, therefor.

In columns 81-82, line 16 (TABLE 2-continued), delete "(CDCl$_3$, 6):" and insert -- (CDCl$_3$, δ): --, therefor.

In columns 81-82, line 16 (TABLE 2-continued), delete "53.3 ,62.3" and insert -- 53.3, 62.3 --, therefor.

CERTIFICATE OF CORRECTION (continued)
U.S. Pat. No. 9,200,016 B2

In columns 81-82, line 19 (TABLE 2-continued), delete "267,32;" and insert -- 267.32; --, therefor.

In columns 81-82, line 26 (TABLE 2-continued), delete "CDCl$_3$, δ):" and insert -- (CDCl$_3$, δ): --, therefor.

In columns 87-88, line 4 (TABLE 3-continued), delete "([MH]$^{+1}$," and insert -- ([MH]$^{+1}$, --, therefor.

In column 89, line 6, delete "Using" and insert -- Using Cs$_2$CO$_3$ or K$_2$CO$_3$ (compounds 23, 27, 32, 41, 46, 55, 73, --, therefor.

In columns 91-92, line 13 (TABLE 4), delete "(185 pL," and insert -- (185 μL, --, therefor.

In columns 91-92, line 30 (TABLE 4), delete "mmole);" and insert -- mmol); --, therefor.

In columns 93-94, line 11 (TABLE 4-continued), delete "mothyl)" and insert -- methyl) --, therefor.

In columns 93-94, line 19 (TABLE 4-continued), delete "mothyl)" and insert -- methyl) --, therefor.

In columns 93-94, line 19 (TABLE 4-continued), delete "othyl)" and insert -- ethyl) --, therefor.

In column 98, lines 37-38, delete "57032a, ANP 53184a," and insert -- 57032A, ANP 53184A, --, therefor.

In column 98, line 40, delete "57032a, ANP 53184a," and insert -- 57032A, ANP 53184A, --, therefor.

In columns 99-100, line 5 (TABLE 5), delete "2xCH2)," and insert -- 2xCH$_2$), --, therefor.

In columns 99-100, line 5 (TABLE 5), delete "CH2)," and insert -- CH$_2$), --, therefor.

In columns 99-100, line 7 (TABLE 5), delete "142.20 ;" and insert -- 142.20; --, therefor.

In columns 99-100, line 7 (TABLE 5), delete "([MH]$^{+1}$" and insert -- ([MH]$^{+1}$, --, therefor.

In columns 99-100, line 11 (TABLE 5), delete "(63 pL," and insert -- (63 μL, --, therefor.

In columns 101-102, line 31 (TABLE 5), delete "([MH]$^{+1}$," and insert -- ([MH]$^{+1}$, --, therefor.

In columns 101-102, line 32 (TABLE 5), delete "99.6%.?" and insert -- 99.6%. --, therefor.

In columns 103-104, line 4 (TABLE 5-continued), delete "N-phenylbis-" and insert -- N-phenyl bis- --, therefor.

In columns 103-104, line 11 (TABLE 5-continued), delete "97.5%" and insert -- 97.5%. --, therefor.

In columns 103-104, line 13 (TABLE 5-continued), delete "Rf:" and insert -- R$_f$: --, therefor.

In columns 103-104, line 25 (TABLE 5-continued), delete "5 00 (s 2H," and insert -- 5.00 (s, 2H, --, therefor.

In columns 103-104, line 25 (TABLE 5-continued), delete "7 33" and insert -- 7.33 --, therefor.

In column 108, line 22, delete "table 7)" and insert -- table 7). --, therefor.

In columns 111-112, line 23 (TABLE 6-continued), delete "$^1$H- NMR" and insert -- $^1$H-NMR --, therefor.

In columns 113-114, line 15 (TABLE 6-continued), delete "Yield :" and insert -- Yield: --, therefor.

In columns 113-114, line 16 (TABLE 6-continued), delete "$^1$H- NMR" and insert -- $^1$H-NMR --, therefor.

In columns 113-114, line 18 (TABLE 6-continued), delete "TR" and insert -- RT --, therefor.

In columns 115-116, line 12 (TABLE 6-continued), delete "(100 pL," and insert -- (100 μL, --, therefor.

In column 117, line 4, delete "46118a" and insert -- 46118A --, therefor.

In column 117, line 20, delete "50188a" and insert -- 50188A --, therefor.

In columns 119-120, line 10 (Table 7), delete "(965 mg) ;" and insert -- (965 mg); --, therefor.

In columns 125-126, line 11 (Structure), delete " 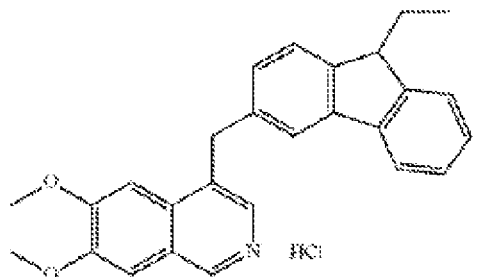 " and insert -- 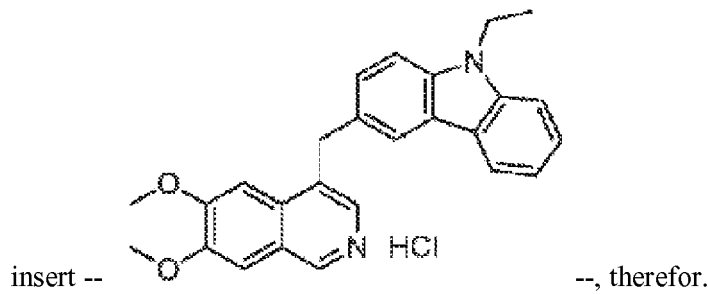 --, therefor.

In columns 125-126, line 20 (Table 7-continued), delete "129%;" and insert -- 29%; --, therefor.

In columns 127-128, line 9 (Table 7-continued), delete "383.4, 385.4" and insert -- 383.4/385.4 --, therefor.

In columns 129-130, line 4 (Table 7-continued), delete "$d^6$," and insert -- $d_6$, --, therefor.

In columns 129-130, lines 13-14 (Table 7-continued), delete "7.68- .75" and insert -- 7.68-7.75 --, therefor.

In columns 129-130, lines 22-23 (Table 7-continued), delete "7.80- .82" and insert -- 7.80-7.82 --, therefor.

In columns 129-130, line 32 (Table 7-continued), delete "CD$_3$OD," and insert -- (CD$_3$OD, --, therefor.

In columns 133-134, line 13 (Table 7-continued), delete "CH2)," and insert -- CH$_2$), --, therefor.

In columns 133-134, line 15 (Table 7-continued), delete "(CD$_3$OD,δ ):" and insert -- (CD$_3$OD, δ): --, therefor.

In columns 133-134, line 26 (Table 7-continued), delete "R$_f$:." and insert -- R$_f$: --, therefor.

In columns 135-136, line 24 (Table 7-continued), delete "CH2)," and insert -- CH$_2$), --, therefor.

In columns 137-138, line 13 (Table 7-continued), delete "1.32 (t, 3H, Hz, 3H J = 6.7 Hz CH$_3$)," and insert -- 1.32 (t, 3H, J = 6.7 Hz, CH$_3$), --, therefor.

In columns 139-140, line 5 (Table 7-continued), delete "1 93-1 98" and

CERTIFICATE OF CORRECTION (continued)
U.S. Pat. No. 9,200,016 B2 insert -- 1.93-1.98 --, therefor.

In columns 139-140, line 6 (Table 7-continued), delete "ArH): 7.45- 7.58" and insert -- ArH), 7.45-7.58 --, therefor.

In columns 139-140, line 7 (Table 7-continued), delete "1H" and insert -- 1H, --, therefor.

In columns 139-140, line 27 (Table 7-continued), delete "dihydroclorìde" and insert -- dihydrochloride --, therefor.

In columns 145-146, line 6 (Table 7-continued), delete "CH2)," and insert -- $CH_2$), --, therefor.

In columns 147-148, line 20 (Table 7-continued), delete "ethypacetamide" and insert -- ethyl)acetamide --, therefor.

In columns 149-150, line 6 (Table 7-continued), delete "4.10," and insert -- 4.10 --, therefor.

In columns 149-150, line 7 (Table 7-continued), delete "37.76" and insert -- 7.76 --, therefor.

In columns 149-150, line 13 (Table 7-continued), delete "$R_f$." and insert -- $R_f$: --, therefor.

In columns 149-150, line 15 (Table 7-continued), delete "(s" and insert -- (s, --, therefor.

In columns 149-150, line 17 (Table 7-continued), delete "(CD3OD," and insert -- ($CD_3OD$, --, therefor.

In columns 151-152, line 5 (Table 7-continued), delete "δ)," and insert -- δ): --, therefor.

In columns 151-152, line 16 (Table 7-continued), delete "(t," and insert -- (t, 1H, --, therefor.

In columns 153-154, line 5 (Table 7-continued), delete "l00:0" and insert -- 100:0 --, therefor.

In columns 153-154, line 13 (Table 7-continued), delete "SSA 481000" and insert -- SSA 48100 --, therefor.

In columns 153-154, line 14 (Table 7-continued), delete "7. 3 Hz," and insert -- 7.3 Hz, --, therefor.

In columns 153-154, line 14 (Table 7-continued), delete "CH3)," and insert -- $CH_3$), --, therefor.

In columns 155-156, line 23 (Table 7-continued), delete "($CD_3OD$, .δ):" and insert -- ($CD_3OD$, δ): --, therefor.

In columns 155-156, line 26 (Table 7-continued), delete "$^{13}C$ -NMR" and insert -- $^{13}C$-NMR --, therefor.

In columns 157-158, line 25 (Table 7-continued), delete "5xCH2)," and insert -- 5x$CH_2$), --, therefor.

In columns 159-160, line 4 (Table 7-continued), delete "$R^f$:" and insert -- $R_f$: --, therefor.

In columns 159-160, line 36 (Table 7-continued), delete "99.9%" and insert -- 99.9%. --, therefor.

In columns 161-162, line 8 (Table 7-continued), delete "$CD_3OD$," and insert -- ($CD_3OD$, --, therefor.

In columns 163-164, line 20 (Table 7-continued), delete "99.9%" and insert -- 99.9%. --, therefor.

In columns 165-166, line 6 (Table 7-continued), delete "dihydrobenzo[o]" and insert -- dihydrobenzo[d] --, therefor.

In columns 165-166, line 6 (Table 7-continued), delete "C<u>H2</u>CH2CH3)," and insert

CERTIFICATE OF CORRECTION (continued)
U.S. Pat. No. 9,200,016 B2

-- C$\underline{H}_2$CH$_2$CH$_3$), --, therefor.

In columns 167-168, line 6 (Table 7-continued), delete "CH2)," and insert -- CH$_2$), --, therefor.

In columns 167-168, line 7 (Table 7-continued), delete "DMSO-d$_6$," and insert -- (DMSO-d$_6$, --, therefor.

In columns 167-168, line 14 (Table 7-continued), delete "7.51-7.543(m," and insert -- 7.51-7.54 (m, --, therefor.

In columns 169-170, line 10 (Table 7-continued), delete "([MH]*," and insert -- ([MH]$^+$, --, therefor.

In columns 169-170, line 21 (Table 7-continued), delete "dirnethoxyisoquinolin" and insert -- dimethoxyisoquinolin --, therefor.

In columns 171-172, line 3 (Table 7-continued), delete "rnethyl)" and insert -- methyl) --, therefor.

In columns 171-172, line 12 (Table 7-continued), delete "dirnethoxyisoquinolin" and insert -- dimethoxyisoquinolin --, therefor.

In columns 171-172, line 14 (Table 7-continued), delete "2xCH3)," and insert -- 2xCH$_3$), --, therefor.

In columns 171-172, line 14 (Table 7-continued), delete "CH2," and insert -- CH$_2$, --, therefor.

In columns 171-172, line 19 (Table 7-continued), delete "MSS-ESI" and insert -- MS-ESI --, therefor.

In columns 171-172, line 20 (Table 7-continued), delete "95.0%" and insert -- 95.0%. --, therefor.

In columns 173-174, line 15 (Table 7-continued), delete "7.481(s," and insert -- 7.48 (s, --, therefor.

In columns 173-174, line 20 (Table 7-continued), delete "dimethoxylsoquinolin-4-yl)rnethyl)quinolin-6-arnine" and insert -- dimethoxyisoquinolin-4-yl)methyl)quinolin-6-amine --, therefor.

In columns 173-174, line 21 (Table 7-continued), delete "207- 208.7;" and insert -- 207-208.7; --, therefor.

In columns 175-176, line 3 (Table 7-continued), delete "1-(3-(0 -ethyl-6,7-dirnethoxyisoquinolin-4-yl)" and insert -- 1-(3-((1-ethyl-6,7-dimethoxyisoquinolin-4-yl) --, therefor.

In columns 175-176, line 9 (Table 7-continued), delete "pyrolidinone" and insert -- pyrrolidinone --, therefor.

In columns 175-176, line 23 (Table 7-continued), delete "(CH$_2$Cl$_2$:MeOH" and insert -- (CH$_2$Cl$_2$:MeOH --, therefor.

In columns 175-176, line 24 (Table 7-continued), delete "CH2Cl2" and insert -- CH$_2$Cl$_2$ --, therefor.

In columns 175-176, line 35 (Table 7-continued), delete "(s,1H, ArH);" and insert -- (s, 1H, ArH); --, therefor.

In columns 177-178, line 7 (Table 7-continued), delete "ArH) ," and insert -- ArH), --, therefor.

In columns 177-178, line 14 (Table 7-continued), delete "(CH$_2$Cl$_2$:MeOH)" and insert -- (CH$_2$Cl$_2$:MeOH) --, therefor.

In columns 177-178, line 16 (Table 7-continued), delete "7.75- 7.80" and insert -- 7.75-7.80 --, therefor.

In columns 177-178, line 21 (Table 7-continued), delete "(39.7 mg) ;" and insert -- (39.7 mg); --, therefor.

In columns 177-178, line 24 (Table 7-continued), delete "7.63- 7.67" and insert -- 7.63-7.67 --, therefor.

In columns 179-180, line 7 (Table 7-continued), delete "$^{13}$C NMR" and insert -- $^{13}$C-NMR --, therefor.

In columns 179-180, line 9 (Table 7-continued), delete "41.89," and insert -- 141.89, --, therefor.

In columns 179-180, line 11 (Structure) (Table 7-continued),

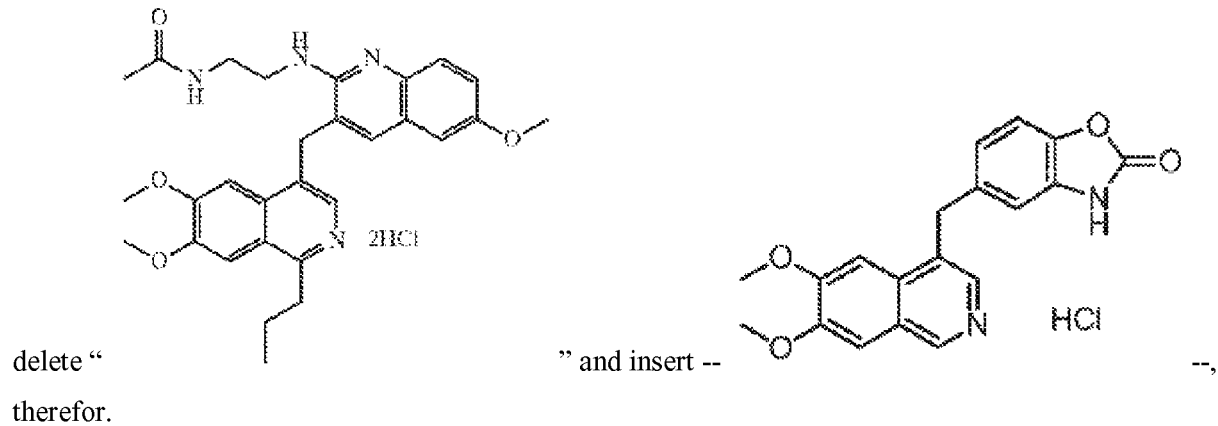

delete " " and insert -- --, therefor.

In columns 181-182, line 16 (Table 7-continued), delete "δ)" and insert -- δ): 13.99, --, therefor.

In columns 181-182, line 26 (Table 7-continued), delete "(CD$^3$OD," and insert -- (CD$_3$OD, --, therefor.

In columns 183-184, line 28, (Table 7-continued), delete "1H-NMR" and insert -- $^1$H-NMR --, therefor.

In columns 183-184, line 30 (Table 7-continued), delete "(m 2H," and insert -- (m, 2H, --, therefor.

In columns 183-184, line 30 (Table 7-continued), delete "8.34 (s 1H ArH)," and insert -- 8.34 (s, 1H, ArH), --, therefor.

In columns 183-184, line 30 (Table 7-continued), delete "8.99 (s 1H ArH);" and insert -- 8.99 (s, 1H, ArH); --, therefor.

In columns 185-186, line 3 (Table 7-continued), delete "benzo[o]" and insert -- benzo[d] --, therefor.

In columns 185-186, line 10 (Table 7-continued), delete "(161.mg, 0.71 mmol) )" and insert -- (161 mg, 0.71 mmol) --, therefor.

In columns 185-186, line 34 (Table 7-continued), delete "MeOH/ H$_2$O" and insert -- MeOH/H$_2$O --, therefor.

In columns 187-188, line 12 (Table 7-continued), delete "137,%;." and insert -- 17%; --, therefor.

In columns 187-188, line 12 (Table 7-continued), delete "R$_f$." and insert -- R$_f$: --, therefor.

In columns 187-188, line 13 (Table 7-continued), delete "CH$_3$) 3 86" and insert -- CH$_3$), 3.86 --, therefor.

CERTIFICATE OF CORRECTION (continued)
U.S. Pat. No. 9,200,016 B2

In columns 187-188, line 25 (Table 7-continued), delete "( DMSO-d₆," and insert -- (DMSO-d₆, --, therefor.

In columns 189-190, line 22 (Table 7-continued), delete "1H-NMR" and insert -- ¹H-NMR --, therefor.

In columns 191-192, line 24 (Table 7-continued), delete "Hz)" and insert -- Hz), --, therefor.

In columns 191-192, line 25 (Table 7-continued), delete "ArH)" and insert -- ArH), --, therefor.

In columns 191-192, line 25 (Table 7-continued), delete "(m 2H," and insert -- (m, 2H, --, therefor.

In columns 193-194, line 24 (Table 7-continued), delete "(CDCl₃, 6):" and insert -- (CDCl₃, δ): --, therefor.

In columns 193-194, line 25 (Table 7-continued), delete "(s 2H," and insert -- (s, 2H, --, therefor.

In columns 193-194, line 25 (Table 7-continued), delete "(d, 1H" and insert -- (d, 1H, --, therefor.

In columns 195-196, line 22 (Structure) (Table 7-continued), delete "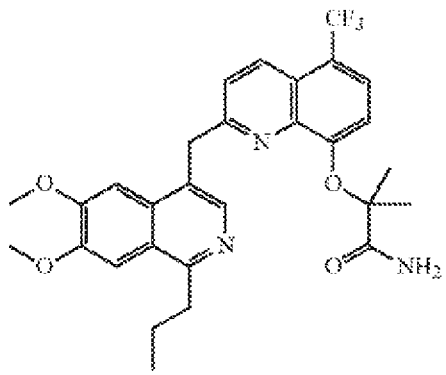 [SMILES: CCCc1ncc(Cc2ccc3c(C(F)(F)F)ccc(OC(C)(C)C(N)=O)c3n2)c2cc(OC)c(OC)cc12]" and insert --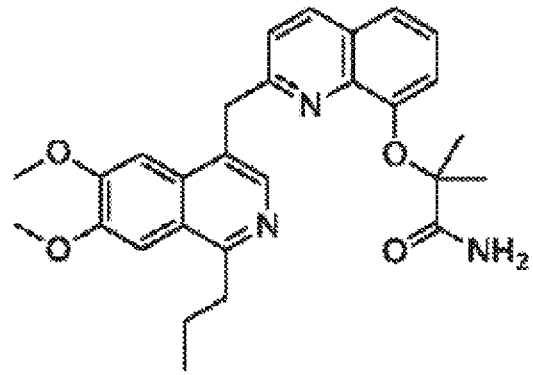--, therefor.

In columns 195-196, line 24 (Table 7-continued), delete "7.4 Hz )" and insert -- 7.4 Hz), --, therefor.

In columns 195-196, line 25 (Table 7-continued), delete "3.9.7" and insert -- 3.97 --, therefor.

In columns 197-198, line 4 (Table 7-continued), delete "10%" and insert -- 10%; --, therefor.

In columns 197-198, line 4 (Table 7-continued), delete "94.6);" and insert -- 94:6); --, therefor.

In columns 197-198, line 5 (Table 7-continued), delete "3 23" and insert -- 3.23 --, therefor.

In columns 197-198, line 13 (Table 7-continued), delete "1H-NMR" and insert -- ¹H-NMR --, therefor.

In columns 197-198, line 14 (Table 7-continued), delete "(CDC1₃" and insert -- (CDCl₃ --, therefor.

CERTIFICATE OF CORRECTION (continued)
U.S. Pat. No. 9,200,016 B2

In columns 197-198, line 22 (Table 7-continued), delete "CH2)," and insert -- $C_{H2}$), --, therefor.

In columns 199-200, line 22 (Table 7-continued), delete "4.61," and insert -- 4.61 --, therefor.

In columns 201-202, line 6 (Table 7-continued), delete "17.47-7.56" and insert -- 7.47-7.56 --, therefor.

In columns 201-202, line 12 (Table 7-continued), delete "(8A56.5 mg," and insert -- (856.5 mg, --, therefor.

In columns 201-202, line 13 (Table 7-continued), delete "$CH_2$," and insert -- $CH_2$, J = 7.7 Hz), --, therefor.

In columns 201-202, line 14 (Table 7-continued), delete "H. z)," and insert -- Hz), --, therefor.

In columns 201-202, line 30 (Table 7-continued), delete "1H-NMR" and insert -- $^1$H-NMR --, therefor.

In columns 203-204, line 3 (Table 7-continued), delete "benzo[o]" and insert -- benzo[d] --, therefor.

In columns 203-204, line 4 (Table 7-continued), delete "white" and insert -- White --, therefor.

In columns 203-204, line 19 (Table 7-continued), delete "oxobenzo[o]" and insert -- oxobenzo[d] --, therefor.

In columns 203-204, line 19 (Table 7-continued), delete "ypacetamide" and insert -- yl)acetamide --, therefor.

In columns 203-204, line 24 (Table 7-continued), delete "43.80 ,55.58," and insert -- 43.80, 55.58, --, therefor.

In column 205-206, line 13 (Table 7-continued), delete "$_1$H-NMR" and insert -- $^1$H-NMR --, therefor.

In columns 205-206, line 16 (Table 7-continued), delete "$^{13}$C- NMR" and insert -- $^{13}$C-NMR --, therefor.

In columns 205-206, line 20 (Table 7-continued), delete "(a )" and insert -- (a) --, therefor.

In columns 209-210, line 17 (Table 7-continued), delete "2xArH)i" and insert -- 2xArH), --, therefor.

In columns 209-210, line 18 (Table 7-continued), delete "(DMSO-d6," and insert -- (DMSO-$d_6$, --, therefor.

In column 209-210, line 23 (Table 7-continued), delete "1H-NMR" and insert -- $^1$H-NMR --, therefor.

In columns 211-212, line 23 (Table 7-continued), delete "CH2)," and insert -- $CH_2$), --, therefor.

In columns 211-212, line 23 (Table 7-continued), delete "7 27-7.37" and insert -- 7.27-7.37 --, therefor.

In columns 213-214, line 4 (Table 7-continued), delete "$CDCl_3$, δ)," and insert -- $CDCl_3$, δ): --, therefor.

In columns 213-214, line 21 (Table 7-continued), delete "Cyclohexane.EtOAc" and insert -- Cyclohexane:EtOAc --, therefor.

In columns 213-214, line 25 (Table 7-continued), delete "$^{13}$C- NMR" and insert -- $^{13}$C-NMR --, therefor.

In columns 213-214, line 27 (Table 7-continued), delete "([MH]$^{+1}$,26);" and insert -- ([MH]$^{+1}$, 26); --, therefor.

In columns 215-216, line 4 (Table 7-continued), delete "157.7." and insert -- 157.7; --, therefor.

In columns 215-216, line 15 (Table 7-continued), delete "ArH) ," and insert -- ArH), --, therefor.

In columns 217-218, line 5 (Table 7-continued), delete "l00:0" and insert -- 100:0 --, therefor.

In columns 217-218, line 7 (Table 7-continued), delete "$^{13}$C- NMR" and insert -- $^{13}$C-NMR --, therefor.